(12) United States Patent
Duan et al.

(10) Patent No.: US 6,403,632 B1
(45) Date of Patent: Jun. 11, 2002

(54) LACTAM METALLOPROTEASE INHIBITORS

(76) Inventors: Jingwu Duan, 17 Springbrook La.; Carl P. Decicco, 17 Ridgewood Turn, both of Newark, DE (US) 19711; Zelda R. Wasserman, 1904 Academy Pl., Wilmington, DE (US) 19806; Thomas P. Maduskuie, Jr., 613 Foulkstone Rd., Wilmington, DE (US) 19803

( * ) Notice: Subject to any disclaimer, the term of this patent is extended or adjusted under 35 U.S.C. 154(b) by 0 days.

(21) Appl. No.: 09/516,709

(22) Filed: Mar. 1, 2000

(51) Int. Cl.[7] .................. A61K 31/40; C07D 209/96; C07D 295/00; C07D 495/00
(52) U.S. Cl. ................. 514/422; 514/424; 514/425; 548/413; 548/517; 548/518
(58) Field of Search ................. 514/422, 424, 514/425; 548/413, 517, 518

(56) References Cited

U.S. PATENT DOCUMENTS 5,795,889 A    8/1998    Spada et al.

FOREIGN PATENT DOCUMENTS

| EP | 0574758 | 12/1993 |
|----|---------|---------|
| GB | 2268934 | 1/1994 |
| WO | 9424140 | 10/1994 |
| WO | 9509841 | 4/1995 |
| WO | 9629313 | 9/1996 |
| WO | 9716425 | 5/1997 |
| WO | 9732846 | 9/1997 |

OTHER PUBLICATIONS

Wei, CA125: 114389, abstract of US Patent #5,523,400, 1996.*

* cited by examiner

*Primary Examiner*—D. Margaret Seaman
(74) *Attorney, Agent, or Firm*—David H. Vance; Jing S. Belfield

(57) ABSTRACT

The present application describes novel lactams and derivatives thereof of formula I:

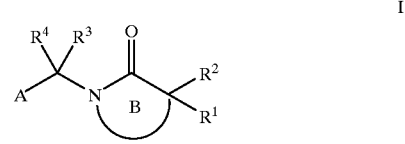

or pharmaceutically acceptable salt forms thereof, wherein rings ring B is a 4–8 membered cyclic amide containing from 0–3 additional heteroatoms selected from N, O, and S, which are useful as metalloprotease inhibitors.

18 Claims, No Drawings

LACTAM METALLOPROTEASE INHIBITORS

FIELD OF THE INVENTION

This invention relates generally to novel lactam metalloprotease inhibitors, pharmaceutical compositions containing the same, and methods of using the same.

BACKGROUND OF THE INVENTION

There is now a body of evidence that metalloproteinases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMP (tissue inhibitor of metalloproteinase), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A, 1970, 424–434). There are four classes of protein degradative enzymes in mammalian cells: serine, cysteine, aspartic and metalloproteinases. The available evidence supports that it is the metalloproteinases which are responsible for the degradation of the extracellular matrix of articullar cartillage in OA and RA. Increased activities of collagenases and stromelysin have been found in OA cartilage and the activity correlates with severity of the lesion (Mankin et al. Arthritis Rheum. 21, 1978, 761–766, Woessner et al. Arthritis Rheum. 26, 1983, 63–68 and Ibid. 27, 1984, 305–312). In addition, aggrecanase (a newly identified metalloproteinase enzymatic activity) has been identified that provides the specific cleavage product of proteoglycan, found in RA and OA patients (Lohmander L. S. et al. Arthritis Rheum. 36, 1993, 1214–22).

Therefore metalloproteinases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. Ann. Rep. Med. Chem. 25, 175–184, AP, San Diego, 1990).

Tumor necrosis factor (TNF) is a cell associated cytokine that is processed from a 26 kd precursor form to a 17 kd active form. TNF has been shown to be a primary mediator in humans and in animals, of inflammation, fever, and acute phase responses, similar to those observed during acute infection and shock. Excess TNF has been shown to be lethal. There is now considerable evidence that blocking the effects of TNF with specific antibodies can be beneficial in a variety of circumstances including autoimmune diseases such as rheumatoid arthritis (Feldman et al, Lancet, 1994, 344, 1105) and non-insulin dependent diabetes melitus. (Lohmander L. S. et al. Arthritis Rheum. 36, 1993, 1214–22) and Crohn's disease (Macdonald T. et al. Clin. Exp. Immunol. 81, 1990, 301).

Compounds which inhibit the production of TNF are therefore of therapeutic importance for the treatment of inflammatory disorders. Recently it has been shown that a matrix metalloproteinase or family of metalloproteinases, hereafter known as TNF-convertases (TNF-C), as well as other Mp's are capable of cleaving TNF from its inactive to active form (Gearing et al Nature, 1994, 370, 555). This invention describes molecules that inhibit this conversion and hence the secretion of active TNF-a from cells. These novel molecules provide a means of mechanism based therapeutic intervention for diseases including but not restricted to septic shock, haemodynamic shock, sepsis syndrom, post ischaemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, osteo and rheumatoid arthritis, multiple sclerosis, radiation damage, hyperoxic alveolar injury, periodontal disease, HIV and non-insulin dependent diabetes melitus.

Since excessive TNF production has been noted in several disease conditions also charactarized by MMP-mediated tissue degradation, compounds which inhibit both MMPs and TNF production may also have a particular advantage in diseases where both mechanisms are involved.

There are several patents which disclose hydroxamate and carboxylate based MMP inhibitors.

WO95/09841 describes compounds that are hydroxamic acid derivatives and are inhibitors of cytokine production.

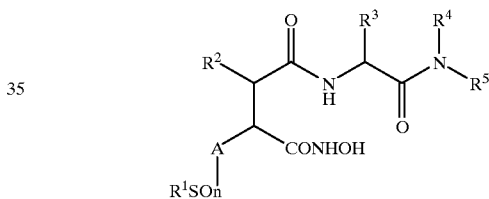

European patent Application Publication No. 574,758 A1, discloses hydroxamic acid derivatives as collagenase inhibitors having the general formula:

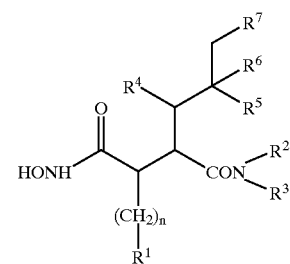

GB 2 268 934 A and WO 94/24140 claim hydroxamate inhibitors of MMPs as inhibitors of TNF production.

The compounds of the current invention act as inhibitors of MMPS, in particular aggrecanase and TNF. These novel molecules are provided as anti-inflammatory compounds and cartilage protecting therapeutics. The inhibiton of aggrecanase, TNF-C, and other metalloproteinases by molecules of the present invention indicates they are anti-inflammatory and should prevent the degradation of cartilage by these enzymes, thereby alleviating the pathological conditions of osteo- and rheumatoid arthritis.

SUMMARY OF THE INVENTION

Accordingly, one object of the present invention is to provide novel lactams which are useful as metalloprotease inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating inflammatory disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formula (I):

$$I$$

or pharmaceutically acceptable salt or prodrug forms thereof, wherein A, B, $R^1$, $R^2$, $R^3$, and $R^4$ are defined below, are effective metalloprotease inhibitors.

DETAILED DESCRIPTION OF PREFERRED EMBODIMENTS

[1] Thus, in a first embodiment, the present invention provides a novel compound of formula I:

$$I$$

or a stereoisomer or pharmaceutically acceptable salt form thereof, wherein;

A is selected from $COR^5$, $-CO_2H$, $CH_2CO_2H$, $-CO_2R^6$, $-CONHOH$, $-CONHOR^5$, $-CONHOR^6$, $NHR^a$, $-N(OH)COR^5$, $-SH$, $-CH_2SH$, $-SO_2NHR^a$, $SN_2H_2R^a$, $PO(OH)_2$, and $PO(OH)NHR^a$;

ring B is a 4–8 membered cyclic amide containing from 0–3 additional heteroatoms selected from O, $NR^a$, and $S(O)_p$, 0–1 additional carbonyl groups and 0–1 double bonds;

$R^1$ is $U-X-Y-Z-U^a-X^a-Y^a-Z^a$;

U is absent or is selected from: O, $NR^a$, C(O), C(O)O, OC(O), $C(O)NR^a$, $NR^aC(O)$, OC(O)O, $OC(O)NR^a$, $NR^aC(O)O$, $NR^aC(O)NR^a$, $S(O)_p$, $S(O)_pNR^a$, $NR^aS(O)_p$, and $NR^aSO_2NR^a$;

X is absent or selected from $C_{1-10}$ alkylene, $C_{2-10}$ alkenylene, and $C_{2-10}$ alkynylene;

Y is absent or selected from O, $NR^a$, $S(O)_p$, and C(O);

Z is absent or selected from a $C_{3-13}$ carbocyclic residue substituted with 0–5 $R^b$ and a 5–14 membered heterocyclic system containing from 1–4 heteroatoms selected from the group consisting of N, O, and S and substituted with 0–5 $R^b$;

$U^a$ is absent or is selected from: O, $NR^a$, C(O), C(O)O, OC(O), $C(O)NR^a$, $NR^aC(O)$, OC(O)O, $OC(O)NR^a$, $NR^aC(O)O$, $NR^aC(O)NR^a$, $S(O)_p$, $S(O)_pNR^a$, $NR^aS(O)_p$, and $NR^aSO_2NR^a$;

$X^a$ is absent or selected from $C_{1-10}$ alkylene, $C_{2-10}$ alkenylene, $C_{2-10}$ alkynylene;

$Y^a$ is absent or selected from O, $NR^a$, $S(O)_p$, and C(O);

$Z^a$ is selected from H, a $C_{3-13}$ carbocyclic residue substituted with 0–5 $R^c$ and a 5–14 membered heterocyclic system containing from 1–4 heteroatoms selected from the group consisting of N, O, and S and substituted with 0–5 $R^c$;

$R^2$ is selected from H, Q', $C_{1-10}$ alkylene-Q', $C_{2-10}$ alkenylene-Q', $C_{2-10}$ alkynylene-Q', $(CRR')_rO(CRR')_r-Q'$, $(CRR')_rNR^a(CRR')_r-Q'$, $(CRR')_rNR^aC(O)(CRR')_r-Q'$, $(CRR')_rC(O)NR^a(CRR')_r-Q'$, $(CRR')_rC(O)(CRR')_r-Q'$, $(CRR')_rC(O)O(CRR')_r-Q'$, $(CRR')_rS(O)_p(CRR')_r-Q'$, $(CRR')_rSO_2NR^a(CRR')_r-Q'$, $(CRR')_rNR^aC(O)NR^a(CRR')_r-Q'$, $(CRR')_rOC(O)NR^a(CRR')_r-Q'$, and $(CRR')_rNR^aC(O)O(CRR')_r-Q'$;

R, at each occurrence, is independently selected from H, $CH_3$, $CH_2CH_3$, $CH=CH_2$, $CH=CHCH_3$, and $CH_2CH=CH_2$;

R', at each occurrence, is independently selected from H, $CH_3$, $CH_2CH_3$, and $CH(CH_3)_2$;

alternatively, $R^1$ and $R^2$ combine to form a $C_{3-13}$ carbocyclic residue substituted with $R^{1'}$ and 0–3 $R^b$ or a 5–14 membered heterocyclic system containing from 1–4 heteroatoms selected from the group consisting of N, O, and S and substituted with $R^{1'}$ and 0–3 $R^b$;

Q' selected from H, a $C_{3-13}$ carbocyclic residue substituted with 0–5 $R^b$ and a 5–14 membered heterocyclic system containing from 1–4 heteroatoms selected from the group consisting of N, O, and and substituted with 0–5 $R^b$;

$R^{1'}$ is $U^a-X^a-Y^a-Z^a$;

$R^3$ is selected from H, Q, $C_{1-10}$ alkylene-Q, $C_{2-10}$ alkenylene-Q, $C_{2-10}$ alkynylene-Q, $(CRR')_rO(CRR')_r-Q$, $(CRR')_rNR^a(CRR')_r-Q$, $(CRR')_rC(O)(CRR')_r-Q$, $(CRR')_rC(O)O(CRR')_r-Q$, $(CRR')_rOC(O)(CRR')_r-Q$, $(CRR')_rC(O)NR^a(CRR')_r-Q$, $(CRR')_rNR^aC(O)(CRR')_r-Q$, $(CRR')_rOC(O)O(CRR')_r-Q$, $(CRR')_rOC(O)NR^a(CRR')_r-Q$, $(CRR')_rNR^aC(O)O(CRR')_r-Q$, $(CRR')_rNR^aC(O)NR^a(CRR')_r-Q$, $(CRR')_rS(O)_p(CRR')_r-Q$, $(CRR')_rSO_2NR^a(CRR')_r-Q$, $(CRR')_rNR^aSO_2(CRR')_r-Q$, $(CRR')_rNR^aSO_2NR^a(CRR')_r-Q$, $(CRR')_rNR^aC(O)(CRR')_rNHQ$, $(CRR')_rNR^aC(O)(CRR')_rNHC(O)OR^a$, and $(CRR')_rNR^aC(O)(CRR')_rNHC(O)(CRR')_rNHC(O)OR^a$, Q is selected from H, a $C_{3-13\ 4}$ carbocyclic residue substituted with 0–5 $R^b$ and a 5–14 membered heterocyclic system containing from 1–4 hete3oatoms selected from the group consisting of N, O, and and substituted with 0–5 $R^b$;

$R^4$ is selected from H, $C_{1-10}$ alkylene-H, $C_{2-10}$ alkenylene-H, $C_{2-10}$ alkynylene-H, $(CRR')_rO(CRR')_r-H$, $(CRR')_rNR^a(CRR')_r-H$, $(CRR')_rC(O)(CRR')_r-H$, $(CRR')_rC(O)O(CRR')_r-H$, $(CRR')_rOC(O)(CRR')_r-H$, $(CRR')_rC(O)NR^a(CRR')_r-H$, $(CRR')_rNR^aC(O)(CRR')_r-H$, $(CRR')_rOC(O)O(CRR')_r-H$, $(CRR')_rOC(O)NR^a(CRR')_r-H$, $(CRR')_rNR^aC(O)O(CRR')_r$ —H, (CRR')$_{r'}$NR$^a$C(O)NR$^a$(CRR')$_r$—H, (CRR')$_r$S(O)$_p$(CRR')$_r$—H, (CRR')$_r$SO$_2$NR$^a$(CRR')$_r$—H, (CRR')$_{r'}$ NR$^a$SO$_2$(CRR')$_r$—H, and (CRR')$_{r'}$NR$^a$SO$_2$NR$^a$(CRR')$_r$—H;

alternatively, R$^3$ and R$^4$ combine to form a C$_{3-13}$ carbocyclic residue substituted with R$^{1'}$ and 0–3 R$^b$ or a 5–14 membered heterocyclic system containing from 1–4 heteroatoms selected from the group consisting of N, O, and S and substituted with R$_{1'}$ and 0–3 R$^b$;

R$^a$, at each occurrence, is independently selected from H, C$_{1-4}$ alkyl, phenyl and benzyl;

R$^{a'}$, at each occurrence, is independently selected from H, C$_{1-4}$ alkyl, phenyl and benzyl;

R$^{a''}$, at each occurrence, is in independently selected from H, C$_{1-4}$ alkyl, benzyl, C$_{3-7}$ carbocyclic residue, or a 5 to 6 membered heteroaromatic ring containing 1–4 heteroatoms selected from the group consisting of N, O, and S;

alternatively, R$^a$ and R$^{a'}$ taken together with the nitrogen to which they are attached form a 5 or 6 membered ring containing from 0–1 additional heteroatoms selected from the group consisting of N, O, and S;

R$^b$, at each occurrence, is independently selected from C$_{1-6}$ alkyl, OR$^a$, Cl, F, Br, I, =O, CN, NO$_2$, NR$^a$R$^{a'}$, C(O)R$^{a''}$, C(O)OR$^a$, C(O)NR$^a$R$^{a'}$, S(O)$_2$NR$^a$R$^{a'}$, S(O)$_p$R$^a$, CF$_3$, and CF$_2$CF$_3$;

R$^c$, at each occurrence, is inependently selected from C$_{1-6}$ alkyl, OR$^a$, Cl, F, Br, I, =O, CN, NO$_2$, NR$^a$R$^{a'}$, C(O)R$^a$, C(O)OR$^a$, C(O)NR$^a$R$^{a'}$, NR$^a$C(O)NR$^a$R$^{a'}$, S(O)$_2$NR$^a$R$^{a'}$, S(O)$_p$R$^a$, CF$_3$, CF$_2$CF$_3$, —CH(=NOH), —C(=NOH)CH$_3$, (CRR')$_s$O(CRR')$_s$R$^d$, (CRR')$_s$S(O)$_p$(CRR')$_s$R$^d$, (CRR')$_s$NR$^a$(CRR')$_s$R$^d$, phenyl, and a 5–14 membered heterocyclic system containing from 1–4 heteroatoms selected from the group consisting of N, O, and S;

R$^5$, at each occurrence, is selected from C$_{1-10}$ alkyl substituted with 0–2 R$^b$, and C$_{1-8}$ alkyl substituted with 0–2 R$^d$;

R$^d$, at each occurrence, is independently selected from phenyl substituted with 0–3 R$^b$, biphenyl substituted with 0–2 R$^b$, naphthyl substituted with 0–3 R$^b$ and a 5–10 membered heteroaryl system containing from 1–4 heteroatoms selected from the group consisting of N, O, and S and substituted with 0–3 R$^b$;

R$^6$, at each occurrence, is selected from phenyl, naphthyl, C$_{1-10}$ alkyl-phenyl-C$_{1-6}$ alkyl-, C$_{3-11}$ cycloalkyl, C$_{1-6}$ alkylcarbonyloxy-C$_{1-3}$ alkyl-, C$_{1-6}$ alkoxycarbonyloxy-C$_{1-3}$ alkyl-, C$_{2-10}$ alkoxycarbonyl, C$_{3-6}$ cycloalkylcarbonyloxy-C$_{1-3}$ alkyl-, C$_{3-6}$ cycloalkoxycarbonyloxy-C$_{1-3}$ alkyl-, C$_{3-6}$ cycloalkoxycarbonyl, phenoxycarbonyl, phenyloxycarbonyloxy-C$_{1-3}$ alkyl-, phenylcarbonyloxy-C$_{1-3}$ alkyl-, C$_{1-6}$ alkoxy-C$_{1-6}$ alkylcarbonyloxy-C$_{1-3}$ alkyl-, [5-(C$_{1-5}$ alkyl)-1,3-dioxa-cyclopenten-2-one-yl]methyl, (5-aryl-1,3-dioxa-cyclopenten-2-one-yl)methyl, -C$_{1-10}$ alkyl-NR$^7$R$^{7a}$, —CH(R$^8$)OC(=O)R$^9$, —CH(R$^8$)OC(=O)OR$^9$, and

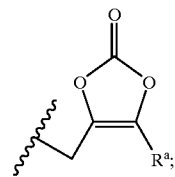

R$^7$ is selected from H and C$_{1-10}$ alkyl, C$_{2-6}$ alkenyl, C$_{3-6}$ cycloalkyl-C$_{1-3}$ alkyl-, and phenyl-C$_{1-6}$ alkyl-;

R$^{7a}$ is selected from H and C$_{1-10}$ alkyl, C$_{2-6}$ alkenyl, C$_{3-6}$ cycloalkyl-C$_{1-3}$ alkyl-, and phenyl-C$_{1-6}$ alkyl-;

R$^8$ is selected from H and C$_{1-4}$ linear alkyl;

R$^9$ is selected from H, C$_{1-8}$ alkyl substituted with 1–2 R$^e$, C$_{3-8}$ cycloalkyl substituted with 1–2 R$^e$, and phenyl substituted with 0–2 R$^b$;

R$^e$, at each occurrence, is selected from C$_{1-4}$ alkyl, C$_{3-8}$ cycloalkyl, C$_{1-5}$ alkoxy, phenyl substituted with 0–2 R$^b$;

p, at each occurrence, is selected from 0, 1, and 2;

r, at each occurrence, is selected from 0, 1, 2, 3, 4, and 5;

r', at each occurrence, is selected from 0, 1, 2, 3, 4, and 5;

r", at each occurrence, is selected from 1, 2, and 3;

s, at each occurrence, is selected from 0, 1, 2, and 3; and, s', at each occurrence, is selected from 0, 1, 2, and 3.

[2] In a preferred embodiment, the present invention provides a novel compound of formula I, wherein;

A is selected from COR$^5$, —CO$_2$H, CH$_2$CO$_2$H, —CONHOH, —CONHOR$^5$, —CONHOR$^6$, —N(OH)COR$^5$, —SH, and —CH$_2$SH;

ring B is a 4–7 membered cyclic amide containing from 0–2 additional heteroatoms selected from O, NR$^a$, and S(O)$_p$, and 0–1 additional carbonyl groups and 0–1 double bonds;

U is absent;

Y is absent;

Z is absent or selected from C$_{5-10}$ carbocyclic residue substituted with 0–5 R$^b$ and a 5–10 membered heterocyclic system containing from 1–4 heteroatoms selected from the group consisting of N, O, and S and substituted with 0–5 R$^b$;

U$^a$ is absent or is selected from: O, NR$^a$, C(O), C(O)NR$^a$, NR$^a$C(O), OC(O)NR$^a$, NR$^a$C(O)O, NR$^a$C(O)NR$^a$, S(O)$_p$NR$^a$, and NR$^a$S(O)$_p$;

R$^2$ is selected from H, Q', C$_{1-5}$ alkylene-Q', C$_{2-5}$ alkenylene-Q', C$_{2-5}$ alkynylene-Q', (CRR')$_r$O(CRR')$_r$—Q', (CRR')$_r$NR$^a$(CRR')$_r$—Q', (CRR')$_r$NR$^a$C(O)(CRR')$_r$—Q', (CRR')$_r$C(O)NR$^a$(CRR')$_r$—Q', (CRR')$_r$NR$^a$C(O)NR$^a$(CRR')$_r$—Q', (CRR')$_r$C(O)(CRR')$_r$—Q', (CRR')$_r$C(O)O(CRR')$_r$—Q', (CRR')$_r$S(O)$_p$(CRR')$_r$—Q', and (CRR')$_r$SO$_2$NR$^a$(CRR')$_r$—Q';

Q' is selected from H, phenyl substituted with 0–3 R$^b$ and a 5–6 membered heteroaryl system containing from 1–4 heteroatoms selected from the group consisting of N, O, and S and substituted with 0–3 R$^b$;

R$^3$ is selected from H, Q, C$_{1-10}$ alkylene-Q, C$_{2-10}$ alkenylene-Q, C$_{2-10}$ alkynylene-Q, (CRR')$_r$O(CRR')$_r$—Q, (CRR')$_r$NR$^a$(CRR')$_r$—Q, (CRR')$_s$C(O)(CRR')$_r$—Q, (CRR')$_r$C(O)NR$^a$(CRR')$_r$—Q, (CRR')$_r$NR$^a$C(O)(CRR')$_r$—Q, (CRR')$_r$OC(O)NR$^a$(CRR')$_r$—Q, (CRR')$_{r'}$NR$^a$C(O)O(CRR')$_r$—Q, (CRR')$_{r'}$NR$^a$C(O)NR$^a$(CRR')$_r$—Q, (CRR')$_{r'}$S(O)$_p$(CRR')$_r$—Q, (CRR')$_{r'}$ $SO_2NR^a(CRR')_r$—Q, $(CRR')_rNR^aSO_2(CRR')_r$—Q, and $(CRR')_rNR^aSO_2NR^a(CRR')_r$—Q;

R, at each occurrence, is independently selected from H, $CH_3$, and $CH_2CH_3$;

R', at each occurrence, is independently selected from H and $CH_3$;

Q is selected from H, a $C_{3-10}$ carbocyclic residue substituted with 0–5 $R^b$ and a 5–10 membered heterocyclic system containing from 1–4 heteroatoms selected from the group consisting of N, O, and S and substituted with 0–5 $R^b$; and, $R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $S(O)_2NR^aR^{a'}$, $S(O)_p R^a$, $CF_3$, $CF_2CF_3$, and a 5–10 membered heterocylic system containing from 1–4 heteroatoms selected from the group consisting of N, O, and S.

[3] In a more preferred embodiment, the present invention provides a novel compound of formula I, wherein;

A is selected from —$CO_2H$, $CH_2CO_2H$, —CONHOH, —$CONHOR^5$, and —$N(OH)COR^5$;

ring B is a 4–6 membered cyclic amide containing from 0–2 additional heteroatoms selected from O, $NR^a$, and $S(O)_p$, and 0–1 additional carboryl groups and 0–1 double bonds;

Z is absent or selected from a $C_{5-6}$ carbocyclic residue substituted with 0–3 $R^b$ and a 5–9 membered heterocyclic system containing from 1–4 heteroatoms selected from the group consisting of N, O, and S and substituted with 0–5 $R^b$;

$U^a$ is absent or is selected from: O, $NR^a$, C(O), $C(O)NR^a$, $NR^aC(O)$, and $S(O)_pNR^a$;

$X^a$ is absent or $C_{1-10}$ alkylene;

$R^2$ is selected from H, $C_{1-5}$ alkylene-Q', $(CH_2)_rO(CH_2)_r$—Q', $(CH_2)_rNR^a(CH_2)_r$—Q', $(CRR')_rNR^aC(O)(CRR')_r$—Q', $(CH_2)_rC(O)NR^a(CH_2)_r$—Q', $(CRR')_rNR^aC(O)NR^a(CRR')_r$—Q', and $(CH_2)_rC(O)(CH_2)_r$—Q';

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $S(O)_2NR^aR^{a'}$, $S(O)_p R^a$, $CF_3$, $CF_2CF_3$, and a 5–9 membered heterocyclic system containing from 1–4 heteroatoms selected from the group consisting of N, O, and S; and, Q is selected from H, a $C_{5-6}$ carbocyclic residue substituted with 0–5 $R^b$ and a 5–6 membered heterocyclic system containing from 1–4 heteroatoms selected from the group consisting of N, O, and S and substituted with 0–5 $R^b$.

[4] In a further preferred embodiment, the present invention provides a novel compound of formula I, wherein;

A is selected from —$CO_2H$, $CH_2CO_2H$, —CONHOH, and —$CONHOR^5$;

ring B is a 4–5 membered cyclic amide containing from 0–2 additional heteroatoms selected from O, $NR^a$, and $S(O)_p$, and 0–1 additional carbonyl groups and 0–1 double bonds;

X is absent or selected from $C_{1-4}$ alkylene, $C_{2-4}$ alkenylene, and $C_{2-4}$ alkynylene, Z is absent or selected from phenyl substituted with 0–3 $R^b$ and a 5–9 membered aromatic heterocyclic system containing from 1–4 heteroatoms selected from the group consisting of N, O, and S and substituted with 0–3 $R^b$;

$X^a$ is absent or $C_{1-4}$ alkylene;

$Y^a$ is absent or selected from O and $NR^a$;

$Z^a$ is selected from H, a $C_{5-10}$ carbocyclic residue substituted with 0–5 $R^c$ and a 5–10 membered heterocyclic system containing from 1–4 heteroatoms selected from the group consisting of N, O, and S and substituted with 0–5 $R^c$;

$R^4$ is selected from H, $C_{1-4}$ alkylene-H, $(CH_2)_rO(CH_2)_r$—H, and $(CH_2)_rNR^a(CH_2)_r$—H; and, $R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $S(O)_2NR^aR^{a'}$, $S(O)_p R^a$, $CF_3$, $CF_2CF_3$, and a 5–6 membered heterocyclic system containing from 1–4 heteroatoms selected from the group consisting of N, O, and S.

[5] In another preferred embodiment, the present invention provides novel compounds selected from:

[1(R)]-N-hydroxy-α,3-dimethyl-2-oxo-3-[4-(phenylmethoxy)phenyl]-1-pyrrolidineacetamide;

[1(R)]-N-hydroxy-α,3-dimethyl-2-oxo-3-(4-methoxyphenyl)-1-pyrrolidineacetamide;

[1(R)]-N-hydroxy-α,3-dimethyl-3-[4-(1-methylethoxy)phenyl]-2oxo-1-pyrrolidineacetamide;

[1(R)]-3-[4-(1,1-dimethylethoxy)phenyl]-N-hydroxy-α,3-dimethyl-2-oxo-1-pyrrolidineacetamide;

[1(R)]-3-(4-(cyclohexyloxy)phenyl]-N-hydroxy-α,3-dimethyl-2-oxo-1-pyrrolidineacetamide;

[1(R)]-N-hydroxy-α,3-dimethyl-2-oxo-3-[4-[4-(1,1-dimethylethyl)phenylmethoxy]phenyl]-1-pyrrolidineacetamide;

[1(R)]-N-hydroxy-α,3-dimethyl-2-oxo-3-[4-(trans-3-phenyl-2-propenyloxy)phenyl]-1-pyrrolidineacetamide;

[1(R)]-3-[4-[(3-methylphenyl)methoxy]phenyl]-N-hydroxy-α,3-dimethyl-2-oxo-1-pyrrolidineacetamide;

[1(R)]-3-[4-[(3,5-dimethylphenyl)methoxy]phenyl]-N-hydroxy-α,3-dimethyl-2-oxo-1pyrrolidineacetamide;

[1(R)]-N-hydroxy-α,3-dimethyl-2-oxo-3-[4-(2-propenyloxy)phenyl]-1-pyrrolidineacetamide;

[1(R)]-3-[4-[(3-cyanophenyl)methoxy]phenyl]-N-hydroxy-α,3-dimethyl-2-oxo-1-pyrrolidineacetamide;

[1(R)]-N-hydroxy-α-3-dimethyl-3-[4-[(2-nitrophenyl)methoxy]phenyl]-2-oxo-1-pyrrolidineacetamide;

[1(R)]-N-hydroxy-α-3-dimethyl-3-[4-[(3-nitrophenyl)methoxy]phenyl]-2-oxo-1-pyrrolidineacetamide;

[1(R)]-N-hydroxy-α,3-dimethyl-3-[4-[(4-nitrophenyl)methoxy]phenyl]-2-oxo-1-pyrrolidineacetamide;

[1(R)]-N-hydroxy-α,3-dimethyl-3-[4-[(1-naphthalenyl)methoxy]phenyl]-2-oxo-1-pyrrolidineacetamide;

[1(R)]-N-hydroxy-3-(4-hydroxyphenyl)-α,3-dimethyl-2-oxo-1-pyrrolidineacetamide;

[1(R)]-N-hydroxy-α,3-dimethyl-2-oxo-3-[4-[(2-pyridinyl)methoxy]phenyl]-1-pyrrolidineacetamide;

[1(R)]-N-hydroxy-α,3-dimethyl-2-oxo-3-[4-[(3-pyridinyl)methoxy]phenyl]-1-pyrrolidineacetamide;

[1(R)]-N-hydroxy-α,3-dimethyl-2-oxo-3-[4-[(4-pyridinyl)methoxy]phenyl]-1-pyrrolidineacetamide;

[1(R)]-N-hydroxy-α,3-dimethyl-3-[4-(2-methylpropyl)phenyl]-2-oxo-1-pyrrolidineacetamide;

[1(R)]-N-hydroxy-α,3-dimethyl-2-oxo-3-phenyl-1-pyrrolidineacetamide;

N-hydroxy-2-oxo-3-phenyl-1-pyrrolidineacetamide;

(+/-)-N-hydroxy-3-methyl-2-oxo-3-phenyl-1-pyrrolidineacetamide;

[1(R)]-N-hydroxy-α-methyl-2-oxo-3-phenyl-1-pyrrolidineacetamide;

[1(R)]-N-hydroxy-3-(4-methoxyphenyl)-α-methyl-2-oxo-1-pyrrolidineacetamide;

[1(R)]-3-cyclohexyl-N-hydroxy-α,3-dimethyl-2-oxo-1-pyrrolidineacetamide;

[1(R)]-N-hydroxy-α,3-dimethyl-2-oxo-3-(2-phenylethyl)-1-pyrrolidineacetamide;

[1(R)]-3-(2-cyclohexylethyl)-N-hydroxy-α,3-dimethyl-2-oxo-1-pyrrolidineacetamide;

[1(R)]-N-hydroxy-α-methyl-2-oxo-3-phenyl-3-(phenylmethyl)-2-oxo-1-pyrrolidineacetamide;

[1(R)]-3,4,4',5'-tetrahydro-N-hydroxy-α-methyl-2-oxospiro[naphthalene-2(1H),3'-[3H]pyrrole]-1'(2'H)-acetamide;

[1(R)]-3-[4-[(3,5-dibromophenyl)methoxy]phenyl]-N-hydroxy-α,3-dimethyl-2-oxo-1-pyrrolidineacetamide;

[1(R)]-3-[4-[[3,5-bis(trifluoromethyl)phenyl]methoxy]phenyl]-N-hydroxy-α,3-dimethyl-2-oxo-1-pyrrolidineacetamide;

[1(R)]-3-[4-[(3,5-dichlorophenyl)methoxy]phenyl]-N-hydroxy-α,3-dimethyl-2-oxo-1-pyrrolidineacetamide;

[1(R)]-N-hydroxy-α,3-dimethyl-3-[4-[(2-methyl-1-naphthalenyl)methoxy]phenyl]-2-oxo-1-pyrrolidineacetamide;

[1(R)]-3-[4-[(3,5-dimethoxyphenyl)methoxy]phenyl]-N-hydroxy-α,3-dimethyl-2-oxo-1-pyrrolidineacetamide;

[1(R)]-3-[4-[[4-chloro-2-(trifluoromethyl)-6-quinolinyl]methoxy]phenyl]-N-hydroxy-α,3-dimethyl-2-oxo-1-pyrrolidineacetamide;

[1(R)]-N-hydroxy-α,3-dimethyl-2-oxo-3-[4-[[4-(1,2,3-thiadiazol-4-yl)phenyl]methoxy]phenyl]-1-pyrrolidineacetamide;

[1(R)]-3-[4-([1,1'-biphenyl]-2-ylmethoxy)phenyl]-N-hydroxy-α,3-dimethyl-2-oxo-1-pyrrolidineacetamide;

[1(R)]-3-[4-[(2,6-dichloro-4-pyridinyl)methoxy]phenyl]-N-hydroxy-α,3-dimethyl-2-oxo-1-pyrrolidineacetamide;

[1(R)]-3-[4-(1H-benzotriazol-1-ylmethoxy)phenyl]-N-hydroxy-α,3-dimethyl-2-oxo-1-pyrrolidineacetamide;

[1(R)]-3-[4-[(4,6-dimethyl-2-pyrimidinyl)methoxy]phenyl]-N-hydroxy-α,3-dimethyl-2-oxo-1-pyrrolidineacetamide;

[1(R)]-3-[4-(1,3-benzodioxol-5-ylmethoxy)phenyl]-N-hydroxy-α,3-dimethyl-2-oxo-1-pyrrolidineacetamide;

[1(R)]-3-[4-[(2-chloro-6-ethoxy-4-pyridinyl)methoxy]phenyl]-N-hydroxy-α,3-dimethyl-2-oxo-1-pyrrolidineacetamide;

[1(R)]-N-hydroxy-α,3-dimethyl-2-oxo-3-[4-(4-quinolinylmethoxy)phenyl]-1-pyrrolidineacetamide;

[1(R)]-3-[4-[(4,5-dimethyl-2-thiazolyl)methoxy]phenyl]-N-hydroxy-α,3-dimethyl-2-oxo-1-pyrrolidineacetamide;

[1(R)]-3-[4-[(2,6-dimethyl-4-pyridinyl)methoxy]phenyl]-N-hydroxy-α,3-dimethyl-2-oxo-1-pyrrolidineacetamide;

[1(R)]-N-hydroxy-α,3-dimethyl-3-[4-[(3-methyl-5-nitrophenyl)methoxy]phenyl]-2-oxo-1-pyrrolidineacetamide;

[1(R)]-3-[4-[(3-amino-5-methylphenyl)methoxy]phenyl]-N-hydroxy-α,3-dimethyl-2-oxo-1-pyrrolidineacetamide;

[1(R)]-3-[4-[[3-(acetylamino)-5-methylphenyl]methoxy]phenyl]-N-hydroxy-α,3-dimethyl-2-oxo-1-pyrrolidineacetamide;

[1(R)]-1,1-dimethylethyl [2-[[3-[[4-[1-[2-(hydroxyamino)-1-methyl-2-oxoethyl]-3-methyl-2-oxo-3pyrrolidinyl]phenoxy]methyl]-5-methylphenyl]amino]-2-oxoethyl]carbamate;

[1(R)]-3-[4-[[3-[(aminoacetyl)amino]-5-methylphenyl]methoxy]phenyl]-N-hydroxy-α,3-dimethyl-2-oxo-1-pyrrolidineacetamide;

[1(R)]-1,1-dimethylethyl [2-[[2-[[3-[[4-[1-[2-(hydroxyamino)-1-methyl-2-oxoethyl]-3-methyl-2-oxo-3-pyrrolidinyl]phenoxy]methyl]-5-methylphenyl]amino]-2-oxoethyl]amino]-2-oxoethyl]carbamate;

[1(R)]-3-[4-[[3-[[[(aminoacetyl)amino]acetyl]amino]-5-methylphenyl]methoxy]phenyl]-N-hydroxy-α,3-dimethyl-2-oxo-1-pyrrolidineacetamide;

[1(R)]-N-[3-[[4-[1-[2-(hydroxyamino)-1-methyl-2-oxoethyl]-3-methyl-2-oxo-3-pyrrolidinyl]phenoxy]methyl]-5-methylphenyl]-4-morpholinecarboxamide;

3-[4-[(2,6-dichloro-4-pyridinyl)methoxy]phenyl]-N-hydroxy-α,α,3-trimethyl-2-oxo-1- pyrrolidineacetamide;

[1(R)]-3-[1,1'-biphenyl]-4-yl-N-hydroxy-α,3-dimethyl-2-oxo-1-pyrrolidineacetamide;

[1(R)]-N-hydroxy-α,3-dimethyl-3-(2'-methyl[1,1'-biphenyl]-4-yl)-2-oxo-1-pyrrolidineacetamide;

[1(R)]-N-hydroxy-α,3-dimethyl-3-(4'-methyl[1,1'-biphenyl]-4-yl)-2-oxo-1-pyrrolidineacetamide;

[1(R)-3-(3',4'-dimethoxy[1,1'-biphenyl]-4-yl)-N-hydroxy-α,3-dimethyl-2-oxo-1-pyrrolidineacetamide;

[1(R)]-N-hydroxy-α,3-dimethyl-2-oxo-3-[2'-(trifluoromethyl)[1,1'-biphenyl]-4-yl]-1-pyrrolidineacetamide;

[1(R)]-N-hydroxy-α,3-dimethyl-3-[4-(4-methylphenoxy)phenyl]-2-oxo-1-pyrrolidineacetamide;

[1(R)]-N-hydroxy-α,3-dimethyl-2-oxo-3-(4-phenoxyphenyl)-1-pyrrolidineacetamide;

[1(R)]-N-hydroxy-α,3-dimethyl-3-[4-(2-methylphenoxy)phenyl]-2-oxo-1-pyrrolidineacetamide;

[1(R)]-3-[4-(3,5-dichlorophenoxy)phenyl]-N-hydroxy-α,3-dimethyl-2-oxo-1-pyrrolidineacetamide;

[1(R)]-3-[4-(3,4-dimethoxyphenoxy)phenyl]-N-hydroxy-α,3-dimethyl-2-oxo-1-pyrrolidineacetamide;

[1(R)]-3-[4-(1,3-benzodioxol-5-yloxy)phenyl]-N-hydroxy-α,3-dimethyl-2-oxo-1-pyrrolidineacetamide;

[1(R)]-N-hydroxy-α,3-dimethyl-3-[4-[3-(1-methylethyl)phenoxy]phenyl]-2-oxo-1-pyrrolidineacetamide;

[1(R)]-N-hydroxy-3-[4-(3-methophenoxy)phenyl]-α,3-dimethyl-2-oxo-1-pyrrolidineacetamide;

[1(R)]-N-hydroxy-α,3-dimethyl-2-oxo-3-[4-(3-thienyloxy)phenyl]-1-pyrrolidineacetamide;

[1(R)]-N-hydroxy-α,3-dimethyl-2-oxo-3-[4-(3,4,5-trimethoxyphenoxy)phenyl]-1-pyrrolidineacetamide;

[1(R)]-3-[4-[3,5-bis(trifluoromethyl)phenoxy]phenyl]-N-hydroxy-α,3-dimethyl-2-oxo-1-pyrrolidineacetamide;

[1(R)]-N-hydroxy-α,3-dimethyl-3-[4-(1-naphthalenyloxy)phenyl]-2-oxo-1-pyrrolidineacetamide;

[1(R)]-N-hydroxy-3-[4-[3-[(hydroxyimino)methyl]phenoxy]phenyl]-α,3-dimethyl-2-oxo-1-pyrrolidineacetamide;

[1(R)]-N-hydroxy-3-[4-[4-[1-(hydroxyimino)ethyl]phenoxy]phenyl]-α,3-dimethyl-2-oxo-1-pyrrolidineacetamide;

[1(R)]-3-[4-([1,1'-biphenyl]-4-yloxy)phenyl]-N-hydroxy-α,3-dimethyl-2-oxo-1-pyrrolidineacetamide;

[1(R)]-3-[4-(3,5-dibromophenoxy)phenyl]-N-hydroxy-α,3-dimethyl-2-oxo-1-pyrrolidineacetamide;

[1(R)]-3-[4-[3-(acetylamino)phenoxy]phenyl]-hydroxy-α,3-dimethyl-2-oxo-1-pyrrolidineacetamide;

[1(R)]-N-hydroxy-α,3-dimethyl-3-[4-(1-nitrophenoxy)phenyl]-2-oxo-1-pyrrolidineacetamide;

[1(R)]-N-hydroxy-α,3-dimethyl-3-(4-methylphenyl)-2-oxo-1-pyrrolidineacetamide;

[1(R)]-3-[4-[[(2,6-dimethyl-4-pyridinyl)oxy]methyl]phenyl]-N-hydroxy-α,3-dimethyl-2-oxo-1-pyrrolidineacetamide;

[1(R)]-N-hydroxy-α,3-dimethyl-2-oxo-3-[4-[(4-quinolinyloxy)methyl]phenyl]-1-pyrrolidineacetamide;

[1(R)]-N-hydroxy-α,3-dimethyl-3-(4-nitrophenyl)-2-oxo-1-pyrrolidineacetamide;

[1(R)]-N-hydroxy-α,3-dimethyl-2-oxo-3-[4-[(phenylcarbonyl)amino]phenyl]-1-pyrrolidineacetamide;

[1(R)]-N-hydroxy-α,3-dimethyl-2-oxo-3-[4-[(phenylsulfonyl)amino]phenyl]-1-pyrrolidineacetamide;
[1(R)]-N-hydroxy-α,3-dimethyl-2-oxo-3-[4-[[(phenylamino)carbonyl]amino]phenyl]-1-pyrrolidineacetamide;
[1(R)]-N-hydroxy-α,3-dimethyl-3-[4-[(1-naphthalenylmethyl)amino]phenyl]-2-oxo-1-pyrrolidineacetamide;
[1(R)]-N-hydroxy-α,3-dimethyl-2-oxo-3-[4-[(4-quinolinylmethyl)amino]phenyl]-1-pyrrolidineacetamide;
[1(R)]-3-[4-[[(3,5-dimethoxphenyl)methyl]amino]phenyl]-N-hydroxy-α,3-dimethyl-2-oxo-1-pyrrolidineacetamide;
3-[4-[(3,5-dimethylphenyl)methoxy]phenyl]-N-hydroxy-3-methyl-2-oxo-1-pyrrolidineacetamide;
3-[4-[(2,6-dichloro-4-pyridinyl)methoxy]phenyl]-N-hydroxy-3-methyl-2-oxo-1-pyrrolidineacetamide;
3-[4-[(2,6-dimethyl-4-pyridinyl)methoxy]phenyl]-N-hydroxy-3-methyl-2-oxo-1-pyrrolidineacetamide;
[1(R)]-N-hydroxy-3-methyl-α-(1-methylethyl)-2-oxo-3-[4-(4-quinolinylmethoxy)phenyl]-1-pyrrolidineacetamide;
[1(R)]-N-hydroxy-3-methyl-α-(1-methylethyl)-2-oxo-3-[4-(phenylmethoxy)phenyl]-1-pyrrolidineacetamide;
[1(R)]-3-[4-[(2,6-dimethyl-4-pyridinyl)methoxy]phenyl]-N-hydroxy-3-methyl-α-(1-methylethyl)-2-oxo-1-pyrrolidineacetamide;
[1(R)]-3-[4-[(2,6-dimethyl-4-pyridinyl)methoxy]phenyl]-N-hydroxy-3-methyl-α-(2-methylpropyl)-2-oxo-1-pyrrolidineacetamide;
[1(R)]-3-[4[(2,6-dichloro-4-pyridinyl)methoxy]phenyl]-N-hydroxy-3-methyl-α-(2-methylpropyl)-2-oxo-1-pyrrolidineacetamide;
[1(R)]-3-[4-[[3,5-bis-(trifluoromethyl)phenyl]methoxy]phenyl]-N-hydroxy-3-methyl-α-(2-methylpropyl)-2-oxo-1-pyrrolidineacetamide;
[1(R)]-3-[4-[(3,5-dichlorophenyl)methoxy]phenyl]-N-hydroxy-3-methyl-α-(2-methylpropyl)-2-oxo-1-pyrrolidineacetamide;
[1(R)]-N-hydroxy-3-methyl-α-(2-methylpropyl)-2-oxo-3-[3-(phenylmethoxy)propyl]-1-pyrrolidineacetamide;
[1(R)]-N-hydroxy-3-methyl-3-[2-methyl-4-(phenylmethoxy)phenyl]-α-(2-methylpropyl)-2-oxo-1-pyrrolidineacetamide;
[1(R)]-3-[4-[(2,6-dichloro-4-pyridinyl)methoxy]-2-methylphenyl]-N-hydroxy-3-methyl-α-(2-methylpropyl)-2-oxo-1-pyrrolidineacetamide;
[1(R)]-N-hydroxy-3-methyl-3-[2-methyl-4-(2-naphthalenylmethoxy)phenyl]-α-(2-methylpropyl)-2-oxo-1-pyrrolidineacetamide;
[1(R)]-N-hydroxy-3-methyl-α-(2-methylpropyl)-3-[2-methyl-4-(4-pyridinylmethoxy)phenyl]-2-oxo-1-pyrrolidineacetamide;
[1(R)]-3-[4-[(2,6-dimethyl-4-pyridinyl)methoxy]-2-methylphenyl]-N-hydroxy-3-methyl-α-(2-methylpropyl)-2-oxo-1-pyrrolidineacetamide;
[1(R)]-N-hydroxy-3-methyl-α-[2-(methylthio)ethyl]-2-oxo-3-[4-(phenylmethoxy)phenyl]-1-pyrrolidineacetamide;
[1(R)]-3-[4-(3,5-dibromophenoxy)phenyl]-3-methyl-α-[2-(methylsulfonyl)ethyl]-2-oxo-1-pyrrolidineacetic acid;
[1(R)]-3-[4-[3,5-bis(trifluoromethyl)phenoxy]phenyl]-N-hydroxy-3-methyl-α-[2-(methylsulfonyl)ethyl]-2-oxo-1-pyrrolidineacetamide;
[1(R)]-3-[4-(3,5-dibromophenoxy)phenyl]-N-hydroxy-3-methyl-α-[2-(methylsulfonyl)ethyl]-2-oxo-1-pyrrolidineacetamide;
[1(R)]-3-[4-[(2,6-dichloro-4-pyridinyl)methoxy]phenyl]-N-hydroxy-3-methyl-α-[2-(methylsulfonyl)ethyl]-2-oxo-1-pyrrolidineacetamide;
[1(R)]-3-[4-[(2,6-dimethyl-4-pyridinyl)methoxy]phenyl]-N-hydroxy-3-methyl-α-[2-(methylsulfonyl)ethyl]-2-oxo-1-pyrrolidineacetamide;
[1(R)]-N-hydroxy-3-methyl-α-[2-(methylsulfonyl)ethyl]-2-oxo-3-[4-(4-quinolinylmethoxy)phenyl]-1-pyrrolidineacetamide;
N-hydroxy-1-[3-methyl-2-oxo-3-[4-(phenylmethoxy)phenyl]-1-pyrrolidinyl]cyclopropanecarboxamide;
[1(R)]-N-hydroxy-α-[(4-hydroxyphenyl)methyl]-3-methyl-2-oxo-3-[4-(phenylmethoxy)phenyl]-1-pyrrolidineacetamide;
[1(R)]-3-[4-[(2,6-dichloro-4-pyridinyl)methoxy]phenyl]-N-hydroxy-α-(2-hydroxyethyl)-3-methyl-2-oxo-1-pyrrolidineacetamide;
[1(R)]-1,1-dimethylethyl [5-[3-[4-[(2,6-dichloro-4-pyridinyl)methoxy]phenyl]-3-methyl-2-oxo-1-pyrrolidinyl]-6-(hydroxyamino)-6-oxohexyl]carbamate;
[1(R)]-α-(4-aminobutyl)-3-[4[(2,6-dichloro-4-pyridinyl)methoxy]phenyl]-N-hydroxy-3-methyl-2-oxo-1-pyrrolidineacetamide;
[1(R)]-α-[4-(acetylamino)butyl]-3-[4-[(2,6-dichloro-4-pyridinyl)methoxy]phenyl]-N-hydroxy-3-methyl-2-oxo-1-pyrrolidineacetamide;
[1(R)]-N-[5-[3-[4-[(2,6-dichloro-4-pyridinyl)methoxy]phenyl]-3-methyl-2-oxo-1-pyrrolidinyl]-6-(hydroxyamino)-6-oxohexyl]-3-pyridineacetamide;
[1(R)]-N-[5-[3-[4-[(2,6-dichloro-4-pyridinyl)methoxy]phenyl]-3-methyl-2-oxo-1-pyrrolidinyl]-6-(hydroxyamino)-6-oxohexyl]-4-morpholinecaboxamide;
[1(R)]-3-[4-[(2,6-dichloro-4-pyridinyl)methoxy]phenyl]-N-hydroxy-3-methyl-α-[4-[(methylsulfonyl)amino]butyl]-2-oxo-1-pyrrolidineacetamide;
[1(R)]-α-[4-(acetylamino)butyl]-3-[4-[(2,6-dimethyl-4-pyridinyl)methoxy]phenyl]-N-hydroxy-3-methyl-2-oxo-1-pyrrolidineacetamide;
[1(R)]-1,1-dimethylethyl [5-[3-[4-[(2,6-dimethyl-4-pyridinyl)methoxy]phenyl]-3-methyl-2-oxo-1-pyrrolidinyl]-6-(hydroxyamino)-6-oxohexyl]carbamate;
[1(R)]-α-(4-aminobutyl)-3-[4-[(2,6-dimethyl-4-pyridinyl)methoxy]phenyl]-N-hydroxy-3-methyl-2-oxo-1-pyrrolidineacetamide;
[1(R)]-α-[4-[(aminoacetyl)amino]butyl]-3-[4-[(2,6-dimethyl-4-pyridinyl)methoxy]phenyl]-N-hydroxy-3-methyl-2-oxo-1-pyrrolidineacetamide;
[1(R)]-α-[4-(acetylamino)butyl]-3-[4-[[3,5-bis(trifluoromethyl)phenyl]methoxy]phenyl]-N-hydroxy-3-methyl-2-oxo-1-pyrrolidineacetamide;
[1(R)]-1,1-dimethylethyl [5-[3-[4(3,5-dibromophenoxy)phenyl]-3-methyl-2-oxo-1-pyrrolidinyl]-6-(hydroxyamino)-6-oxohexyl]carbamate;
[1(R)]-α-(4-aminobutyl)-3-[4-(3,5-dibrbomophenoxy)phenyl]-N-hydroxy-3-methyl-2-oxo-1-pyrrolidineacetamide;
[1(R)]-1,1-dimethylethyl [3-[3-[4-[(2,6-dichloro-4-pyridinyl)methoxy]phenyl]-3-methyl-2-oxo-1-pyrrolidinyl]-4-(hydroxyamino)-4-oxobutyl]carbamate;
[1(R)]-α-(2-aminoethyl)-3-[4-[(2,6-dichloro-4-pyridinyl)methoxy]phenyl]-N-hydroxy-3-methyl-2-oxo-1-pyrrolidineacetamide;
[1(R)]-α-[2-(acetylamino)ethyl]-3-[4-[(2,6-dichloro-4-pyridinyl)methoxy]phenyl]-N-hydroxy-3-methyl-2-oxo-1-pyrrolidineacetamide;
[1(R)]-1,1-dimethylethyl [3-[3-[4-[(2,6-dimethyl-4-pyridinyl)methoxy]phenyl]-3-methyl-2-oxo-1-pyrrolidinyl]-4-(hydroxyamino)-4-oxobutyl]carbamate;
[1(R)]-α-(2-aminoethyl)-3-[4-[(2,6-dimethyl-4-pyridinyl)methoxy]phenyl]-N-hydroxy-3-methyl-2-oxo-1-pyrrolidineacetamide;

N-[3-[3-[4-[(2,6-dimethyl-4-pyrridinyl)methoxy]phenyl]-3-methyl-2-oxo-1-pyrrolidinyl]-4-(hydroxyamino)-4-oxobutyl]-3-pyridinecarboxamide;

[1(R)]-N-[3-[3-[4-[(2,6-dimethyl-4-pyridinyl)methoxy]phenyl]-3-methyl-2-oxo-1-pyrrolidinyl]-4-(hydroxyamino)-4-oxobutyl]-4-morpholinecarboxamide;

[1(R)]-1,1-dimethylethyl [2-[[3-[3-[4-[(2,6-dimethyl-4-pyridinyl)methoxy]phenyl]-3-methyl-2-oxo-1-pyrrolidinyl-]4-(hydroxyamino)-4-oxobutyl]amino]-2-oxoethyl]carbamate;

[1(R)]-α-[2-[(aminoacetyl)amino]ethyl]-3-[4-[(2,6-dimethyl-4-pyridinyl)methoxy]phenyl]-N-hydroxy-3-methyl-2-oxo-1-pyrrolidineacetamide;

[1(R)]-1,1-dimethylethyl [2-[[2-[[3-[3-[4-[(2,6-dimethyl-4-pyridinyl)methoxy]phenyl]-3-methyl-2-oxo-1-pyrrolidinyl]-4-(hydroxyamino)-4-oxobutyl]amino]-2-oxoethyl]amino]-2-oxoethyl]carbamate;

[1(R)]-α-[2-[[[(aminoacetyl)amino]acetyl]amino]ethyl]-3-[4-[(2,6-dimethyl-4-pyridinyl)methoxy]phenyl]-N-hydroxy-3-methyl-2-oxo-1-pyrrolidineacetamide;

[1(R)]-N-hydroxy-3-methyl-2-oxo-α-[(phenylmethoxy)methyl]-3-[4-(phenylmethoxy)phenyl]-1-pyrrolidineacetamide;

[1(R)]-3-[4-[(2,6-dichloro-4-pyridinyl)methoxy]phenyl]-N-hydroxy-α-(hydroxymethyl)-3-methyl-2-oxo-1-pyrrolidineacetamide;

[1(R)]-1,1-dimethylethyl 4-[2-(hydroxyamino)-1-[3-methyl-2-oxo-3-[4-(4-quinolinylmethoxy)phenyl]-1-pyrrolidinyl]-2-oxoethyl]-1-piperidinecaboxylate;

[1(R)]-N-hydroxy-α-[3-methyl-2-oxo-3-[4-(4-quinolinylmethoxy)phenyl]-1-pyrrolidinyl]-4-piperidineacetamide;

[1(R)]-N-hydroxy-α-[3-methyl-2-oxo-3-[4-(4-quinolinylmethoxy)phenyl]-1-pyrrolidinyl]-1-(methylsulfonyl)-4-piperidineacetamide;

[1(R)]-1-(2-furanylcarbonyl)-N-hydroxy-α-[3-methyl-2-oxo-3-[4-(4-quinolinylmethoxy)phenyl]-1-pyrrolidinyl]-4-piperidineacetamide;

[1(R)]-1,1-dimethylethyl 4-[1-[3-[4-[(2,6-dimethyl-4-pyridinyl)methoxy]phenyl]-3-methyl-2-oxo-1-pyrrolidinyl]-2-(hydroxyamino)-2-oxoethyl]-1-piperidinecarboxylate;

[1(R)]-α-[3-[4-[(2,6-dimethyl-4-pyridinyl)methoxy]phenyl]-3-methyl-2-oxo-1-pyrrolidinyl]-N-hydroxy-4-piperidineacetamide;

[1(R)]-methyl 4-[1-[3-[4-[(2,6-dimethyl-4-pyridinyl)methoxy]phenyl]-3-methyl-2-oxo-1-pyrrolidinyl]-2-(hydroxyamino)-2-oxoethyl]-1-piperidinecarboxylate;

[1(R)]-α-[3-[4-[(2,6-dimethyl-4-pyridinyl)methoxy]phenyl]-3-methyl-2-oxo-1-pyrrolidinyl]-N-hydroxy-1-(methylsulfonyl)-4-piperidineacetamide;

[1(R)]-1-acetyl-α-[3-[4-[(2,6-dimethyl-4-pyridinyl)methoxy]phenyl]-3-methyl-2-oxo-1-pyrrolidinyl]-N-hydroxy-4-piperidineacetamide;

[1(R)]-1-(2,2-dimethyl-1-oxopropyl)-α-[3-[4-[(2,6-dimethyl-4-pyridinyl)methoxy]phenyl]-3-methyl-2-oxo-1-pyrrolidinyl]-N-hydroxy-4-piperidineacetamide;

[1(R)]-α-[3-[4-[(2,6-dimethyl-4-pyridinyl)methoxy]phenyl]-3-methyl-2-oxo-1-pyrrolidinyl]-N-hydroxy-1-methyl-4-piperidineacetamide;

[1(R)]-α-[3-[4-[(2,6-dimethyl-4-pyridinyl)methoxy]phenyl]-3-methyl-2-oxo-1-pyrrolidinyl]-N-hydroxy-1-(1-methylethyl)-4-piperidineacetamide;

[1(R)]-3-amino-N-hydroxy-alpha-(2-methylpropyl)-2-oxo-3-[4-(2-quinolinylmethoxy)phenyl]-1-pyrrolidineacetamide;

[1(R)]-3-amino-3-[4-[(3,5-dimethylphenyl)methoxy]phenyl]-N-hydroxy-alpha-methyl-2-oxo-1-pyrrolidineacetamide;

[1(R)]-3-[4-[(3,5-dimethylphenyl)methoxy]phenyl]-3-[[(ethylamino)carbonyl]amino]-N-hydroxy-alpha-methyl-2-oxo-1-pyrrolidineacetamide;

[1(R)]-3-[4-[(3,5-dimethylphenyl)methoxy]phenyl]-N-hydroxy-alpha-methyl-3-[(methylsulfonyl)amino]-2-oxo-1-pyrrolidineacetamide;

[1(R)]-N-[3-[4-[(3,5-dimethylphenyl)methoxy]phenyl]-1-[2-(hydroxyamino)-1-methyl-2-oxoethyl]-2-oxo-3-pyrrolidinyl]-3-pyridineacetamide;

[1(R)]-N-[3-[4-[(3,5-dimethylphenyl)methoxy]phenyl]-1-[2-(hydroxyamino)-1-methyl-2-oxoethyl]-2-oxo-3-pyrrolidinyl]-4-pyridinecarboxamide;

[1(R)]-3-amino-3-[4-[(2,6-dichloro-4-pyridinyl)methoxy]phenyl]-N-hydroxy-alpha-methyl-2-oxo-1-pyrrolidineacetamide;

[1(R)]-N-[3-[4-[(2,6-dichloro-4-pyridinyl)methoxy]phenyl]-1-[2-(hydroxyamino)-1-methyl-2-oxoethyl]-2-oxo-3-pyrrolidinyl]-4-pyridinecarboxamide;

[1(R)]-3-[4-[(2,6-dichloro-4-pyridinyl)methoxy]phenyl]-3-[[(ethylamino)carbonyl]amino]-N-hydroxy-alpha-methyl-2-oxo-1-pyrrolidineacetamide;

[1(R)]-1,1-dimethylethyl [2-[[3-[4-[(2,6-dichloro-4-pyridinyl)methoxy]phenyl]-1-[2-(hydroxyamino)-1-methyl-2-oxoethyl]-2-oxo-3-pyrrolidinyl]amino]-2-oxoethyl]carbamate;

[1(R)]-3-[(aminoacetyl)amino]-3-[4-[(2,6-dichloro-4-pyridinyl)methoxy]phenyl]-N-hydroxy-alpha-methyl-2-oxo-1-pyrrolidineacetamide;

[1(R)]-N-[3-[4-[(2,6-dichloro-4-pyridinyl)methoxy]phenyl]-1-[2-(hydroxyamino)-1-methyl-2-oxoethyl]-2-oxo-3-pyrrolidinyl]-3-pyridineacetamide;

[1(R)]-3-[4-[(2,6-dichloro-4-pyridinyl)methoxy]phenyl]-N-hydroxy-alpha-methyl-2-oxo-3 [[[(phenylmethyl)amino]carbonyl]amino]-1-pyrrolidineacetamide;

[1(R)]-3-[4-[(2,6-dichloro-4- pyridinyl)methoxy]phenyl]-3-[[[(2,4-dimethoxyphenyl)amino]carbonyl]amino]-N-hydroxy-alpha-methyl-2-oxo-1-pyrrolidineacetamide;

[1(R)]-3-[4-[(2,6-dichloro-4-pyridinyl)methoxy]phenyl]-N-hydroxy-alpha-methyl-2-oxo-3-[[(phenylamino)carbonyl]amino]-1-pyrrolidineacetamide;

[1(R)]-1,1-dimethylethyl [3-[4-[(2,6-dichloro-4-pyridinyl)methoxy]phenyl]-1-[2-(hydroxyamino)-1-methyl-2-oxoethyl]-2-oxo-3-pyrrolidinyl]carbamate;

[1(R)]-3-[4-[(2,6-dichloro-4-pyridinyl)methoxy]phenyl]-N-hydroxy-alpha-methyl-3-[[[[2-(4-morpholinyl)ethyl]amino]carbonyl]amino]-2-oxo-1-pyrrolidineacetamide;

[1(R)]-1,1-dimethylethyl N-[[[3-[4-[(2,6-dichloro-4-pyridinyl)methoxy]phenyl]-1-[2-(hydroxyamino)-1-methyl-2-oxoethyl]-2-oxo-3-pyrrolidinyl]amino]carbonyl]glycine;

[1(R)]-3-[4-[(2,6-dichloro-4-pyridinyl)methoxy]phenyl]-N-hydroxy-alpha-methyl-2-oxo-3-[[(2-thiazolylamino)carbonyl]amino]-1-pyrrolidineacetamide;

[1(R)]-3-[4-[(2,6-dichloro-4-pyridinyl)methoxy]phenyl]-N-hydroxy-alpha-methyl-2-oxo-3-[[(4-pyridinylamino)carbonyl]amino]-1-pyrrolidineacetamide;

[1(R)]-3-[4-[(2,6-dichloro-4-pyridinyl)methoxy]phenyl]-N-hydroxy-3-[[[(3-hydroxyphenyl)amino]carbonyl]amino]-alpha-methyl-2-oxo-1-pyrrolidineacetamide;

[1(R)]-3-[4-[(2,6-dichloro-4-pyridinyl)methoxy]phenyl]-3-[[[(2,3-dihydro-2-oxo-1H-benzimidazol-5-yl)amino]carbonyl]amino]-N-hydroxy-alpha-methyl-2-oxo-1-pyrrolidineacetamide;

[1(R)]-3-amino-3-[4-[(2,6-dichloro-4-pyridinyl)methoxy]phenyl]-N-hydroxy-alpha-[2-(methylsulfonyl)ethyl]-2-oxo-1-pyrrolidineacetamide;

[1(R)]-3-amino-3-[4-[(2,6-dimethyl-4-pyridinyl)methoxy]phenyl]-N-hydroxy-alpha-[2-(methylsulfonyl)ethyl]-2-oxo-1-pyrrolidine acetamide;

[1(R)]-3-[4-[(2,6-dichloro-4-pyridinyl)methoxy]phenyl]-N-hydroxy-alpha-[2-(methylsulfonyl)ethyl]-2-oxo-3-[[(2-thiazolylamino)carbonyl]amino]-1-pyrrolidineacetamide;

[1(R)]-3-[4-[(2,6-dimethyl-4-pyridinyl)methoxy]phenyl]-N-hydroxy-alpha-[2-(methylsulfonyl)ethyl]-2-oxo-3-[[(2-thiazolylamino)carbonyl]amino]-1-pyrrolidineacetamide;

[5(R)]-2-propenyl [5-[3-amino-3-[4-[(2,6-dichloro-4-pyridinyl)methoxy]phenyl]-2-oxo-1-pyrrolidinyl]-6-(hydroxyamino)-6-oxohexyl]carbamate;

[5(R)]-2-propenyl [5-[3-amino-3-[4-[(2,6-dimethyl-4-pyridinyl)methoxy]phenyl]-2-oxo-1-pyrrolidinyl]-6-(hydroxyamino)-6-oxohexyl]carbamate;

[1(R)]-3-amino-3-[4-[(2,6-dichloro-4-pyridinyl)methoxy]phenyl]-N-hydroxy-alpha-(2-methylpropyl)-2-oxo-1-pyrrolidineacetamide;

[1(R)]-3-[4-[(2,6-dichloro-4-pyridinyl)methoxy]phenyl]-N-hydroxy-alpha-(2-methylpropyl)-2-oxo-3-[[(2-thiazolylamino)carbonyl]amino]-1-pyrrolidineacetamide;

[1(R)]-3-[4-[(2,6-dimethyl-4-pyridinyl)methoxy]phenyl]-N-hydroxy-alpha-(2-methylpropyl)-2-oxo-3-[[(2-thiazolylamino)carbonyl]amino]-1-pyrrolidineacetamide;

[1(R)]-3-[4-[(2,6-dichloro-4-pyridinyl)methoxy]phenyl]-N-hydroxy-alpha-(2-methylpropyl)-2-oxo-3-[[(2-pyridinylamino)carbonyl]amino]-1-pyrrolidineacetamide;

[1(R)]-3-[4-[(2,6-dimethyl-4-pyridinyl)methoxy]phenyl]-N-hydroxy-alpha-(2-methypropyl)-2-oxo-3-[(trifluoroacetyl)amino]-1-pyrrolidineacetamide;

[1(R)]-3-[4-[(2,6-dimethyl-4-pyridinyl)methoxy]phenyl]-N-hydroxy-alpha-(2-methylpropyl)-2-oxo-3-[[(2-pyridinylamino)carbonyl]amino]-1-pyrrolidineacetamide;

[1(R)]-3-[4-[(2,6-dichloro-4-pyridinyl)methoxy]phenyl]-N-hydroxy-alpha-(2-methylpropyl)-2-oxo-3-[[[(phenylsulfonyl)amino]carbonyl]amino]-1-pyrrolidineacetamide;

[1(R)]-3-[4-[(2,6-dimethyl-4-pyridinyl)methoxy]phenyl]-N-hydroxy-alpha-(2-methylpropyl)-2-oxo-3-[[[(phenylsulfonyl)amino]carbonyl]amino]-1-pyrrolidineacetamide;

[1(R)]-3-[4-[(2,6-dichloro-4-pyridinyl)methoxy]phenyl]-N-hydroxy-3-[[[(3-methyl-5-isothiazolyl)amino]carbonyl]amino]-alpha-(2-methylpropyl)-2-oxo-1-pyrrolidineacetamide;

[1(R)]-3-[[(1H-benzimidazol-2-ylamino)carbonyl]amino]-3-[4-[(2,6-dichloro-4-pyridinyl)methoxy]phenyl]-N-hydroxy-alpha-(2-methylpropyl)-2-oxo-1-pyrrolidineacetamide;

[1(R)]-3-[[(1H-benzimidazol-2 ylamino)carbonyl]amino]-3-[4-[(2,6-dimethyl-4-pyridinyl)methoxy]phenyl]-N-hydroxy-alpha-(2-methylpropyl)-2-oxo-1-pyrrolidineacetamide;

[1(R)]-3-[4-[(2,6-dimethyl-4-pyridinyl)methoxy]phenyl]-N-hydroxy-alpha-(2-methylpropyl)-2-oxo-3-[[(phenylamino)carbonyl]amino]-1-pyrrolidineacetamide;

[1(R)]-3-[4-[(2,6-dichloro-4-pyridinyl)methoxy]phenyl]-N-hydroxy-alpha-(2-methylpropyl)-2-oxo-3-[[(phenylamino)carbonyl]amino]-1-pyrrolidineacetamide;

[1(R)]-1-[1-[(hydroxyamino)carbonyl]-3-methylbutyl]-N,N,N-trimethyl-2-oxo-3-[4-(phenylmethoxy)phenyl]-1-pyrrolidinemethanaminium;

[1(R)]-3-amino-N-hydroxy-alpha-(2-methylpropyl)-2-oxo-3-[4-(4-quinolinylmethoxy)phenyl]-1-pyrrolidineacetamide;

[1(R)]-3-amino-N-hydroxy-alpha-(2-methylpropyl)-2-oxo-3-[4-(2-oxo-2-phenylethoxy)phenyl]-1-pyrrolidineacetamide;

[1(R)]-3-amino-3-[4-[(3,5-dimethyl-4-isoxazolyl)methoxy]phenyl]-N-hydroxy-alpha-(2-methylpropyl)-2-oxo-1-pyrrolidineacetamide;

[1(R)]-3-amino-3-[4-[(2,6-dimethyl-4-pyridinyl)methoxy]phenyl]-N-hydroxy-alpha-(2-methylpropyl)-2-oxo-1-pyrrolidineacetamide;

[1(R)]-3-amino-3-[4-[2-(2-benzothiazolylamino)-2-oxoethoxy]phenyl]-N-hydroxy-alpha-(2-methylpropyl)-2-oxo-1-pyrrolidineacetamide;

[1(R)]-3-amino-N-hydroxy-3-[4-[(2-methoxy-4-quinolinyl)methoxy]phenyl]-alpha-(2-methylpropyl)-2-oxo-1-pyrrolidineacetamide;

[1(R)]-3-amino-N-hydroxy-alpha-(2-methylpropyl)-2-oxo-3-[4-[(2-phenyl-4-quinolinyl)methoxy]phenyl]-1-pyrrolidineacetamide;

[1(R)]-3-amino-3-[4-[(2,6-dimethyl-4-quinolinyl)methoxy]phenyl]-N-hydroxy-alpha-(2-methylpropyl)-2-oxo-1-pyrrolidineacetamide;

[1(R)]-3-amino-3-[4-[(2-chloro-4-quinolinyl)methoxy]phenyl]-N-hydroxy-alpha-(2-methylpropyl)-2-oxo-1-pyrrolidineacetamide;

[1(R)]-3-amino-3-[4-[2-(2,5-dimethoxyphenyl)-2-(hydroxyimino)ethoxy]phenyl]-N-hydroxy-alpha-(2-methylpropyl)-2-oxo-1-pyxrolidineacetamide;

[1(R)]-3-amino-N-hydroxy-3-[4-[(2-methylimidazo[1,2-a]pyridin-3-yl)methoxy]phenyl]-alpla-(2-methylpropyl)-2-oxo-1-pyrrolidineacetamide;

[1(R)]-3-amino-3-[4-[[1,4-dimethyl-2-(methylthio)-1H-imidazol-5-yl]methoxy]phenyl]-N-hydroxy-alpha-(2-methylpropyl)-2-oxo-1-pyrrolidineacetamide;

[1(R)]-3-amino-3-[4-[[1,5-dimethyl-2-(methylthio)-1H-imidazol-4-yl]methoxy]phenyl]-N-hydroxy-alpha-(2-methylpropyl)-2-oxo-1-pyrrolidineacetamide;

[1(R)]-3-amino-3-[4-[(2,4-dimethyl-5-thiazolyl)methoxy]phenyl]-alpha-(2-methylpropyl)-2-oxo-1-pyrrolidineacetamide;

[1(R)]-3-amino-N-hydroxy-alpha-(2-methylpropyl)-3-[4-[(2-methyl-4-quinolinyl)methoxy]phenyl]-2-oxo-1-pyrrolidineacetamide;

[1(R)]-3-amino-3-[4-[(2-chloro-4-quinolinyl)methoxy]phenyl]-N-hydroxy-alpha-[2-(methylsulfonyl)ethyl]-2-oxo-1-pyrrolidineacetamide;

[1(R)]-3-amino-N-hydroxy-3-[4-[(2-methyl-4-quinolinyl)methoxy]phenyl]-alpha-[2-(methylsulfonyl)ethyl]-2-oxo-1-pyrrolidineacetamide;

[1(R)]-3-amino-3-[4-[(3,5-dimethoxyphenyl)methoxy]phenyl]-N-hydroxy-alpha-[2-(methylsulfonyl)ethyl]-2-oxo-1-pyrrolidineacetamide;

[1(R)]-3-amino-N-hydroxy-3-[4-[(2-methoxy-4-quinolinyl)methoxy]phenyl]-alpha-[2-(methylsulfonyl)ethyl]-2oxo-1-pyrrolidineacetamide;

[1(R)]-3-amino-3-[4-[(3,5-dimethoxyphenyl)methoxy]phenyl]-N-hydroxy-alpha-(2-methylpropyl)-2-oxo-1-pyrrolidineacetamide;

[1(R)]-3-(aminomethyl)-3-[4-[(2,6-dimethyl-4-pyridinyl)methoxy]phenyl]-N-hydroxy-alpha-(2-methylpropyl)-2-oxo-1-pyrrolidineacetamide;

[1(R)]-3-[4-[(2,6-dimethyl-4-pyridinyl)methoxy]phenyl]-N-hydroxy-alpha-(2-methylpropyl)-2-oxo-3-[[[(2-thiazolylamino)carbonyl]amino]methyl]-1-pyrrolidineacetamide;

[1(R)]-3-(aminomethyl)-3-[4-[(2,6-dichloro-4-pyridinyl)methoxy]phenyl]-N-hydroxy-alpha-methyl-2-oxo-1-pyrrolidineacetamide;

[1(R)]-3-[4-[(2,6-dichloro-4-pyridinyl)methoxy]phenyl]-N-hydroxy-alpha-methyl-2-oxo-3-[[[(2-thiazolylamino)carbonyl]amino]methyl]-1-pyrrolidineacetamide;

[1(R)]-4-[4-[(3,5-dimethylphenyl)methoxy]phenyl]-N-hydroxy-alpha,4-dimethyl-5-oxo-1-imidazolidineacetamide;

[1(R)]-3-[4-[(3,5-dimethylphenyl)methoxy]phenyl]-N-hydroxy-3-(hydroxymethyl)-alpha-methyl-2-oxo-1-pyrrolidineacetamide;

[1(R)]-[3-[4-[(3,5-dimethylphenyl)methoxy]phenyl]-1-[2-(hydroxyamino)-1-methyl-2-oxoethyl]-2-oxo-3-pyrrolidinyl]methyl ethycarbamate;

[1(R)]-3-[4-[(2,6-dichloro-4-pyridinyl)methoxy]phenyl]-N-hydroxy-3-(hydroxymethyl)-alpha-methyl-2-oxo-1-pyrrolidineacetamide;

[1(R)]-3-[4-[(3,5-dimethylphenyl)methoxy]phenyl]-N-hydroxy-alpha,3-dimethyl-2-oxo-1-azetidineacetamide;

[1(R)]-3-[5-[(3,5-dimethylphenoxy)methyl]-2-thiazolyl]-N-hydroxy-alpha,3-dimethyl-2-oxo-1-pyrrolidineacetamide;

[1(R)]-4-[4-[(3,5-dimethylphenyl)methoxy]phenyl]-N-hydroxy-alpha-methyl-2,5-dioxo-4-(2-propenyl)-1-imidazolidineacetamide;

[1(R)]-N-hydroxy-alpha,3-dimethyl-2-oxo-3-[[4-(phenylmethoxy)phenyl]methyl]-1-pyrrolidineacetamide;

[1(R)]-3-[4-[(2,6-dimethyl-4-pyridinyl)methoxy]phenyl]-N-hydroxy-3-(methylamino)-alpha-(2-methylpropyl)-2-oxo-1-pyrrolidineacetamide;

[1(R)]-N-hydroxy-3-(methylamino)-alpha-(2-methylpropyl)-3-[4-[(2-methyl-4-quinolinyl)methoxy]phenyl]-2-oxo-1-pyrrolidineacetamide;

[1(R)]-alpha,3-dimethyl-N-hydroxy-2-oxo-3-[4-(phenylmethoxy)phenyl]-1-piperidineacetamide;

[1(R)]-α-[3-amino-2-oxo-3-[4-(4-quinolinylmethoxy)phenyl]-1-pyrrolidinyl]-N-hydroxy-4-piperidineacetamide;

[1(R)]-α-[3-amino-3-[4-[(2,6-dichloro-4-pyridinyl)methoxy]phenyl]-2-oxo-1-pyrrolidinyl]-N-hydroxy-4-piperidineacetamide;

[1(R)]-1,1-dimethylethyl 4-[1-[3-[[(1,1-dimethylethoxy)carbonyl]amino]-3-[4-[(1,1-dimethyl-4-pyridinyl)methoxy]phenyl]-2-oxo-1-pyrrolidinyl]-2-(hydroxyamino)-2-oxoethyl]-1-piperidinecarboxylate;

[1(R)]-α-[3-amino-3-[4-[(2,6-dimethyl-4-pyridinyl)methoxy]phenyl]-2-oxo-1-pyrrolidinyl]-N-hydroxy-4-piperidineacetamide;

[1(R)]-α-[3-amino-3-[4-[(2,6-dimethyl-4-pyridinyl)methoxy]phenyl]-2-oxo-1-pyrrolidinyl]-N-hydroxy-1-(methylsulfonyl)-4-piperidineacetamide;

[1(R)]-1-acetyl-α-[3-amino-3-[4-[(2,6-dimethyl-4-pyridinyl)methoxy]phenyl]-2-oxo-1-pyrrolidinyl]-N-hydroxy-4-piperidineacetamide;

[1(R)]-α-[3-amino-3-[4-[(2,6-dimethyl-4-pyridinyl)methoxy]phenyl]-2-oxo-1-pyrrolidinyl]-1-(2,2-dimethyl-1-oxopropyl)-N-hydroxy-4-piperidineacetamide;

[1(R)]-1,1-dimethylethyl 4-[1-[3-amino-3-[4-[(2,6-dimethyl-4-pyridinyl)methoxy]phenyl]-2-oxo-1-pyrrolidinyl]-2-(hydroxyamino)-2-oxoethyl]-1-piperidinecarboxylate;

[1(R)]-methyl 4-[1-[3-amino-3-[4-[(2,6-dimethyl-4-pyridinyl)methoxy]phenyl]-2-oxo-1-pyrrolidinyl]-2-(hydroxyamino)-2-oxoethyl]-1-piperidinecarboxylate;

[1(R)]-α-[3-amino-3-[4-[(2,6-dimethyl-4-pyridinyl)methoxy]phenyl]-2-oxo-1-pyrrolidinyl]-N-hydroxy-1-methyl-4-piperidineacetamide;

[1((R)]-α-[3-amino-3-[4-[(2,6-dimethyl-4-pyridinyl)methoxy]phenyl]-2-oxo-1-pyrrolidinyl]-1-dimethylcarbamyl-N-hydroxy-4-piperidineacetamide;

[1(R)]-α-[3-amino-3-[4-[(2,6-dimethyl-4pyridinyl)methoxy]phenyl]-2-oxo-1-pyrrolidinyl]-1-cyclopropanecarbonyl-N-hydroxy-4-piperidineacetamide;

[1(R)]-3-amino-N-hydroxy-α-(1-methylethyl)-2-oxo-3-[4-(4-quinolinylmethoxy)phenyl]-1-pyrrolidineacetamide;

[1(R)]-3-amino-3-[4-[(2,6-dimethyl-4-pyridinyl)methoxy]phenyl]-N-hydroxy-α-(1-methylethyl)-2-oxo-1-pyrrolidineacetamide;

[1(R)]-3-amino-α-cyclohexyl-N-hydroxy-2-oxo-3-[4-(4-quinolinylmethoxy)phenyl]-1-pyrrolidineacetamide;

[1(R)]-3-amino-α-cyclohexyl-3-[4-[(2,6-dimethyl-4-pyridinyl)methoxy]phenyl]-N-hydroxy-2-oxo-1-pyrrolidineacetamide;

3-amino-α-(1,1-dimethylethyl)-3-[4-[(2,6-dimethyl-4-pyridinyl)methoxy]phenyl]-N-hydroxy-2-oxo-1-pyrrolidineacetamide;

[1(R)]-3-amino-α-(1,1-dimethylethyl)-N-hydroxy-2-oxo-3-[4-(4-quinolinylmethoxy)phenyl]-1-pyrrolidineacetamide;

[1(R)]-3-amino-α-(1,1-dimethylethyl)-N-hydroxy-2-oxo-3-[4-[(2-methyl-4-quinolinyl)methoxy]phenyl]-1-pyrrolidineacetamide;

[1(R)]-3-amino-N-hydroxy-α-(1-methylethyl)-2-oxo-3-[4-[(2-methyl-4-quinolinyl)methoxy]phenyl]-1-pyrrolidineacetamide;

[1(R)]-3-amino-N-hydroxy-α-(1-methylethyl)-2-oxo-3-[4-[(2,6-dimethyl-4-quinolinyl)methoxy]phenyl]-1-pyrrolidineacetamide;

[1(R)]-N-[4-[1-[3-amino-3-[4-[(2,6-dimethyl-4-pyridinyl)methoxy]phenyl]-2-oxo-1-pyrrolidinyl]-2-(hydroxyamino)-2-oxoethyl-1-piperidine]-4-morpholinecarboxamide;

[1(R)]-α-[3-amino-3-[4-[(2,6-dimethyl-4-pyridinyl)methoxy]phenyl]-2-oxo-1-pyrrolidinyl]-1-(2-methyl-1-oxopropyl)-N-hydroxy-4-piperidineacetamide;

[1(R)]-3-amino-3-[4-[(2,6-dimethyl-4-pyridinyl)methoxy]phenyl]-N-hydroxy-α-(4-methoxycyclohexyl)-2-oxo-1-pyrrolidineacetamide;

[1'(R)]-N-hydroxy-1,2-dihydro-α-(1-methylethyl)-2,2'-dioxo-6-(phenylmethoxy)spiro[3H-indole-3,3'-pyrrolidine]-1'-acetamide;

[1(R)]-N-hydroxy-α,3-dimethyl-2-oxo-3-[3-(phenylmethoxy)phenyl]-1-pyrrolidineacetamide;

[1(R)]-3-[3-[(3,5-dimethylphenyl)methoxy]phenyl]-N-hydroxy-α,3-dimethyl-2-oxo-1-pyrrolidineacetamide;

[1(R)]-N-hydroxy-α,3-dimethyl-3-[3-[(3-methylphenyl)methoxy]phenyl]-2-oxo-1-pyrrolidineacetamide;

[1(R)]-N-hydroxy-α,3-dimethyl-3-[3-(1-methylethoxy)phenyl]-2-oxo-1-pyrrolidineacetamide;

[1(R)]-3-[3-(heptyloxy)phenyl]-N-hydroxy-α,3-dimethyl-2-oxo-1-pyrrolidineacetamide;

[1(R)]-3-[4-[(2,6-dichloro-4-pyridinyl)methoxy]phenyl]-N1-hydroxy-α1-methyl-2-oxo-N3-1,3,4-thiadiazol-2-yl-1,3-pyrrolidinediacetamide;

[1(R)]-1,1-dimethylethyl 1-[2-(hydroxyamino)-1-methyl-2-oxoethyl]-2-oxo-3-[4-(phenylmethoxy)phenyl]-3-pyrrolidineacetate;

[1(R)]-1-[2-(hydroxyamino)-1-methyl-2-oxoethyl]-2-oxo-3-[4-(phenylmethoxy)phenyl]-3-pyrrolidineacetic acid;

[1(R)]-3-[4-[(3,5-dimethylphenyl)methoxy]phenyl]-N1-hydroxy-α1-methyl-N3-[2-(methylamino)-2-oxoethyl]-2-oxo-1,3-pyrrolidinediacetamide;

[1(R)]-3-[4-[(3,5-dimethylphenyl)methoxy]phenyl]-N1-hydroxy-α1-methyl-2-oxo-N3-2-thiazolyl-1,3-pyrrolidinediacetamide;

[1(R)]-3-[4-[(3,5-dimethylphenyl)methoxy]phenyl]-N-hydroxy-α-methyl-3-[2-(4-morpholinyl)-2-oxoethyl]-2-oxo-1-pyrrolidineacetamide;

[1(R)]-3-[4-[(2,6-dichloro-4-pyridinyl)methoxy]phenyl]-N1-hydroxy-α1-methyl-2-oxo-N3-2-thiazolyl-1,3-pyrrolidinediacetamide;

[1(R)]-3-[4-[(2,6-dichloro-4-pyridinyl)methoxy]phenyl]-N1-hydroxy-α1-methyl-2-oxo-N3-[2-(4-morpholinyl)ethyl]-1,3-pyrrolidinediacetamide;

[1(R)]-3-[4-[(2,6-dichloro-4-pyridinyl)methoxy]phenyl]-N1-hydroxy-α1-methyl-2-oxo-N3-(4-pyridinylmethyl)-1,3-pyrrolidinediacetamide;

[1(R)]-3-[4-[(2,6-dimethyl-4-pyridinyl)methoxy]phenyl]-N1-hydroxy-α1-methyl-2-oxo-N3-2-thiazolyl-1,3-pyrrolidinediacetamide;

[1(R)]-3-[4-[(2,6-dichloro-4-pyridinyl)methoxy]phenyl]-N1-hydroxy-α1-methyl-2-oxo-N3-(3-pyridinylmethyl)-1,3-pyrrolidinediacetamide;

[1(R)]-3-[4-[(2,6-dichloro-4-pyridinyl)methoxy]phenyl]-N1-hydroxy-α1-methyl-2-oxo-N3-(2-pyridinylmethyl)-1,3-pyrrolidinediacetamide;

[1(R)]-3-[4-[(2,6-dichloro-4-pyridinyl)methoxy]phenyl]-N1-hydroxy-α1-methyl-2-oxo-N3-4-pyridinyl-1,3-pyrrolidinediacetamide;

[1(R)]-3-[4-[(2,6-dichloro-4-pyridinyl)methoxy]phenyl]-N1-hydroxy-α1-methyl-N3-(3-methyl-5-isothiazolyl)-2-oxo-1,3-pyrrolidinediacetamide;

[1(R)]-3-[4-[(2,6-dichloro-4-pyridinyl)methoxy]phenyl]-N3-[5-(1,1-dimethylethyl)-1,3,4-thiadizol-2-yl]-N1-hydroxy-α1-methyl-2-oxo-1,3-pyrrolidinediacetamide;

[1(R)]-1,1-dimethylethyl 2-[[[3-[4-[(2,6-dichloro-4-pyridinyl)methoxy]phenyl]-1-[2-(hydroxyamino)-1-methyl-2-oxoethyl]-2-oxo-3-pyrrolidinyl]acetyl]amino]-4-thiazoleacetate;

[1(R)]-2-[[[3-[4-[(2,6-dichloro-4-pyridinyl)methoxy]phenyl]-1-[2-(hydroxyamino)-1-methyl-2-oxoethyl]-2-oxo-3-pyrrolidinyl]acetyl]amino]-4-thiazoleacetic acid;

[1(R)]-3-[4-[(2,6-dichloro-4-pyridinyl)methoxy]phenyl]-N1-hydroxy-α1-methyl-N3-[4-[2-(methylamino)-2-oxoethyl]-2-thiazolyl]-2-oxo-1,3-pyrrolidinediacetamide;

[1(R)]-3-(1H-benzimidazol-2-ylmethyl)-3-[4-[(2,6-dichloro-4-pyridinyl)methoxy]phenyl]-N-hydroxy-α-methyl-2-oxo-1-pyrrolidineacetamide;

[1(R)]-3-[4-[(2,6dichloro-4-pyridinyl)methoxy]phenyl]-N-hydroxy-3-(3H-imidazo(4,5-c]pyridin-2-ylmethyl)-α-methyl-2-oxo-1-pyrrolidineacetamide;

[1(R)]-3-[4-[3,5-bis(trifluoromethyl)phenoxy]phenyl]-N1-hydroxy-α1-methyl-2-oxo-N3-2-thiazolyl-1,3-pyrrolidinediacetamide;

[1(R)]-3-[4-[3,5-bis(trifluoromethyl)phenoxy]phenyl]-N1-hydroxy-α1-methyl-2-oxo-N3-(4-pyridinylmethyl)-1,3-pyrrolidinediacetamide;

[1(R)]-3-[4-[(2,6-dimethyl-4-pyridinyl)methoxy]phenyl]-N1-hydroxy-α1-(1-methylethyl)-2-oxo-N3-(4-pyridinylmethyl)-1,3-pyrrolidinediacetamide;

[1(R)]-3-[4-[(2,6-dichloro-4-pyridinyl)methoxy]phenyl]-N1hydroxy-α1-(1-methylethyl)-2-oxo-N3-(4-pyridinylmethyl)-1,3-pyrrolidinediacetamide;

[1(R)]-α1-(cyclohexylmethyl)-3-[4-[(2,6-dimethyl-4-pyridinyl)methoxy]phenyl]-N1-hydroxy-2-oxo-N3-(4-pyridinylmethyl)-1,3-pyrrolidinediacetamide;

[1(R)]-α1-(cyclohexylmethyl)-3-[4-[(2,6-dichloro-4-pyridinyl)methoxy]phenyl]-N1-hydroxy-2-oxo-N3-(4-pyridinylmethyl)-1,3-pyrrolidinediacetamide;

[1(R)]-1,1-dimethylethyl [5-[3-[4-[(2,6-dimethyl-4-pyridinyl)methoxy]phenyl]-2-oxo-3-[2-oxo-2-[(4-pyridinylmethyl)amino)ethyl]-1-pyrrolidinyl]-6-(hydroxyamino)-6-oxohexyl]carbamate;

[1(R)]-α1-(4-aminobutyl)-3-[4-[(2,6-dimethyl-4-pyridinyl)methoxy]phenyl]-N1-hydroxy-2-oxo-N3-(4-pyridinylmethyl)-1,3-pyrrolidinediacetamide;

[1(R)]-3-[3-(1H-benzotriazol-1-ylmethoxy)phenyl]-N-hydroxy-α,3-dimethyl-2-oxo-1-pyrrolidineacetamide;

[1(R)]-N-hydroxy-3,4,4-trimethyl-α-[3-methyl-2-oxo-3[4-(phenylmethoxy)phenyl]-1-pyrrolidinyl]-2,5-dioxo-1-imidazolidinepropanamide;

[1(R)]-1,1-dimethylethyl 1-[(hydroxyamino)carbonyl]-3-methylbutyl]-2-oxo-3-[4-(phenyl]-3-pyrrolidineacetate;

[1(R)-N1-hydroxy-3-[4-[(3,5-dimethylphenyl)methoxy]phenyl]-N3-[2-(methylamino)-2-oxoethyl]-α-(2-methylpropyl)-2-oxo--1,3-pyrrolidinediacetamide;

[1(R)]-3-[4-[(2,6-dichloro-4-pyridinyl)methoxy]phenyl]-N1-hydroxy-N3-[2-(methylamino)-2-oxoethyl]-alpha1-(2-methylpropyl)-2-oxo-1,3-pyrrolidinediacetamide;

[1(R)]-3-[4-[(2,6-dichloro-4-pyridinyl)methoxy]phenyl]-N1-hydroxy-α1-(2-methylpropyl)-2-oxo-N3-2-thiazolyl-1,3-pyrrolidinediacetamide;

[1(R)]-3-[4-[3,5-bis(trifluoromethyl)phenoxy]phenyl]-N1-hydroxy-N3-[2-(methylamino)-2-oxoethyl]-α1-(2-methylpropyl)-2-oxo-1,3-pyrrolidinediacetamide;

[1(R)]-3-[4-[3,5-bis(trifluoromethyl)phenoxy]phenyl]-N1-hydroxy-α1-(2-methylpropyl)-2-oxo-N3-(4-pyridinylmethyl)-1,3-pyrrolidinediacetamide;

[1(R)]-3-[4-[(2,6-dichloro-4-pyridinyl)methoxy]phenyl]-N1-hydroxy-α1-(2-methylpropyl)-2-oxo-N3-phenyl-1,3-pyrrolidinediacetamide;

[1(R)]-3-[4-[(2,6-dimethyl-4-pyridinyl)methoxy]phenyl]-N1-hydroxy-N3-methyl-α1-(2-methylpropyl)-2-oxo-1,3-pyrrolidinediacetamide;

[1(R)]-3-[4-[(2,6-dimethyl-4-pyridinyl)methoxy]phenyl]-N1-hydroxy-N3-[2-(1H-imidazol-4-yl)ethyl]-α1-(2-methylpropyl)-2-oxo-1,3-pyrrolidinediacetamide;

[1(R)]-3-[4-[(2,6-dimethyl-4-pyridinyl)methoxy]phenyl]-N1-hydroxy-α1-(2-methylpropyl)-2-oxo-N3-[1-(phenylmethyl)-4-piperidinyl]-1,3-pyrrolidinediacetamide;

[1(R)]-N3-[2-(dimethylamino)ethyl]-3-[4-[(2,6-dimethyl-4-pyridinyl)methoxy]phenyl]-N1-hydroxy-α1-(2-methylpropyl)-2-oxo-1,3-pyrrolidinediacetamide;

[1(R)]-3-[4-[(2,6-dimethyl-4-pyridinyl)methoxy]phenyl]-N1-hydroxy-N3-(4-hydroxyphenyl)-α1-(2-methylpropyl)-2-oxo-1,3-pyrrolidinediacetamide;

[1(R)]-3-[4-[(2,6-dimethyl-4-pyridinyl)methoxy]phenyl]-N3-hydroxy-α1-(2-methylpropyl)-2-oxo-N3-2-thiazolyl-1,3-pyrrolidinediacetamide;

[1(R)]-3-[4-[(2,6-dimethyl-4-pyridinyl)methoxy]phenyl]-N3-hydroxy-3-(2-hydroxyethyl)-α1-(2-methylpropyl)-2-oxo-1-pyrrolidineacetamide;

[1(R)]-3-[4-[(2,6-dimethyl-4-pyridinyl)methoxy]phenyl]-N3-(4,5-dimethyl-2-thiazolyl)-N1-hydroxy-α1-(2-methylpropyl)-2-oxo-1,3-pyrrolidinediacetamide;

[1(R)]-3-[4-[(2,6-dimethyl-4-pyridinyl)methoxy]phenyl]-N1-hydroxy-N3-1H-indazol-5-yl-α1-(2-methylpropyl)-2-oxo-1,3-pyrrolidinediacetamide; and,

[1(R)]-3-[4-[3,5-bis(trifluoromethyl)phenoxy]phenyl]-N1-hydroxy-α1-(2-methylpropyl)-2-oxo-N3-2-thiazolyl-1,3-pyrrolidinediacetamide;

or a pharmaceutically acceptable salt form thereof.

[6] In another preferred embodiment, the present invention provides a novel compound of formula I, wherein:

A is selected from $COR^5$, —$CO_2H$, $CH_2CO_2H$, —CONHOH, —$CONHOR^5$, —$CONHOR^6$, —N(OH)$COR^5$, —SH, and —$CH_2SH$;

ring B is a 4–7 membered cyclic amide containing from 0–3 additional heteroatoms selected from O, $NR^a$, and $S(O)_p$, and 0–1 additional carbonyl groups and 0–1 double bonds;

$R^1$ and $R^2$ combine to form a $C_{5-14}$ carbocyclic residue substituted with $R^{1'}$ and 0–3 $R^b$ or a 5–10 membered heterocyclic system containing from 1–4 heteroatoms selected from the group consisting of N, O, and S and substituted with $R^{1'}$ and 0–3 $R^b$;

$Z^a$ is selected from H, a $C_{5-10}$ carbocyclic residue substituted with 0–5 $R^c$ and a 5–10 membered heterocyclic system containing from 1–4 heteroatoms selected from the group consisting of N, O, and S and substituted with 0–5 $R^c$;

$R^3$ is selected from H, Q, $C_{1-10}$ alkylene-Q, $C_{2-10}$ alkenylene-Q, $C_{2-10}$ alkynylene-Q, $(CRR')_r O(CRR')_r$—Q, $(CRR')_r NR^a(CRR')_r$—Q, $(CRR')_r C(O)(CRR')_r$—Q, $(CRR')_r C(O)NR^a(CRR')_r$—Q, $(CRR')_r NR^a C(O)(CRR')_r$—Q, $(CRR')_r OC(O)NR^a(CRR')_r$—Q, $(CRR')_r NR^a C(O)O(CRR')_r$—Q, $(CRR')_r NR^a C(O)NR^a(CRR')_r$—Q, $(CRR')_r S(O)_p(CRR')_r$—Q, $(CRR')_r SO_2NR^a(CRR')_r$—Q, $(CRR')_r NR^a SO_2(CRR')_r$—Q, and $(CRR')_r NR^a SO_2 NR^a(CRR')_r$—Q;

R, at each occurrence, is independently selected from H, $CH_3$, $CH_2CH_3$, $CH=CH_2$, $CH=CHCH_3$, and $CH_2CH=CH_2$;

R', at each occurrence, is independently selected from H, $CH_3$, $CH_2CH_3$, and $CH(CH_3)_2$;

Q is selected from H, a $C_{3-10}$ carbocyclic residue substituted with 0–5 $R^b$ and a 5–10 membered heterocyclic system containing from 1–4 heteroatoms selected from the group consisting of N, O, and S and substituted with 0–5 $R^b$;

$R^4$ is selected from H;

$R^c$, at each occurrence, is independently selected from $C_{1-6}$ alkyl, $OR^a$, Cl, F, Br, I, =O, CN, $NO_2$, $NR^a R^{a'}$, $C(O)R^a$, $C(O)OR^a$, $C(O)NR^a R^{a'}$, $S(O)_2 NR^a R^{a'}$, $S(O)_p R^a$, $CF_3$, $CF_2 CF_3$, and a 5–10 membered heterocyclic system containing from 1–4 heteroatoms selected from the group consisting of N, O, and S.

[7] In another more preferred embodiment, the present invention provides a novel compound of formula II, wherein:

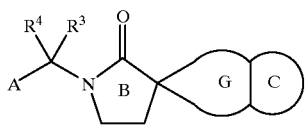

II

A is selected from —$CO_2H$, $CH_2CO_2H$, —CONHOH, and —$CONHOR^5$;

ring C is fused to ring G and is a phenyl ring or 5–6 membered aromatic heterocycle containing from 0–4 heteroatoms selected from O, N, and $S(O)_p$, and ring C is substituted with 1 $R^{1'}$;

ring G is a 4–8 membered carbocylic ring substituted with 0–1 carbonyl groups alternatively, ring G is a 4–8 membered heterocyclic ring containing from 1–2 heteroatoms selected from O and $NR^a$ and substituted with 0–2 carbonyl groups and 0–1 double bonds;

$U^a$ is absent or is selected from: O, $NR^a$, C(O), $C(O)NR^a$, $NR^a C(O)$, and $S(O)_p NR^a$;

$X^a$ is absent or $C_{1-4}$ alkylene;

$Y^a$ is absent or selected from O and $NR^a$;

$Z^a$ is selected from H, phenyl substituted with 0–5 $R^c$ and a 5–9 membered aromatic heterocyclic system containing from 1–4 heteroatoms selected from the group consisting of N, O, and S and substituted with 0–5 $R^c$;

Q is selected from H, a $C_{5-6}$ carbocyclic residue substituted with 0–5 $R^b$ and a 5–6 membered heterocyclic system containing from 1–4 heteroatoms selected from the group consisting of N, O, and S and substituted with 0–5 $R^b$; and, $R^c$, at each occurrence, is independently selected from $C_{1-6}$ alkyl, $OR^a$, Cl, F, Br, I, =O, CN, $NO_2$, $NR^a R^{a'}$, $C(O)R^a$, $C(O)OR^a$, $C(O)NR^a R^{a'}$, $S(O)_2 NR^a R^{a'}$, $S(O)_p R^a$, $CF_3$, $CF_2 CF_3$, and a 5–6 membered heterocyclic system containing from 1–4 heteroatoms selected from the group consisting of N, O, and S.

In a third embodiment, the present invention provides a novel pharmaceutical composition, comprising: a pharmaceutically acceptable carrier and a therapeutically effective amount of a compound of formula (I) or a pharmaceutically acceptable salt form thereof.

In a fourth embodiment, the present invention provides a novel method for treating or preventing an inflammatory disorder, comprising: administering to a patient in need thereof a therapeutically effective amount of a compound of formula (I) or a pharmaceutically acceptable salt form thereof.

In a fifth embodiment, the present invention provides a novel method of treating a condition or disease mediated by MMPs, TNF, aggrecanase, or a combination thereof in a mammal, comprising: administering to the mammal in need of such treatment a therapeutically effective amount of a compound of formula (I) or a pharmaceutically acceptable salt form thereof.

In a sixth embodiment, the present invention provides a novel method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal, comprising: administering to the mammal in need of such treatment a therapeutically effective amount of a compound of formula (I) or a pharmaceutically acceptable salt form thereof.

In a seventh embodiment, the present invention provides a novel method of treating a condition or disease wherein the disease or condition is referred to as fever, cardiovascular effects, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of formula (I) or a pharmaceutically acceptable salt form thereof.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. When a ring system (e.g., carbocyclic or heterocyclic) is said to be substituted with a carbonyl group or a double bond, it is intended that the carbonyl group or double bond be part (i.e., within) of the ring.

When any variable (e.g., $R^b$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. Alkenyl" is intended to include hydrocarbon chains of either a straight or branched configuration and one or more unsaturated carbon-carbon bonds which may occur in any stable point along the chain, such as ethenyl and propenyl. "Alkynyl" is intended to include hydrocarbon chains of either a straight or branched configuration and one or more triple carbon-carbon bonds which may occur in any stable point along the chain, such as ethynyl and propynyl.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 7- membered monocyclic or bicyclic or 7- to 14-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 14-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furnayl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl. Also included are fused ring and spiro compounds containing, for example, the above heterocycles.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) *The Pettides*, 5: 342–429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ohiithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention. "Stable compound" and "stable structure" are meant to indicate a compound that is sufficiently robust to survive isolation to a useful degree of purity from a reaction mixture, and formulation into an efficacious therapeutic agent.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

A series of γ-lactams of formula 10 are prepared by the method outlined in Scheme 1 and 2. $R^1$-substituted methyl acetate 1 is deprotonated to form enolate using bases such as sodium bis(trimethylsilyl)amide, lithium N,N-diisopropylamide, and sodium hydride. Alkylation with $R^2$-X provides 2. Further alkylation with allyl bromide under similar basic conditions gives ester 3. The olefin in 3 is then cleaved by ozonolysis or by dihydroxylation ($OsO_4$/NMO) followed by diol cleavage (NaIO4) to give aldehyde 4. Treatment of the aldehyde 4 and D-amino acid 5 with zinc in acetic acid at elevated temperature leads to reductive amination and lactamization to give γ-lactam 7. The γ-lactamization gives a mixture of two diastereomers epimeric at the quaternary center. The diastereomers of 7 are either separated or taken to the next step as a mixture.

Alternatively, aldehyde 4 is converted to lactam 7 through a stepwise sequence. Condensation of 4 with amino ester 5 through reductive amination provides secondary amine 6. The reductive amination can be affected with reagents such as sodium borohydride, sodium cyanoborohydride, and sodium triacetoxyborohydride. Amine 6 is converted to 7 via thermally induced lactamization or methyl ester hydrolysis followed by amide bond formation using reagents such as BOP.

Lactam 7 can also be prepared from ester 3 through the carboxylic acid 8. Acid 8 and amino ester 5 can be coupled using standard peptide coupling reagents well known in the literature such as DCC, BOP, and TBTU (Bodanszky, M. in Peptide Chemistry A Practical Textbook, 2nd ed. Springer-Verlag, New York, 1993). Olefin degradation ($O_3$/$PPh_3$, or $OsO_4$/$NaIO_4$ and deoxygenation ($Et_3SiH$/$CF_3COOH$) gives lactam 7.

Many of the D-amino acid derivatives 5 are commercially available or are prepared from the commercial material by simple protecting group manipulations. Others are synthesized from glycine using Myers method (Myers, A. G.; Gleason, J. L.; Yoon, T. *J. Am. Chem. Soc.* 1995, 117, 8488), from serine using Mitsunobu reactions (Cherney, R. J.; Wang, L. *J. Org. Chem.* 1996, 61, 2544), or using Evans electrophilic azidations (Evans, D. A.; Britton, T. C.; Ellman, J. A.; Dorow, R. L. *J. Am. Chem. Soc.* 1990, 112, 4011).

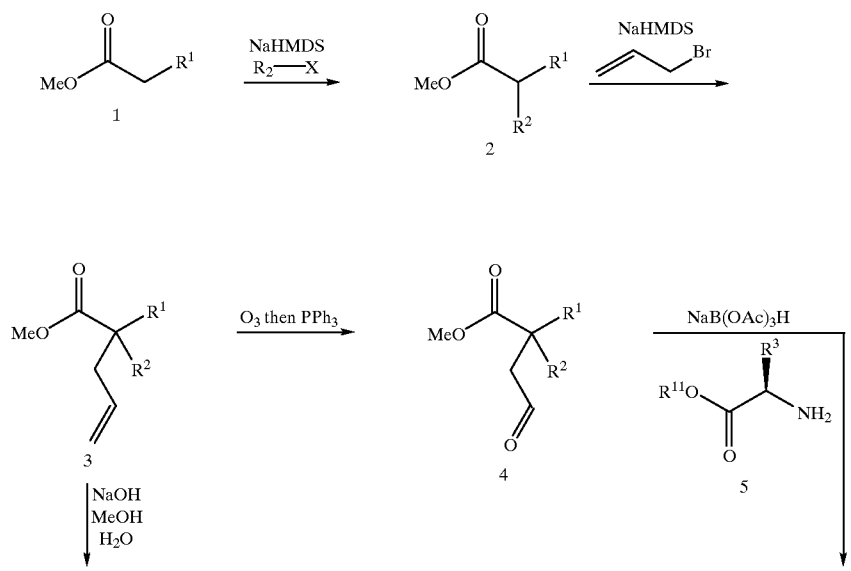

Scheme 1

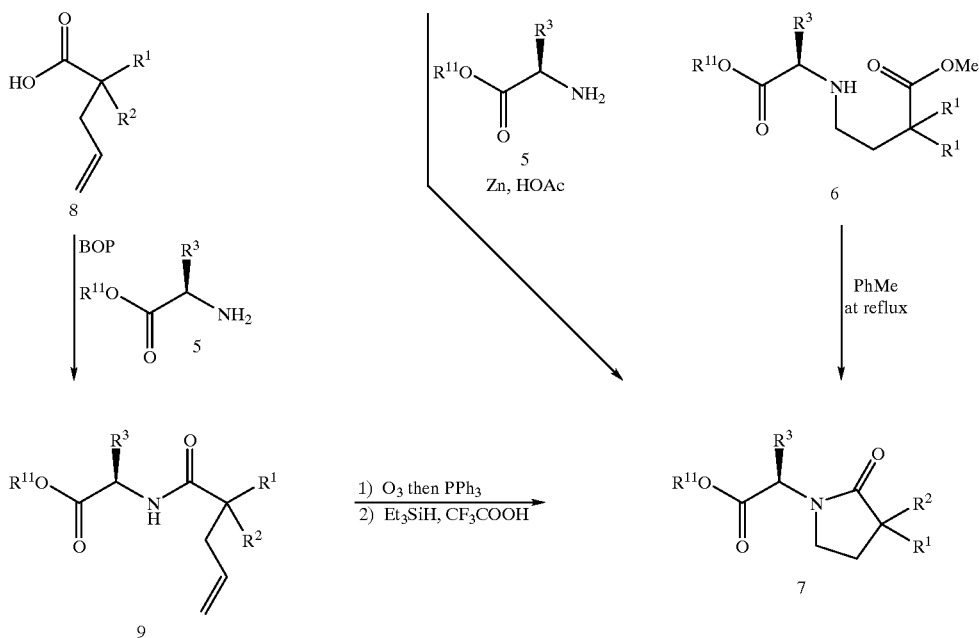

The methyl ester of 7 ($R^{11}$=Me) is converted to hydroxamic acid 10 by treatment with hydroxylamine under basic conditions (KOH or NaOMe) in methanol (Scheme 2). The methyl ester 7 ($R^{11}$=Me) can also be converted to benzyl protected hydroxamic acid with O-benzylhydroxylamine using Weinreb's trimethylalluminum conditions (Levin, J. I.; Turos, E.; Weinreb, S. M. *Syn. Commun.* 1982, 12, 989) or Roskamp's bis[bis(trimethylsilyl)amido]tin reagent (Wang, W.-B.; Roskamp, E. J. *J. Org. Chem.* 1992, 57, 6101). Hydrogenolysis then provides the hydroxamic acid 10. Alternatively, 10 can be prepared through the carboxylic intermediate 11. Carboxylic acid 11 is converted to 10 via coupling with hydroxylamine or NH2OBn followed by deprotection.

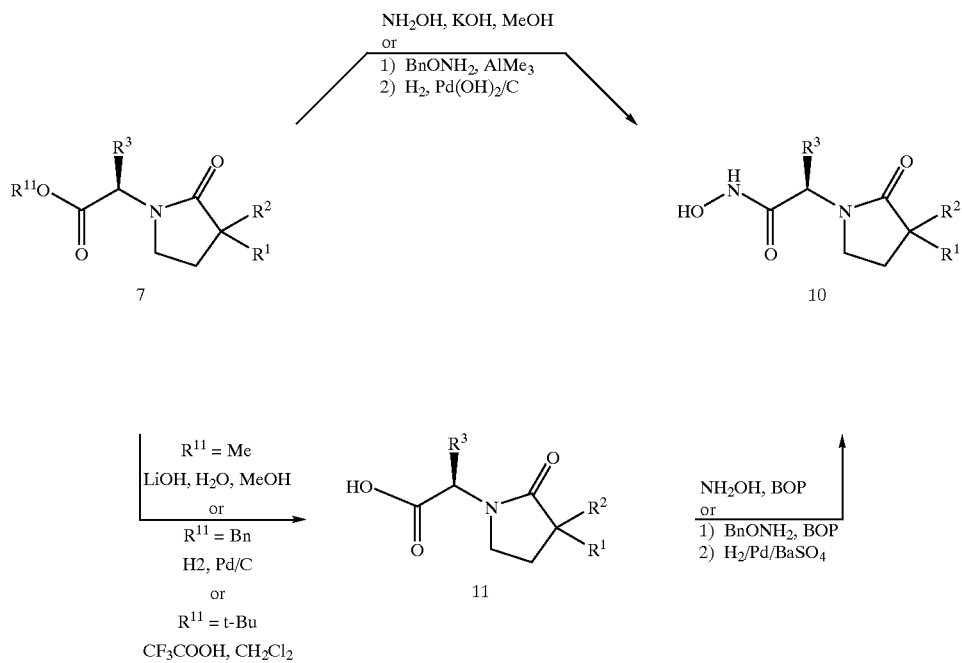

A variety of ethers of 4-hydroxyphenyllactam 13 are prepared using intermediate 7 when $R^1$ is benzyloxyphenyl group (Scheme 3). Removal of benzyl protecting group followed by alkylation with $R^4$—X produces 13. The alkylation can be affected with bases such as $K_2CO_3$, $Cs_2CO_3$, NaH, and t-BuOK. Ester 13 is converted to the hydroxamic acid following the sequences outlined in Scheme 2.

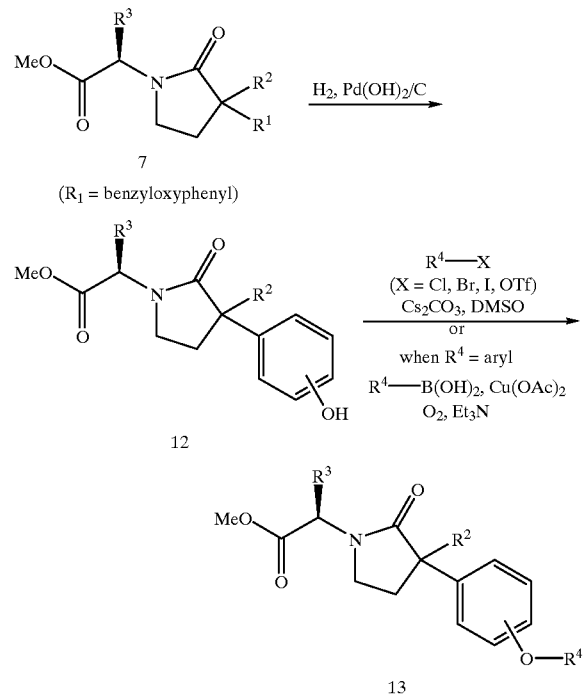

Another series of phenyllactams of formula 15 is prepared following the sequence outlined in Scheme 4. Starting from 7 when $R^1$ methyl group, radical bromonation with N-bromosuccinimide gives bromide 14. Alkylation of 14 with R—OH under basic conditions gives 15. Ester 15 is converted to the hydroxamic acid following the sequences outlined in Scheme 2.

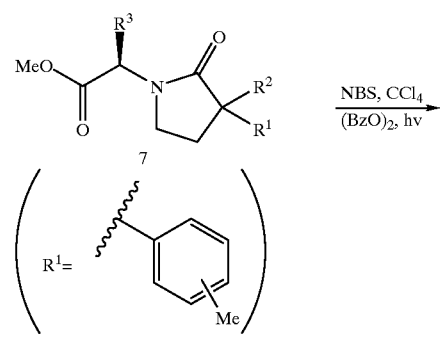

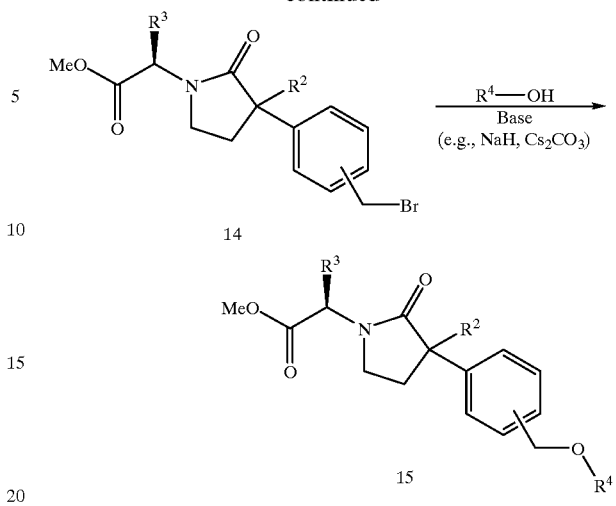

Another series of phenyllactams of formula 17 is prepared following the sequence outlined in Scheme 5. Reaction of 12 with triflic anhydride provides triflate 16. Palladium-mediated coupling of 16 under Stille or Suzuki conditions provides 17. Alternatively, 16 reacts with lower or higher-order cuprates to give 17. Ester 17 is converted to the hydroxamic acid following the sequences outlined in Scheme 2.

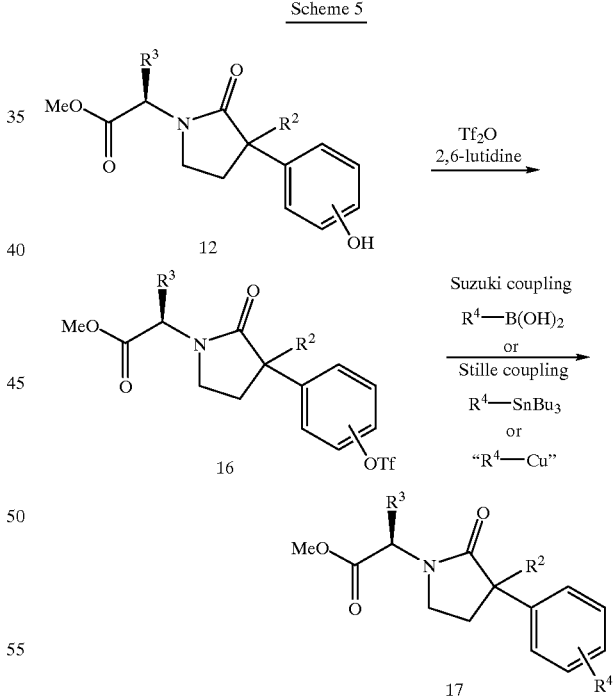

A variety of heterocyclic substituted lactams are prepared from 7 when $R^1$ is carbobenzyloxy group. As a representative example, scheme 6 illustrates the synthesis of the benzimidazole series. Following hydrogenolysis of 7, the resultant acid 18 is coupled with diamine 19 with coupling reagents such as BOP-Cl. Upon heating of 20 in acetic acid, benzimidazole 21 is formed. Ester 21 is converted to the hydroxamic acid following the sequences outlined in Scheme 2.

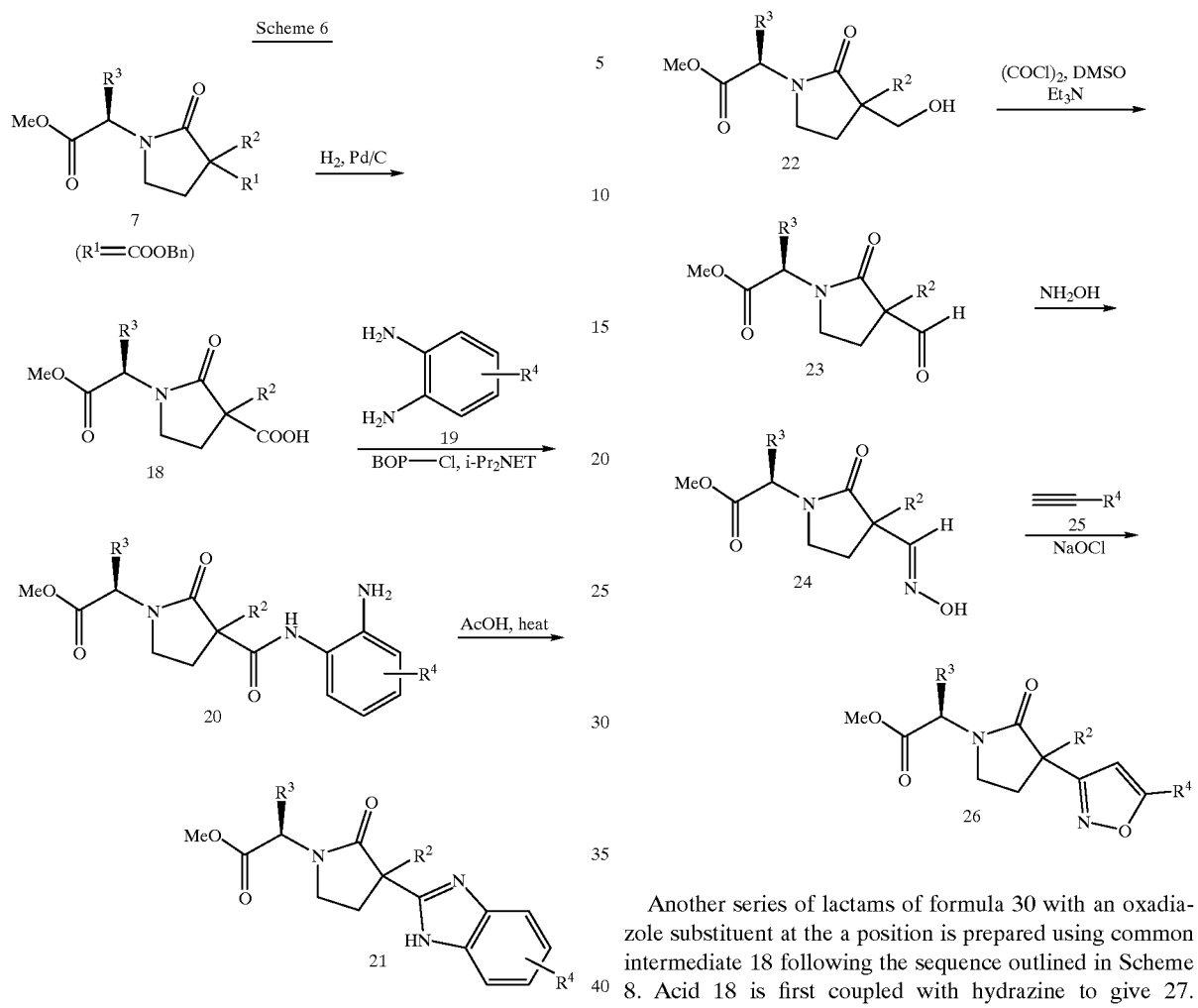

A series of isoxazole-substituted lactams of formula 26 is prepared using common intermediate 18 following the sequence outlined in Scheme 7. The carboxylic acid 18 is converted to aldehyde 23 by hydroboration and Swern oxidation. Oxime formation, in situ oxidation and [3+2] dipolar cycloaddition with acetylene 25 provides isoxazole 26. Ester 26 is converted to the hydroxamic acid following the sequences outlined in Scheme 2.

Another series of lactams of formula 30 with an oxadiazole substituent at the a position is prepared using common intermediate 18 following the sequence outlined in Scheme 8. Acid 18 is first coupled with hydrazine to give 27. Condensation with aldehyde 28 and oxidative cyclization with PhI(OAc)₂ provided oxadiazole 30 (Yang, R. Y.; Dai, L. X. *J. Org. Chem.* 1993, 58, 3381). Ester 30 is converted to the hydroxaxnic acid following the sequences outlined in Scheme 2.

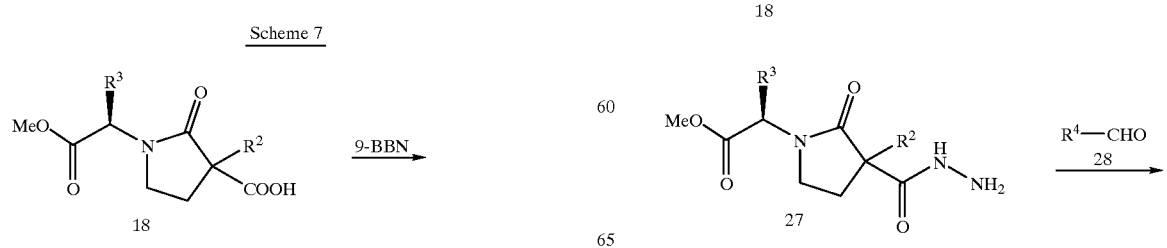

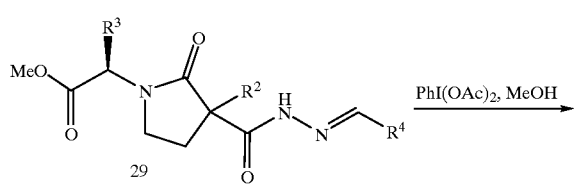

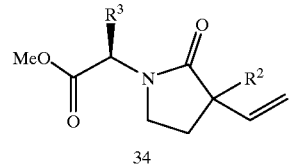

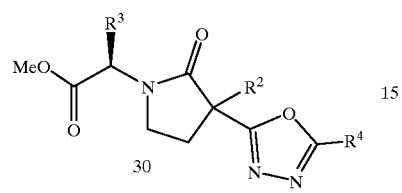

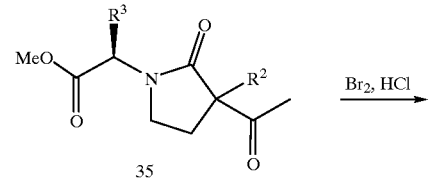

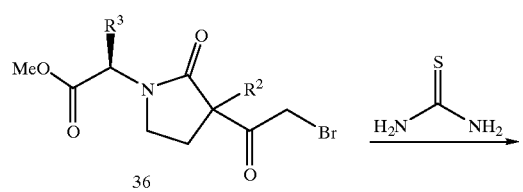

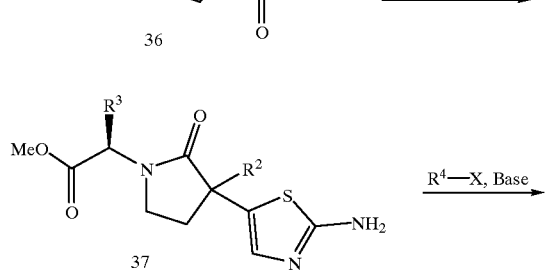

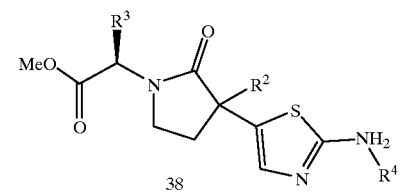

Another series of lactams of formula 38 with an aminothiazole substituent at the α position is prepared following the sequence outlined in Scheme 9. Consecutive alkylations with bromoacetaldehyde dimethyl acetal and $R^2$—X gives 33. Reaction of 33 with D-amino acid 5 using zinc in acetic acid provides lactam 34. Bromoketone 36 is obtained from 34 by Wacker oxidation and bromonatilon. Treatment of bromoketone 36 with thiourea produces aminothiazole 37 (Markees, D. G.; Burger, A. *J. Am. Chem. Soc.* 1948, 70, 3329). Alkylation with $R^4$—X then provides 38. Ester 38 is converted to the hydroxamic acid following the sequences outlined in Scheme 2.

Scheme 9

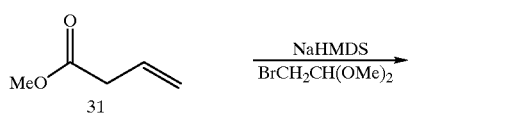

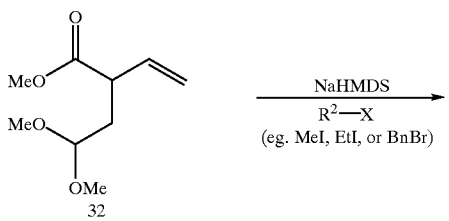

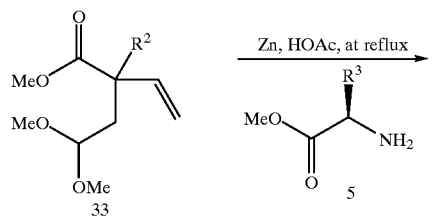

Another series of lactams of formula 42 with an imidazole substituent at the α position is prepared following the sequence outlined in Scheme 10. Consecutive alkylations with bromoacetaldehyde dimethyl acetal and $R^2$—X gives 41. Reaction of 41 with D-amino acid 5 using zinc in acetic acid provides lactam 42. Ester 42 is converted to the hydroxamic acid following the sequences outlined in Scheme 2.

Scheme 10

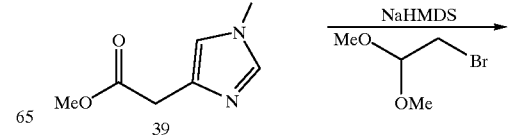

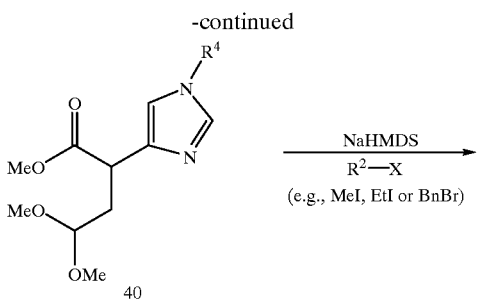

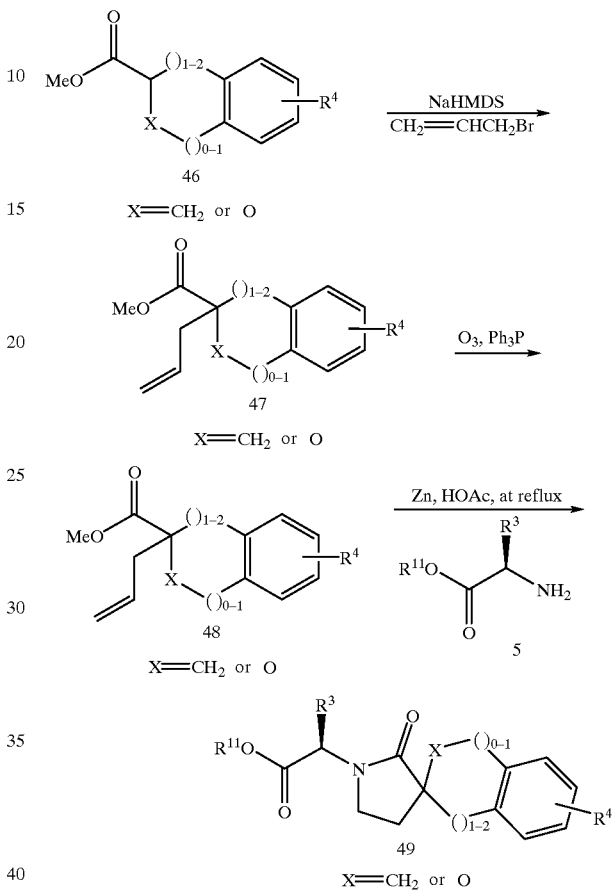

A series of spirolactams of formula 49 is prepared from 46 (Scheme 12). The synthetic sequence is analogous to the strategy in Scheme 1. Ester 49 is converted to the hydroxamic acid following the sequences outlined in Scheme 2.

A series of succinimides of formula 45 is prepared from intermediate 4 (Scheme 11). The synthesis entails oxidation to carboxylic acid 43, coupling with amino acid 5, and succinimide formation. Ester 45 is converted to the hydroxamic acid following the sequences outlined in Scheme 2.

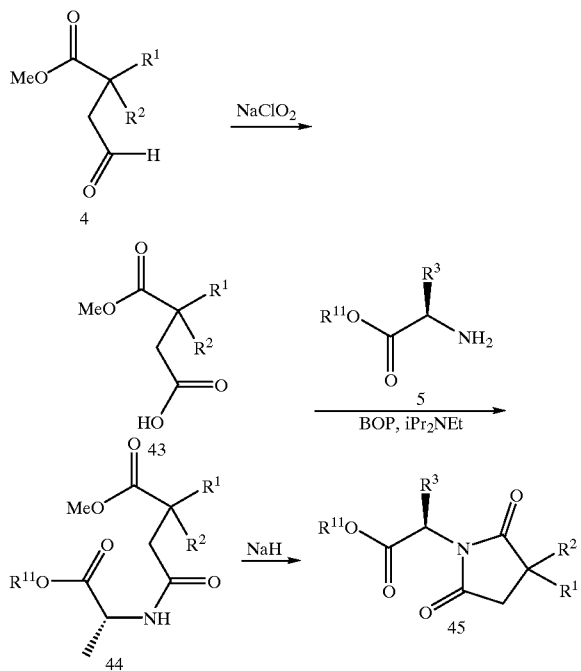

A variety of compounds of formula (I) wherein $R^2$ is NHR can be prepared by methods described in Scheme 13. The p-hydroxyglycine acid was converted to the methyl ester using methanol and HCl to give compound 51, which was converted to the N-Boc protected amino acid 52 by methods described in the literature. The p-benzyloxyphenylglcine compound 53 was prepared by reacting the phenol compound 52 with benzyl bromide in acetone with a base such as potassium carbonate. The 2-allyl phenyl acetic acid compound 54, was prepared by treating compound 53 with LDA (2 eq) and allyl bromide. The olefin compound 54 is oxidized to the aldehyde compound 55 using ozone and triphenylphosphine, then reacted with an appropriate amine to give the imine, which can be reduced with reagent similar to sodium triacetoxyborohydride, to give the amine compound 56. The γ-lactam compound 57 is prepared by heating the amine compound 56 in an appropriate solvent such as toluene. The benzyl ether is removed by methods well known in the literature such as hydrogenation using palladium on carbon in hydrogen, to give compound 58. The compound 59 is prepared by reacting the phenol 58 with an appropriately substituted halide or the like in acetone with a base such as potassium carbonate. The hydroxamic acid compound 61 was prepared from compound 59 by methods well known in the literature for removing N-Boc groups and conversion of the methyl ester previously described. Alternatively the amine compound 60 can be treated with appropriately substituted acid chloride, isocyanate, carboxylic acid with coupling agents such as carbonyldiimidazole or the like, which are well known in the literature for making amide bonds. Alternatively the amine of compound 60 can be converted to an isocyanate by a variety of methods known in the literature like using phosgene and a base such as sodium carbonate, and reacting this with an appropriately substituted amine, to give compound 62. The hydroxamic acid was prepared by methods previously described.

Scheme 13

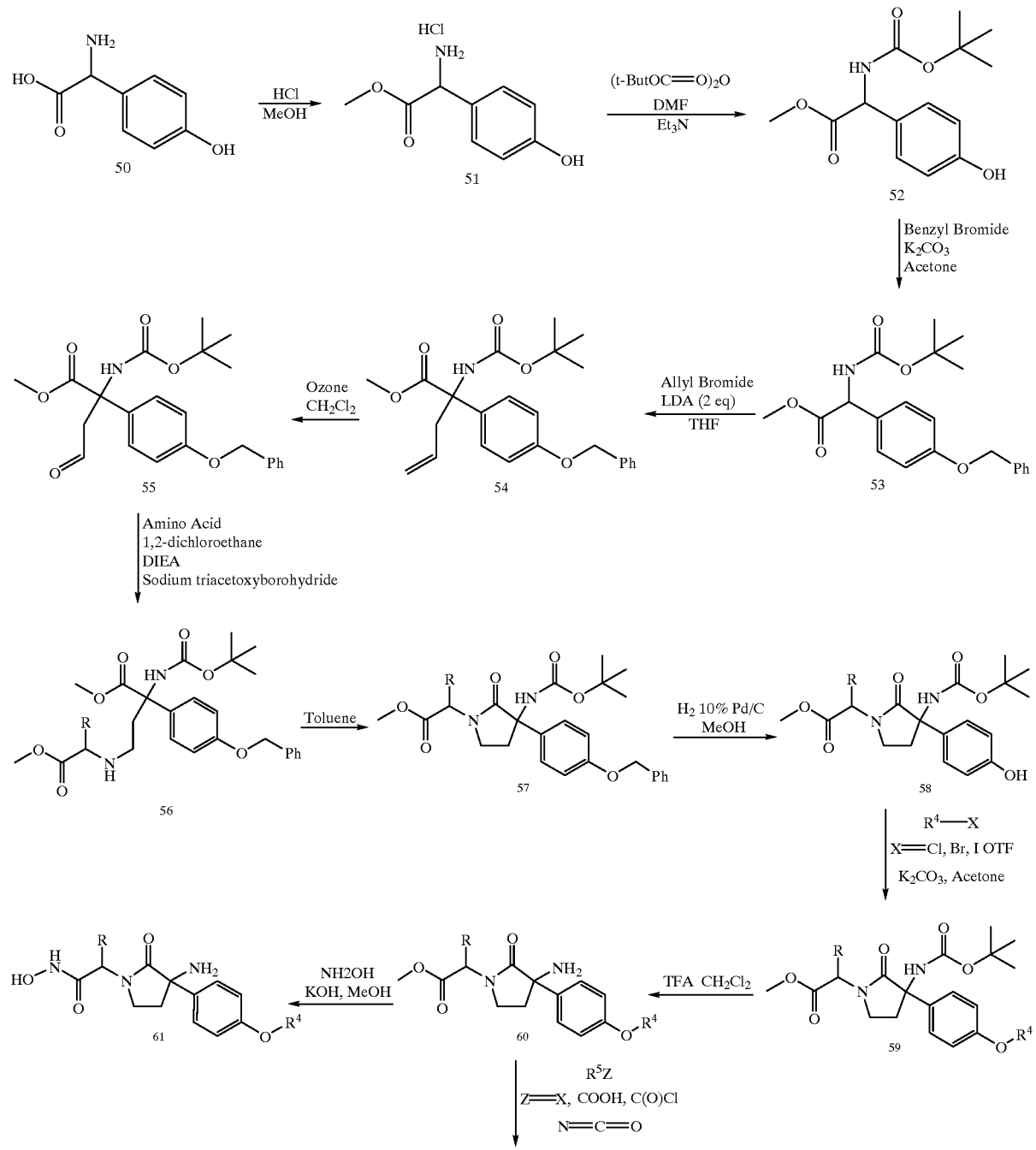

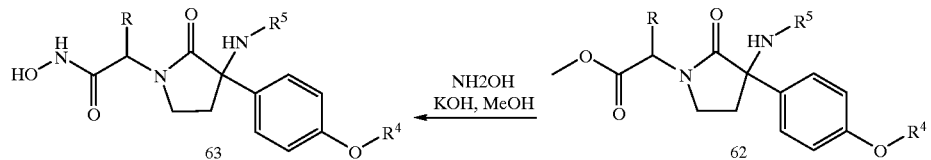

A variety of compounds of formula (I) wherein the lactam is a six member ring can be prepared by methods described in Scheme 14. The ester compound 64 is converted to the acid compound 65 by methods well known in the literature, such as lithium hydroxide in methanol water, then coupled to an appropriately substituted amine by methods well described in the literature for making amide bonds, such as TBTU and N-methyl morpholine in DNF, to give compound 66. The hydroxy compound 67 was prepared from the olefin compound 66 by reduction with 9-BBN and oxidative workup with hydrogen peroxide. The δ-lactam 69 is prepared by converting the hydroxy of compound 67 to a leaving group by methods well known in the literature such as carbon tetrabromide and triphenylphosphine in methylene chloride. The bromide compound 68 was reacted with a base such as sodium hydride in THF to give the δ-lactam 69. The hydroxamic acid compound 70 was prepared by methods previously described.

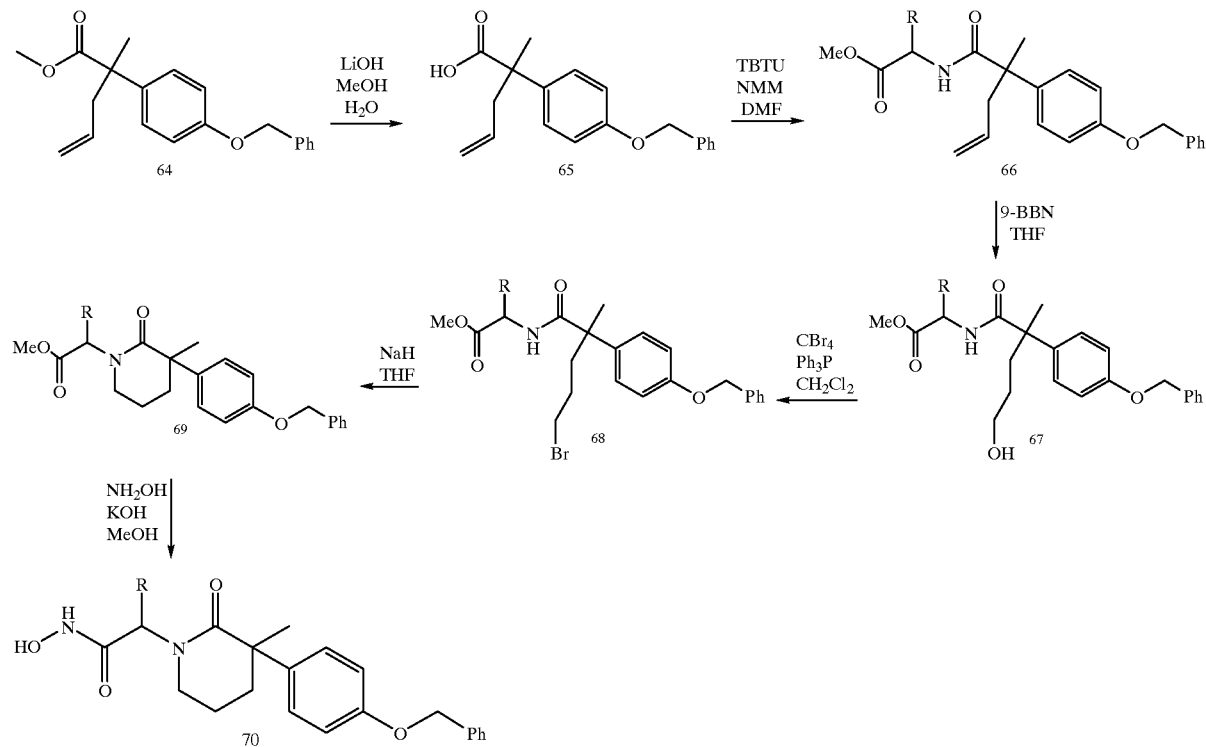

Scheme 14

A variety of compounds of formula (I) wherein the lactam is a four member ring can be prepared by methods described in Scheme 15. The ester compound 71 was converted to the acid compound 72 and coupled to an appropriately substituted amine by methods well known in the literature and previously described. The β-lactam 75 is prepared by converting the hydroxy of compound 73 to a leaving group by methods well known in the literature, such as methanesulfonyl chloride and potassium carbonate in pyridine. The methanesulfonate compound 74 was reacted with a base such as potassium carbonate in acetone to give the β-lactam 75. The hydroxamic acid compound 77 was prepared by methods previously described.

Scheme 15

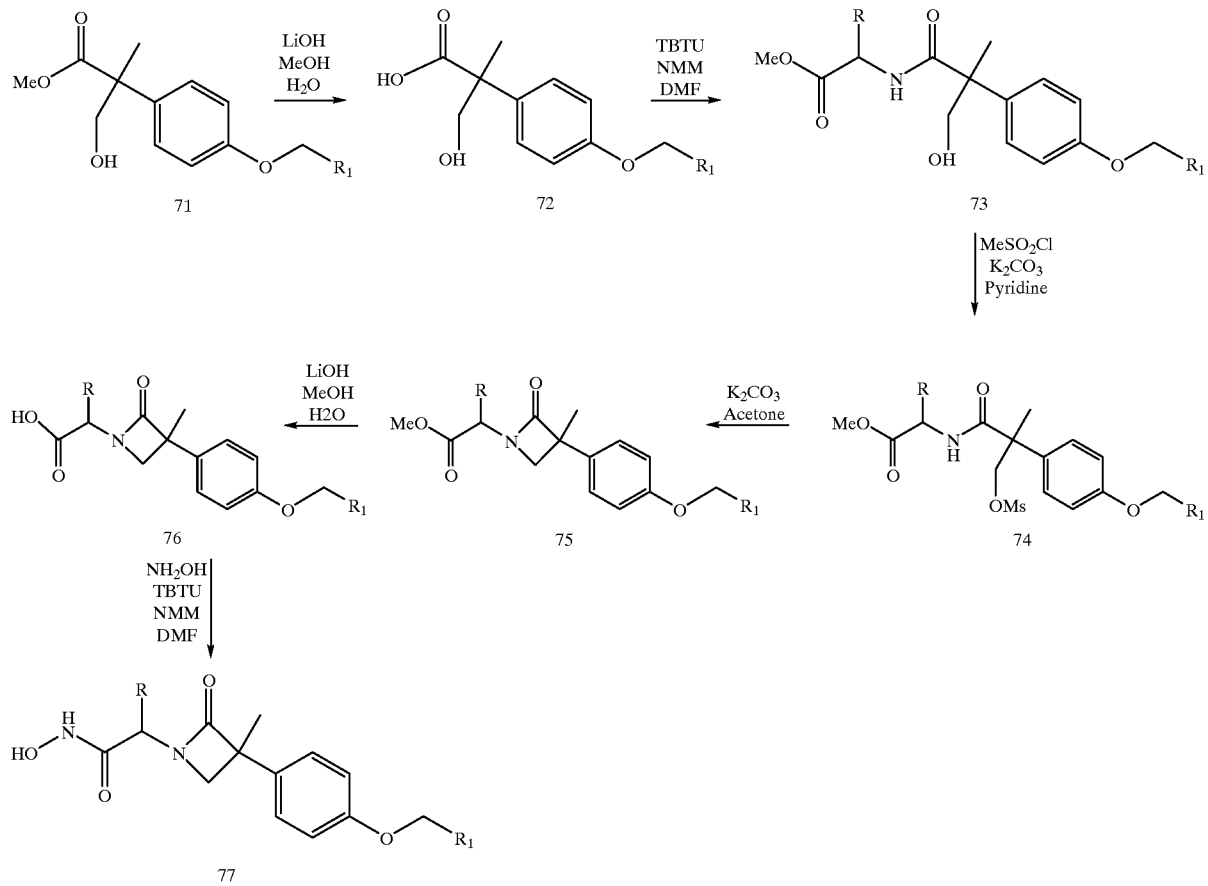

A variety of compounds of formula (I) wherein the lactam is replaced with a hydantoin ring can be prepared by methods described in Scheme 16. The amine compound 78 was prepared from the N-Boc compound 54 by methods previously described for the removal of Boc protecting groups. The urea compound 79 was prepared by converting the amine compound 78 to an isocyanate by methods well known in the literature and previously described, such as triphosgene and DIEA in methylene chloride and reacting this with an appropriately substituted amine. Alternatively, the amine 78 can be reacted with an isocyanate which is commercially available or can be prepared as described above. The hydantoin compound 80 was prepared by reacting the urea compound 79 with potassium carbonate in acetone. The final hydroxamic acid compound 81 was prepared by methods well documented previously.

Scheme 16

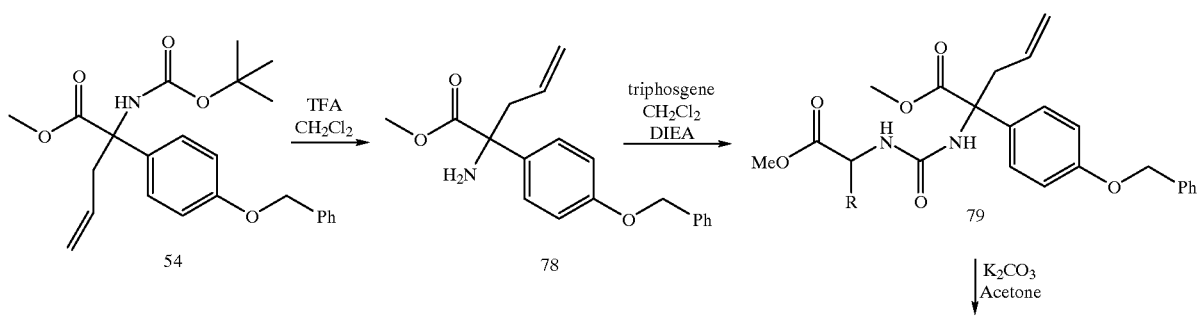

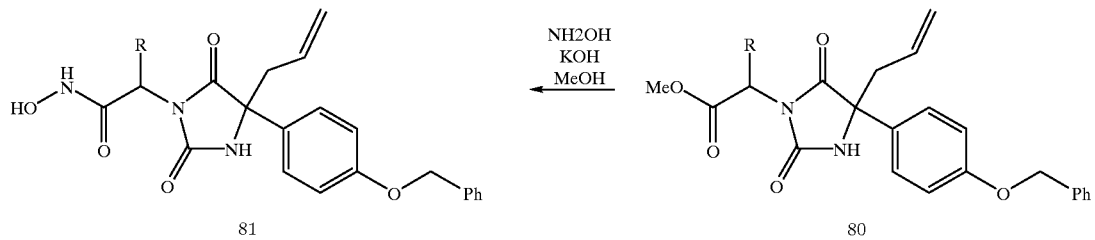

A variety of compounds of formula (I) wherein the lactam is replaced with a aminomethylene lactam ring can be prepared by methods described in Scheme 17. The diamino acid compound 84 was prepared from the 2-methyl phenylglycine compound 82, by hydrolysis to the acid and coupling to an appropriately substituted amine a well described in the literature and previously detailed. The N-Boc group is remove by conventional methods previously described to give the amine compound 85. The heterocyclic compound 86 was prepared by reacting the amine compound 85 with paraformaldehyde in toluene at elevated temperatures. The final hydroxamic acid compound 87 was prepared by methods well documented previously.

ing the p-hydroxyphenylacetonitrile with benzyl bromide in acetone with potassium carbonate to give compound 88, which was in turn reacted with sodium ethoxide and diethylcarbonate in toluene at elevated temperatures. The allyl cyanoacetate compound 90 was prepared from the cyanoacetate compound 89 by generating the anion with a base such as sodium hydride and reacting this with allyl bromide in DMF. The nitrile lactam compound 94 was prepared by a sequence of steps previously described in several other Schemes. The N-Boc methyleneamine compound 96 was prepared by reduction of the nitrile lactam compound 94, using palladium on carbon with HCl in methanol, to give the amino compound 95 which was then protected by conven-

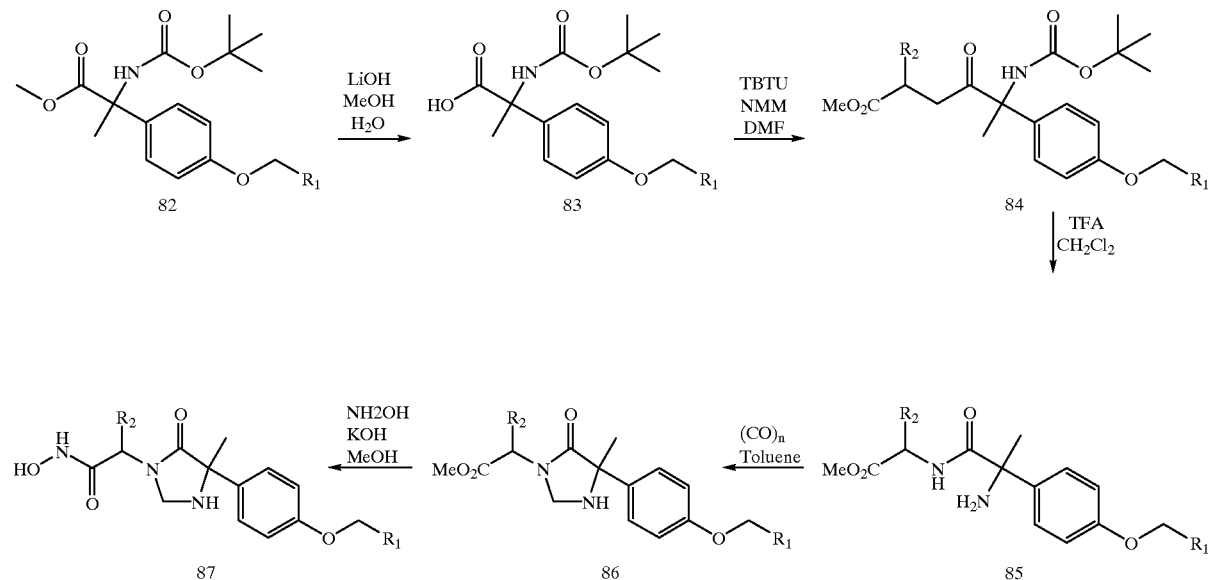

A variety of compounds of formula (I) wherein $R^2$ is $CH_2NHR$ can be prepared by methods described in Scheme 18. The cyanoacetate compound 89 was prepared by reacttional methods with a Boc group to give compound 96. The final hydroxamic acid compounds 99 and 101 were prepared by methods previously described.

Scheme 18

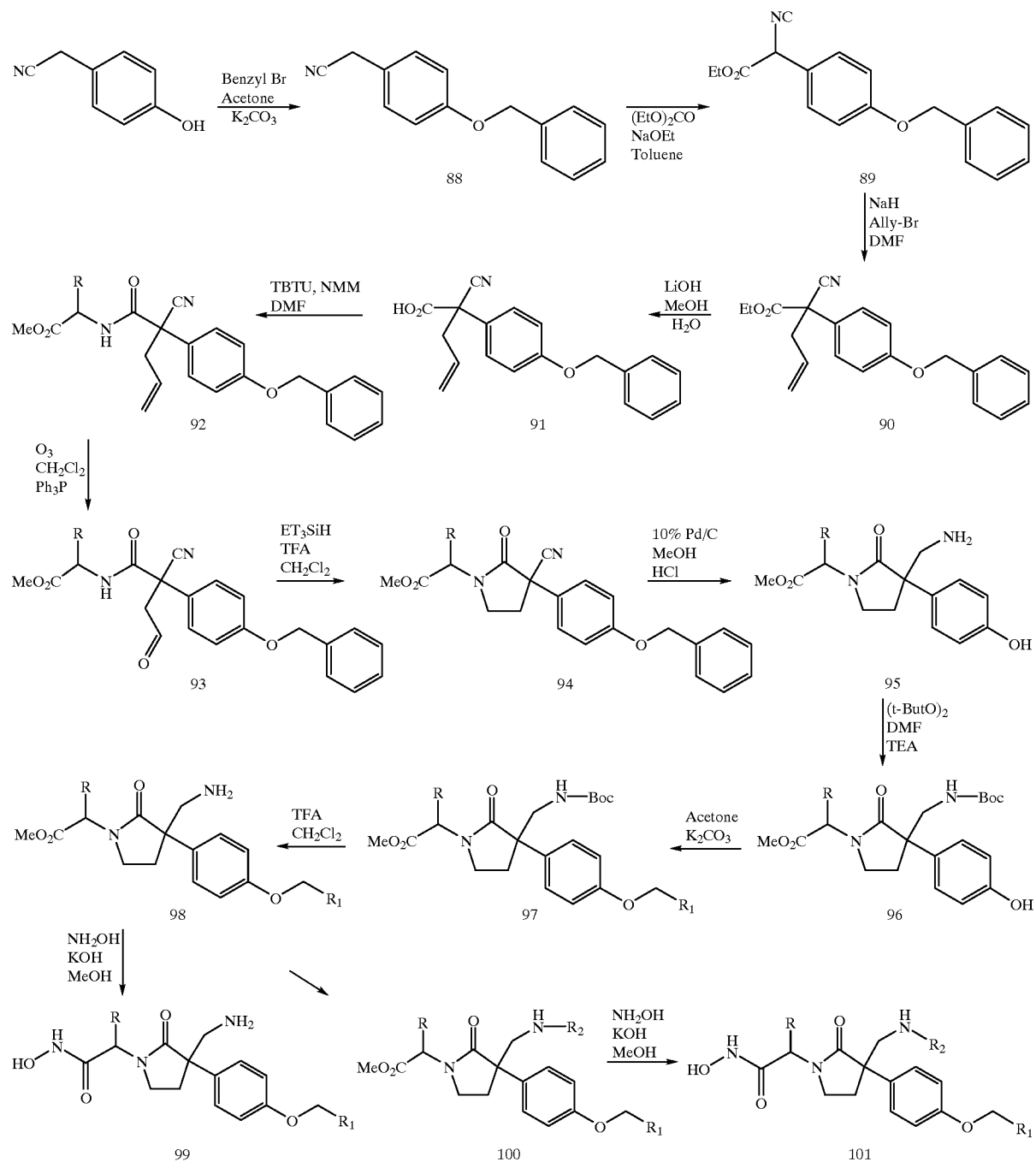

A variety of compounds of formula (I) wherein $R^2$ is $CH_2OH$ can be prepared by methods described in Scheme 19. The allyl compound 104 was prepared from p-hydroxyphenyl acetate, by reaction with benzyl bromide and potassium carbonate in acetone as previously described and then treating the benzyloxy phenyl acetate compound 103 with LDA and allyl bromide in THF. The methylene hydroxy compound 105 was prepared by treating the benzyloxy phenyl acetate compound 103 with paraformaldehyde and sodium methoxide in DMSO. The hydrolysis of the ester and coupling of the carboxylic acid to an appropriately substituted amine was described earlier to give the compound 107. The protected O-silyl compound 108 was prepared by methods well described in the literature, then oxidation to the aldehyde compound 109 with ozone was described previously. The lactam compound 110 was prepared from the aldehyde compound 109 by treatment with triethyl silane and TFA in methylene chloride at ambient temperatures. The final hydroxamic acid compound 112 was prepared by methods previously described.

Scheme 19

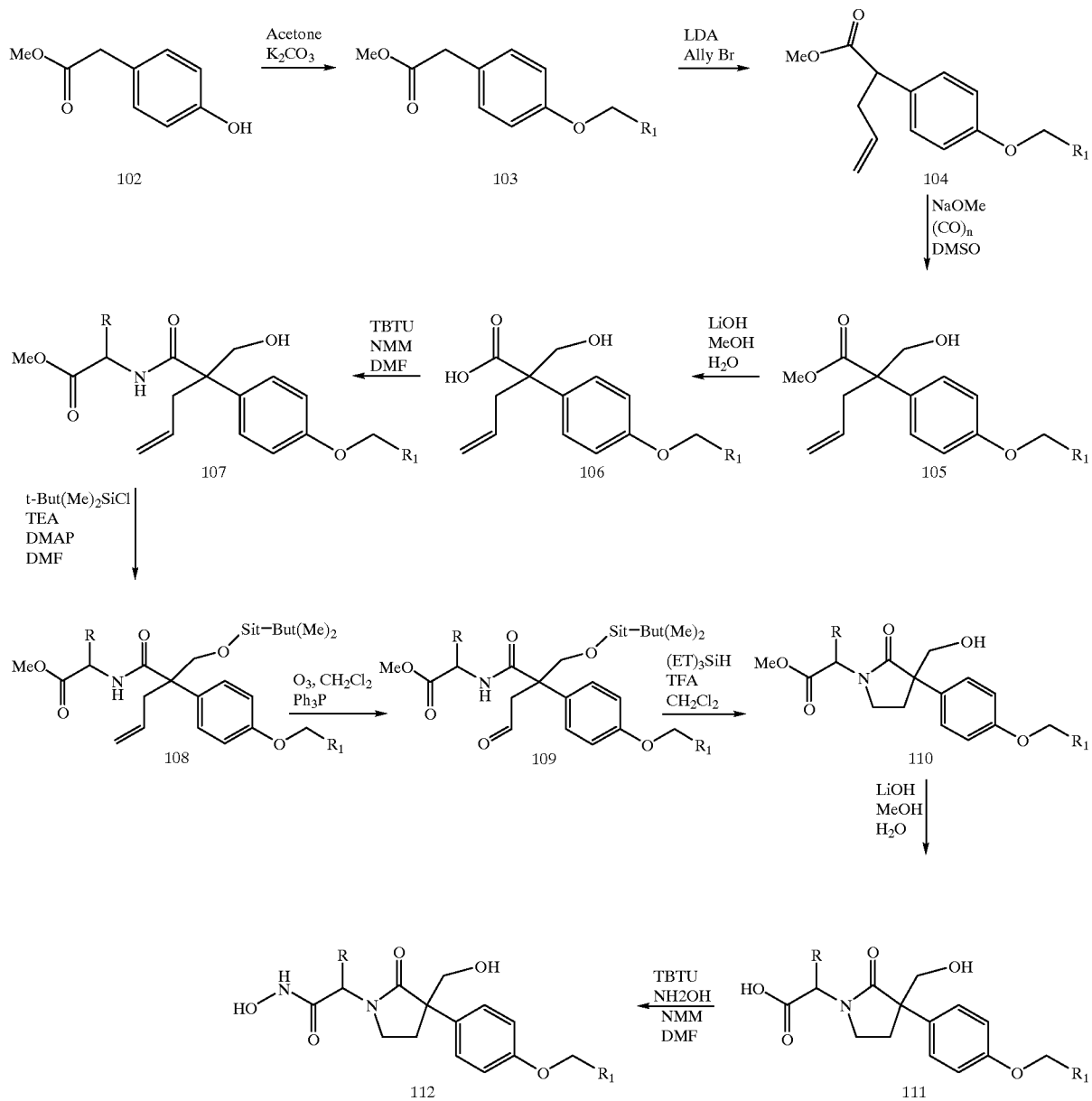

A variety of compounds of formula (I) wherein $R^1$ is a heterocycle, such as thiophene, can be prepared by methods described in Scheme 20. The thiophene substituted compound 115 was prepared by treating the thiophene acetate compound 113 with LDA and allyl bromide to give compound 114, and subsequently with LDA and methyl iodide in THF. The thiophene compound 117 was prepared by methods previously detailed for ester hydrolysis to the acid and coupling the carboxylic acid to an amine. The oxidation of the olefin compound 117, to the aldehyde compound 118, was performed by the action of osmium tetraoxide and NMMO, to give the diol, then treatment with NaIO4. The formation of the lactam ring compound 119 was previously described using triethylsilane and TFA in methylene chloride. The aldehyde thiophene compound 120 was prepared by chemistry well described in the literature, using phosphorus oxychloride in DMF. The aldehyde compound 120 was reacted with sodium borohydride in methanol to give alcohol compound 121 which was reacted with carbon tetrabromide and triphenyl phosphine to give the bromide compound 122. The bromide was treated with phenol and potassium carbonate in acetone to give the phenyl ether compound 123. The final hydroxamic acid compound 124 was prepared by methods previously described.

Scheme 20

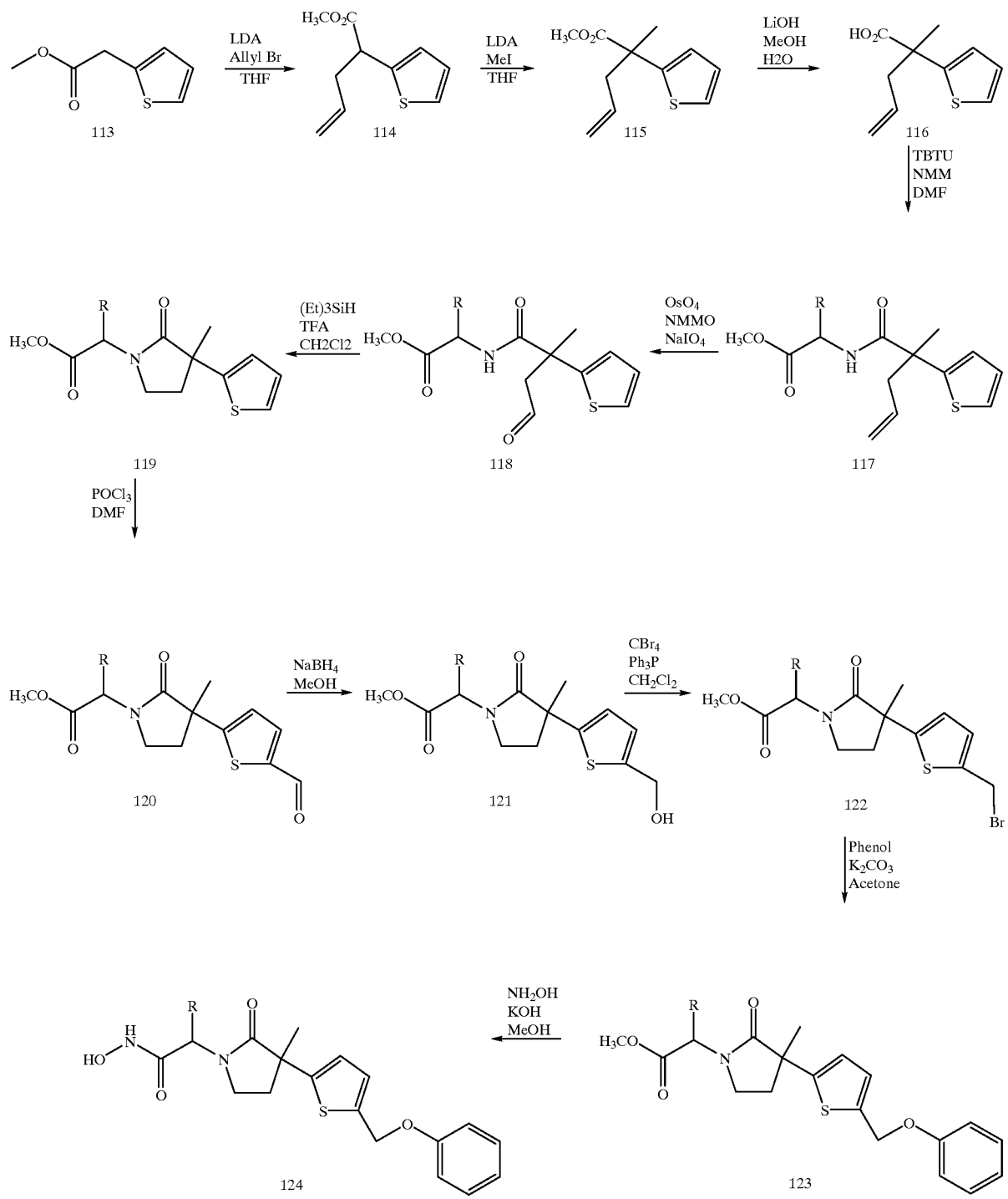

Another series of lactams of formula 135 is prepared following the sequence outlined in Scheme 21. Ester 124 is alkylated with t-butyl bromoacetate to give 126. Ester 126 is converted to 132 following previously described sequence. Removal of t-butyl group and coupling with $NH_2R'$ under literature well known conditions gives 134. Ester 134 is converted to the hydroxamic acid following the sequences outlined in Scheme 2.

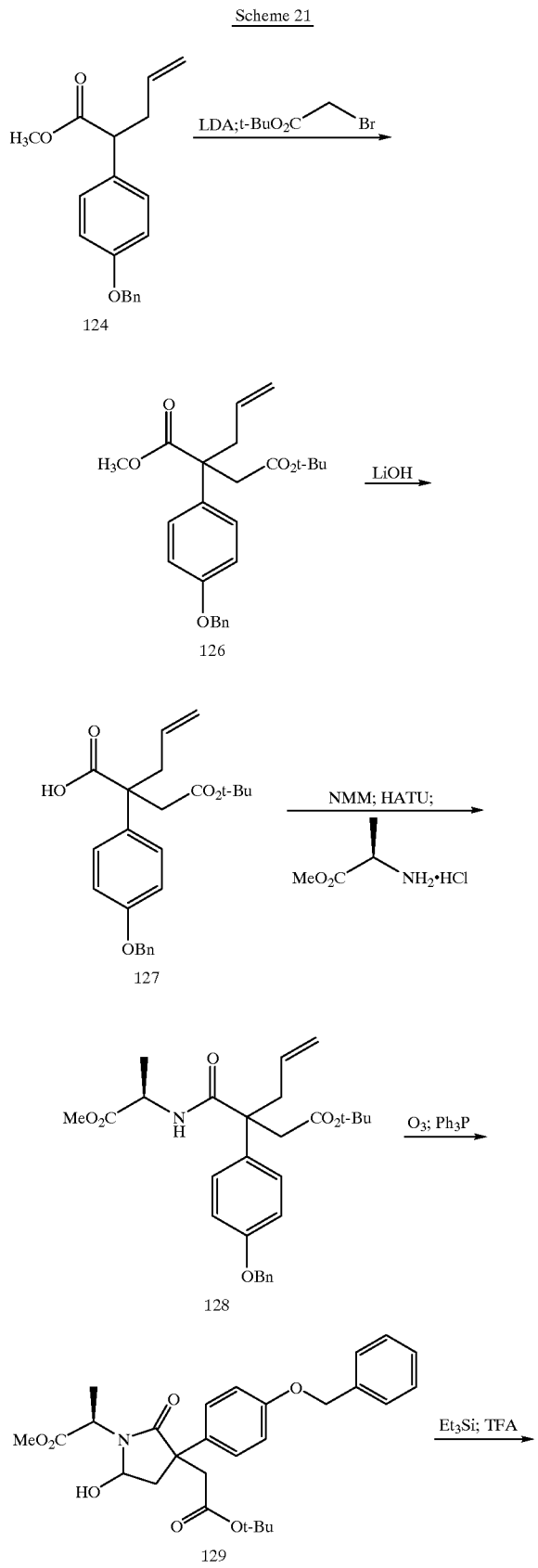
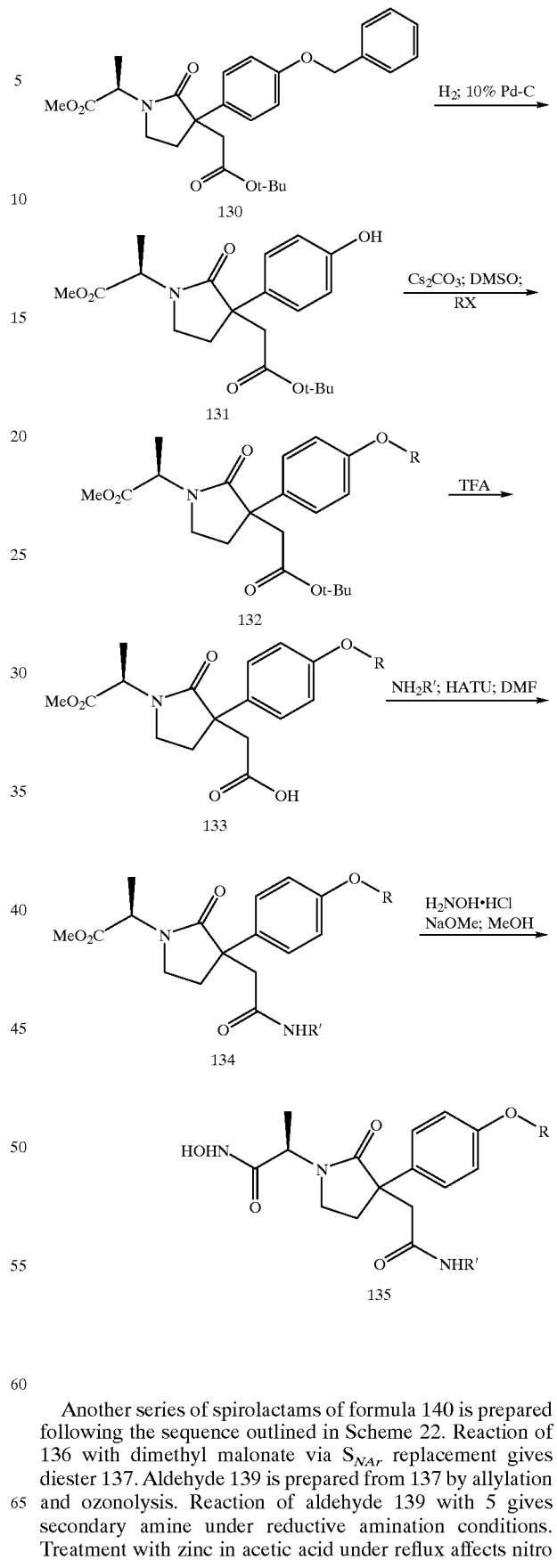

Another series of spirolactams of formula 140 is prepared following the sequence outlined in Scheme 22. Reaction of 136 with dimethyl malonate via $S_{NAr}$ replacement gives diester 137. Aldehyde 139 is prepared from 137 by allylation and ozonolysis. Reaction of aldehyde 139 with 5 gives secondary amine under reductive amination conditions. Treatment with zinc in acetic acid under reflux affects nitro reduction and spirocyclization in one pot to give 140. Ester 140 is converted to the hydroxamic acid following the sequences outlined in Scheme 2.

Scheme 22

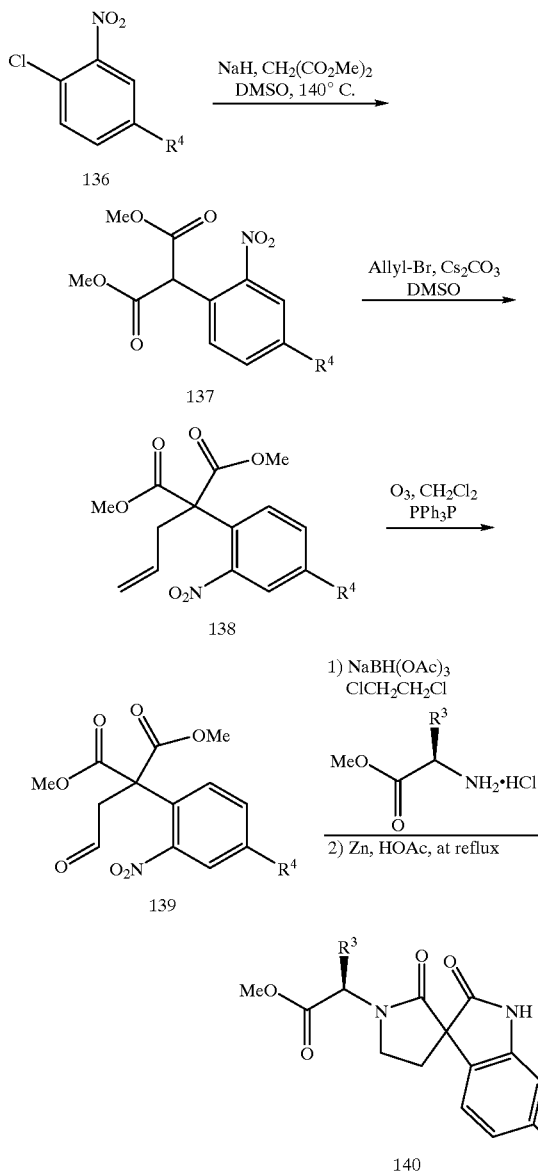

One diasteriomer of a compound of Formula I may display superior activity compared with the others. Thus, the following stereochemistries are considered to be a part of the present invention.

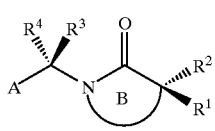

Ia

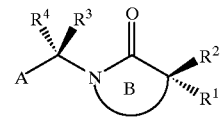

Ib

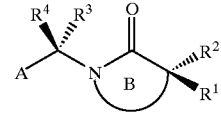

Ic

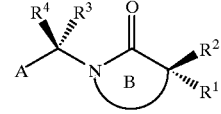

Id

When required, separation of the racemic material can be achieved by HPLC using a chiral column or by a resolution using a resolving agent such as camphonic chloride as in Steven D. Young, et al, *Antimicrobial Agents and Chemotheraphy* 1995, 2602–2605. A chiral compound of Formula I may also be directly synthesized using a chiral catalyst or a chiral ligand, e.g., Andrew S. Thompson, et al, *Tet. lett.* 1995, 36, 8937–8940).

Other features of the invention will become apparent in the course of the following descriptions of exemplary embodiments which are given for illustration of the invention and are not intended to be limiting thereof.

EXAMPLES

Abbreviations used in the Examples are defined as follows: "1×" for once, "2×" for twice, "3×" for thrice, "° C." for degree, Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R" and "S" are stereochemical designations familiar to those skilled in the art.

Example 1

[1(R)]-N-hydroxy-α,3-dimethyl-2-oxo-3-[4-(phenylmethoxy)phenyl]-1-pyrrolidineacetamide (1a) A 1.0 M tetrahydrofuran solution of sodium bis(trimethylsilyl)amide (254 mL, 1.3 eq) was added over 1 h to methyl 4-benzyloxyphenylacetate (50.00 g, 195 mmol) in tetrahydrofuran (600 mL) at −78° C. After 1 h at −78° C., iodomethane (18.2 mL, 1.5 eq) was added. After 2 h at −20° C., saturated ammonium chloride (400 mL), water (600 mL), ether (500 mL) and hexane (500 mL) were added. The two phases were separated and the aqueous phase extracted with 1:1 (v/v) ether-hexane (2×650 mL). The combined organic extracts were washed successively with water (2×500 mL), brine (400 mL) and dried (MgSO4). Removal of solvent in vacuo provided the desired product (49.58 g, 94%) as a yellow viscous oil. MS found: (M+NH$_4$)$^+$=288.

(1b) Following a procedure analogous to (1a), the material from (1a) (48.66 g, 180 mmol) was treated with 1.0 M tetrahydrofuran solution of sodium bis(trimethylsilyl)

amide (234 mL, 1.3 eq) at −78° C. and alkylated with allyl bromide (23.4 mL, 1.5 eq) at −20° C. Workup and concentration gave the desired product (54.77 g, 98%) as a pale yellow solid. MS found: $(M+H)^+=311$, $(M+NH_4)^+=328$.

(1c) Ozone was bubbled through a solution of the olefin from (1b) (54.0 g, 174 mmol) in dichloromethane (500 mL) at −78° C. until starting material disappeared by TLC. The mixture was purged with nitrogen and treated with triphenylphospiline (54.77 g, 1.2 eq). After 1 h at ambient temperature, the mixture was concentrated in vacuo. The residue was purified by short silica gel column (ethyl acetate-hexane, 20:80) to give the desired aldehyde (44.65 g, 82%) as a white solid. MS found: $(M+H)^+=313$, $(M+NH_4)^+=330$.

(1d) Zinc powder (93.74 g, 10 eq) was added in several portions to the aldehyde from (1c) (44.73 g, 143 mmol) and D-alanine methyl ester hydrochloride (22.00 g, 1.1 eq) in acetic acid (1 L) at 5–10° C. The mixture was heated to reflux for 4 h and then cooled to rt. Following addition of chloroform (1 L), the mixture was filtered and the solid residue washed with 1:1 ethanol-chloroform (500 mL). Following removal of solvent in vacuo, ethyl acetate (1 L) was added and the precipitate was removed by filtration. The filtrate was concentrated and purified by silica gel chromatography (ethyl acetate-hexane, 35:65 then 40:60 then 60:40) to give a 1:1 mixture of lactams (42.30 g, 81%). The mixture was separated by repeated silica gel chromatography (ethyl acetate-hexane, 40:60). MS found: $(M+H)^+=368$.

(1e) Preparation of hydroxylamine/potassium hydroxide solution: A solution of potassium hydroxide (2.81 g, 1.5 eq) in methanol (7 mL) was added to a hot solution of hydroxylamine hydrochloride (2.34 g, 33.7 mmol) in methanol (12 mL). After the mixture was cooled to room temperature, the precipitate was removed by filtration. The filtrate was used fresh and assumed hydroxylamine concentration of 1.76 M.

The freshly prepared 1.76 M solution of hydroxylamine (2.3 mL, 4 eq), was added to the less polar isomer from (1d) (369.2 mg, 1.00 mmol) in methanol (2 mL) at rt. After 1 h at this temperature, same portion of hydroxylamine was added and the mixture was stirred for additional 30 min. Upon acidification to pH 4–5 with 1 N HCl, the desired hydroxamic acid precipitated out. The product was collected by filtration and washed with water (3×) to give a white solid (322.6 mg, 87%). MS found: $(M-H)^-=367$.

(1f) Following a procedure analogous to (1e), the more polar isomer from (1d) (378.6 mg, 1.03 mmol) was reacted with hydroxylamine. After adjusting to pH 4 with 1 N HCl, methanol was removed in vacuo. The aqueous residue was extracted with ethyl acetate, dried ($MgSO_4$) and concentrated. Silica gel chromatography (methanol-dichloromethane, 5:95 then 10:90) provided the desired hydroxamic acid (84.0 mg, 22%) as a white solid. MS found: $(M-H)^-=367$.

Example 2

[1(R)]-N-hydroxy-α,3-dimethyl-2-oxo-3-(4-methoxypyenyl)-1-pyrrolidineacetamide (2a) A 1.0 M tetrahydrofuran solution of sodium bis(trimethylsilyl)amide (139 mL, 1.1 eq) and methyl 4-methoxyphenylacetate (20.0 mL, 126 mmol) were added successively to tetrahydrofuran (500 mL) at −78° C. After 1 h at −78° C., allyl bromide (16.4 mL, 1.5 eq) was added. After 1.5 h at −78° C., the cold bath was removed and the mixture stirred at ambient temperature for 1 h. Following addition of saturated ammonium chloride (200 mL), water (800 mL), and hexane (1000 mL), the two phases were separated and the aqueous phase extracted with hexane (2×500 mL). The combined organic extracts were washed successively with water (2×100 mL), brine (100 mL), dried ($MgSO_4$) and concentrated to provide the product (28.00 g) as a yellow liquid. This material was used in the subsequent reaction without purification.

(2b) Following a procedure analogous to (1a), the crude material from (2a) (8.20 g) was reacted with potassium bis(trimethylsilyl)amide and iodomethane to yield the desired product (8.50 g, 97%) as a yellow oil. MS found: $(M+H)^+=235$, $(M+NH_4)^+=252$.

(2c) Ozone was bubbled through a solution of the olefin from (2b) (8.40 g, 35.85 mmol) in dichloromethane (500 mL) at −78° C. until the solution turned blue. The mixture was purged with nitrogen, treated with dimethyl sulfide (13.1 mL, 5 eq) and stirred at rt overnight. Concentration in vacuo provided crude aldehyde (10.65 g). The material was used in the subsequent reaction without purification.

(2d) Following a procedure analogous to (1d), the aldehyde from (2c) (6.36 g) was reacted with D-alanine methyl ester hydrochloride. Silica gel chromatography (ethyl acetate-hexane, 35:65 then 40:60) gave less polar lactam (630 mg), more polar lactam (1.12 g), and a 5:3 mixture of the two isomers (1.17 g). The total yield of the two isomers is 2.92 g (47% for two steps). MS found: $(M+H)^+=292$.

(2e) Following a procedure analogous to (1e), the less polar isomer from (2d) (226.8 mg, 0.778 mmol) was reacted with hydroxylamine. Preparative thin layer chromatography (methanol-dichloromethane, 10:90) gave the hydroxamic acid (183.3 mg, 81%) as a light yellow powder. MS found: $(M-H)^-=291$.

(2f) Following a procedure analogous to (1e), the more polar isomer from (2d) (197.0 mg, 0.676 mmol) was reacted with hydroxylamine. Preparative thin layer chromatography (methanol-dichloromethane, 10:90) gave the hydroxamic acid (158.4 mg, 80%) as a light yellow powder. MS found: $(M-H)^-=291$.

Example 3

[1(R)]-N-hydroxy-α,3-dimethyl-3-[4-(1-methylethoxy)phenyl]-2-oxo-1-pryrrolidineacetamide (3a) A 1:1 mixture of the benzyl ether from (1d) (16.26 g, 44.25 mmol), 20% palladium hydroxide on carbon (3.0 g) and methanol (500 mL) was stirred under balloon pressure hydrogen for 2 h. The catalyst was removed by filtration. The filtrate was concentrated to give the phenol (11.87 g, 97%) as a 1:1 mixture of two isomers. MS found: $(M+H)^+=278$.

(3b) A mixture of the phenol from (3a) (460 mg, 1.66 mmol) and N,N'-dimethyl-O-isopropylisourea (5 mL) was heated to 70° C. for 4 h and then cooled to rt. Following addition of acetic acid (2 mL) and dichloromethane (2 mL), the mixture was stirred for 30 min. The mixture was then filtered through a silica gel pad and the filter cake washed with ethyl acetate-hexane (40:60). The filtrate was concentrated and purified by silica gel chromatography (ethyl acetate-hexane, 40:60) to give the isopropyl ether (123.2 mg, 23%) as a 1:1 mixture of two isomers. MS found: $(M+H)^+=320$.

(3c) Following a procedure analogous to (1e), the isopropyl ether from (3b) (99.1 mg, 0.310 mmol) was reacted with hydroxylamine to give the hydroxamic acid (29.1 mg, 29%) as a 1:1 mixture of two isomers. MS found: $(M-H)^- = 319$.

Example 4

[1(R)]-3-[4-(1,1-dimethylethoxy)phenyl]-N-hydroxy-α,3-dimethyl-2oxo-1-pyrrolidineacetamide (4a) Following a procedure analogous to (3b), the phenol from (3a) (270 mg, 0.97 mmol) was reacted with N,N'-dimethyl-O-t-butylisourea. Silica gel chromatography (ethyl acetate-hexane, 20:80) gave the t-butyl ether (50.2 mg, 15%) as a 1:1 mixture of two isomers. MS found: $(M+H)^+ = 334$.

(4b) Following a procedure analogous to (1e), the t-butyl ether from (4a) (45 mg, 0.135 mmol) was reacted with hydroxylamine to give the hydroxamic acid (26.1 mg, 58%) as a 1:1 mixture of two isomers. MS found: $(M-H)^- = 333$.

Example 5

[1(R)]-3-(4-(cyclohexyloxy)phenyl]-N-hydroxy-α,3-dimethyl-2-oxo-1-pyrrolidineacetamide (5a) Following a procedure analogous to (3b), the phenol from (3a) (350 mg, 1.26 mmol) was reacted with N,N'-dimethyl-O-cyclohexylisourea. Silica gel chromatography (ethyl acetate-hexane, 40:60) gave the cyclohexyl ether (70 mg, 15%) as a 1:1 mixture of two isomers. MS found: $(M+H)^+ = 360$.

(5b) Following a procedure analogous to (1e), the cyclohexyl ether from (5a) (61.5 mg, 0.171 mmol) was reacted with hydroxylamine to give the hydroxamic acid (39.5 mg, 64%) as a 1:1 mixture of two isomers. MS found: $(M-H)^- = 359$.

Example 6

[1(R)]-N-hydroxy-α,3-dimethyl-2-oxo-3-[4-[4-(1,1-dimethylethyl)phenylmethoxy]phenyl]-1-pyrrolidineacetamide (6a) Following a procedure analogous to (3a), the more polar isomer from (1d) (2.35 g, 6.40 mmol) was hydrogenolyzed to give the phenol (1.77 g, 100%) as a colorless viscous oil. MS found: $(M+H)^+ = 278$.

(6b) Cesium carbonate (225 mg, 1.8 eq) was added to a solution of the phenol from (6a) (106.3 mg, 0.383 mmol), and p-t-butylbenzyl bromide (174 mg, 2 eq) in methyl sulfoxide (2 mL). After 1.5 h at rt, saturated ammonium chloride (3 mL) and ethyl acetate (100 mL) were added. The mixture was washed with water (2×5 mL), brine (5 mL), dried (MgSO4) and concentrated. Silica gel chromatography (ethyl acetate-hexane, 30:70 then 35:75) gave the ether (149.5 mg, 92%) as a colorless oil. MS found; $(M+H)^+ = 424$.

(6c) Following a procedure analogous to (1f), the ester from (6b) (142.0 mg, 0.335 mmol) was reacted with hydroxylamine. Upon neutralization and removal of methanol in vacuo, product precipitated out of solution. The precipitate was collected by filtration and washed with water several times to give the hydroxamic acid (113.3 mg, 80%) as a white powder. MS found: $(M-H)^- = 423$.

Example 7

[1(R)]-N-hydroxy-α,3-dimethyl-2-oxo-3-[4-(trans-3-phenyl-2-propenyloxy)phenyl]-1-pyrrolidineacetamide (7a) Following a procedure analogous to (6b), the phenol from (3a) (510 mg, 1.84 mmol) was reacted with cinnamyl bromide and potassium carbonate in N,N-dimethylformamide. Silica gel chromatography (ethyl acetate-hexane, 30:70 then 40:60) gave less polar isomer (87 mg), more polar isomer (102 mg), and a 1:1 mixture of the two isomers (300 mg). The total yield is 489 mg (68%). MS found: $(M+H)^+ = 394$.

(7b) Following a procedure analogous to (1e), the less polar isomer from (7a) (82 mg, 0.208 mmol) was reacted with hydroxylamine. Silica gel chromatography (methanol-dichloromethane, 5:95) gave the hydroxamic acid (37 mg, 45%) as a solid. MS found: $(M-H)^- = 393$.

(7c) Following a procedure analogous to (1e), the more polar isomer from (7a) (97 mg, 0.247 mmol) was reacted with hydroxylamine. Silica gel chromatography (methanol-dichloromethane, 5:95) gave the hydroxamic acid (52 mg, 54%) as a solid. MS found: $(M-H)^- = 393$.

Example 8

[1(R)]-3-[4-[(3-methylphenyl)methoxy]phenyl]-N-hydroxy-α,3-dimethyl-2-oxo-1-pyrrolidineacetamide (8a) Following a procedure analogous to (6b), the phenol from (3a) (277.6 mg, 1.00 mmol) was reacted with α-bromo-m-xylene and cesium carbonate in N,N-dimethylformamide. Silica gel chromatography (ethyl acetate-hexane, 30:70 then 40:60) gave the less polar isomer (53 mg), the more polar isomer (50.8 mg), and a 1:1 mixture the two isomers (40.0 mg). The total yield is 143.8 mg (38%). MS found: $(M+H)^+ = 382$.

(8b) Following a procedure analogous to (1e), the less polar isomer from (8a) (53 mg, 0.139 mmol) was reacted with hydroxylamine. Silica gel chromatography (methanol-dichloromethane, 5:95) gave the hydroxamic acid (31.7 mg, 60%) as a solid. MS found: $(M-H)^- = 381$.

(8c) Following a procedure analogous to (1e), the more polar isomer from (8a) (50.8 mg, 0.133 mmol) was reacted with hydroxylamine. Silica gel chromatography (methanol-dichloromethane, 5:95) gave the hydroxamic acid (33.7 mg, 66%) as a solid. MS found: $(M-H)^- = 381$.

Example 9

[1(R)]-3-[4-[(3,5-dimethylphenyl)methoxy]phenyl]-N-hydroxy-α,3-dimethyl-2-oxo-1-pyrrolidineacetamide (9a) Following a procedure analogous to (6b), the phenol from (3a) (450 mg, 1.62 mmol) was reacted with α-bromomesitylene and cesium carbonate in N,N-dimethylformamide. Silica gel chromatography (ethyl acetate-hexane, 30:70 then 40:60) gave the less polar isomer (130.8 mg), the more polar isomer (125.0 mg), and a 1:1 mixture of the two isomers (73.7 mg). The total yield is 329.5 mg (51%). MS found: $(M+H)^+ = 396$.

(9b) Following a procedure analogous to (1e), the less polar isomer from (9a) (50 mg, 0.126 mmol) was reacted with hydroxylamine. Silica gel chromatography (methanol-dichloromethane, 5:95) gave the hydroxamic acid (37.6 mg, 75%) as a solid. MS found: $(M-H)^- = 395$.

(9c) Following a procedure analogous to (1e), the more polar isomer from (9a) (46.0 mg, 0.116 mmol) was reacted with hydroxylamine. Silica gel chromatography (methanol-dichloromethane, 5:95) gave the hydroxamic acid (25.0 mg, 54%) as a solid. MS found: $(M-H)^- = 395$.

Example 10

[1(R)]-N-hydroxy-α,3-dimethyl-2-oxo-3-[4-(2-propenyloxy)phenyl]-1-pyrrolidineacetamide (10a) Following a procedure analogous to (6b), the phenol from (3a) (480 mg, 1.73 mmol) was reacted with allyl bromide and potassium carbonate in N,N-dimethylformamide. Silica gel chromatography (ethyl acetate-hexane, 30:70 then 40:60) gave the less polar isomer (111 mg), the more polar isomer (57 mg), and a 5:6 mixture of the two isomers (45.6 mg). The total yield is 213.6 mg (39%). MS found: $(M+H)^+=318$.

(10b) Following a procedure analogous to (1e), the less polar isomer from (10a) (110 mg, 0.347 mmol) was reacted with hydroxylamine. Silica gel chromatography (methanol-dichloromethane, 5:95) gave the hydroxamic acid (68 mg, 62%) as a solid. MS found: $(M-H)^-=317$.

(10c) Following a procedure analogous to (1e), the more polar isomer from (10a) (57 mg, 0.18 mmol) was reacted with hydroxylamine. Silica gel chromatography (methanol-dichloromethane, 5:95) gave the hydroxamic acid (51 mg, 89%) as a solid. MS found: $(M-H)^-=317$.

Example 11

[1(R)]-3-[4-[(3-cyanophenyl)methoxy]phenyl]-N-hydroxy-α,3-dimethyl-2-oxo-1-pyrrolidineacetamide (11a) Following a procedure analogous to (6b), the phenol from (6a) (99.7 mg, 0.360 mmol) was reacted with α-bromo-m-tolunitrile. Silica gel chromatography (ethyl acetate-hexane, 40:60 then 50:50) gave the ether (130.2 mg, 92%) as a colorless glass. MS found: $(M+H)^+=393$.

(11b) Following a procedure analogous to (1e), the ester from (11a) (56.9 mg, 0.145 mmol) was reacted with hydroxylamine. Silica gel chromatography (methanol-dichloromethano, 8:92 then 15:85) gave the hydroxamic acid (24 mg, 42%) as a viscous oil. MS found: $(M-H)^-=392$.

Example 12

[1(R)]-N-hydroxy-α-3-dimethyl-3-[4-[(2-nitrophenyl)methoxy]phenyl]-2-oxo-1-pyrrolidineacetamide (12a) Following a procedure analogous to (5b), the phenol from (5a) (93.0 mg, 0.335 mmol) was reacted with o-nitrobenzyl bromide. Silica gel chromatography (ethyl acetate-hexane, 40:60) gave product (130 mg, 94%) as a colorless glass. MS found: $(M+H)^+=413$.

(12b) Following a procedure analogous to (1e), the ester from (12a) (110 mg, 0.267 mmol) was reacted with hydroxylamine to give the hydroxamic acid (106.6 mg, 97%) as a solid. MS found: $(M-H)^-=412$.

Example 13

[1(R)]-N-hydroxy-α-3-dimethyl-3-[4-[(3-nitronphenyl)methoxy]phenyl]-2-oxo-1-pyrrolidineacetamide (13a) Following a procedure analogous to (6b), the phenol from (6a) (95.2 mg, 0.343 mmol) was reacted with m-nitrobenzyl bromide. Silica gel chromatography (ethyl acetate-hexane, 40:60) gave the desired product (57.6 mg, 41%). MS found: $(M+H)^+=413$.

(13b) Following a procedure analogous to (1e), the ester from (13a) (50 mg, 0.121 mmol) was reacted with hydroxylamine to give the hydroxamic acid (44.3 mg, 89%) as a solid. MS found: $(M-H)^-=412$.

Example 14

[1(R)]-N-hydroxy-α,3-dimethyl-3-[4-[(4-nitrophenyl)methoxy]phenyl]-2-oxo-1-pyrrolidineacetamide (14a) Following a procedure analogous to (6b), the phenol from (6a) (93.0 mg, 0.326 mmol) was reacted with p-nitrobenzyl bromide. Silica gel chromatography (ethyl acetate-hexane, 40:60 then 50:50) gave the desired product (126.7 mg, 94%) as a yellow glass. MS found: $(M+H)^+=413$.

(14b) Following a procedure analogous to (1e), the ester from (14a) (120 mg, 0.291 mmol) was reacted with hydroxylamine to give the hydroxamic acid (108.0 mg, 90%) as a solid. MS found: $(M-H)^-=412$.

Example 15

[1(R)]-N-hydroxy-α,3-dimethyl-3-[4-[(1-naphthalenyl)methoxy]phenyl]-2-oxo-1-pyrrolidineacetamide (15a) Following a procedure analogous to (6b), the phenol from (6a) (115.6 mg, 0.417 mmol) was reacted with 2-bromomethylnaphthalene and cesium carbonate. Silica gel chromatography (ethyl acetate-hexane, 35:65 then 45:55) gave the desired product (168.5 mg, 97%) as a white solid. MS found: $(M+H)^+=418$.

(15b) Following a procedure analogous to (1e), the ester from (15a) (162.4 mg, 0.399 mmol) was reacted with hydroxylamine to give the hydroxamic acid (140.1 mg, 86%) as a white powder. MS found: $(M-H)^-=417$.

Example 16

[1(R)]-N-hydroxy-3-(4-hydroxyphenyl)-α,3-dimethyl-2-oxo-1-pyrrolidineacetamide (16a) A mixture of the hydroxamic acid from (1e) (163.3 mg, 0.44 mmol), 20% palladium hydroxide on carbon (40.8 mg) and methanol (6 mL) was stirred under balloon pressure hydrogen for 1 h. Filtration and concentration of the filtrate gave the hydroxamic acid (117 mg, 95%) as a white solid. MS found: $(M-H)^-=277$.

(16b) Following a procedure analogous to (16a), the product from (1f) (45.2 mg, 123 mmol) was hydrogenolyzed to furnish the hydroxamic acid (34.1 mg, 100%) asa white solid. MS found: $(M-H)^-=277$.

Example 17

[1(R)]-N-hydroxy-α,3-dimethyl-2-oxo-3-[4-[(2-pyridinyl)methoxy]phenyl]-1-pyrrolidineacetamide (17a) Cesium carbonate (306 mg, 2.8 eq) was added to the phenol from (6a) (92.8 mg, 0.335 mmol), and 2-picolyl chloride hydrochloride-(110 mg, 2 eq) in methyl suilfoxide (2mL). After 20 h at rt, same portions of cesium carbonate and 2-picolyl chloride were added. After 1 h at 50° C., saturated ammonium chloride (6 mL) and ethyl acetate (100 mL) were added. The mixture was washed with water (6 mL), brine (6 mL), dried (MgSO4) and concentrated. Silica gel chromatography (ethyl acetate-hexane, 80:20 then 100:0) gave the desired product (112.7 mg, 91%) as a colorless oil. MS found: $(M+H)^+=369$.

(17b) Following a procedure analogous to (1e), the ester from (17a) (106.6 mg, 0.289 mmol) was reacted with hydroxylamine to give the hydroxamic acid (86.4 mg, 81%) as a white solid. MS found: $(M-H)^-=368$.

Example 18

[1(R)]-N-hydroxy-α,3-dimethyl-2-oxo-3-[4-[(3-pyridinyl)methoxy]phenyl]-1-pyrrolidineacetamide (18a) Cesium carbonate (311 mg, 2.8 eq) was added to the phenol from (6a) (94.7 mg, 0.341 mmol), and 3-picolyl chloride hydrochloride (112 mg, 2 eq) in methyl sulfoxide (2 mL). After 20 h at rt, same portions of cesium carbonate and 3-picolyl chloride hydrochloride were added. After 2 h at 75° C., saturated ammonium chloride (6 mL) and ethyl acetate (100 mL) were added. The mixture was washed with water (6 mL), brine (6 mL), dried (MgSO$_4$) and concentrated. Silica gel chromatography (ethyl acetate-hexane, 80:20 then 100:0) gave the desired product (99.8 mg, 79%) as a colorless oil. Proton NMR indicated a 3:2 mixture of isomers due to partial epimerization at alanine chiral center. MS found: (M+H)$^+$=369.

(18b) Following a procedure analogous to (1e), the ester from (18a) (94.5 mg, 0.256 mmol) was reacted with hydroxylamine to give the hydroxamic acid (90.1 mg, 95%) as a white solid. MS found: (M–H)$^-$=368.

Example 19

[1(R)]-N-hydroxy-α,3-dimethyl-2-oxo-3-[4-[(4-pyridinyl)methoxyl]phenyl]-1-pyrrolidineacetamide (19a) Cesium carbonate (331 mg, 2.8 eg) was added to the phenol from (7a) (100.7 mg, 0.363 mmol), and 4-picolyl chloride hydrochloride (119 mg, 2 eq) in methyl sulfoxide (2 mL). After 20 h at rt, same portions of cesium carbonate and 4-picolyl chloride hydrochloride were added. After 30 min at 75° C., saturated ammonium chloride (6 mL) and ethyl acetate (100 mL) were added. The mixture was washed with water (6 mL), brine (6 mL), dried (MgSO4) and concentrated. Silica gel chromatography (ethyl acetate) gave the desired product (106.7 mg, 80%) as a colorless oil. Proton NMR indicated a 4.5:1 mixture of isomers due to partial epimerization at alanine chiral center. MS found: (M+H)$^+$=369.

(19b) Following a procedure analogous to (1e), the ester from (19a) (99.8 mg, 0.271 mmol) was reacted with hydroxylamine to give the hydroxamic acid (81.2 mg, 81%) as a white solid. MS found: (M–H)$^-$=368.

Example 20

[1(R)]-N-hydroxy-α,3-dimethyl-3-[4-(2-methylproyl)phenyl]-2-oxo-1-pyrrolidineacetamide (20a) Iodomethane (3.82 mL, 2.5 eq.) was added to a mixture of ibuprofen (4.97 g, 24.1 mmol), 1,8-diazabicyclo[4.3.0]non-5-ene (4.32 mL, 1.2 eq.) and benzene (100 mL) and the mixture was heated to reflux for 1 h. Following addition of hexane (100 mL), the mixture was filtered through a silica gel pad nd the filter cake washed with ether-hexane (1:1, v/v) until free of product. The filtrate was concentrated in vacuo to give the methyl ester as a colorless liquid (5.12 g, 96%).

(20b) Following a procedure analogous to (1a), ibuprofen methyl ester from (20a) (4.655 g) was reacted with sodium bis(trimethylsilyl)amide and allyl bromide to yield crude product (6.39 g) as a yellow liquid. This material was used in the subsequent reaction without purification.

(20c) Following a procedure analogous to (1c), the crude material from (20b) (6.19 g) was ozonolyzed to give crude aldehyde (6.53 g) as a yellow oil. This material was used in the subsequent reaction without purification.

(20d) Following a procedure analogous to (1d), crude aldehyde from (20c) (2.05 g) was-reacted with D-alanine methyl ester hydrochloride. Silica gel chromatography (ethyl acetate-hexane, 20:80 then 30:70) gave less polar isomer (371.8 mg), more polar isomer (289.6 mg), and a 1:3 mixture of the two isomers (337.8 mg). The total yield is 999.2 mg (49% for three steps). MS found: (M+H)$^+$=318.

(20e) Following a procedure analogous to (1e), the less polar isomer from (20d) (210 mg, 0.660 mmol) was reacted with hydroxylamine to give the hydroxamic acid (186.7 mg, 89%). MS found: (M–H)$^-$=317.

(20f) Following a procedure analogous to (1e), the more polar isomer from (20d) (200 mg, 0.630 mmol) was reacted with hydroxylamine to give the hydroxamic acid (167.2 mg, 83%) as a white solid. MS found: (M–H)$^-$=317.

Example 21

[1(R)]-N-hydroxy-α,3-dimethyl-2-oxo-3-phenyl-1-pyrrolidineacetamide (21a) Following a procedure analogous to (20a), 2-phenylpropionic acid (10.0 g, 66.5 mmol) was reacted with iodomethane and 1,8-diazabicyclo[4.3.0]non-5-ene to give the ester (9.57 g, 88%) as a colorless liquid.

(21b) Following a procedure analogous to (1a), the methyl ester from (21a) (9.28 g, 56.5 mmol) was reacted with sodium bis(trimethylsilyl)amide and allyl bromide to yield crude product (11.96 g) as a yellow liquid. This material was used in the subsequent reaction without purification.

(21c) Following a procedure analogous to (1c), the crude material from (21b) (6.76 g) was ozonolyzed to give crude aldehyde (8.53 g) as a yellow oil. This material was used in the subsequent reaction without purification.

(21d) Following a procedure analogous to (1d), the crude aldehyde from (21c) (1.93 g) was reacted with D-alanine methyl ester hydrochloride. Silica gel chromatography (ethyl acetate-hexane, 30:70 then 40:60) gave less polar isomer (230 mg), more polar isomer (270 mg), and a 3:2 mixture of the two isomers (380 mg). The total yield is 880 mg (47% for three steps). MS found: (M+H)$^+$=262.

(21e) Following a procedure analogous to (1e), the less polar isomer from (21d) (141.1 mg, 0.540 mmol) was reacted with hydroxylamine to give the hydroxamic acid (141.5 mg, 100%) as a solid. MS found: (M–H)$^-$=261.

(21f) Following a procedure analogous to (1e), the more polar isomer from (21d) (165.2 mg, 0.632 mmol) was reacted with hydroxylamine to give the hydroxamic acid (149.6 mg, 90%) as a solid. MS found: (M–H)$^-$=261.

Example 22

N-hydroxy-2-oxo-3-phenyl-1-pyrroldiecetamide (22a) Following a procedure analogous to (1a), methyl phenylacetate (10.0 mL, 69.2 mmol) was reacted with sodium bis(trimethylsilyl)amide and allyl bromide to yield the desired (13.10 g, 100%) as a colorless liquid.

(22b) Following a procedure analogous to (1c), the material from (22a) (7.06 g, 36.8 mmol) was ozonolyzed to give crude aldehyde (9.00 g) as a yellow oil. This material was used in the subsequent reaction without purification.

(22c) Following a procedure analogous to (1d), the crude aldehyde from (22b) (2.00 g) was reacted with glycine methyl ester hydrochloride. Silica gel chromatography (ethyl acetate-hexane, 50:50) gave the desired lactam (1.05 g, 55% for two steps).

(22d) Following a procedure analogous to (1e), the lactam from (22c) (433.8 mg, 1.86 mmol) was reacted with hydroxylamine to give the hydroxamic acid (261 mg, 60%) as a yellow powder. MS found: (M–H)$^-$=233.

Example 23

(+/−)-N-hydroxy-3-methyl-2-oxo-3-phenyl-1-pyrrolidineacetamide (23a) Following a procedure analogous to (1d), the crude. aldehyde from (21c) (2.19 g) was reacted with glycine methyl ester hydrochloride. Silica gel chromatography (ethyl acetate-hexane, 35:65) gave the desired lactam (650 mg, 32%

(23b) Following a procedure analogous to (1e), the lactam from (23a) (433.8 mg, 1.86 mmol) was reacted with hydroxylamine to give the hydroxamic acid (261 mg, 90%) as a white powder. MS found: (M−H)⁻=247.

Example 24

[1(R)]-N-hydroxy-α-methyl-2-oxo-3-phenyl-1-pyrrolidineacetamide (24a) Following a procedure analogous to (1d), the crude aldehyde from (22b) (2.00 g) was reacted with D-alanine methyl ester hydrochloride. Silica gel chromatography (ethyl acetate-hexane, 30:70 then 40:60 then 50:50) gave less polar isomer (309.3 mg), more polar isomer (347.2 mg), and a 1:1 mixture of the two isomers (163.4 mg). The total yield is 819.9 mg (41% for two steps). MS found: (M+H)⁺=248.

(24b) Following a procedure analogous to (1e), the less polar isomer from (24a) (243.7 mg, 0.985 mmol) was reacted with hydroxylamine to give the hydroxamic acid (210 mg, 86%) as a white solid. MS found: (M−H)⁻=247.

(24c) Following a procedure analogous to (1e), the more polar isomer from (24a) (202.8 mg, 0.820 mmol) was reacted with hydroxylamine to give the hydroxamic acid (180 mg, 88%) as a white solid. MS found: (M−H)⁻=247.

Example 25

[1(R)]-N-hydroxy-3-(4-methoxyphenyl)-α-methyl-2-oxo-1-pyrrolidineacetamide (25a) Following a procedure analogous to (1c), the crude material from (2a) (8.22 g) was ozonolyzed to give crude aldehyde (8.22 g) as a yellow oil. This material was used in the subsequent reaction without purification.

(25b) Following a procedure analogous to (1d), the crude aldehyde from (25a) (2.21 g) was reacted with D-alanine methyl ester hydrochloride. Silica gel chromatography (ethyl acetate-hexane, 45:55 then 50:50) gave less polar isomer (215.8 mg), more polar isomer (181.1 mg), and a 1:1 mixture of the two isomers (623 g). The total yield is 1.020 g (49% for three steps). MS found: (M+H)⁺=278.

(25c) Following a procedure analogous to (1e), the less polar isomer from (25b) (154.6 mg, 0.557 mmol) was reacted with hydroxylamine to give the hydroxamic acid (120.4 mg, 78%) as a viscous oil. MS found: (M−H)⁻=277.

(25d) Following a procedure analogous to (1e), the more polar isomer from (25b) (130.3 mg, 0.470 mmol) was reacted with hydroxylamine to give the hydroxamic acid (117.9 mg, 90%) as a solid. MS found: (M−H)⁻=277.

Example 26

[1(R)]-3-cyclohexyl-N-hydroxy-α,3-dimethyl-2-oxo-1-pyrrolidineacetamide (26a) A mixture of the more polar isomer from (24a) (36.5 mg, 0.14 mmol), rhodium on alumina (17 mg), 4 N dioxane solution of hydrogen chloride (2 drops) and methanol (2 mL) was hydrogenated under 45 psi overnight. The mixture was filtered through a celite pad and the filter cake washed with ethyl acetate-hexane (40:60). The filtrate was concentrated to give the desired product (37.4 mg, 100%) as a colorless liquid. MS found: (M+H)⁺=268.

(26b) Following a procedure analogous to (1e), the ester from (26a) (52.4 mg, 0.196 mmol) was reacted with hydroxylamine to give the hydroxamic acid (25.2 mg, 48%) as a solid. MS found: (M−H)⁻=267.

Example 27

[1(R)]-N-hydroxy-α,3-dimethyl-2-oxo-3-(2-phenylethyl)-1-pyrrolidineacetamide (27a) A 2.5 M hexane solution of n-butyllithium (5.12 mL, 1.1 eq) was added dropwise to diisopropylamine (1.80 mL, 1.1 eq) in tetrahydrofuran (50 mL) at 0° C. The resultant mixture was stirred for 20 min at 0° C. and cooled to −78° C. A solution of ethyl 2-methyl-4-pentenoate (1.90 mL, 11.7 mmol) in tetrahydrofuran (25 mL) was added. The mixture was stirred at −78° C. for 30 min and warmed to 0° C. 2-Phenylethyl bromide (1.71 mL, 1.05 eq) in tetrahydrofuran (25 mL) was added dropwise. After additional 2 h at 0° C., saturated ammonium chloride (50 mL) was added and the mixture extracted with ethyl acetate (3×). The combined extracts were washed with brine, dried (MgSO4) and concentrated. Silica gel chromatography (ethyl acetate-hexane, 0:100 then 5:95) gave the desired product (1.95 g, 68%) as a liquid. MS found: (M+H)⁺=247.

(27b) Following a procedure analogous to (1c), the olefin from (27a) (1.86 g, 7.55 mmol) was ozonolyzed. Silica gel chromatography (ethyl acetate-hexane, 10:90) gave the desired aldehyde (1.67 g, 89%) as a colorless oil. MS found: (M+H)⁺=249.

(27c) Following a procedure analogous to (1d), the aldehyde from (27b) (1.66 g, 6.68 mmol) was reacted with D-alanine methyl ester hydrochloride. Silica gel chromatography (ethyl acetate-hexane, 35:65 then 40:60) gave the lactam (1.32 g, 68%) as a 1:1 mixture of two diastereomers. MS found: (M+H)⁺=290.

(27d) Following a procedure analogous to (1e), the ester from (27c) (52.4 mg, 0.196 mmol) was reacted with hydroxylamine to give the hydroxamic acid (226.6 mg, 96%) as a 1:1 mixture of two isomers. MS found: (M−H)⁻=289.

Example 28

[1(R)]-3-(2-cyclohexylethyl)-N-hydroxy-α,3-dimethyl-2-oxo-1-pyrrolidineacetamide (28a) Following a procedure analogous to (26a), the ester from (27c) (180 mg, 0.622 mmol) was hydrogenated to give the desired product (184 mg, 100%) as a colorless oil. MS found: (M+H)⁺=296.

(28b) Following a procedure analogous to (1e), the ester from (28a) (160 mg, 0.542 mmol) was reacted with hydroxylamine to give the hydroxamic acid (158 mg, 98%) as a 1:1 mixture of two isomers. MS found: (M−H)⁻=295.

Example 29

[1(R)]-N-hydroxy-α-methyl-2-oxo-3-phenyl-3-(phenylmethyl)-2-oxo-1-pyrrolidineacetamide (29a) Following a procedure analogous to (20a), 2,3-diphenylacetic acid (10.26 g, 45.34 mmol) was reacted with iodomethane and 1,8-diazabicyclo[4.3.0]non-5-ene to give the ester (10.86 g, 100%) as a colorless liquid. MS found: (M+H)$^+$=241.

(29b) Following a procedure analogous to (1a), the ester from (29a) (10.56 g, 43.9 mmol) was reacted with sodium bis(trimethylsilyl)amide and allyl bromide to yield crude product (13.13 g) as a pale yellow oil. This material was used in the subsequent reaction without purification.

(29c) Following a procedure analogous to (1c), the crude material from (29b) (6.07 g) was ozonolyzed to give the crude aldehyde (7.10 g) as a yellow oil. This material was used in the subsequent reaction without purification.

(29d) Following a procedure analogous to (1d), the crude aldehyde from (29c) (2.08 g) was reacted with D-alanine methyl ester. Silica gel chromatography (ethyl acetate-hexane, 20:80 then 30:70) gave a 1:1 mixture of lactams (1.07 g, 53% for three steps) as a colorless viscous oil. MS found: (M+H)$^+$=338.

(29e) Following a procedure analogous to (1e), the ester from (29d) (980 mg, 2.90 mmol) was reacted with hydroxylamine to give the hydroxamic acid as a as a 1:1 mixture of two isomers. MS found: (M−H)$^-$=337.

Example 30

[1(R)]-3,4,4',5'-tetrahydro-N-hydroxy-α-methyl-2-oxopiro[naphthalene-2(1H),3'-[3H]pyrrole]-1'(2'H)-acetamide (30a) Following a procedure analogous to (20a), 1,2,3,4-tetrahydro-2-naphthoic acid (4.50 g, 25.5 mmol) was reacted with iodomethane and 1,8-diazabicyclo[4.3.0]non-5-ene to give the ester (4.62 g, 95%) as a pale yellow liquid. MS found: (M+H)$^+$=191.

(30b) Following a procedure analogous to (1a), the ester from (30a) (4.52 g) was reacted with sodium bis(trimethylsilyl)amide and allyl bromide to yield crude product (5.20 g) as a yellow oil. This material was used in the subsequent reaction without purification.

(30c) Following a procedure analogous to (1c), the crude olefin from (30b) (5.00 g) was ozonolyzed to give crude aldehyde (5.83 g) as a yellow oil. This material was used in the subsequent reaction without purification.

(30d) Following a procedure analogous to (1d), the crude aldehyde from (30c) (2.03 g) was reacted with D-alanine methyl ester hydrochloride. Silica gel chromatography (ethyl acetate-hexane, 30:70 then 40:60) gave a 1:1 mixture of lactams (732.1 mg, 34% for three steps). MS found: (M+H)$^+$=288.

(30e) Following a procedure analogous to (1e), the ester from (30d) (510.7 mg, 1.788 mmol) was reacted with hydroxylamine to give the hydroxamic acid (431 mg, 84%) as a 1:1 mixture of two isomers. MS found: (M−H)$^-$=287.

Example 31

[1(R)]-3-[4-[3,5-dibromophenyl)methoxy]phenyl]-N-hydroxy-α,3-dimethyl-2-oxo-1-pyrrolidineacetamide Beginning with the phenol from (6a) and 3,5-dibromobenzyl bromide, example 31 was prepared in an analogous series of reactions to (6b) and (6c). MS found: (M−H)$^-$=523.

Example 32

[1(R)]-3-[4-[[3,5-bis(trifluoromethyl)phenyl]methoxy]phenyl]-N-hydroxy-α,3-dimethyl-2-oxo-1-pyrrolidineacetamide Beginning with the phenol from (6a) and 3,5-bis(trifluoromethyl)benzyl bromide, example 32 was prepared in an analogous series of reactions to (6b) and (6c). MS found: (M−H)$^-$=503.

Example 33

[1(R)]-3-[4-[(3,5-dichlorophenyl)methoxy]phenyl]-N-hydroxy-α,3-dimethyl-2-oxo-1-pyrrolidineacetamide Beginning with the phenol from (6a) and 3,5-dichlorobenzyl chloride, example 33 was prepared in an analogous series of reactions to (6b) and (6c). MS found: (M−H)$^-$=435.

Example 34

[1(R)]-N-hydroxy-α,3-dimethyl-3-[4-[(2-methyl-1-naphthalenyl)methoxy]phenyl]-2-oxo-1-pyrrolidineacetamide Beginning with the phenol from (6a) and 1-chloromethyl-2-methylnaphthalene, example 34 was prepared in an analogous series of reactions to (6b) and (6c). MS found: (M+Na)$^+$=455.

Example 35

[1(R)]-3-[4-[(3,5-dimethoxyphenyl)methoxy]phenyl]-N-hydroxy-α,3-dimethyl-2-oxo-1-pyrrolidineacetamide Beginning with the phenol from (6a) and 3,5-dimethoxybenzyl chloride, example 35 was prepared in an analogous series of reactions to (6b) and (6c). MS found: (M−H)$^-$=427.

Example 36

[1(R)]-3-[4-[[4-chloro-2-(trifluoromethyl)-6-quinolinyl]methoxy]phenyl]-N-hydroxy-α,3-dimethyl-2-oxo-1-pyrrolidineacetamide Beginning with the phenol from (6a) and 6-bromomethyl-4-chloro-2-trifluoromethylquinoline, example 36 was prepared in an analogous series of reactions to (6b) and (6c). MS found: (M−H)$^-$=520.

Example 37

[1(R)]-N-hydroxy-α,3-dimethyl-2-oxo-3-[4-[[4-(1,2,3-thiadiazol-4-yl)phenyl]methoxy]phenyl]-1pyrrolidineacetamide Beginning with the phenol from (6a) and 4-(4-bromomethylphenyl)-1,2,3-thiadiazole, example 37 was prepared in an analogous series of reactions to (6b) and (6c). MS found: (M−H)$^-$=451.

Example 38

[1(R)]-3-[4-([1,1-biphenyl]-2-ylmethoxy)phenyl]-N-hydroxy-α,3-dimethyl-2-oxo-1-pyrrolidineacetamide Beginning with the phenol from (6a) and 2-phenylbenzyl bromide, example 38 was prepared in an analogous series of reactions to (6b) and (6c). MS found: (M−H)$^-$=443.

Example 39

[1(R)]-3-[4-[(2,6-dichloro-4-pyridinyl)methoxy]phenyl]-N-hydroxy-α,3-dimethyl-2-oxo-1-pyrrolidineacetamide Beginning with the phenol from (6a) and 4-bromomethyl-2,6-dichloropyridine, example 39 was prepared in an analogous series of reactions to (6b) and (6c). MS found: (M−H)$^-$=436.

Example 40

[1(R)]-3-[4-(1H-benzotriazol-1-ylmethoxy)phenyl]-N-hydroxy-α,3-dimethyl-2-oxo-1-pyrrolidineacetamide Beginning with the phenol from (6a) and 1-chloromethylbenzotriazole, example 40 was prepared in an analogous series of reactions to (6b) and (6c). MS found: (M−H)⁻=408.

Example 41

[1(R)]-3-[4-[(4,6-dimethyl-2-pyrimidinyl)methoxy]phenyl]-N-hydroxy-α,3-dimethyl-2-oxo-1-pyrrolidineacetamide Beginning with the phenol from (6a) and 2-chloromethyl-4,6-dimethylpyrimidine (Sakamoto et al, Heterocycles 1997, 6, 525), example 41 was prepared in an analogous series of reactions to (6b) and (6c). MS found: (M−H)⁻=397.

Example 42

[1(R)]-3-[4-(1,3-benzodioxol-5-ylmethoxy)phenyl]-N-hydroxy-α,3-dimethyl-2-oxo-1-pyrrolidineacetamide Beginning with the phenol from (6a) and 3,4-methylenedioxybenzyl chloride, example 42 was prepared in an analogous series of reactions to (6b) and (6c). MS found: (M−H)⁻=411.

Example 43

[1(R)]-3-[4-[(2-chloro-6-ethoxy-4-pyridinyl)methoxy]phenyl]-N-hydroxy-α,3-dimethyl-2-oxo-1-pyrrolidineacetamide Beginning with the phenol from (6a) and 4-bromomethyl-2-chloro-6-ethoxypyridine, example 43 was prepared in an analogous series of reactions to (6b) and (6c). MS found: (M−H)⁻=446.

Example 44

[1(R)]-N-hydroxy-α,3-dimethyl-2-oxo-3-[4-(4-quinolinylmethoxy)phenyl]-1-pyrrolidineacetamide Beginning with the phenol from (6a) and 4-chloromethylquinoline, example 44 was prepared in an analogous series of reactions to (6b) and (6c). MS found: (M+H)⁺=420.

Example 45

[1(R)]-3-[4-[(4,5-dimethyl-2-thiazolyl)methoxy]phenyl]-N-hydroxy-α,3-dimethyl-2-oxo-1-pyrrolidineacetamide Beginning with the phenol from (6a) and 2-bromomethyl-4,5-dimethylthiazole, example 45 was prepared in an analogous series of reactions to (6b) and (6c). MS found: (M−H)⁻=402.

Example 46

[1(R)]-3-[4-[(2,6-dimethyl-4-pyridinyl)methoxy]phenyl]-N-hydroxy-α,3-dimethyl-2-oxo-1-pyrrolidineacetamide mono(trifluoroacetate)

Beginning with the phenol from (6a) and 4-chloromethyl-2,6-dimethylpyridine, example 46 was prepared in an analogous series of reactions to (6b) and (6c). MS found: (M+H)⁺=398.

Example 47

[1(R)]-N-hydroxy-α,3-dimethyl-3-[4-[(3-methyl-5-nitrophenyl)methoxy]phenyl]-2-oxo-1-pyrrolidineacetamide (47a) Following a procedure analogous to (6b), the phenol from (6a) (500 mg, 1.80 mmol) was reacted with 5-methyl-3-nitrobenzyl bromide to give the desired ether (690 mg, 90%). MS found: (M+Na)⁺=449.

(47b) Following a procedure analogous to step (1f), the ester from (47a) (67.4 mg, 0.158 mmol) was reacted with hydroxylamine to give the hydroxamic acid (48.7 mg, 72%). MS found: (M−H)⁻=426.

Example 48

[1(R)]-3-[4-[(3-amino-5-methylphenyl)methoxy]phenyl]-N-hydroxy-α,3-dimethyl-2-oxo-1-pyrrolidineacetamide (48a) Zinc powder (2.5 g) was added to the ester from (47a) (670 mg, 1.57 mmol) in acetic acid (10 mL) and the mixture was stirred at 50° C. for 2 h. The solid was removed by filtration and washed with ethyl acetate. The filtrate was concentrated, treated with brine (15 mL) and 1 N NaOH (15 mL), and extracted with ethyl acetate (3×). The combined extracts were dried (MgSO4) and concentrated. Silica gel chromatography (ethyl acetate-hexane, 45:55 then 55;45) gave the desired aniline (610 mg, 98%). MS found: (M+H)⁺=397.

(48b) Following a procedure analogous to step (1f), the ester from (48a) (80 mg, 0.202 mmol) was reacted with hydroxylamine to give the hydroxamic acid (63 mg, 79%). MS found: (M−H)⁻=396.

Example 49

[1(R)]-3-[4-[[3-(acetylamino)-5-methylphenyl]methoxy]phenyl]-N-hydroxy-α,3-dimethyl-2-oxo-1-pyrrolidineacetamide (49a) Hunig's base (74 mg, 5 eq) and acetyl chloride (23 mg, 2 eq) were added sequentially to the aniline from (48a) (58 mg, 0.146 mmol) in dichloromethane (2.5 mL) at 0° C. After 30 min at this temperature, saturated NaHCO3 (5 mL) and ethyl acetate (100 mL) were added. The organic phase was separated, washed with brine (5 mL), dried (MgSO4) and concentrated. Silica gel chromatography (ethyl acetate-hexane, 70:30) gave the acetamide (45 mg, 78%). MS found: (M+Na)⁺=461.

(49b) Following a procedure analogous to step (1f), the ester from (49a) (40 mg, 0.091 mmol) was reacted with hydroxylamine to give the hydroxamic acid (27 mg, 67%). MS found: (M−H)⁻=438.

Example 50

[1(R)]-1,1-dimethylethyl [2-[[3-[[4-[1-[2-(hydroxyamino)-1-methyl-2-oxoethyl]-3-methyl-2-oxo-3-pyrrolidinyl]phenoxy]methyl]-5-methylphenyl]amino]-2-oxoethyl]carbamate (50a) A mixture of the aniline from (48a) (100 mg, 0.252 mmol), N-(t-butoxycarbonyl)glycine (53 mg, 1.2 eq), BOP-Cl (70.6 mg, 1.1 eq), NMM (76.5 mg, 3 eq) and THF (10 mL) were heated to reflux for 30 min. Following addition of water (15 mL) and sat K2CO3, THF was removed in vacuo. The aqueous residue was extracted with ethyl acetate (3×40 mL). The combined organic extracts were dried (MgSO4) and concentrated. Silica gel chromatography (MeOH—CH2Cl2, 5:95) gave the desired amide (130 mg, 93%). MS found: $(M+Na)^+$=576.

(50b) Following a procedure analogous to step (1f), the ester from (50a) (120 mg, 0.217 mmol) was reacted with hydroxylamine to give the hydroxamic acid (100 mg, 83%). MS found: $(M-H)^-$=553.

Example 51

[1(R)]-3-[4-[[3-[(aminoacetyl)amino]-5-methylphenyl]methoxy]phenyl]-N-hydroxy-α,3-dimethyl-2-oxo-1-pyrrolidineacetamide mono (trifluoroacetate)

The hydroxamic acid from (50b) (60 mg, 0.108 mmol) was stirred with trifluoroacetic acid (1 mL) and $CH_2Cl_2$ (1 mL) for 2 h at rt and concentrated to give the TFA salt (58 mg, 94%). MS found: $(M+H)^+$=455.

Example 52

[1(R)]-1,1-dimethylethyl [2-[[2-[[3-[[4-[1-[2-(hydroxyamino)-1-methyl-2-oxoethyl]-3-methyl-2-oxo-3-pyrrolidinyl]phenoxy]methyl]-5-methylphenyl]amino]-2-oxoethyl]amino]-2-oxoethyl]carbamate Beginning with the aniline from (48a) and BOC-Gly-Gly-OH, example 52 was prepared in an analogous series of reactions to (50a) and (50b). MS found: $(M+Na)^+$=634.

Example 53

[1(R)]-3-[4-[[3-[[[(aminoacetyl)amino]acetyl] amino]-5-methylphenyl]methoxy]phenyl]-N-hydroxy-α,3-dimethyl-2-oxo-1-pyrrolidineacetamide mono(trifluoroacetate)

Beginning with the hydroxamic acid from example 52, example 53 was prepared following a procedure analogous to example 51. MS found: $(M+H)^+$=512.

Example 54

[1(R)]-N-[3-[[4-[1-[2-(hydroxyamino)-1-methyl-2-oxoethyl]-3-methyl-2-oxo-3-pyrrolidinyl]phenoxy] methyl]-5-methylphenyl]-4-morpholinecarboxamide Beginning with the aniline from (48a) and 4-morpholinecarbonyl chloride, example 54 was prepared in an analogous series of reactions to example 49. MS found: $(M-H)^-$=509.

Example 55

3-[4-[(2,6-dichloro-4-pyridinyl)methoxy]phenyl]-N-hydroxy-α,α,3-trimethyl-2-oxo-1-pyrrolidineacetamide (55a) Following a procedure analogous to step (1d), the aldehyde from (1c) (1.50 g, 4.81 mmol) was reacted with α-aminoisobutyric acid methyl ester hydrochloride to give the lactam (396 mg, 22%). MS found: $(M+H)^+$=382.

(55b) Following a procedure analogous to step (3a), the lactam from (55a) (379 mg, 992 mmol) was hydrogenolized to give the phenol (270 mg, 93%). MS found: $(M+H)^+$=290.

(55c) Following a procedure analogous to step (6b), the phenol from (55b) (128 mg, 0.440 mmol) was reacted with 4-bromomethyl-2,6-dichloropyridine to give the picolyl ether (153 mg, 77%). MS found: $(M+Na)^+$=473.

(55d) The ester from (55c) was stirred in THF (3 mL) and 1 N NaOH (10 mL) at rt overnight. The mixture was acidified to pH 4 with 1 N HCl and THF removed in vacuo. The aqueous residue was extracted with ethyl acetate. The combined extracts were washed with brine, dried (MgSO4) and concentrated to give the carboxylic acid (137 mg, 94%). MS found: $(M-H)^-$=435.

(55e) Hunig's base (148 mg, 4 eq), hydroxylamine hydrochloride (40 mg, 2 eq) and BOP (152 mg, 1.2 eq) were added to the acid from (55d) (125 mg, 0.286 mmol) in DMF (5 mL) at 0° C. the mixture was stirred at rt for 24 h and at 60° C. for 3 h. Sat ammonium chloride was added and the mixture extracted with ethyl acetate (2x). The extracts were washed with sat NaHCO3, water and brine, dried (MgSO4) and concentrated. Silica gel chromatography (methanol-chloroform, 8:92) provided the hydroxamic acid (50 mg, 39%). MS found: $(M+Na)^+$=479.

Example 56

[1(R)]-3-[1,1'-biphenyl]-4-yl-N-hydroxy-α,3-dimethyl-2-oxo-1-pyrrolidineacetamide (56a) Triflic anhydride (1.45 mL, 2.2 eq) was added dropwise to a solution of the phenol from (6a) (1.09 g, 3.93 mmol) and 2,6-lutidine (1.01 mL, 2.2 eq) in CH2Cl2 (50 mL) at 0° C. After 10 min at this temperature, hexane (200 mL) was added. The mixture was filtered through a silica gel pad and the filter cake washed with ethyl acetate-hexane (1:1) until free of product. The filtrate was concentrated to give the triflate (1.49 g, 93%). MS found: $(M-H)^-$=408.

(56b) A mixture of the triflate from (56a) (150 mg, 0.366 mmol), benzeneboronic acid (89.3 mg, 2 eq), triphenylphosphine (96 mg, 1 eq), potassium carbonate (202 mg, 4 eq) and anhydrous toluene (10 mL) was pumped then filled with nitrogen for 10 cycles to remove oxygen. Palladium(II) acetate (16.4 mg, 0.2 eq) was then quickly added and the flask was again deoxygenated for 10 cycles. This mixture was heated to reflux for 18 h. Following addition of ethyl acetate, the mixture was washed with water (2x), brine, dried (MgSO4) and concentrated. Silica gel chromatography (ethyl acetate-hexane, 25:75 then 50:50) give the biphenyl (118 mg, 96%). MS found: $(M+Na)^+$=360.

(56c) Following a procedure analogous to step (1f), the ester from (56b) (100 mg, 0.297 mmol) was reacted with hydroxylamine to give the hydroxamic acid (52 mg, 52%). MS found: $(M+H)^+$=339.

Example 57

[1(R)]-N-hydroxy-α,3-dimethyl-3-(2'-methyl[1,1'-biphenyl]-4-yl)-2-oxo-1-pyrrolidineacetamide Beginning with the triflate from (56a) and 2-methylbenzeneboronic acid, example 57 was prepared in an analogous series of reactions to (56b) and (56c). MS found: $(M+H)^+$=353.

Example 58

[1(R)]-N-hydroxy-α,3-dimethyl-3-(4'-methyl[1,1-biphenyl]-4-yl)-2-oxo-1-pyrrolidineacetamide Beginning with the triflate from (56a) and 4-methylbenzeneboronic acid, example 58 was prepared in an analogous series of reactions to (56b) and (56c). MS found: (M+H)⁺=353.

Example 59

[1(R)-3-(3',4'-dimethoxy[1,1'-biphenyl]-4-yl)-N-hydroxy-α,3-dimethyl-2-oxo-1-pyrrolidineacetamide Beginning with the triflate from (56a) and 3,4-dimethoxybenzeneboronic acid, example 59 was prepared in an analogous series of reactions to (56b) and (56c). MS found: (M–H)⁻=397.

Example 60

[1(R)]-N-hydroxy-α,3-dimethyl-2-oxo-3-[2'-(trifluoromethyl)[1,1'-biphenyl]-4-yl]-1-pyrrolidineacetamide Beginning with the triflate from (56a) and 2-trifluoromethylbenzeneboronic acid, example 60 was prepared in an analogous series of reactions to (56b) and (56c). MS found: (M–H)⁻=405.

Example 61

[1(R)]-N-hydroxy-α,3-dimethyl-3-[4-(4-methylphenoxy)phenyl]-2-oxo-1-pyrrolidineacetamide (61a) Copper(II) acetate monohydrate (108 mg, 1 eq), p-tolueneboronic acid (147 mg, 1 eq), and 4 A molecular sieve (400 mg) were added sequentially to the phenol from (6a) (150 mg, 0.541 mmol) and pyridine (0.219 mL, 5 eq) in dichloromethane. The resultant mixture was stirred at rt open to atmosphere for 20 h. The mixture was filtered through a silica gel pad and the filter cake washed with ethyl acetate until free of product. The filtrate was concentrated and purified by silica gel chromatography (ethyl acetate-hexane, 30:70 then 40:60) to give the phenyl ether (167.4 mg, 84%). MS found: (M+Na)⁺=390.
(61b) Following a procedure analogous to step (1f), the ester from (61a) (154 mg, 0.419 mmol) was reacted with hydroxylamine to give the hydroxamic acid (144 mg, 93%). MS found: (M–H)⁻=367.

Example 62

[1(R)]-N-hydroxy-α,3-dimethyl-2-oxo-3-(4-phenoxyphenyl)-1-pyrrolidineacetamide

Beginning with the phenol from (6a) and benzeneboronic acid, example 62 was prepared in an analogous series of reactions to (61a) and (61b). MS found: (M–H)⁻=353.

Example 63

[1(R)]-N-hydroxy-α,3-dimethyl-3-[4-(2-methylphenoxy)phenyl]-2-oxo-1-pyrrolidineacetamide Beginning with the phenol from (6a) and 2-methylbenzeneboronic acid, example 63 was prepared in an analogous series of reactions to (61a) and (61b). MS found: (M–H)⁻=367.

Example 64

[1(R)]-3-[4-(3,5-dichlorohenoxy)phenyl]-N-hydroxy-α,3-dimethyl-2-oxo-1-pyrrolidineacetamide Beginning with the phenol from (6a) and 3,5-dichlorobenzeneboronic acid, example 64 was prepared in an analogous series of reactions to (61a) and (61b). MS found: (M–H)⁻=421.

Example 65

[1(R)]-3-[4-(3,4-dimethoxyphenoxy)phenyl]-N-hydroxy-α,3-dimethyl-2-oxo-1-pyrrolidineacetamide Beginning with the phenol from (6a) and 3,4-dimethoxybenzeneboronic acid, example 65 was-prepared in an analogous series of reactions to (61a) and (61b). MS found: (M–H)⁻=413.

Example 66

[1(R)]-3-[4-(1,3-benzodioxol-5-yloxy)phenyl]-N-hydroxy-α,3-dimethyl-2-oxo-1-pyrrolidineacetamide Beginning with the phenol from (6a) and 3,4-methylenedioxybenzeneboronic acid, example 66 was prepared in an analogous series of reactions to (61a) and (61b). MS found: (M–H)⁻=397.

Example 67

[1(R)]-N-hydroxy-α,3-dimethyl-3-[4-[3-(1-methylethyl)phenoxy]phenyl]-2-oxo-1-pyrrolidineacetamide Beginning with the phenol from (6a) and 3-isopropylbenzeneboronic acid, example 67 was prepared in an analogous series of reactions to (61a) and (61b). MS found: (M–H)⁻=395.

Example 68

[1(R)]-N-hydroxy-3-[4-(3-methoxyphenoxy)phenyl]-α,3-dimethyl-2-oxo-1-pyrrolidineacetamide Beginning with the phenol from (6a) and 3-methoxybenzeneboronic acid, example 68 was prepared in an analogous series of reactions to (61a) and (61b). MS found: (M–H)⁻=383.

Example 69

[1(R)]-N-hydroxy-α,3-dimethyl-2-oxo-3-[4-(3-thienyloxy)phenyl]-1-pyrrolidineacetamide Beginning with the phenol from (6a) and thiophene-3-boronic acid, example 69 was prepared in an analogous series of reactions to (61a) and (61b). MS found: (M–H)⁻=359.

Example 70

[1(R)]-N-hydroxy-α,3-dimethyl-2-oxo-3-[4-(3,4,5-trimethoxyphenoxy)phenyl]-1-pyrrolidineacetamide Beginning with the phenol from (6a) and 3,4,5-trimethoxybenzeneboronic acid, example 70 was prepared in an analogous series of reactions to (61a) and (61b.). MS found: (M–H)⁻=443.

Example 71

[1(R)]-3-[4-[3,5-bis(trifluoromethyl)phenoxy]phenyl]-N-hydroxy-α,3-dimethyl-2-oxo-1-pyrrolidineacetamide Beginning with the phenol from (6a) and 3,5-bis(trifluoromethyl)benzeneboronic acid, example 71 was prepared in an analogogus series of reactions to (61a) and (61b). MS found: (M+H)⁻=491.

Example 72

[1(R)]-N-hydroxy-α,3-dimethyl-3-[4-(1-naphthalenyloxy)phenyl]-2-oxo-1-pyrrolidineacetamide Beginning with the phenol from (6a) and 1-naphthaleneboronic acid, example 72 was prepared in an analogous series of reactions to (61a) and (61b). MS found: (M+H)⁻=405.

Example 73

[1(R)]-N-hydroxy-3-[4-[3-[(hydroxyimino)methyl]phenoxy]phenyl]-α,3-dimethyl-2-oxo-1-pyrrolidineacetamide Beginning with the phenol from (6a) and 3-formylbenzeneboronic acid, example 73 was prepared in an analogous series of reactions to (61a) and (61b). MS found: (M+H)⁺=398.

Example 74

[1(R)]-N-hydroxy-3-[4-[4-[1-(hydroxyimino)ethyl]phenoxy]phenyl]-α,3-dimethyl-2-oxo-1-pyrrolidineacetamide Beginning with the phenol from (6a) and 4-acetylbenzeneboronic acid, example 74 was prepared in an analogous series of reactions to (61a) and (61b). MS found: (M−H)⁻=410.

Example 75

[1(R)]-3-[4-([1,1'-biphenyl]-4-yloxy)phenyl]-N-hydroxy-α,3-dimethyl-2-oxo-1-pyrrolidineacetamide Beginning with the phenol from (6a) and 4-biphenylboronic acid, example 75 was prepared in an analogous series of reactions to (61a) and (61b). MS found: (M+H)⁻=431.

Example 76

[1(R)]-3-[4-(3,5-dibromophenoxy)phenyl]-N-hydroxy-α,3-dimethyl-2-oxo-1-pyrrolidineacetamide Beginning with the phenol from (6a) and 3,5-dibromobenzeneboronic acid, example 76 was prepared in an analogous series of reactions to (61a) and (61b). MS found: (M+H)⁻=510.

Example 77

[1(R)]-3-[4-[3-(acetylamino)phenoxy]phenyl]-N-hydroxy-α,3-dimethyl-2-oxo-1-pyrrolidineacetamide Beginning with the phenol from (6a) and 3-acetamidobenzeneboronic acid, example 77 was prepared in an analogous series of reactions to (61a) and (61b). MS found: (M+H)⁻=412.

Example 78

[1(R)]-N-hydroxy-α,3-dimethyl-3-[4-(4-nitrophenoxy)pyenyl]-2-oxo-1-pyrrolidineacetamide (78a) Cesium carbonate (254 mg, 1.8 eq) was added to the phenol from (6a) (120 mg, 0.433 mmol) and 1-fluoro-4-nitrobenzene (122 mg, 2 eq) in DMSO (2 mL). After 1 h at rt, sat ammonium chloride (3 mL) and ethyl acetate (100 mL) were added. The mixture was washed with water (2×5 mL), brine (5 mL), dried (MgSO4) and concentrated. Silica gel chromatography (ethyl acetate-hexane, 50:50) gave the phenyl ether (139.7 mg, 81%). MS found: (M+H)⁻=399.

(78b) Following a procedure analogous to step (1f), the ester from (78a) (125 mg, 0.314 mmol) was reacted with hydroxylamine to give the hydroxamic acid (80.6 mg, 64%). MS found: (M−H)⁻=398.

Example 79

[1(R)]-N-hydroxy-α,3-dimethyl-3-(4-methylphenyl)-2-oxo-1-pyrrolidineacetamide

Beginning with methyl (4-methylphenyl)acetate, example 79 was prepared in an analogous series of reactions to example 1. MS found: (M−H)⁻=275.

Example 80

[1(R)]-3-[4-[[(2,6-dimethyl-4-pyridinyl)oxy]methyl]phenyl]-N-hydroxy-α,3-dimethyl-2-oxo-1-pyrrolidineacatamida mono(trifluoroacetate)

(80a–d) Beginning with methyl (4-methylphenyl)acetate, methyl (R)-α,3-dimethyl-2-oxo-3-(4-methyl phenyl)-1-pyrrolidineacetate was prepared in an analogous series of reactions to (1a–d). The two isomers were separated by silica gel chromatography (ethyl acetate-hexane, 20:80 then 25:75). The more polar isomer was used for subsequent reactions. MS found: (M+H)⁺=276.

(80e) N-bromosuccinimide (1.45 g, 1.05 eq) and benzoyl peroxide (28.2 mg, 0.015 eq) were added to the more polar ester from (80d) (2.14 g, 7.77 mmol) in carbon tetrachloride (50 mL). The suspension was stirred under two 250 W sun lamp radiation for 2 h. The mixture was concentrated and purified by silica gel chromatography (ethyl acetate-hexane, 20:80 then 30:70) to give the bromide (1.784 g, 65%). MS found: (M+H)⁺=354.

(80f) Cesium carbonate (199 mg, 1.8 eq) was added to the bromide from (80e) (120 mg, 0.339 mmol) and 2,6-dimethyl-4-phenol (83 mg, 2 eq) in DMSO (4 mL). After 3 h at rt, sat ammonium chloride was added. The mixture was extracted with ethyl acetate (3×). The combined extracts were washed with brine, dried (MgSO4) and concentrated. Silica gel chromatography (methanol-chloroform, 7:93) gave the pyridinyl ether (35 mg, 26%). MS found: (M+H)⁺=397.

(80a) Following a procedure analogous to step (1f), the ester from (80f) (30 mg, 0.0758 mmol) was reacted with hydroxylamine. The hydroxamic acid was isolated as a TFA salt (15 mg, 39%). MS found: (M+H)⁺=398.

Example 81

[1(R)]-N-hydroxy-α,3-dimethyl-2-oxo-3-[4-[(4-quinolinyloxy)methyl]phenyl]-1-pyrrolidineacetamide mono(trifluoroacetate)

Beginning with the bromide from (80e). and 4-hydroxyquinoline, example 81 was prepared in an analogous series of reactions to (80f) and (80g). MS found: (M+H)⁺=420.

Example 82

[1(R)]-N-hydroxy-α,3-dimethyl-3-(4-nitrophenyl)-2-oxo-1-pyrrolidineacetamide (82a) DBU (25.33 mL, 1.1 eq) was added dropwise to a mixture of 2-(4-nitrophenyl)propionic acid (30.00 g, 154 mmol) and iodomethane (10.55 mL, 1.1 eq) in toluene (250 mL). After 30 min at rt, ether (200 mL) was added. The mixture was filtered through a silica gel pad and the filter cake washed with ethyl acetate-hexane (1:1) until free of solvent. The combined filtrate was concentrated to give the ester (25.85 g, 80%). MS found: M$^+$=209.

(82b) Sodium hydride (2.76 g, 1.2 eq, 60% in mineral oil) was added to the ester from (82a) (12.00 g, 57.4 mmol) and allyl bromide (9.93 mL, 2 eq) in DMF (200 mL) at 0° C. After 30 min at rt, sat NH4Cl (200 mL) was added and the mixture was concentrated to dryness in vacuo. The solid was treated with water (200 mL) and extracted with ether (3×200 mL). The combined extracts were washed with water, brine, dried (MgSO4) and concentrated. The crude material was used in the next step without purification.

(82c) A 1 N solution of NaOH (100 mL) was added to half of the crude material from (82b) in methanol (200 mL). The mixture was stirred at rt overnight and at reflux for 1 h. Following removal of methanol in vacuo, the aqueous residue was washed with hexane (2×100 mL) to remove mineral oil. The combined hexane washings were back extracted with 1 N NaOH (30 mL). The combined aqueous layer was acidified with 1 N HCl (180 mL), saturated with solid NaCl, and extracted with ethyl acetate (3×250 mL). The combined organic extracts were washed with brine (30 mL), dried (MgSO4) and concentrated to give the carboxylic acid (6.38 g, 94% for 2 steps).

(82d) HATU (11.17 g 1.1 eq) and NMM (10.27 mL, 3.5 eq) were added to the acid from (82c) (6.28 g, 26.7 mmol) and D-alanine methyl ester hydrochloride (4.10 g, 1.1 eq) in DMF (50 mL). After 2 h at rt, ethyl acetate (750 mL) was added. The mixture was washed with 1 N HCl (3×50 mL), water (50 mL), sat NaHCO3 (2×50 mL), water (50 mL), and brine (50 mL), dried (MgSO4) and concentrated. The crude material was used in the next step without purification. NS found; (M+H)$^+$=321.

(82e) Ozone was bubbled through a solution of the crude olefin from (82d) in dichloromethane (200 mL) and methanol (100 mL) at −78 ° C. until starting material consumed. the mixture was purged with oxygen and treated with triphenylphosphine (7.00 g, 1.0 eq). After 1 h at rt, the mixture was concentrated. The crude material was used in the next step without purification.

(82f) Triethylsilane (42.6 mL, 10 eq) and trifluroacetic acid (20.6 mL, 10 eq) were added successively to the crude aldehyde from (82e) in dichloromethane at 0° C. After 2 h at rt, the mixture was concentrated and purified by silica gel chromatography (ethyl acetate-toluene-hexane, 20:10:70 then 25:10:65 then 30:10:60 then 35:10:55) to give less polar lactam (2.211 mg), more polar lactam (2.184 g), and a 1:1 mixture of the two isomers (0.44 g). The total yield of the two isomers is 4.835 g (59% for three steps). MS found: (M+H)$^+$=307.

(82a) Following a procedure analogous to step (1f), the more polar ester from (82f) (100 mg, 0.326 mmol) was reacted with hydroxylamine to give the hydroxamic acid (93.8 mg, 94%). MS found: (M−H)$^-$=306.

Example 83

[1(R)]-N-hydroxy-α,3-dimethyl-2-oxo-3-[4-[(phenylcarbonyl)amino]phenyl]-1-pyrrolidineacetamide (83a) The more polar isomer from (82f) (1.97 g, 6.43 mmol) and 10% Pd on carbon (0.5 g) in methanol (50 mL) and chloroform (50 mL) was stirred under balloon pressure hydrogen for 2 h. Following removal of catalyst by filtration, the filtrate was concentrated to give the aniline (1.83 g, 100%). MS found: (M+H)$^+$=277.

(83b) Following a procedure analogous to step (49a), the aniline from (83a) (100 mg, 0.362 mmol) was reacted with benzoyl chloride to give the benzamide (124 mg, 90%). MS found: (M+Na)$^+$=403.

(83c) Following a procedure analogous to step (1f), the benzamide from (83b) (110 mg, 0.289 mmol) was reacted with hydroxylamine to give the hydroxamic acid (100 mg, 91%). MS found: (M−H)$^-$=380.

Example 84

[1(R)]-N-hydroxy-α,3-dimethyl-2-oxo-3-[4-[(phenylsulfonyl)amino]phenyl]-1-pyrrolidineacetamide Beginning with the aniline from (83b) and benzenesulfonyl chloride, example 84 was prepared in an analogous series of reactions to (49a) and (1f). MS found: (M+Na)$^+$=440.

Example 85

[1(R)]-N-hydroxy-α,3-dimethyl-2-oxo-3-[4-[[(phenylamino)carbonyl]amino]phenyl]-1-pyrrolidineacetamide Beginning with the aniline from (83b) and phenyl isocyanate, example 85 was prepared in an analogous series of reactions to (49a) and (1f). MS found: (M+Na)$^+$=419.

Example 86

[1(R)]-N-hydroxy-α,3-dimethyl-3-[4-[(1-naphthalenylmethyl)amino]phenyl]-2-oxo-1-pyrrolidineacetamide (86a) Hunig's base (0.13 mL, 2 eq), 1-naphthaldehyde (62.2 mg, 1.1 eq) and 4 A molecular sieves (300 mg) were added to the aniline from (83a) (100 mg, 0.362 mmol) in 1,2-dichloroethane (3 mL). After 30 min at rt, NaBH (OAc)3 (230 mg, 3 eq) was added and the mixture was stirred for 36 h. The precipitate was removed by filtration. The filtrate was concentrated and purified by silica gel chromatography (ethyl acetate-hexane, 50:50) to give the secondary amine (117 mg, 78%). MS found: (M+Na)$^+$=439.

(86b) Following a procedure analogous to step (1f), the ester from (86a) (108 mg, 0.260 mmol) was reacted with hydroxylamine to give the hydroxamic acid (75.4 mg, 70%). MS found: (M+Na)$^+$=440.

Example 87

[1(R)]-N-hydroxy-α,3-dimethyl-2-oxo-3-[4-[(4-quinolinylmethyl)amino]phenyl]-1-pyrrolidineacetamide Beginning with the aniline from (83b) and quinoline-4-carboxaldehyde, example 87 was prepared in an analogous series of reactions to (86a) and (1f). MS found: (M+H)$^+$=419.

Example 88

[1(R)]-3-[4-[[(3,5-dimethoxyphenyl)methyl]amino]phenyl]-N-hydroxy-α,3-dimethyl-2-oxo-1-pyrrolidineacetamide Beginning with the aniline from (83b) and 3,5-dimethoxybenzaldehyde, example 88 was prepared in an analogous series of reactions to (86a) and (1f). MS found: (M−H)$^-$=426.

Example 89

3-[4-[(3,5-dimethylphenyl)methoxy]phenyl]-N-hydroxy-3-methyl-2-oxo-1-pyrrolidineacetamide Beginning with the aldehyde from (1c) and glycine methyl ester hydrochloride, example 89 was prepared in an analogous series of reactions to (1d), (3a), (6b) and (1f), but using 3,5-dimethylbenzyl bromide in step (6b). MS found: $(M+Na)^+=405$.

Example 90

3-[4-[(2,6-dichloro-4-pyridinyl)methoxy]phenyl]-N-hydroxy-3-methyl-2-oxo-1-pyrrolidinesactamide Beginning with the aldehyde from (1c) and glycine methyl ester hydrochloride, example 90 was prepared in an analogous series of reactions to (1d), (3a), (6b) and (1f), but using 4-bromomethyl-2,6-dichloropyridine in step (6b). MS found: $(M+H)^+=424$.

Example 91

3-[4-[(2,6-dimethyl-4-pyridinyl)methoxy]phenyl]-N-hydroxy-3-methyl-2-oxo-1-pyrrolidineacetamide Beginning with the aldehyde from (1c) and glycine methyl ester hydrochloride, example 91 was prepared in an analogous series of reactions to (1d), (3a), (6b) and (1f), but using 4-bromomethyl-2,6-dimethylpyridine hydrochloride in step (6b). MS found: $(M+H)^+=424$.

Example 92

[1(R)]-N-hydroxy-3-methyl-α-(1-methylethyl)-2-oxo-3-[4-(4-quinolinylmethoxy)phenyl]-1-pyrrolidineacetamide mono(trifluoroacetate)

(92a) Following a procedure analogous to step (1d), the aldehyde from (1c) (3.00 g, 9.61 mmol) was reacted with D-valine methyl ester hydrochloride to give the lactam as mixture of two isomers. Silica gel chromatography (ether-hexane, 50:50 then 85:15) provided the less polar isomer (1.25 g, 30%). MS found: $(M+Na)^+=418$.

(92b) Following a procedure analogous to step (3a), the less polar lactam from (92a) (1.25 g, 3.18 mmol) was hydrogenolized to give the phenol (0.915 g, 94%). MS found: $(M+H)^+=300$.

(92c) Following a procedure analogous to step (6b), the phenol from (92b) (106 mg, 0.348 mmol) was reacted with 4-chloromethylquinoline to give the phenyl ether (134 mg, 86%). MS found: $(M+H)^+=447$.

(92d) The 1.76 M NH2OH/KOH solution in methanol was prepared fresh following the procedure described in (1e). The ester from (92c) (134 mg, 0.300 mmol) was treated with the hydroxylamine solution (3.4 mL, 20 eq). Additional hydroxylamine (2 mL, 0.5 mL and 2 mL) were added after 20 min, 40 min and 1.5 h, respectively. After a total of 2 h, the mixture was neutralized to pH 7 with 1 N HCl and concentrated. Purification by HPLC (acetonitrile-water-TFA, 15:85:0.1 to 50:50:0.1) provided the hydroxamic acid as a TFA salt (69 mg, 41%). MS found: $(M-H)^-=446$.

Example 93

[1(R)]-N-hydroxy-3-methyl-α-(1-methylethyl)-2-oxo-3-[4-(phenylmethoxy)phenyl]-1-pyrrolidineacetamide Following a procedure analogous to step (1f), the less polar lactam from (92a) was reacted with hydroxylamine to give the hydroxamic acid. MS found: $(M-H)^-=395$.

Example 94

[1(R)]-3-[4-[(2,6-dimethyl-4-pyridinyl)methoxy]phenyl]-N-hydroxy-3-methyl-α-(1-methylethyl)-2-oxo-1-pyrrolidineacetamide mono(trifluoroacetate)

Beginning with the phenol from (92b) and 4-chloromethyl-2,6-dimethylpyridine, example 94 was prepared in an analogous series of reactions to (6b) and (92d). MS found: $(M+H)^+=426$.

Example 95

[1(R)]-3-[4-[(2,6-dimethyl-4-pyridinyl)methoxy]phenyl]-N-hydroxy-3-methyl-α-(2-methylpropyl)-2-oxo-1-pyrrolidineacetamide (95a) Following a procedure analogous to step (1d), the aldehyde from (1c) (3.00 g, 9.61 mmol) was reacted with D-leucine methyl ester hydrochloride to give the lactam as mixture of two isomers. Silica gel chromatography (ether-toluene, 10:90) provided the less polar isomer (1.20 g, 31%). MS found: $(M+Na)^+=432$.

(95b) Following a procedure analogous to step (3a), the less polar lactam from (95a) (1.20 g, 2.93 mmol) was hydrogenolized to give the phenol (0.94 g, 100%). MS found: $(M+H)^+=320$.

(95c) Following a procedure analogous to step (6b), the phenol from (95b) (155 mg, 0.486 mmol) was reacted with 4-chloromethyl-2,6-dimethylpyridine to give the phenyl ether (191 mg, 90%). MS found: $(M+H)^+=439$.

(95d) Following a procedure analogous to step (1f), the ester from (95c) (140 mg, 0.320 mmol) was reacted with hydroxylamine to give the hydroxamic acid (115 mg, 82%). MS found: $(M+H)^+=440$.

Example 96

[1(R)]-3-[(4-[(2,6-dichloro-4-pyridinyl)methoxy]phenyl]-N-hydroxy-3-methyl-α-(2-methylpropyl)-2-oxo-1-pyrrolidineacetamide Beginning with the phenol from (95b) and 4-bromomethyl-2,6-dichloropyridine, example 96 was prepared in an analogous series of reactions to (6b) and (1f). MS found: $(M-H)^-=479$.

Example 97

[1(R)]-3-[4-[[3,5-bis(trifluoromethyl)phenyl]methoxy]phenyl]-N-hydroxy-3-methyl-α-(2-methylpropyl)-2-oxo-1-pyrrolidineacetamide Beginning with the phenol from (95b) and 3,5-bis(trifluoromethyl)benzyl bromide, example 97 was prepared in an analogous series of reactions to (6b) and (1f). MS found; $(M-H)^-=454$.

Example 98

[1(R)]-3-[4-[(3,5-dichlorophenyl)methoxy]phenyl]-N-hydroxy-3-methyl-α-(2-methylpropyl)-2-oxo-1-pyrrolidineacetamide Beginning with the phenol from (95b) and 3,5-dichlorobenzyl bromide, example 98 was prepared in an analogous series of reactions to (6b) and (1f). MS found: $(M+H)^+=479$.

Example 99

[1(R)]-N-hydroxy-3-methyl-α-(2-methylpropyl)-2-oxo-3-[3-(phenylmethoxy)propyl]-1-pyrrolidineacetamide (99a) Following a procedure analogous to step (1a), ethyl 2-methyl-4-pentenoate (3.00 g, 21.1 mmol) was reacted with 3-benzyloxy-1-bromopropane to give the crude ester. MS found: $(M+NH_4)^+=308$.

(99b) Following a procedure analogous to step (1c), the crude ester from (99a) was ozonolized to give the aldehyde (5.19 g, 84% for 2 steps). MS found: $(M+NH_4)^+=310$.

(99c) Following a procedure analogous to step (1d), the aldehyde from (99b) (5.06 g, 17.3 mmol) was reacted with D-leucine methyl ester hydrochloride to give the lactam as mixture of two isomers. Silica gel chromatography (ethyl acetate-hexane, 20:80 then 25:75 then 30:70) provided the less polar isomer (1.94 g), the more polar isomer (1.66 g) and a 1:1.1 mixture of both isomers (1.86 g). The total yield of both isomers is 5.4 g (84%). MS found: $(M+H)^+=376$.

(99d) Following a procedure analogous to step (1f), the less polar lactam from (99c) (100 mg, 0.266 mmol) was reacted with hydroxylamine to give the hydroxamic acid (80.6 mg, 80%). MS found: $(M-H)^-=375$.

(99e) Following a procedure analogous to step (1f), the more polar lactam from (99c) (100 mg, 0.266 mmol) was reacted with hydroxylamine to give the hydroxamic acid (81.8 mg, 82%). MS found: $(M-H)^-=375$.

Example 101

[1(R)]-N-hydroxy-3-methyl-3-[2-methyl-4-(phenylmethoxy)phenyl]-α-(2-methylpropyl)-2-oxo-1-pyrrolidineacetamide (101a) Following a procedure analogous to step (1a), methyl (4-benzyloxy-2-methylphenyl)acetate (5.00 g, 18.5 mmol) was reacted with iodomethane to give the crude ester. MS found: $(M+NH_4)^+=302$.

(101b). Following a procedure analogous to step (1b), the crude material from (101a) was reacted with allyl bromide to give the crude ester. MS found: $(M+NH_4)^+=342$.

(101c) Following a procedure analogous to step (1c), the crude ester from (101b) was ozonolized to give the aldehyde (5.42 g, 90% for 3 steps). MS found: $(M+NH_4)^+=344$.

(101d) Following a procedure analogous to step (1d), the aldehyde from (10c) (5.28 g, 16.2 mmol) was reacted with D-leucine methyl ester hydrochloride to give the lactam as mixture of two isomers. Silica gel chromatography (ethyl acetate-hexane, 20:80) provided the less polar isomer (1.363 g) and the more polar isomer (1.412 g). MS found: $(M+Na)^+=446$.

(101e) Following a procedure analogous to step (1f), the less polar lactam from (101d) (100 mg, 0.262 mmol) was reacted with hydroxylamine to give the hydroxamic acid (65.2 mg, 65%). MS found: $(M-H)^-=423$.

Example 102

[1(R)]-3-[4-[(2,6-dichloro-4-pyridinyl)methoxy]-2-methylphenyl]-N-hydroxy-3-methyl-α-(2-methylpropyl)-2-oxo-1-pyrrolidineacetamide (102a) Following a procedure analogous to step (3a), the less polar lactam from (101d) (1.05 g, 2.48 mmol) was hydrogenolized to give the phenol (731 mg, 88%). MS found: $(M-H)^-=332$.

(102b) Following a procedure analogous to step (6b), the phenol from (102a) (100 mg, 0.300 mmol) was reacted with 4-bromomethyl-2,6-dichloropyridine to give the picolyl ether (116 mg, 78%). MS found: $(M+Na)^+=515$.

(102c) Following a procedure analogous to step (1f), the ester from (102b) (105 mg, 0.213 mmol) was reacted with hydroxylamine to give the hydroxamic acid (70.2 mg, 67%). MS found: $(M-H)^-=492$.

Example 103

[1(R)]-N-hydroxy-3-methyl-3-[2-methyl-4-(2-naphthalenylmethoxy)phenyl]-α-(2-methylpropyl)-2-oxo-1-pyrrolidineacetamide Beginning with the phenol from (102a) and 1-bromomethylnaphthlene, the desired product was prepared in an analogous series of reactions to (6b) and (1f). MS found: $(M+H)^+=475$.

Example 104

[1(R)]-N-hydroxy-3methyl-α-(2-methylpropyl)-3-[2-methyl-4-(4-pyridinylmethoxy)phenyl]-2-oxo-1-pyrrolidineacetamide Beginning with the phenol from (102a) and 4-chloromethylpyridine, example 104 was prepared in an analogous series of reactions to (6b) and (1f). MS found: $(M+H)^+=426$.

Example 105

[1(R)]-3-[4-[(2,6-dimethyl-4-pyridinyl)methoxy]-2-methylphenyl]-N-hydroxy-3-methyl-α-(2-methylpropyl)-2-oxo-1-pyrrolidineacetamide Beginning with the phenol from (102a) and 4-chloromethyl-2,6-dimethylpyridine, example 105 was prepared in an analogous series of reactions to (6b) and (1f). MS found: $(M+H)^+=454$.

Example 106

[1(R)]-N-hydroxy-3-methyl-α-[2-(methylthio)ethyl]-2-oxo-3-[4-(phenylmethoxy)phenyl]-1-pyrrolidineacetamide (106a) Following a procedure analogous to step (1d), the aldehyde from (1c) (4.19 g, 13.4 mmol) was reacted with D-methionine methyl ester hydrochloride to give the lactam as a 1:1 mixture of two isomers (4.39 g, 77%). MS found: $(M+H)^+=428$.

(106b) Following a procedure analogous to step (1f), the lactam from (106a) (144 mg, 0.337 mmol) was reacted with hydroxylamine to give the hydroxamic acid (90.7 mg, 63%). MS found: $(M-H)^-=427$.

Example 107

[1(R)]-3-[4-(3,5-dibromophenoxy)phenyl]-3-methyl-α-[2-(methylsulfonyl)ethyl]-2-oxo-1-pyrrolidineacetic acid (107a) Oxone (19.0 g, 3 eq) in water (100 mL) was added to the lactam from (106a) (8.80 g, 20.6 mmol) in methanol (100 mL) at 0° C. After 30 min at 0° C. and 4 h at rt, methanol was removed in vacuo. The aqueous residue was diluted with water (300 mL) and extracted with chloroform (3×400 ml). The combined organic extracts were washed with water (50 mL) and brine (50 mL), dried (MgSO4) and concentrated. Silica gel chromatography (ethyl acetate-hexane, 60:40 then 70:30 then 100:0) provided the more polar sulfone (2.88 g, 30%). MS found: $(M+Na)^+=482$.

(107b) Following a procedure analogous to step (3a), the sulfone from (107a) (2.88 g, 6.27 mmol) was hydrogenolizea to give the phenol (2.15 g, 93%). MS found: $(M+H)^+=370$.

(107c) Following a procedure analogous to step (61a), the phenol from (107b) (120 mg, 0.325 mmol) was reacted with 3,5-dibromobenzeneboronic acid to give the phenyl ether (150 mg, 77%). MS found: $(M+H)^+=604$.

(107d) A 1 N solution of LiOH (0.28 mL, 1.3 eq) was added to the ester from (107c) (128 mg, 0.212 mmol) in THF (1.5 mL) at 0° C. After 30 min at this temperature, the mixture was acidified to pH 2–3. The mixture was concentrated to dryness, treated with ethyl acetate (100 mL), and filtered. The filtrate was concentrated to give the carboxylic acid (121 mg, 97%). MS found: $(M-H)^-=492$.

Example 108

[1(R)]-3-[4-[3,5-bis(trifluoromethyl)phenoxy]phenyl]-N-hydroxy-3-methyl-α-[2-(methylsulfonyl)ethyl]-2-oxo-1-pyrrolidineacetamide Beginning with the phenol from (107b) and 3,5-bis(trifluoromethyl)benzene boronic acid, example 108 was prepared in an analogous series of reactions to (61a) and (1f). MS found: $(M-H)^-=581$.

Example 109

[1(R)]-3-[4-(3,5-dibromophenoxy)phenyl]-N-hydroxy-3-methyl-α-[2-(methylsulfonyl)ethyl]-2-oxo-1-pyrrolidineacetamide Following a procedure analogous to step (1f), the lactam from (107c) (156 mg, 0.259 mmol) was reacted with hydroxylamine to give the hydroxamic acid (110 mg, 70%). MS found: $(M-H)^-=603$.

Example 110

[1(R)]-3-[4-[(2,6-dichloro-4-pyridinyl)methoxy]phenyl]-N-hydroxy-3-methyl-α-[2-(methylsulfonyl)ethyl]-2-oxo-1-pyrrolidineacetamide Beginning with the phenol from (107b) and 4-bromomethyl-2,6-dichloropyridine, example 110 was prepared in an analogous series of reactions to (6b) and (1f). MS found: $(M-H)^-=528$.

Example 111

[1(R)]-3-[4-[(2,6-dimethyl-4-pryridinyl)methoxy]phenyl]-N-hydroxy-3-methyl-α-[2-(methylsulfonyl)ethyl]-2-oxo-1-pyrrolidineacetamide Beginning with the phenol from (107b) and 4-chloromethyl-2,6-dimethylpyridine, example 111 was prepared in an analogous series of reactions to (6b) and (1f). MS found: $(M+H)^+=490$.

Example 112

[1(R)]-N-hydroxy-3-methyl-α-[2-(methylsulfonyl)ethyl]-2-oxo-3-[4-(4-quinolinylmethoxy)phenyl]-1-pyrrolidineacetamide mono(trifluoroacetate)

Beginning with the phenol from (107b) and 4-chloromethylquinoline hydrochloride, example 112 was prepared in an analogous series of reactions to (6b) and (1f). MS found: $(M+H)^+=512$.

Example 113

N-hydroxy-1-[3-methyl-2-oxo-3-[4-(phenylmethoxy)phenyl]-1-pyrrolidinyl]cyclopropanecarboxamide (113a) Following a procedure analogous to step (1d), the aldehyde from (1c) (400 mg, 1.28 mmol) was reacted with 1-aminocyclopropane-1-carboxylic acid methyl ester hydrochloride to give the lactam (280 mg, 58%). MS found: $(M+H)^+=380$.

(113b) Following a procedure analogous to step (1f), the ester from (113a) (100 mg, 0.264 mmol) was reacted with hydroxylamine to give the hydroxamic acid (76 mg, 76%). MS found: $(M-H)^-=379$.

Example 114

[1(R)]-N-hydroxy-α-[(4-hydroxyphenyl)methyl]-3-methyl-2-oxo-3-[4-(phenylmethoxy)phenyl]-1-pyrrolidineacetamide Beginning with the aldehyde from (1c) and D-tyrosine methyl ester hydrochloride, example 114 was prepared in an analogous series of reactions to (1d) and (1f). MS found: $(M-H)^-=395$.

Example 115

[1(R)]-3-[4-[(2,6-dichloro-4-pyridinyl)methoxy]phenyl]-N-hydroxy-α-(2-hydroxyethyl)-3-methyl-2-oxo-1-pyrrolidineacetamide (115a) A mixture of D-homoserine (25.00 g, 210 mmol), 35–37% hydrochloric acid (200 mL) and water (200 mL) was heated to reflux for 3 h. Removal of solvent in vacuo provided the aminolactone hydrochloride (27.68 g, 96%). MS found: $(M+NH4)^+=119$.

(115b) Following a procedure analogous to step (1d), the aldehyde from (1c) (3.00 g, 9.60 mmol) was reacted with the aminolactone hydrochloride from (115a) (1.45 g, 1.1 eq) to give the lactam as mixture of two isomers. Silica gel chromatography (ethyl acetate-hexane, 20:80) provided the less polar isomer (1.51 g) and the more polar isomer (1.45 g). MS found: $(M+NH4)^+=383$.

(115c) Following a procedure analogous to step (3a), the more polar lactam from (115b) (1.40 g, 3.83 mmol) was hydrogenolized to give the phenol (1.06g, 100%). MS found: $(M+H)^+=276$.

(115d) Following a procedure analogous to step (6b), the phenol from (115c.) (1.03 g, 3.74 mmol) was reacted with 4-bromomethyl-2,6-dichloropyridine to give the picolyl ether (1.36 g, 84%). MS found: $(M+H)^+=435$.

(115e) Following a procedure analogous to step (1f), the ester from (115d) (71.0 mg, 0.163 mmol) was reacted with hydroxylamine to give the hydroxamic acid (59.1 mg, 77%) as a 85:15 mixture due to partial epimerization. MS found: $(M-H)^-=466$.

Example 116

[1(R)]-1,1-dimethylethyl [5-[3-[4-[(2,6-dichloro-4-pyridinyl)methoxy]phenyl]-3-methyl-2-oxo-1-pyrrolidinyl]-6-(hydroxyamino)-6-oxohexyl]carbamate (116a) Following a procedure analogous to step (1d), the aldehyde from (1c) (5.05 g, 16.2 mmol) was reacted with H-D-Lys(BOC)-OMe hydrochloride (5.28 g, 1.1 eq) to give the crude lactam as mixture of two isomers. The BOC protecting group came off during the cyclization.

(116b) The crude material from (116a) in methylene chloride (100 mL) and DMF (10 mL) was treated with Hunig's base (12.0 mL, 2 eq) and di-t-butyl dicarbonate (8.33 g, 1.2 eq) for 1 h at rt. Following addition of sat ammonium chloride (50 mL) and ethyl acetate (800 mL), the mixture was washed with water (2×50 mL), brine (50 mL), dried (MgSO4) and concentrated. Silica gel chromatography (ethyl acetate-hexane, 40:60 then 50:50) gave the BOC protected lactams (5.49 g, 65% for 2 steps) as a 1:1 mixture. MS found: $(M+Na)^+=547$.

(116c) Following a procedure analogous to step (3a), the lactam from (116b) (5.40 g, 10.3 mmol) was hydrogenolized. Silica gel chromatography (isopropanol-chloroform, 3:97 then 5:95) gave more polar phenol (1.29 g), a 1:1 mixture of both isomers (1.46 g), as well as the less polar isomer. MS found: $(M+Na)^+=457$.

(116d) Following a procedure analogous to step (6b), the more polar phenol from (116c) (300 mg, 0.690 mmol) was reacted with (360 mg, 88%). MS found: $(M+Na)^+=616$.

(116e) Following a procedure analogous to step (1f), the ester from (116d) (152 mg, 0.256 mmol) was reacted with hydroxylamine to give the hydroxamic acid (71.0 mg, 47%). MS found: $(M-H)^-=593$.

Example 117

[1(R)]-α-(4-aminobutyl)-3-[4-[(2,6-dichloro-4-pyridinyl)methoxy]phenyl]-N-hydroxy-3-methyl-2-oxo-1-pyrrolidineacetamide mono(trifluoroacetate)

The hydroxamic acid example 116 (39 mg, 0.065 mmol) was stirred with trifluoroacetic acid (0.5 mL) and $CH_2Cl_2$ (2 mL) for 1 h at rt and concentrated to give example 117 (40 mg, 100%). MS found: $(M+H)^+=495$.

Example 118

[1(R)]-α-[4-(acetylamino)butyl]-3-[4-[(2,6-dichloro-4-pyridinyl)methoxy]phenyl]-N-hydroxy-3-methyl-2-oxo-1-pyrrolidineacetamide (118a) The picolyl ether from (116d) (351 mg, 0.590 mmol) was stirred with trifluoroacetic acid (2 mL) and $CH_2Cl_2$ (8 mL) for 2 h at rt and concentrated to give the free amine trifluoroacetate in quantitative yield. MS found: $(M+H)^+=494$.

(118b) Beginning with the amine from (118a) and acetyl chloride, example 118 was prepared in an analogous series of reactions to (49a) and (1f). MS found: $(M-H)^-=535$.

Example 119

[1(R)]-N-[5-[3-[4-[(2,6-dichloro-4-pyridinyl)methoxy]phenyl]-3-methyl-2-oxo-1-pyrrolidinyl]-6-(hydroxyamino)-6-oxohexyl]-3-pyridineacetamide Beginning with the amine from (li8a) and nicotinoyl chloride, example 119 was prepared in an analogous series of reactions to (49a) and (1f). MS found: $(M+H)^+=600$.

Example 120

[1(R)]-N-[5-[3-[4-[(2,6-dichloro-4-pyridinyl)methoxy]phenyl]-3-methyl-2-oxo-1-pyrrolidinyl]-6-(hydroxyamino)-6-oxohexyl]-4-morpholinecarboxamide Beginning with the amine from (118a) and 4-morpholinecarbonyl chloride, example 120 was prepared in an analogous series of reactions to (49a) and (1f). MS found: $(M+Na)^+=630$.

Example 121

[1(R)]-3-[4-[(2,6-dichloro-4-pyridinyl)methoxy]phenyl]-N-hydroxy-3-methyl-α-[4-[(methylsulfonyl)amino]butyl]-2-oxo-1-pyrrolidineacetamide Beginning with the amine from (118a) and methanesulfonyl chloride, example 121 was prepared in an analogous series of reactions to (49a) and (1f). MS found: $(M+Na)^+=595$.

Example 122

[1(R)]-α-[4-(acetylamino)butyl]-3-[4-[(2,6-dimethyl-4-pyridinyl)methoxy]phenyl]-N-hydroxy-3-methyl-2-oxo-1-pyrrolidineacetamide (122a) Following a procedure analogous to step (6b), the more polar phenol from (116c) (1.00 g, 2.30 mmol) was reacted with 4-bromomethyl-2,6-dimethylpyridine to give the picolyl ether (1.00 g, 79%). MS found: $(M+H)^+=554$.

(122b) Following a procedure analogous to step (118a), the picolyl ether from (122a) (1.00 g, 1.81 mmol) was deprotected with trifluoroacetic acid to give the amine trifluoroacetate (1.28, 100%). MS found: $(M+H)^+=454$.

(122c) Beginning with the aminie from (122b) and acetyl chloride, example 122 was prepared in an analogous series of reactions to (49a) and (1f). MS found: $(M+H)^+=497$.

Example 123

[1(R)]-1,1-dimethylethyl [5-[3-[4-[(2,6-dimethyl-4-pyridinyl)methoxy]phenyl]-3-methyl-2-oxo-1-pyrrolidinyl]-6-(hydroxyamino)-6-oxohexyl] carbamate Beginning with the picolyl ether from (122a), example 123 was prepared in an analogous series of reactions to (55d) and (55e). MS found: $(M+H)^+=555$.

Example 124

[1(R)]-α-(4-aminobutyl)-3-[4-[(2,6-dimethyl-4-pyridinyl)methoxy]phenyl]-N-hydroxy-3-methyl-2-oxo-1-pyrrolidineacetamide bis(trifluoroacetate)

Starting with the hydroxamic acid from example 123, example 124 was prepared in a procedure analogous to example 117. MS found; $(M+H)^+=455$.

Example 125

[1(R)]-α-[4-[(aminoacetyl)amino]butyl]-3-[4-[(2,6-dimethyl-4-pyridinyl)methoxy]phenyl]-N-hydroxy-3-methyl-2-oxo-1-pyrrolidineacetamide bis(trifluoroacetate)

Beginning with the amine from (122b) and N-(t-butoxycarbonyl)glycine, example 125 was prepared in an analogous series of reactions to (50a), (1e) and example 51. MS found: $(M+H)^+=512$.

Example 126

[1(R)]-α-[4-(acetylamino)butyl]-3-[4-[[3,5-bis(trifluoromethyl)phenyl]methoxy]phenyl]-N-hydroxy-3-methyl-2-oxo-1-pyrrolidineacetamide Beginning with the more polar phenol from (116c) and 3,5-bis(trifluoromethyl)benzyl bromide, example 126 was prepared in an analogous series of reactions to (6b), (118a), (49a) and (1f). MS found: $(M+Na)^+=626$.

Example 127

[1(R)]-1,1-dimethylethyl [5-[3-[4-(3,5-dibromophenoxy)phenyl]-3-methyl-2-oxo-1-pyrrolidinyl]-6-hydroxyamxno)-6-oxohexyl] carbamate Beginning with the more polar phenol from (116c) and 3,5-dibromobenzeneboronic acid, example 127 was prepared in an analogous series of reactions to (61a) and (1f). MS found: (M−H)⁻=668.

Example 128

[1(R)]-α-(4-aminobutyl)-3-[4-(3,5-dibromophenoxy)phenyl]-N-hydroxy-3-methyl-2-oxo-1-pyrrolidineacetamide mono(trifluoroacetate)

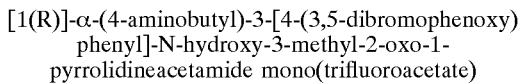

Starting with the hydroxamic acid from example 127, example 128 was prepared in a procedure analogous to example 117. MS found: (M+H)⁺=570.

Example 129

[1(R)]-1,1-dimethylethyl [3-[3-[4-[(2,6-dichloro-4-pyridinyl)methoxy]phenyl]-3-methyl-2-oxo-1-pyrrolidinyl]-4-(hydroxyamino)-4-oxobutyl] carbamate

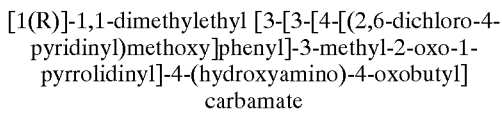

(129a) Ioaobenzene diacetate (38.6 g, 1.2 eq) was added to a mixture of Z-D-Gln-OH (28.1 g, 100 mmol), ethyl acetate (134 mL), acetonitrile (134 mL) and water (67 mL) at 5–10° C. After 30 min at 10° C. and 4 h at 16° C., the organic solvent was removed in vacuo. The aqueous residue was washed with ethyl acetate (2×20 mL) and concentrated to small volume. The product was precipitated out by addition of ethyl acetate (100 mL). Filtration and washing with ethyl acetate (50 mL) provided the diamino acid (16.3 g, 64.5%). MS found: (M+H)⁺=253.

(129b) Following a procedure analogous to (82a), the diamino acid from (129a) (5.40 g, 21.4 mmol) was cyclized with BOP reagent to give the lactam (2.33 g, 47%). MS found: (M+Na)⁺=257.

(129c) Following a procedure analogous to (3a), the lactam from (129b) (9.10 g, 38.8 mmol) was hydrogenolized to give the free aminolactam hydrochloride (5.33 g, 100%). MS found: (M+NH4)⁺=118.

(129d) Following a procedure analogous to (1d), the aldehyde from (1c) (2.39 g, 7.65 mmol) and the lactam from (129c) (1.3 mixture of two isomers. MS found: (M+Na)⁺=387.

(129e) Following a procedure analogous to (3a), the lactam from (129d) (2.23 g, 6.12 mmol) was hydrogenolized to give the phenol (1.60 g, 95%). MS found: (M+H)⁺=275.

(129f) Following a procedure analogous to (6b), the phenol from (129e) (1.51 g, 5.50 mmol) was coupled with 4-bromomethyl-2,6-dichloropyridine to give the picolyl ether (1.03 g, 43%). MS found: (M+Na)⁺=456.

(129g) Triethylamine (0.32 mL, 1 eq), (BOC)20 (1.00 g, 2 eq) and DMAP (0.281 g, 1 eq) were added to the lactam from (129f) (1.00 g, 2.30 mmol) in dichloromethane (10 mL) and the mixture was stirred at rt overnight. The solvent was removed and the mixture purified by silica gel chromatography (ethyl acetate-hexane, 40:60 then S0:50 then 60:40) to provide the less polar isomer (380 mg) and the more polar isomer (310 mg). MS found: (M+Na)⁺=556.

(129h) Following a procedure analogous to (1f), the more polar lactam from (129g) (102 mg, 0.191 mmol) was converted to the hydroxamic acid (50.0 mg, 50%). MS found: (M−H)⁻=565.

Example 130

[1(R)]-α-2-aminoethyl)-3-[4-[(2,6-dichloro-4-pyridinyl)methoxy]phenyl]-N-hydroxy-3-methyl-2-oxo-1-pyrrolidineacetamide mono(trifluoroacetate)

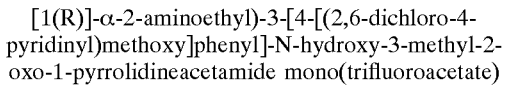

Starting with the hydroxamic acid from example 129, example 130 was prepared in a procedure analogous to example 117. MS found: (M+H)⁺=467.

Example 131

[1(R)]-α-[2-(acetylamino)ethyl]-3-[4-](2,6-dichloro-4-pyridinyl)methoxy]phenyl]-N-hydroxy-3-methyl-2-oxo-1-pyrrolidineacetamide

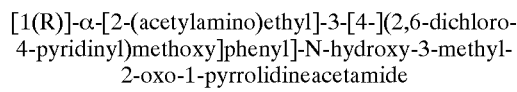

(131a) Chlorotrimethylsilane (0.20 mL, 10 eq) was added to the more polar lactam from (129g) (90.0 mg, 0.168 mmol) in methanol at rt. After 12 h at reflux, additional chlorotrimethylsilane (10 eq) was added and the mixture kept at reflux for another 24 h. Concentration and purification by silica gel chromatography (methanol-dichloromethane, 5:95 then 10:90) provided the aminoester (70 mg, 89%). MS found: (M+H)⁺=466.

(131b) Following a procedure analogous to (49a), the aminoester from (131a) (64 mg, 0.137 mmol) was converted to the acetamide (70 mg, 100%). MS found: (M+Na)⁺=630.

(131c) Following a procedure analogous to (1f), the acetamide from (131b) (65 mg, 0.128 mmol) was converted to the hydroxamic acid (15 mg, 23%). MS found: (M−H)⁻=508.

Example 132

[1(R)]-1,1-dimethylethyl [3-[3-[4-](2,6-dimethyl-4-pyridinyl)methoxy]phenyl-]-3-methyl-2-oxo-1-pyrrolidinyl]-4-(hydroxyamino)-4-oxobutyl] carbamate mono(trifluoroacetate)

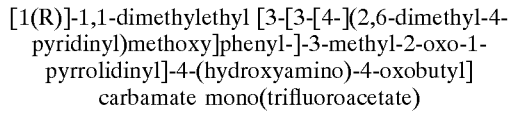

(132a) Following a procedure analogous to (129g), the lactam mixture from (129d) (6.36 g, 17.4 mmol) was converted to the BOC protected lactam. Silica gel chromatography (ethyl acetate-hexane, 40:60 then 50:50 then 60:40) provided the less polar isomer (3.70 g) and the more polar isomer (3.19 g). The total yield is 85%. MS found: (M+Na)⁺=487.

(132b) Following a procedure analogous to example 117, the more polar isomer from (132a) (3.13 g, 8.59 mmol) was deprotected to give the lactam (1.70 g, 69%). MS found: (M+H)⁺=365.

(132c) Following a procedure analogous to (3a), the lactam from (132b) (1.68 g, 4.61 mmol) was hydrogenolized to give the phenol (1.23 g, 97%). MS found: (M+H)⁺=275.

(132d) Following a procedure analogous to (6b), the phenol from (132c) (1.20 g, 4.37 mmol) was coupled with 4-bromomethyl-2,6-dimethylpyridine to give the picolyl ether (1.63 g, 95%). MS found: (M+H)⁺=394.

(132e) Following a procedure analogous to (131a), the lactam from (132d) (1.58 g, 4.02 mmol) was converted to the methyl ester bis(hydrochloride) (2.00 g, 100%). MS found: (M+H)⁺=426.

(132f) Following a procedure analogous to (49a), the aminoester from (132e) (100 mg, 0.183 mmol) was reacted with (BOC)2O to give the t-butyl carbamate (70 mg, 60%). MS found: (M+H)⁺=526.

(132g) Following a procedure analogous to (1f), the ester from (132f) (65 mg, 0.124 mmol) was converted to the hydroxamic acid (23.5 mg, 30%). MS found: (M+H)⁺=527.

Example 133

[1(R)]-α-(2-aminoethyl)-3-[4-[(2,6-dimethyl-4-pyridinyl)methoxy]phenyl]-N-hydroxy-3-methyl-2-oxo-1-pyrrolidineacetamide bis(trifluoroacetate)

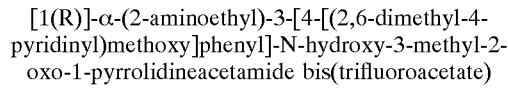

Starting with the hydroxamic acid from example 132, example 133 was prepared in a procedure analogous to example 117. MS found: (M+H)⁺=427.

Example 134

N-[3-[3-[4-[(2,6-dimethyl-4-pyridinyl)methoxy] phenyl]-3-methyl-2-oxo-1-pyrrolidinyl]-4-(hydroxyamino)-4-oxobutyl]-3-pyridinecarboxamide Beginning with the amine from (132e) and nicotinoyl chloride, example 134 was prepared in an analogous series of reactions to (49a) and (1f). MS found: $(M+H)^+ = 523$.

Example 135

[1(R)]-N-[3-[3-[4-[(2,6-dimethyl-4-pyridinyl) methoxy]phenyl]-3-methyl-2-oxo-1-pyrrolidinyl]-4-(hydroxyamino)-4-oxobutyl]-4-morpholinecarboxamide mono(trifluoroacetate)

Beginning with the amine from (132e) and 4-morpholinecarbonyl chloride, example 120 was prepared in an analogous series of reactions to (49a) and (1f). MS found: $(M+H)^+ = 540$.

Example 136

[1(R)]-1,1-dimethylethyl [2-[[3-[3-[4-[(2,6-dimethyl-4-pyridinyl)methoxy]phenyl]-3-methyl-2-oxo-1-pyrrolidinyl]-4-(hydroxyamino)-4-oxobutyl] amino]-2-oxoethyl]carbamate mono(trifluoroacetate)

Beginning with the amine from (132e) and N-(t-butoxycarbonyl)glycine, example 136 was prepared in an analogous series of reactions to (50a) and (1e). MS found: $(M+H)^+ = 584$.

Example 137

[1(R)]-α-[2-[(aminoacetyl)amino]ethyl]-3-[4-[(2,6-dimethyl-4-pyridinyl)methoxy]phenyl]-N-hydroxy-3-methyl-2-oxo-1-pyrrolidineacetamide bis (trifluoroacetate)

Starting with the hydroxamic acid from example 136, example 137 was prepared in a procedure analogous to example 117. MS found: $(M+H)^+ = 484$.

Example 138

[1(R)]-1,1-dimethylethyl [2-[[2-[[3-[3-[4-[(2,6-dimethyl-4-pyridinyl)methoxy]phenyl]-3-methyl-2-oxo-1-pyrrolidinyl]-4-(hydroxyamino)-4-oxobutyl] amino]-2-oxoethyl]amino]-2-oxoethyl]carbamate mono(trifluoroacetate)

Beginning with the amine from (132e) and BOC-Gly-Gly-OH, example 138 was prepared in an analogous series of reactions to (50a) and (1e). MS found: $(M+H)^+ = 641$.

Example 139

[1(R)]-α-[2-[[[(aminoacetyl)amino]acetyl]amino] ethyl]-3-[4-[(2,6-dimethyl-4-pyridinyl)methoxy] phenyl]-N-hydroxy-3-methyl-2-oxo-1-pyrrolidineacetamide bis(trifluoroacetate)

Starting with the hydroxamic acid from example 138, example 139 was prepared in a procedure analogous to example 117. MS found: $(M+H)^+ = 541$.

Example 140

[1(R)]-N-hydroxy-3-methyl-2-oxo-α-[(phenylmethoxy)methyl]-3-[4-(phenylmethoxy) phenyl]-1-pyrrolidineacetamide Beginning with the aldehyde from (1c) and (D)-Ser (OBn)-OMe, example 140 was prepared in an analogous series of reactions to (1d) and (1e). MS found: $(M-H)^- = 473$.

Example 141

[1(R)]-3-[4-[(2,6-dichloro-4-pyridinyl)methoxy] phenyl]-N-hydroxy-α-(hydroxymethyl)-3-methyl-2-oxo-1-pyrrolidineacetamide Beginning with the aldehyde from (1c) and (D)-Ser (OBn)-OMe, example 141 was prepared in an analogous series of reactions to (1d), (3a), (6b) and (1e). MS found; $(M-H)^- = 437$.

Example 142

[1(R)]-1,1-dimethylethyl 4-[2-(hydroxyamino)-1-[3-methyl-2-oxo-3-[4-(4-quinolinylmethoxy)phenyl]-1-pyrrolidinyl]-2-oxoethyl]-1-piperidinecarboxylate mono(trifluoroacetate)

(142a) To 2-(R)-azido-2-(N-t-BOC-4-piperidinyl)acetic acid (50.0 g, 213 mmol, Ciba-Geigy, EP606046 1994) in methanol (125 mL) and benzene (500 mL) was added a 2 M hexane solution of trimethylsilyl diazomethane (110 mL, 1.03 eq). After 10 min at rt, the mixture was concentrated. Silica gel chromatography (ethyl acetate-hexane, 10:90 then 20:80) gave the methyl ester (36.8 g, 58%). MS found: $(M+H)^+ = 299$.

(142b) A mixture of the azido ester from (142a) (36.8 g, 123 mmol), 10% Pd on carbon (8.0 g) in water (600 mL), THF (600 mL) and acetic acid (200 mL) was stirred under balloon pressure hydrogen at rt overnight. The catalyst was removed by filtration and the filtrate was concentrated to give the amino ester (29.5 g, 88%). MS found: $(M+H)^+ = 273$.

(142c) Following a procedure analogous to step (1d), the aldehyde from (1c) (2.00 g, 6.40 mmol) was reacted with the amino ester from (142b) (2.09 g, 1 eq) to give the crude lactam as mixture of two isomers. The BOC protecting group came off during the cyclization. MS found: $(M+H)^+ = 437$.

(142d) Following a procedure analogous to step (116b), the crude material from (142c) was reacted with (BOC)2O to provide the carbamate (2.13 g, 62%) as a 1:1 mixture. MS found: $(M+Na)^+ = 559$.

(142e) Following a procedure analogous to step (3a), the lactam from (142d) (2.13 g, 3.97 mmol) was hydrogenolized to give the phenol (1.72 g, 97%). MS found: $(M-H)^- = 445$.

(142f) Following a procedure analogous to step (6b), the phenol from (142e) (700 mg, 1.57 mmol) was reacted with 4-chloromethylquinoline hydrochloride to give the ether (744 mg, 81%). MS found: $(M+H)^+ = 588$.

(142g) Following a procedure analogous to step (92d), the ester from (142f) (160 mg, 0.272 mmol) was reacted with hydroxylamine. The product was purified by reverse phase HPLC on a Dynamax C-18 semiprep column eluting an acetonitrile:water:TFA gradient, to give the fast moving isomer (61.5 mg) and the slow moving isomer (53.0 mg). MS found: $(M+H)^+ = 589$.

Example 143

[1(R)]-N-hydroxy-α-[3-methyl-2-oxo-3-[4-(4-quinolinylmethoxy)phenyl]-1-pyrrolidinyl]-4-piperidineacetamide mono(trifluoroacetate)

Starting with the slow moving isomer from example 142, example 143 was prepared in a procedure analogous to example 117. MS found: $(M+H)^+ = 489$.

Example 144

[1(R)]-N-hydroxy-α-[3-methyl-2-oxo-3-[4-(4-quinolinylmethoxy)phenyl]-1-pyrrolidinyl]-1-(methylsulfonyl)-4-piperidineacetamide mono (trifluoroacetate)

(144a) Following a procedure analogous to example 117, the lactam from (142f) (553 mg, 0.941 mmol) was reacted with TFA to give the piperidine mono(trifluoroacetate) (1.04, 100%). MS found: (M+H)$^+$=488.

(144b) Following a procedure analogous to (49a), the piperidine from (144a) (200 mg, 0.278 mmol) was reacted with MsCl to give the sulfonamile (112 mg, 71%). Mg found: (M+H)$^+$=566.

(144c) Following a procedure analogous to step (92d), the ester from (144b) (112 mg, 0.198 mmol) was reacted with hydroxylamine. The product was purified by reverse phase HPLC on a Dynamax C-18 semiprep column eluting an acetonitrile:water:TFA gradient, to give the fast moving isomer (14.0 mg) and the slow moving isomer (13.5 mg). MS found: (M+H)$^+$=567.

Example 145

[1(R)]-1-(2-furanylcarbonyl)-N-hydroxy-α-[3-methyl-2-oxo-3-[4-(4-quinolinylmethoxy)phenyl]-1-pyrrolidinyl]-4-piperidineacetamide mono (trifluoroacetate)

Beginning with the piperidine from (144a) and 2-furic acid, example 145 was prepared in an analogous series of reactions to (50a) and (92d). MS found: (M+H)$^+$=583.

Example 146

[1(R)]-1,1-dimethylethyl 4-[1-[3-[4-[(2,6-dimethyl-4-pyridinyl)methoxy]phenyl]-3-methyl-2-oxo-1-pyrrolidinyl]-2-(hydroxyamino)-2-oxoethyl]-1-piperidinecarboxylate mono(trifluoroacetate)

(146a) Following a procedure analogous to step (6b), the phenol from (142e) (1.07 g, 2.40 mmol) was reacted with 4-chloromethyl-2,6-dimethylpyridine hydrochloride to give the picolyl ether (1.15 g, 85%). MS found: (M+Na)$^+$=588.

(146b) Following a procedure analogous to step (92d), the ester from (146a) (124 mg, 0.219 mmol) was reacted with hydroxylamine. The product was purified by reverse phase HPLC on a Dynamax C-18 semiprep column eluting an acetonitrile:water:TFA gradient, to give the fast moving isomer (40.0 mg) and the slow moving isomer (30.0 mg). MS found; (M+H)$^+$=567.

Example 147

[1(R)]-α-[3-[4-[(2,6-dimethyl-4-pyridinyl)methoxy] phenyl]-3-methyl-2-oxo-1-pyrrolidinyl]-N-hydroxy-4-piperidineacetamide bis(trifluoroacetaate)

Starting with the slow moving isomer from example 146, example 147 was prepared in a procedure analogous to example 117. MS found: (M+H)$^+$=467.

Example 148

[1(R)]-methyl 4-[1-[3-[4-[(2,6-dimethyl-4-pyridinyl) methoxy]phenyl]-3-methyl-2-oxo-1-pyrrolidinyl]-2-(hydroxyamino)-2-oxoethyl]-1-piperidinecarboxylate mono(trifluoroacetate)

(148a) Following a procedure analogous to example 117, the 1:1 mixture of lactams from (146a) (1.01 g, 1.79 mmol) was reacted with TFA to give the piperidine mono (trifluoroacetate) (1.22 g, 100%). MS found: (M+H)$^+$=466.

(148b) Following a procedure analogous to (49a), the piperidine from (148a) (75.4 mg, 0.109 mmol) was reacted with methyl chloroformate to give the crude carbamate. MS found: (M+H)$^+$=524.

(148c) Following a procedure analogous to step (92d), the crude ester from (148b) was reacted with hydroxylamine. The diastereomeric mixture was purified by reverse phase HPLC on a Dynamax C-18 semiprep column eluting an acetonitrile:water:TFA gradient, to give the slow moving isomer (14.1 mg). MS found: (M+H)$^+$=525.

Example 149

[1(R)]-α-[3-[4-[(2,6-dimethyl-4-pyridinyl)methoxy] phenyl]-3-methyl-2-oxo-1-pyrrolidinyl]-N-hydroxy-1-(methylsulfonyl)-4-piperidineacetamide mono (trifluoroacetate)

Beginning with the piperidine from (148a) and mathanesulfonyl chloride, example 149 was prepared in an analogous series of reactions to (49a) and (92d). MS found: (M+H)$^+$=545.

Example 150

[1(R)]-1-acetyl-α-[3-[4-[2,6-dimethyl-4-pyridinyl) methoxy]phenyl]-3-methyl-2-oxo-1-pyrrolidinyl]-N-hydroxy-4-piperidineacetamide mono (trifluoroacetate)

Beginning with the piperidine from (148a) and acetyl chloride, example 150 was prepared in an analogous series of reactions to (49a) and (92d). MS found: (M+H)$^+$=509.

Example 151

[1(R)]-1-(2,2-dimethyl-1-oxypropyl)-α-[3-[4-[(2,6-dimethyl-4-pyridinyl)methoxy]phenyl]-3-methyl-2-oxo-1-pyrrolidinyl]-N-hydroxy-4-piperidineacetamide mono(trifluoroacetate)

Beginning with the piperidine from (148a) and trimethylacetyl chloride, example 151 was prepared in an analogous series of reactions to (49a) and (92d). MS found: (M+H)$^+$=551.

Example 152

[1(R)]-α-[3-[4-[(2,6-dimethyl-4-pyridinyl)methoxy] phenyl]-3-methyl-2-oxo-1-pyrrolidinyl]-N-hydroxy-1-methyl-4-piperidineacetamide bis(trifluoroacetate)

Beginning with the piperidine from (148a) and formaldehyde, example 152 was prepared in an analogous series of reactions to (86a) and (92d). MS found: (M+H)$^+$=481.

Example 153

[1(R)]-α-[3-[4-[(2,6-dimethyl-4-pyridinyl)methoxy] phenyl]-3-methyl-2-oxo-1-pyrrolidinyl]-N-hydroxy-1-(1-methylethyl)-4-piperidineacetamide bis (trifluoroacetate)

Beginning with the piperidine from (148a), sodium cyanoborohydride and acetone, example 153 was prepared in an analogous series of reactions to (86a) and (92d). MS found: (M+H)$^+$=510.

Example 300

[1(R)]-3-amino-N-hydroxy-alpha-(2-methylpropyl)-2-oxo-3-[4-(2-quinolinylmethoxy)phenyl]-1-pyrrolidineacetamide mono(trifluoroacetate (300a) The p-hydroxy phenyl glycine (74.0 g, 442 mmol) was suspended in methanol (500 mL), cooled in an ice bath and HCl (gas) was bubbled through the reaction mixture for 20 minutes, to give a clear solution. The reaction was stirred at rt for 48 h, concentrated in vacuo to give an oil which was triturated with ethyl ether to give the p-hydroxy phenyl glycine methyl ester (95.8 g, 99%) as a white powder. MS found: (M+H)$^+$=182.

(300b) The Di-t-butyl dicarbonate (105.0 g, 484 mmol) dissolved in DMF (100 mL) was added slowly to an ice cooled solution of p-hydroxy phenyl glycine methyl ester (95.8 g, 440 mmol), triethyl amine (101 mL) and DMF (800 mL). The reaction was allowed to warm to rt, stirred for 5 h, partitioned between ethyl acetate and 1N HCl. The organic layer was washed with brine, dried over magnesium sulfate and was concentrated in vacuo to give the N-Boc product (123.0 g, 100%) an amber oil. MS (M−H)$^-$=280.

(300c) The N-Boc p-hydroxy phenyl glycine methyl ester from step (300a) (123.0 g, 440 mmol) was combined with benzyl bromide (90.3 g, 528 mmol), potassium carbonate (182 g, 1.3 mol) and acetone (800 mL) under a nitrogen atmosphere. The reaction was heated to reflux for 5 h, allowed to cool to rt, diluted with ethyl acetate (800 mL) filtered to remove the solids and concentrated in vacuo to give a semisolid residue. The product was crystallized from ethyl ether to give the N-Boc p-benzyloxy phenyl glycine methyl ester (106.7 g, 65%) as a white powder. MS (M+H)$^+$=372, (M+NH4)$^+$=389.

(300d) The LDA (148.1 mL, 296.2 mmol) was added slowly to a solution of the N-Boc p-benzyloxy phenyl glycine methyl ester from step (300c) (55.0 g, 148.1 mmol) in THF (500 mL) cooled to −78° C. under a nitrogen atmosphere. The reaction was allowed to stir for 1 h and the allyl bromide (17.9 g, 148.1 mmol) was added. The reaction was allowed to warm to 0° C. and stir for 1.5 h. The reaction was partitioned between ethyl dried over magnesium sulfate and concentrated in vacuo to give an oil. The product was purified by flash chromatography on silica gel (hexane:ethyl acetate, 85:15, v:v) to give olefin (50,1 g, 82%). MS (M+Na)$^+$=434.

(300e) Following a procedure analogous to that used in step (1c), the olefin from (300d) (5.0 g, 11.37 mmol) was oxidized to the aldehyde. The product was purified by flash chromatography on silica gel (hexane:ethyl acetate, 70:30, v:v) to give the desired aldehyde (4.6 g, 98%). MS (M+Na)$^+$=436.

(300f) The aldehyde from (300e) (4.0 g, 9.67 mmol) was combined with leucine methyl ester hydrochloride (2.1 g, 11.6 mmol) and DIEA (1.49 g, 11.6 mmol) in 1,2 1,2-dichloroethane (50 mL) at rt and stirred for 1 h. To this solution the sodium triacetoxyborohydride (3.1 g, 14.5 mmol) was added. The reaction was stirred for 2 h, diluted with methylene chloride washed with brine, dried over magnesium sulfate and concentrated in vacuo, to give the amine (5.2 g, 100%) as a clear oil. MS (M+H)$^+$=543.

(300g) The amine from (300f) (5.2 g, 9.67 mmol) was dissolved in toluene (100 mL) under a nitrogen atmosphere and was heated to 90° C. for 4 h. The reaction was allowed to cool to rt, concentrated in vacuo to give a crude oil which was purified by flash chromatography on silica gel (hexane: ethyl acetate, 85:15, v:v) to give the desired lactam as two separated diastereomers (4.8 g, 97%) as a glass. MS (M+H)$^+$=511.

(300h) The lactam from (300g) (2,6 g, 3.9 mmol) was dissolved in methanol (50 mL), degassed with nitrogen, 10% Pd/C was added and the reaction was charged to 50 PSI hydrogen. The reaction was shaken for 3 h, filtered through celite to remove the catalyst, concentrated in vacuo to give the phenol product (1.6 g, 100%) as a white foam. MS (M+H)$^+$=421, MS (M+Na)$^+$=443.

(300i) The phenol product from (300h) (0.15 g, 0.35 mmol) was combined with 2(chloromethyl)quinoline (0.15 g, 0.71 mmol), cesium carbonate (3 eq) and sodium iodide in acetone (15 mL), then heated to reflux. The reaction was heated for 3 h, cooled, diluted with ethyl acetate, filtered to remove the solids and concentrated in vacuo to give a crude oil. The product was purified by flash chromatography on silica gel (methylene chloride:ethyl acetate, 80:20, v:v) to give the desired lactam product (0.15 g, 76%) as a white foam. MS (M+H)$^+$=562 (M−NH2)$^+$=445.

(300j) The N-Boc lactam from (300i) (0.14 g, 0.25 mmol) was dissolved in methylene chloride (2 mL) and TFA (2 mL) under a nitrogen atmosphere. The reaction was stirred for 2 h, concentrated in vacuo to give the expected amino lactam (0.14 g, 100%) as an oil. MS (M+H)$^+$=462, (M−NH2)$^+$=445.

(300k) Following a procedure analogous to that used in step (1f), the methyl ester amino lactam product from (300j) (0.14 g, 0.30 mmol) was converted to the crude hydroxamic acid which was purified by reverse phase HPLC on a Vydac C-18 semiprep column eluting an acetonitrile-:water:TFA gradient, to give the hydroxamic acid product (0.085 g, 49%) as a white amorphous solid. MS (M+H)$^+$= 463, (M−NH2)$^+$=446.

Example 301

[1(R)]-3-amino-3-[4-[(3,5-dimethylphenyl)methoxy] phenyl]-N-hydroxy-alpha-methyl-2-oxo-1-pyrrolidineacetamide mono(trifluoroacetate)

(301a) Following the procedures analogous to that used for the preparation of example (300), but using alanine methyl ester in step (300f) and 3,5-dimethyl benzyl bromide in step (300i), the crude hydroxamic acid was prepared. The product was purified by reverse phase HPLC on a Vydac C-18 semiprep column eluting an acetonitrile:water:TFA gradient, to give the hydroxamic acid product (0.021 g, 42%) as a white amorphous solid. MS (M+H)$^+$=398, (M−NH2)$^+$=381.

Example 302

[1(R)]-3-[4-[(3,5-dimethylphenyl)methoxy]phenyl-3-[[(ethylamino]carbonyl]amino]-N-hydroxy-alpha-methyl-2-oxo-1-pyrrolidineacetamide (302a) Following the procedures analogous to that used for the preparation of example (300), but using alanine methyl ester in step (300f) and 3,5-dimethyl benzyl bromide in step (300i), the amino lactam methyl ester from step (j) was prepared and purified by crystallization from ethyl ether (0.28 g, 40%). MS (M+Na)$^+$=419, (M−NH2)$^+$=380.

(302b) The ethyl isocyanate (0.0035 g, 0.05 mmol) was added to a solution of amino lactam methyl ester (302a) (0.025 g, 0.05 mmol), methylene chloride (1 mL) and N-methyl morpholine (2 eq) at rt under a nitrogen atmosphere. After stirring for 1 h the reaction was concentrated in vacuo to give the ethyl urea (0.023 g, 98%) as a viscous oil. MS (M+H)$^+$=468.

(302c) Following a procedure analogous to that used in step (1f), the ethyl urea lactam methyl ester product from (302b) (0.023 g, 0.049 mmol) was converted to the crude hydroxamic acid which was purified by reverse phase HPLC on a Vydac C-18 semiprep column eluting an acetonitrile:water:TFA gradient, to give the title compound (0.015 g, 64%) as a white amorphous solid. MS (M+Na)⁺=491.

Example 303

[1(R)]-3-[4-[(3,5-dimethylphenyl)methoxy]phenyl]-N-hydroxy-alpha-methyl-3-[(methylsulfonyl)amino]-2-oxo-1-pyrrolidineacetamide

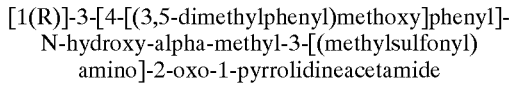

(303a) Following the procedures analogous to that used for the preparation of example (302), but using methane sulfonyl chloride in step (302b) the crude hydroxamic acid was prepared. The product was purified by reverse phase HPLC on a Vydac C-18 semiprep column eluting an acetonitrile:water:TFA. gradient, to give the title compound (0.010 g, 35%) as a white amorphous solid. MS (M+Na)⁺=498.

Example 304

[1(R)]-N-[3-[4-[(3,5-dimethylphenyl)methoxy]phenyl]-1-[2-(hydroxyamino)-1-methyl-2-oxoethyl]-2-oxo-3-pyrrolidinyl]-3-[pyridineacetamide mono (trifluoroacetate)

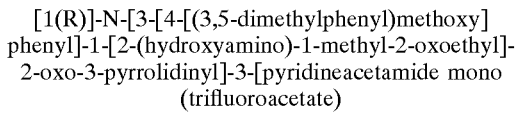

(304a) The amino lactam methyl ester (302a) (0.05 g, 0.098 mmol) was combined with 3-pyridinyl acetic acid (0.026 g, 0.15 mmol), HATU (0.057 g, 0.15 mmol), NMM (3 eq), and DMF (1 mL) at rt under nitrogen atmosphere. The reaction was stirred for 18 h, partitioned between ethyl acetate and 1 N HCl. The organic layer was washed with brine, dried over MgSO4, and concentrated in vacuo to give the amide product as a crude oil. MS (M+H)⁺=515, MS (M+Na)⁺=538.

(304b) Following a procedure analogous to that used in step (1f), the pyridinyl acetamide lactam methyl ester from step (304a) (0.05 g, 0.098 mmol) was converted to the crude hydroxamic acid which was purified by reverse phase HPLC on a Vydac C-18 semiprep column eluting an acetonitrile:water:TFA gradient, to give the title compound (0.025 g, 49%) as a white amorphous solid. MS (M+H)⁺=517.

Example 305

[1(R)]-N-[3-[4-[(3,5-dimethylphenyl)methoxy]phenyl]-1-[2-(hydroxyamino)-1-methyl-2-oxoethyl]-2-oxo-3-pyrrolidinyl-4-pyridinecarboxamide mono (trifluoroacetate)

(305a) Following the procedures analogous to that used for the preparation of example (302), but using isonicotinoyl chloride in step (302b) the crude hydroxamic acid was prepared. The product was purified by reverse phase HPLC on a Vydac C-18 semiprep column eluting an acetonitrile:water:TFA gradient, to give the title compound (0.035 g, 71%) as a white amorphous solid. MS (M+H)⁺=503.

Example 306

[1(R)]-3-amino-3-[4-[(2,6-dichloro-4-pyridinyl)methoxy]phenyl]-N-hydroxy-alpha-methyl-2-oxo-1-pyrrolidineacetamide bis(trifluoroacetate)

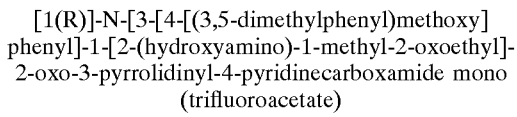

(306a) Following the procedures analogous to that used for the preparation of example (300), but using alanine methyl ester in step (300f) and 3,5-dichloro-4-picolyl chloride hydrochloride in step (300i), the crude hydroxamic acid was prepared. The product was purified by reverse phase HPLC on a Vydac C-18 semiprep column eluting an acetonitrile:water:TFA gradient, to give the title compound (0.045 g, 33%) as a white amorphous solid. MS (M−H)⁻=437, 439.

Example 307

[1(R)]-N-[3-[4-[(2,6-dichloro-4-pyridinyl)methoxy]phenyl]-1-[2-(hydroxyamino)-1-methyl-2-oxoethyl]-2-oxo-3-pyrrolidinyl]-4-pyridinecarboxamide bis (trifluoroacetate)

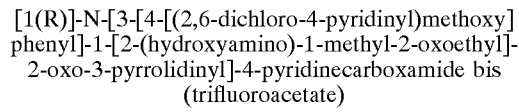

(307a) Following the procedures analogous to that used for the preparation of example (300), but using alanine methyl ester in step (300f) and 3,5-dichloro-4-picolyl chloride hydrochloride in step (300i), the amino lactam methyl ester from step (j) was reacted with isonicotinoyl chloride similar to example (305a), to prepare the title compound. The product was purified by reverse phase HPLC on a Vydac C-18 semiprep column eluting an acetonitrile:water:TFA gradient, to give the hydroxamic acid product (0.02 g, 20%) as a white amorphous solid. MS (M+H)⁺=544, 546.

Example 308

[1(R)]-3-[4-[(2,6dichloro-4-pyridinyl)methoxy]phenyl]-3-[[(ethylamino)carbonyl]amino]-N-hydroxy-alpha-methyl-2-oxo-1-pyrrolidineacetamide mono(trifluoroacetate)

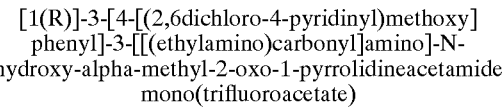

(308a) Following the procedures analogous to that used for the preparation of example (300), but using alanine methyl ester in step (300f) and 3,5-dichloro-4-picolyl chloride hydrochloride in step (300i), the amino lactam methyl ester from step (j) was reacted with ethyl isocyanate similar to example (302b), to prepare the title compound. The product was purified by reverse phase HPLC on a Vydac C-18 semiprep column eluting an acetonitrile:water:TFA gradient, to give the hydroxamic acid product (0.04 g, 25%) as a white amorphous solid. MS (M+Na)⁺=532, 534.

Example 309

[1(R)]-1,1-dimethylethyl [2-[[3-[4-[(2,6-dichloro-4-pyridinyl)methoxy]phenyl]-1-[2-(hydroxyamino)-1-methyl-2-oxoethyl]-2-oxo-3-pyrrolidinyl]amino]-2-oxoethyl]carbamate mono(trifluoroacetate)

(309a) Following the procedures analogous to that used for the preparation of example (300), but using alanine methyl ester in step (300f) and 3,5-dichloro-4-picolyl chloride hydrochloride in step (300i), the amino lactam methyl ester from step (j) was reacted with N-Boc glycine acid similar to example (304a), to prepare the title compound. The product was purified by reverse phase HPLC on a Vydac C-18 semiprep column eluting an acetonitrile:water:TFA gradient, to give the hydroxamic acid product (0.02 g, 25%) as a white amorphous solid. MS (M+Na)⁺=618,620.

Example 310

[1(R)]-3-[(aminoacetyl)amino]-3-[4-[(2,6-dichloro-4-pyridinyl)methoxy]phenyl]-N-hydroxy-alpha-methyl-2-oxo-1-pyrrolidineacetamide bis (trifluoroacetate)

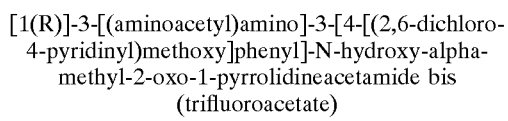

(310a) The N-Boc glycine compound example (309) was dissolved in methylene chloride (0.5 mL) and TFA (0.5 mL) at rt under a nitrogen atmosphere. The reaction was stirred for 1 h, concentrated in vacuo to give a residue which was triturated with ethyl ether to give the title compound (0.01 g 82%) as a white solid. MS (M+H)$^+$= 496,498.

Example 311

[1(R)]-N-[3-[4-[(2,6-dichloro-4-pyridinyl)methoxy] phenyl]-1-[2-(hydroxyamino)-1-methyl-2-oxoethyl]-2-oxo-3-pyrrolidinyl]-3-pyridineacetamide bis (trifluoroacetate)

(311a) Following the procedures analogous to that used for the preparation of example (300), but using alanine methyl ester in step (300f) and 3,5-dichloro-4-picolyl chloride hydrochloride in step (300i), the amino lactam methyl ester from step (j) was reacted with 3-pyridinyl acetic acid similar to example (304a), to prepare the title compound. The product was purified by reverse phase HPLC on a Vydac C-18 semiprep column eluting an acetonitrile:water:TFA-gradient, to give the hydroxamic acid product (0.045 g, 23%) as a white amorphous solid. MS (M+H)$^+$=558, 560.

Example 312

[1(R)]-3-[4-[(2,6-dichloro-4-pyridinyl)methoxy] phenyl]-N-hydroxy-alpha-methyl-2-oxo-3 [[[(phenylmethyl)amino]carbonyl]amino]-1-pyrrolidineacetamide (312a) Following the procedures analogous to that used for the preparation of example (300), but using alanine methyl ester in step (300f) and 3,5-dichloro-4-picolyl chloride hydrochloride in step (300i), the amino lactam methyl ester from step (j) was reacted with benzyl isocyanate similar to example (302b), to prepare the title compound. The product was purified by reverse phase HPLC on a Vydac C-18 semiprep column eluting an acetonitrile:water:TFA gradient, to give the hydroxamic acid product (0.05 g, 33%) as a white amorphous solid. MS (M+Na)$^+$=594, 596.

Example 313

[1(R)]-3-[4-[(2,6-dichloro-4-pyridinyl)methoxy] phenyl]-3-[[[(2,4-dimethoxyphenyl)amino]carbonyl] amino]-N-hydroxy-alpha-methyl-2-oxo-1-pyrrolidineacetamide (313a) Following the procedures analogous to that used for the, preparation of example (300), but using alanine methyl ester in step (300f) and 3,5-dichloro-4-picolyl chloride hydrochloride in step (300i), the amino lactam methyl ester from step (j) was reacted with 2,4-dimethoxy phenylisocyanate similar to example (302b), to prepare the title compound. The product was purified by reverse phase HFLC on a Vydac C-18 semiprep column eluting an acetonitrile:water:TFA gradient, to give the hydroxamic acid product (0.035 g, 27%) as a white amorphous solid. MS (M+Na)$^+$=640,642.

Example 314

[1(R)]-3-[4-[-(2,6-dichloro-4-pyridinyl)methoxy] phenyl]-N-hydroxy-alpha-methyl-2-oxo-3-[[(phenylamino)carbonyl]amino]-1-pyrrolidineacetamide (314a) Following the procedures analogous to that used for the preparation of example (300), but using alanine methyl ester in step (300f) and 3,5-dichloro-4-picolyl chloride hydrochloride in step (300i), the amino lactam methyl ester from step (j) was reacted with phenylisocyanate similar to example (302b), to prepare the title compound. The product was purified by reverse phase HPLC on a Vydac C-18 semiprep column eluting an acetonitrile:water:TFA gradient, to give the hydroxamic acid product (0.016 g, 13%) as a white amorphous solid. MS (M+Na)$^+$=580,582.

Example 315

[1(R)]-1,1-dimethylethyl [3-[4-[(2,6-dichloro-4-pyridinyl)methoxy]phenyl]-1-[2-(hydroxyamino)-1-methyl-2-oxoethyl]-2-oxo-3-pyrrolidinyl]carbamate (315a) Following the procedures analogous to that used for the preparation of example (300), but using alanine methyl ester in step (300f) and 3,5-dichloro-4-picolyl chloride hydrochloride in step (300i), the N-Boc lactam methyl ester from step (i) was reacted with hydroxylamine hydrochloride similar to example (1f), to prepare the title compound. The product was purified by reverse phase HPLC on a Vydac C-18 semiprep column eluting an acetonitrile:water:TFA gradient, to give the hydroxamic acid product (0.04 g, 42%) as a white amorphous solid. MS (M+Na)$^+$=561, 563.

Example 316

[1(R)]-3-(4-[(2,6-dichloro-4-pyridinyl)methoxy] phenyl]-N-hydroxy-alpha-methyl-3-[[[[2-(4-morpholinyl)ethyl]amino]carbonyl]amino]-2-oxo-1-pyrrolidineacetamide (316a) Following the procedures analogous to that used for the preparation of example (300), but using alanine methyl ester in step (300f) and 3,5-dichloro-4-picolyl chloride hydrochloride in step (300i), the amino lactam methyl ester from step (j) (0.10 g, 0.18 mmol) was dissolved in methylene chloride (3 mL) and saturated sodium bicarbonate solution (1 mL), cooled to 0° C., phosgene in toluene solution was added and the reaction was stirred vigorously for 15 minutes. The reaction was diluted with methylene chloride washed with brine, dried over magnesium sulfate and concentrated to give an oil. The oil was taken up in methylene chloride (2 mL) and the amino ethyl morpholine (0.047 g, 0.36 mmol) was added. The reaction was stirred for 0.5 h at rt and was concentrated to give the urea (0.09 g, 84%) as a crude product. MS (M+H)$^+$=594, 596.

(316b) The urea lactam methyl ester from step (316a) was reacted with hydroxylamine hydrochloride similar to example (1f), to prepare the title compound. The product was purified by reverse phase HPLC on a Vydac C-18 semiprep column eluting an acetonitrile:water:TFA gradient, to give the hydroxamic acid product (0.03 g, 28%) as a white amorphous solid. MS (M+H)$^+$=595, 597.

Example 317

[1(R)]-1,1-dimethylethyl N-[[[3-[4-[(2,6-dichloro-4-pyridinyl)methoxy]phenyl]-1-(2-(hydroxyamino)-1-methyl-2-oxoethyl]-2-oxo-3-pyrrolidinyl]amino] carbonyl]glycine (317a) Following the procedures analogous to that used for the preparation of example (300), but using alanine methyl ester in step (300f) and 3,5-dichloro-4-picolyl chloride hydrochloride in step (300i), the amino lactam methyl ester from step (j) was reacted with t-butyl glycine ester similar to steps (316a and 316b), to prepare the title compound. The product was purified by reverse phase HPLC on a Vydac C-18 semiprep column eluting an acetonitrile:water:TFA gradient, to give the hydroxamic acid product (0.04 g, 37%) as a white amorphous solid. MS (M+Na)⁺=618, 620.

Example 318

[1(R)]-3-[4-[(2,6-dichloro-4-pyridinyl)methoxy]phenyl]-N-hydroxy-alpha-methyl-2-oxo-3-[[(2-thiazolylamino)carbonyl]amino]-1-pyrrolidineacetamide

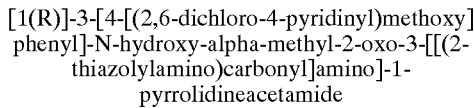

(318a) Following the procedures analogous to that used for the preparation of example (300), but using alanine methyl ester in step (300f) and 3,5-dichloro-4-picolyl chloride hydrochloride in step (300i), the amino lactam methyl ester from step (j) was reacted 2-amino thiazole similar to steps (316a and 316b), to prepare the title compound. The product was purified by reverse phase HPLC on a Vydac C-18 semiprep column eluting an acetonitrile:water:TFA gradient, to give the hydroxamic acid product (0.045 g, 44%) as a white amorphous solid. MS (M+H)⁺=565, 567.

Example 319

[1(R)]-3-[4-[(2,6-dichloro-4-pyridinyl)methoxy]phenyl]-N-hydroxy-alpha-methyl-2-oxo-3-[[(4-pyridinylamino)carbonyl]amino]-1-pyrrolidineacetamide mono(trifluoroacetate)

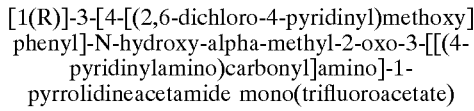

(319a) Following the procedures analogous to that used for the preparation of example (300), but using alanine methyl ester in step (300f) and 3,5-dichloro-4-picolyl chloride hydrochloride in step (300i), the amino lactam methyl ester from step (j) was reacted with 4-amino pyridine similar to steps (316a and 316b), to prepare the title compound. The product was purified by reverse phase HPLC on a Vydac C-18 semiprep column eluting an acetonitrile:water:TFA gradient, to give the hydroxamic acid product (0.035 g, 32%) as a white amorphous solid. MS (M+Na)⁺=581, 583.

Example 320

[1(R)]-3-[4-[(2,6-dichloro-4-pyridinyl)methoxy]phenyl]-N-hydroxy-3-[[[(3-hydroxyphenyl)amino]carbonyl]amino]-alpha-methyl-2-oxo-1-pyrrolidineacetamide

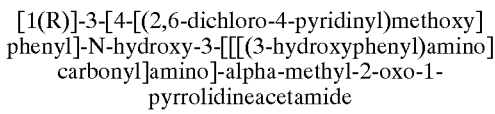

(320a) Following the procedures analogous to that used for the preparation of example (300), but using alanine methyl ester hydrochloride in step (300i), the amino lactam methyl ester from step (j) was reacted 3-hydroxy aniline similar to steps (316a and 316b), to prepare the title compound. The product was purified by reverse phase HPLC on a Vydac C-18 semiprep column eluting an acetonitrile:water:TFA gradient, to give the hydroxamic acid product (0.011 g, 14%) as a white amorphous solid. MS (M+Na)⁺=596,598.

Example 321

[1(R)]-3-[4-[(2,6-dichloro-4-pyridinyl)methoxy]phenyl]-3-[[[(2,3-dihydro-2-oxo-1H-benzimidazol-5-yl)amino]carbonyl]amino]-N-hydroxy-alpha-methyl-2-oxo-1-pyrrolidineacetamide

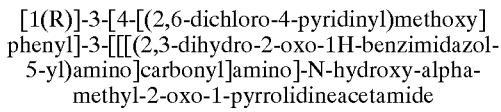

(321a) Following the procedures analogous to that used for the preparation of example (300), but using alanine methyl ester in step (300f) and 3,5-dichloro-4-picolyl chloride hydrochloride in step (300i), the amino lactam methyl ester from step (j) was reacted with 5-amino-1,3-dihydro-2H-benzimiazol-2-one similar to steps (316a and 316b), to prepare the title compound. The product wag purified by reverse phase HPLC on a Vydac C-18 semiprep column eluting an acetonitrile:water:TFA gradient, to give the hydroxamic acid product (0.02 g, 22%) as a white amorphous solid. MS (M+Na)⁺=636, 638.

Example 322

[1(R)]-3-amino-3-[4-[(2,6-dichloro-4-pyridinyl)methoxy]phenyl]-N-hydroxy-alpha-[2-(methylsulfonyl)ethyl]-2-oxo-1-pyrrolidineacetamide mono(trifluoroacetate)

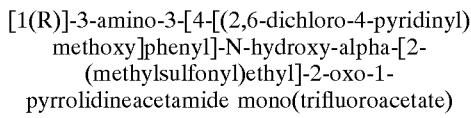

(322a) Following the procedures analogous to that used for the preparation of example (300), but using methionine methyl ester in step (300f), the sulphide from step (g) was oxidized (2.6 g, 5.10 mmol) by Oxone (12.55 g, 20.5 mmol) in methanol water solution, at rt. The methanol was removed in vacuo and the aqueous layer was extracted with methylene chloride (2×). The combined organic layer was washed with brine, dried over sulfone (2.6 g, 91%) as a white foam. MS (M+Na)⁺=583.

(322b) Following the procedures analogous to that used for the preparation of example (300) steps (h through k), but using the sulfide compound from step (322a) and 3,5-dichloro-4-picolyl chloride hydrochloride in step (300i), the title compound was prepared. The product was purified by reverse phase HPLC on a Vydac C-18 semiprep column eluting an acetonitrile:water:TFA gradient, to give the hydroxamic acid product (0.03 g, 30%) as a white amorphous solid. MS (M+H)⁺=532, 533.

Example 323

[1(R)]-3-amino-3-[4-[(2,6-dimethyl-4-pyridinyl)methoxy]phenyl]-N-hydroxy-alpha-[2-(methylsulfonyl)ethyl]-2-oxo-1-pyrrolidine acetamide mono(trifluoroacetate)

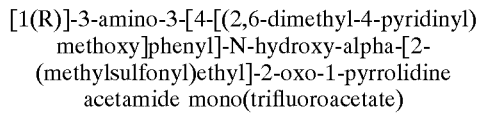

(323a) Following the procedures analogous to that used for the preparation of example (300), but using methionine methyl ester in step (300f), oxidation methods similar to example (322a) and 3,5-dimethyl-4-picolyl chloride hydrochloride in step (300i), the title compound was prepared. The product was purified by reverse phase HPLC on a Vydac C-18 semiprep column eluting an acetonitrile:water:TFA gradient, to give the hydroxamic acid product (0.035 g, 35%) as a white amorphous solid. MS (M+H)⁺=491.

Example 324

[1(R)]-3-[4-[(2,6-dichloro-4-pyridinyl)methoxy]phenyl]-N-hydroxy-alpha-[2-(methylsulfonyl)ethyl]-2-oxo-3-[[(2-thiazolylamino)carbonyl]amino]-1-pyrrolidineacetamide

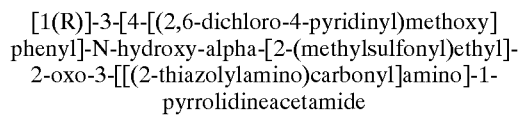

(324a) Following the procedures analogous to that used for the preparation of example (300), but using methionine methyl ester in step (300f), oxidation methods similar to example (322a) and 3,5-dichloro-4-picolyl chloride hydrochloride in step (300i), the amino lactam methyl ester from step (j) was reacted 2-amino thiazole similar to example (316a), to prepare HPLC on a Vydac C-18 semiprep column eluting an acetonitrile:water:TFA gradient, to give the hydroxamic acid product (0.054 g, 20%) as a white amorphous solid. MS (M+H)$^+$=657, 659.

Example 325

[1(R)]-3-[4-[(2,6-dimethyl-4-pyridinyl)methoxy]phenyl]-N-hydroxy-alpha-[2-(methylsulfonyl)ethyl]-2-oxo-3-[[2-thiazolylamino)carbonyl]amino]-1-pyrrolidineacetamide mono(trifluoroacetate)

(325a) Following the procedures analogous to that used for the preparation of example (300), but using methionine methyl ester in step (300f), oxidation methods similar to example (322a) and 3,5-dimethyl-4-picolyl chloride hydrochloride in step (300i), the amino lactam methyl ester from step (j) was reacted 2-amino thiazole similar to example (316a), to prepare the title compound. The product was purified by reverse phase HPLC on a Vydac C-18 semiprep column eluting an acetonitrile:water:TFA gradient, to give the hydroxamic acid product (0.055 g, 40%) as a white amorphous solid. MS (M+H)$^+$=617.

Example 326

[5(R)]-2-propenyl [5-[3-amino-3-[4-[(2,6-dichloro-4-pyridinyl)methoxy]phenyl]-2-oxo-1-pyrrolidinyl]-6-(hydroxyamino)-6-oxohexyl]carbamate mono (trifluoroacetate)

(326a) Following the procedures analogous to that used for the preparation of example (300), but using g-N-Alloc lysine methyl ester in step (300f) and 3,5-dichloro-4-picolyl chloride hydrochloride in step (300i), the title compound was prepared. The product was purified by reverse phase HPLC on a Vydac C-18 semiprep column eluting an acetonitrile:water:TFA gradient, to give the hydroxamic acid product (0.012 g, 18%) as a white amorphous solid. MS (M+H)$^+$=580, 582.

Example 327

[5(R)]-2-[propenyl [5-[3-amino-3-[4-[(2,6-dimethyl-4-pyridinyl)methoxy]phenyl]-2-oxo-1-pyrrolidinyl]-6-(hydroxyamino)-6-oxohexyl]carbamate bis (trifluoroacetate)

(327a) Following the procedures analogous to that used for the preparation of example (300), but using g-N-Alloc lysine methyl ester in step (300f) and 3,5-dimethyl-4-picolyl chloride hydrochloride in step (300i), the title compound was prepared. The product was purified by reverse phase HPLC on a Vydac C-18 semiprep column eluting an acetonitrile:water:TFA gradient, to give the hydroxamic acid product (0.025 g, 25%) as a white amorphous solid. MS (M+Na)$^+$=562.

Example 328

[1(R)]-3-amino-3-[4-[(2,6-dichloro-4-pyridinyl)methoxy]phenyl]-N-hydroxy-alpha-(2-methylpropyl)-2-oxo-1-[pyrrolidineacetamide mono (trifluoroacetate)

(328a) Following the procedures analogous to that used for the preparation of example (300), but using 3,5-dichloro-4-picolyl chloride hydrochloride in step (300i), the title compound was prepared. The product was purified by reverse phase HPLC on a Vydac C-18 semiprep column eluting an acetonitrile:water:TFA gradient, to give the hydroxamic acid product (0.03 g, 35%) as a white amorphous solid. MS (M+H)$^+$=481,483.

Example 329

[1(R)]-3-[4-[(2,6-dichloro-4-pyridinyl)methoxy]phenyl]-N-hydroxy-alpha-(2-methylpropyl)-2-oxo-3-[[(2-thiazolylamino)carbonyl]amino]-1-pyrrolidineacetamide (329a) Following the procedures analogous to that used for the preparation of example (300), but using 3,5-dichloro-4-picolyl chloride hydrochloride in step (300i), the amino lactam methyl ester from step (j) was reacted 2-amino thiazole similar to step (316a), the title compound was prepared. The product was purified by reverse phase HPLC on a Vydac C-18 semiprep column eluting an acetonitrile:water:TFA gradient, to give the hydroxamic acid product (0.01 g, 25%) as a white amorphous solid. MS (M+Na)$^+$=629,621.

Example 330

[1(R)]-3-[4-[(2,6-dimethyl-4-pyridinyl)methoxy]phenyl]-N-hydroxy-alpha-(2-methylpropyl)-2-oxo-3-[[(2-thiazolylamino)carbonyl]amino]-1-pyrrolidineacetamide mono(trifluoroacetate)

(330a) Following the procedures analogous to that used for the preparation of example (300), but using 3,5-dimethyl-4-picolyl chloride hydrochloride in step (300i), the amino lactam methyl ester from step (j) was reacted 2-amino thiazole similar to step (316a), the title compound was prepared. The product was purified by reverse phase HPLC on a Vydac C-18 semiprep column eluting an acetonitrile:water:TFA gradient to give the hydroxamic acid product (0.01 g, 20%) as a white amorphous solid. MS (M+H)$^+$=567.

Example 331

[1(R)]-3-[4-[(2,6-dichloro-4-pyridinyl)methoxy]phenyl]-N-hydroxy-alpha-(2-methylpropyl)-2-oxo-3-[[(2-pyridinylamino)carbonyl]amino]-1-pyrrolidineacetamide mono(trifluoroacetate)

(331a) Following the procedures analogous to that used for the preparation of example (300), but using 3,5-dichloro-4-picolyl chloride hydrochloride in step (300i), the amino lactam methyl ester from step (j) was reacted with 2-amino pyridine similar to step (316a), the title compound was prepared. The product was purified by reverse phase HPLC on a Vydac C-18 semiprep column eluting an acetonitrile:water:TFA gradient, to give the hydroxamic acid product (0.02 g, 20%) as a white amorphous solid. MS (M+Na)$^+$=623,625.

Example 332

[1(R)]-3-[4-[(2,6-dimethyl-4-pyridinyl)methoxy]phenyl]-N-hydroxy-alpha-(2-methylpropyl)-2-oxo-3-[(trifluoroacetyl)amino]-1-pyrrolidineacetamide mono(trifluoroacetate)

(332a) Following the procedures analogous to that used for the preparation of example (300), but using 3,5-dimethyl- 4-picolyl chloride hydrochloride in step (300i), the amino lactam methyl ester from step (j) was reacted with trifluoroacetic anhydride similar to step (302b), the title compound was prepared. The product was purified by reverse phase HPLC on a Vydac C-18 semiprep column eluting an acetonitrile:water:TFA gradient, to give the hydroxamic acid product (0.051 g, 25%) as a white amorphous solid. MS $(M+H)^+=537$.

Example 333

[1(R)]-3-[4-[(2,6-dimethyl-4-pyridinyl)methoxy] phenyl]-N-hydroxy-alpha-(2-methylpropyl)-2-oxo-3-[[(2-pyridinylamino)carbonyl]amino]-1-pyrrolidineacetamide bis(trifluoroacetate)

(333a) Following the procedures analogous to that used for the preparation of example (300), but using 3,5-dimethyl-4-picolyl chloride hydrochloride in step (300i), the amino lactam methyl ester from step (j) was reacted with 2-amino pyridine similar to step (316a), the title compound was prepared. The product was purified by reverse phase HPLC on a Vydac C-18 semiprep column eluting an acetonitrile:water:TFA gradient, to give the hydroxamic acid product (0.03 g, 25%) as a white amorphous solid. MS $(M+H)^+=561$.

Example 334

[1(R)]-3-[4-[(2,6-dichloro-4-pyridinyl)methoxy] phenyl]-N-hydroxy-alpha-(2-methylpropyl)-2-oxo-3-[[[(phenylsulfonyl)amino]carbonyl]amino]-1-pyrrolidineacetamide (334a) Following the procedures analogous to that used for the preparation of example (300), but using 3,5-dichloro-4-picolyl chloride hydrochloride in step (300i), the amino lactam methyl ester from step (j) was reacted with benzenesulfonyl isocyanate similar to step (302b), the title compound was prepared. The product was purified by reverse phase HPLC on a Vydac C-18 semiprep column eluting an acetonitrile:water:TFA gradient, to give the hydroxamic acid product (0.025 g, 20%) as a white amorphous solid. MS $(M+Na)^+=686,688$.

Example 335

[1(R)]-3-[4-[(2,6-dimethyl-4-pyridinyl)methoxy] phenyl]-N-hydroxy-alpha-(2-methylpropyl)-2-oxo-3-[[[(phenylsulfonyl)amino]carbonyl]amino]-1-pyrrolidineacetamide mono(trifluoroacetate)

(335a) Following the procedures analogous to that used for the preparation of example (300), but using 3,5-dimethyl-4-picolyl chloride hydrochloride in step (300i), the amino lactam methyl ester from step (j) was reacted with benzenesulfonyl isocyanate similar to step (302b), the title compound was prepared. The product was purified by reverse phase HPLC on a Vydac C-18 semiprep column eluting an acetonitrile:water:TFA gradient, to give the hydroxamic acid product (0.035 g, 30%) as a white amorphous solid. MS $(M+H)^+=624$.

Example 336

[1(R)]-3-[4-[(2,6-dichloro-4-pyridinyl)methoxy] phenyl]-N-hydroxy-3-[[[(3-methyl-5-isothiazolyl) amino]carbonyl]amino]-alpha-(2-methylpropyl)-2-oxo-1-[pyrrolidineacetamide (336a) Following the procedures analogous to that used for the preparation of example (300), but using 3,5-dichloro-4-picolyl chloride hydrochloride in step (300i), the amino lactam methyl ester from step (j) was reacted with 5-amino-3-methyl isothiazole similar to step (316a), the title compound was prepared. The product was purified by reverse phase HPLC on a gradient, to give the hydroxamic acid product (0.01 g, 20%) as a white amorphous solid. MS $(M+H)^+=621,623$.

Example 337

[1(R)]-3-[[(1H-benzimidazol-2-ylamino)carbonyl] amino]-3-[4-[(2,6-dichloro-4-[pyridinyl)methoxy] phenyl]-N-hydroxy-alpha-(2-methylpropyl)-2-oxo-1-pyrrolidineacetamide (337a) Following the procedures analogous to that used for the preparation of example (300), but using 3,5-dichloro-4-picolyl chloride hydrochloride in step (300i), the amino lactam methyl ester from step (j) was reacted with 2-amino benzimidazole similar to step (316a), the title compound was prepared. The product was purified by reverse phase HPLC on a Vydac C-18 semiprep column eluting an acetonitrile:water:TFA gradient, to give the hydroxamic acid product (0.005 g, 5%) as a white amorphous solid. MS $(M+H)^+=640, 642$.

Example 338

[1(R)]-3-[[(1H-benzimidazol-2-ylamino)carbonyl] amino]-3-[4-[(2,6-dimethyl-4-pyridinyl)methoxy] phenyl]-N-hydroxy-alpha-(2-methylpropyl)-2-oxo-1-pyrrolidineacetamide mono(trifluoroacetate)

(338a) Following the procedures analogous to that used for the preparation of example (300), but using 3,5-dimethyl-4-picolyl chloride hydrochloride in step (300i), the amino lactam methyl ester from step (j) was reacted with 2-amino benzimidazole similar to step (316a), the title compound was prepared. The product was purified by reverse phase HPLC on a Vydac C-18 semiprep column eluting an acetonitrile:water:TFA gradient, to give the hydroxamic acid product (0.015 g, 25%) as a white amorphous solid. MS $(M+H)^+=600$.

Example 339

[1(R)]-3-[4-[(2,6-dimethyl-4-pyridinyl)methoxy] phenyl]-N-hydroxy-alpha-(2-methylpropyl)-2-oxo-3-[[(phenylamino)carbonyl]amino]-1-pyrrolidineacetamide mono(trifluoroacetate)

(339a) Following the procedures analogous to that used for the preparation of example (300), but using 3,5-dimethyl-4-picolyl chloride hydrochloride in step (300i), the amino lactam methyl ester from step (j) was reacted with benzene isocyanate similar to step (302b), the title compound was prepared. The product was purified by reverse phase HPLC on a Vydac C-18 semiprep column eluting an acetonitrile:water:TFA gradient, to give the hydroxamic acid product (0.02 g, 20) as a white amorphous solid. MS $(M+H)^+=560$.

Example 340

[1(R)]-3-[4-[(2,6-dichloro-4-pyridinyl)methoxy] phenyl]-N-hydroxy-alpha-(2-methylpropyl)-2-oxo-3-[[(phenylamino)carbonyl]amino]-1-pyrrolidineacetamide (340a) Following the procedures analogous to that used for the preparation of example (300), but using 3,5-dichloro- 4-picolyl chloride hydrochloride in step (300i), the amino lactam methyl ester from step (j) was reacted with benzene isocyanate similar to step (302b), the title compound was prepared. The product was purified by reverse phase HPLC on a Vydac C-18 semiprep column eluting an acetonitrile:water:TFA gradient, to give the hydroxamic acid product (0.015 g, 20%) as a white amorphous solid. MS (M+Na)$^+$=622,624.

Example 341

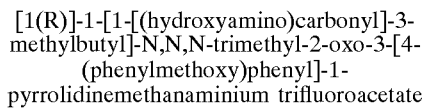
[1(R)]-1-[1-[(hydroxyamino)carbonyl]-3-methylbutyl]-N,N,N-trimethyl-2-oxo-3-[4-(phenylmethoxy)phenyl]-1-pyrrolidinemethanaminium trifluoroacetate (341a) Following the procedures analogous to that used for the preparation of example (300), but using benzyl bromide in step (300i), the amino lactam methyl ester from step (j) was reacted with methyl iodide and triethylamine in DMSO at rt. The reaction was partitioned between ethyl acetate and saturated sodium bicarbonate. The organic layer was washed with brine, dried over magnesium sulfate and concentrated in vacuo to give an oil. The product was purified by reverse phase HPLC on a Vydac C-18semiprep column eluting an acetonitrile:water:TFA gradient, to give the trimethyl amino lactam product (0.025 g, 61%) as an oil. MS (M+H)$^+$=453.

(341b) Following the procedures analogous to that used for the preparation of step (1f) the title compound was prepared. The product was purified by reverse phase HPLC on a Vydac C-18 semiprep column eluting an acetonitrile:water:TFA gradient, to give the hydroxamic acid product (0.01 g, 50%) as a white amorphous solid. MS (M+H)$^+$=454.

Example 342

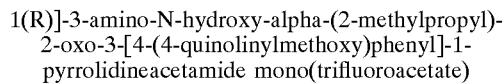
1(R)]-3-amino-N-hydroxy-alpha-(2-methylpropyl)-2-oxo-3-[4-(4-quinolinylmethoxy)phenyl]-1-pyrrolidineacetamide mono(trifluoroacetate)

(342a) Following the procedures analogous to that used for the preparation of example (300), but using 4-chloromethyl quinoline hydrochloride in step (300i), the title compound was prepared. The product was purified by reverse phase HPLC on a Vydac C-18 semiprep column eluting an acetonitrile:water:TFA gradient, to give the hydroxamic acid product (0.075 g, 52%) as a white amorphous solid. MS (M+H)$^+$=463, MS (M−NH2)$^+$=446.

Example 343

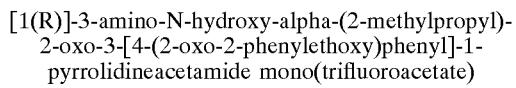
[1(R)]-3-amino-N-hydroxy-alpha-(2-methylpropyl)-2-oxo-3-[4-(2-oxo-2-phenylethoxy)phenyl]-1-pyrrolidineacetamide mono(trifluoroacetate)

(343a) Following the procedures analogous to that used for the preparation of example (300), but using 2-bromoacetophenone in step (300i), the title compound was prepared. The product was purified by reverse phase HPLC on a Vydac C-18 semiprep column eluting an acetonitrile:water:TFA gradient, to give the hydroxamic acid product (0.075 g, 52%) as a white amorphous solid. MS (M+H)$^+$=455.

Example 344

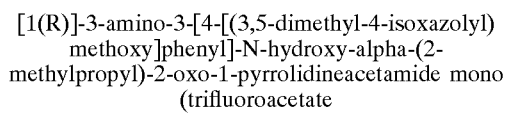
[1(R)]-3-amino-3-[4-[(3,5-dimethyl-4-isoxazolyl)methoxy]phenyl]-N-hydroxy-alpha-(2-methylpropyl)-2-oxo-1-pyrrolidineacetamide mono (trifluoroacetate (344a) Following the procedures analogous to that used for the preparation of example (300), but using 4-(chloromethyl)-3,5-dimethyl-isoxazole in step (300i), the title compound was prepared. The product was purified by reverse phase HPLC on a Vydac C-18 semiprep column eluting an acetonitrile:water:TFA gradient, to give the hydroxamic acid product (0.075 g, 53%) as a white amorphous solid. MS (M+H)$^+$=431, MS (M−NH2)$^+$=414.

Example 345

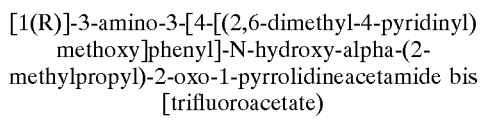
[1(R)]-3-amino-3-[4-[(2,6-dimethyl-4-pyridinyl)methoxy]phenyl]-N-hydroxy-alpha-(2-methylpropyl)-2-oxo-1-pyrrolidineacetamide bis [trifluoroacetate]

(345a) Following the procedures analogous to that used for the preparation of example (300), but using 3,5-dimethyl-4-picolyl chloride hydrochloride in step (300i), the title compound was prepared. The product was purified by reverse phase HPLC on a Vydac C-18 semiprep column eluting an acetonitrile:water:TFA gradient, to give the hydroxamic acid product (0.160 g, 55%) as a white amorphous solid. MS (M+H)$^+$=441.

Example 346

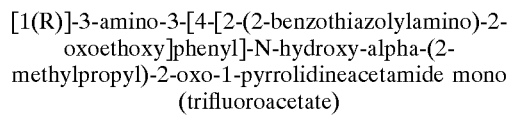
[1(R)]-3-amino-3-[4-[2-(2-benzothiazolylamino)-2-oxoethoxy]phenyl]-N-hydroxy-alpha-(2-methylpropyl)-2-oxo-1-pyrrolidineacetamide mono (trifluoroacetate)

(346a) Following the procedures analogous to that used for the preparation of example (300), but using 2-chloro-N (2-benzthiazole)acetamide in step (300i), the title compound was prepared. The product was purified by reverse phase HPLC on a Vydac C-18 semiprep column eluting an acetonitrile:water:TFA gradient, to give the hydroxamic acid product (0.08 g, 56%) as a white amorphous solid. MS (M+H)$^+$=512, MS (M−NH2)$^+$=495.

Example 347

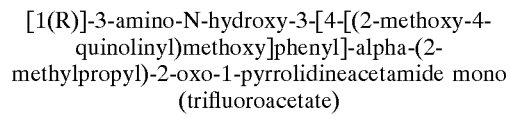
[1(R)]-3-amino-N-hydroxy-3-[4-[(2-methoxy-4-quinolinyl)methoxy]phenyl]-alpha-(2-methylpropyl)-2-oxo-1-pyrrolidineacetamide mono (trifluoroacetate)

(360a) Following the procedures analogous to that used for the preparation of example (300), but using 2-methoxy-4-bromomethyl quinoline in step (300i) the title compound was prepared. The product was purified by reverse phase HPLC on a Vydac C-18 semiprep column eluting an acetonitrile:water:TFA gradient, to give the hydroxamic acid product (0.12 g, 34%) as a white amorphous solid. MS (M+H)$^+$=493, MS (M−NH2)$^+$=476.

Example 348

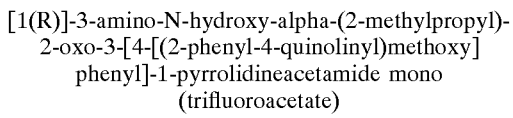
[1(R)]-3-amino-N-hydroxy-alpha-(2-methylpropyl)-2-oxo-3-[4-[(2-phenyl-4-quinolinyl)methoxy] phenyl]-1-pyrrolidineacetamide mono (trifluoroacetate)

(362a) Following the procedures analogous to that used for the preparation of example (300), but using 2-phenyl]-4-chloromethyl quinoline hydrochloride in step (300i) the title compound was prepared. The product was purified by reverse phase HPLC on a Vydac C-18 semiprep column eluting an acetonitrile:water:TFA gradient, to give the hydroxamic acid product (0.12 g, 34%) as a white amorphous solid. MS (M+H)+=539.

Example 349

[1(R)]-3-amino-3-[4-[(2,6-dimethyl-4-quinolinyl)methoxy]phenyl]-N-hydroxy-alpha-(2-methylpropyl)-2-oxo-1-pyrrolidineacetamide mono (trifluoroacetate)

(363a) Following the procedures analogous to that used for the preparation of example (300), but using 2,6-dimethyl-4-chloromethyl quinoline hydrochloride in step (300i) the title compound was prepared. The product was purified by reverse phase HPLC on a Vydac C-18 semiprep column eluting an acetonitrile:water:TFA gradient, to give the hydroxamic acid product (0.12 g, 34%) as a white amorphous solid. MS (M+H)+=491.

Example 350

[1(R)]-3-amino-3-[4-[(2-chloro-4-quinolinyl)methoxy]phenyl]-N-hydroxy-alpha-(2-(trifluoroacetate)

(350a) Following the procedures analogous to that used for the preparation of example (300), but using 2-chloro-4 (chloromethyl)quinoline hydrochloride in step (300i), the title compound was prepared. The product was purified by reverse phase HPLC on a Vydac C-18 semiprep column eluting an acetonitrile:water:TFA gradient, to give the hydroxamic acid product (0.03 g, 20%) as a white amorphous solid. MS (M+H)+=497,499.

Example 351

[1(R)]-3-amino-3-[4-[2-(2,5-dimethoxyphenyl)-2-(hydroxyimino)ethoxy]phenyl]-N-hydroxy-alpha-(2-methylpropyl)-2-oxo-1-pyrrolidineacetamide mono (trifluoroacetate)

(351a) Following the procedures analogous to that used for the preparation of example (300), but using 2-bromo-2',5'-dimethoxy acetophenone in step (300i), the title compound was prepared. The product was purified by reverse phase HPLC on a Vydac C-18 semiprep column eluting an acetonitrile:water:TFA gradient, to give the hydroxamic acid product (0.0 g, %) as a white amorphous solid. MS (M+H)+=515.

Example 352

[1(R)]-3-amino-N-hydroxy-3-[4-[(2-methylimidazol[1,2-a]pyridin-3-yl)methoxy]phenyl]-alpha-(2-methylpropyl)-2-oxo-1-pyrrolidineacetamide mono (trifluoroacetate)

(352a) Following the procedures analogous to that used for the preparation of example (300), the phenol from step (300h) (0.15 g, 0.35 mmol)was combined with 3-hydroxylmethyl-2-methyl-imidazoylpyridine (0.086 g, 0.53 mmol), DEAD, triphenylphosphine and benzene at rt. The reaction was stirred for 2 h, partitioned between ethyl acetate and water, the organic layer was washed with brine dried over magnesium sulfate and concentrated in vacuo to give an oil. The product was purified by flash chromatography on silica gel eluting ethyl acetate to give the alkylated product (0.088 g, 44%)as an oil. MS (M+H)+=565.

(352b) Following the procedures analogous to that used for the preparation of example (300) and step (1f) the compound from step (352a) was reacted to prepare the title compound. The product was purified by reverse phase HPLC on a Vydac C-18 semiprep column eluting an acetonitrile:water:TFA gradient, to give the hydroxamic acid product (0.065 g, 72%) as a white amorphous solid. MS (M+H)+=466.

Example 353

[1(R)]-3-amino-3-[4-[[1,4-dimethyl-2-(methylthio)-1H-imidazol-5-yl]methoxy]phenyl]-N-hydroxy-alpha-(2-methylpropyl)-2-oxo-1-pyrrolidineacetamide mono(trifluoroacetate)

(353a) Following the procedures analogous to that used for the preparation of example (300), the phenol from step (h) was treated with 2-thiomethyl-3N-5-dimethyl-4-hydroxymethyl imidazole similar to step (352a), to prepare the title compound. The product was purified by reverse phase HPLC on a Vydac C-18 semiprep column eluting an acetonitrile:water:TFA gradient, to give the hydroxamic acid product (0.09 g, 44%) as a white amorphous solid. MS (M+H)+=476.

Example 354

[1(R)]-3-amino-3-[4-[[1,5-dimethyl-2-(methylthio)-1H-imidazol-4-yl]methoxy]phenyl]-N-hydroxy-alpha-(2-methylpropyl)-2-oxo-1-pyrrolidineacetamide mono(trifluoroacetate)

(354a) Following the procedures analogous to that used for the preparation of example (300), the phenol from step (h) was treated with 2-thiomethyl-3N-methyl-4-methyl-5-hydroxymethyl imidazole similar to step (352a), to prepare the title compound. The product was purified by reverse phase HPLC on a Vydac C-18 semiprep column eluting an acetonitrile:water:TFA gradient, to give the hydroxamic acid product (0.04 g, 45%) as a white amorphous solid. MS (M+H)+=476.

Example 355

[1(R)]-3-amino-3-[4-[(2,4-dimethyl-5-thiazolyl)methoxy]phenyl]-alpha-(2-methylpropyl)-2-oxo-1-pyrrolidineacetamide mono(trifluoroacetate)

(355a) Following the procedures analogous to that used for the preparation of example (300), the phenol from step (h) was treated with 2,4-dimethyl-5-hydroxymethyl thiazole similar to step (352a), to prepare the title compound. The product was purified by reverse phase HPLC on a Vydac C-18 semiprep column eluting an acetonitrile:water:TFA gradient, to give the hydroxamic acid product (0.150 g, 75%) as a white amorphous solid. MS (M+H)+=447.

Example 356

[1(R)]-3-amino-N-hydroxy-alpha-(2-methylpropyl)-3-[4-[(2-methyl-4-quinolinyl)methoxy]phenyl]-2-oxo-1-pyrrolidineacetamide bis(trifluoroacetate)

(356a) Following the procedures analogous to that used for the preparation of example (300), but using 2-methyl-4-chloromethyl quinoline hydrochloride similar to step (300i), the title compound was prepared. The product was

Example 357

[1(R)]-3-amino-3-[4-[(2-chloro-4-quinolinyl)
methoxy]phenyl]-N-hydroxy-alpha-[2-
(methylsulfonyl)ethyl]-2-oxo-1-
[pyrrolidineacetamide mono(trifluoroacetate)

(357a) Following the procedures analogous to that used for the preparation of example (300), but using methionine methyl ester in step (300f), oxidation methods similar to example (322a), and 2-chloro-4-chloromethyl quinoline hydrochloride in step (300i), the title compound was prepared. The product was purified by reverse phase HPLC on a Vydac C-18 semiprep column hydroxamic acid product (0.12 g, 34%) as a white amorphous solid. MS $(M+H)^+$=547,549, MS $(M-NH_2)^+$530,532.

Example 358

[1(R)]-3-amino-N-hydroxy-3-[4-[(2-methyl-4-
quinolinyl)methoxy]phenyl]-alpha-(2-
(methylsulfonyl)ethyl]-2-oxo-1-
pyrrolidineacetamide mono(trifluoroacetate)

(358a) Following the procedures analogous to that used for the preparation of example (300), but using methionine methyl ester in step (300f), oxidation methods similar to step (322a) and 2-methyl-4-chloromethyl quinoline hydrochloride in step (300i), the title compound was prepared. The product was purified by reverse phase HPLC on a Vydac C-18 semiprep column eluting an acetonitrile:water:TFA gradient, to give the hydroxamic acid product (0.12 g, 34%) as a white amorphous solid. MS $(M+H)^+$=527.

Example 359

[1(R)]-3-amino-3-[4-[(3,5-dimethoxyphenyl)
methoxy]phenyl]-N-hydroxy-alpha-[2-
(methylsulfonyl)ethyl]-2-oxo-1-
pyrrolidineacetamide mono(trifluoroacetate)

(359a) Following the procedures analogous to that used for the preparation of example (300), but using methionine methyl ester in step (300f), oxidation methods similar to step (322a),3,5-dimethoxy benzyl bromide in step (300i) and the title compound was prepared. The product was purified by reverse phase HPLC on a Vydac C-18 semi-prep column eluting an acetonitrile:water:TFA gradient, to give the hydroxamic acid product (0.12 g, 34%) as a white amorphous solid. MS $(M+H)^+$=522, MS $(M-NH_2)^+$ 505.

Example 360

[1(R)]-3-amino-N-hydroxy-3-[4-[(2-methoxy-4-
quinolinyl)methoxy]phenyl]-alpha-(2-
(methylsulfonyl)ethyl]-2-oxo-1-
pyrrolidineacetamide mono(trifluoroacetate)

(361a) Following the procedures analogous to that used for the preparation of example (300), but using methionine methyl ester in step (300f), 2-methoxy-4-bromomethyl quinoline in step (300i) and oxidation similar to prep (322a) the title compound was prepared. The product was purified by reverse phase HPLC on a Vydac C-18 semi-prep column eluting an acetonitrile:water:TFA gradient, to give the hydroxamic acid product (0.12 g, 34%) as a white amorphous solid. MS $(M+H)^+$=543, MS $(M-NH_2)^+$ 526.

Example 361

[1(R)]-3-amino-3-[4-[(3,5-dimethoxyphenyl)
methoxy]phenyl]-N-hydroxy-alpha-(2-
methylpropyl)-2-oxo-1-[pyrrolidineacetamide mono
(trifluoroacetate)

(361a) Following the procedures analogous to that used for the preparation of example (3), but using 3,5-dimethoxy benzyl bromide in step (300i), the title compound was prepared. The product was purified by reverse phase HPLC on a Vydac C-18 semiprep column eluting an acetonitrile:water:TFA gradient, to give the hydroxamic acid product (0.12 g, 34%) as a white amorphous solid. MS $(M-NH_2)^+$=455.

Example 362

[1(R)]-3-amino-3-[4-[(2-methoxy-5-nitro-phenyl)
methoxy]phenyl]-N-hydroxy-alpha-(2-
methylpropyl)-2-oxo-1-pyrrolidineacetamide mono
(trifluoroacetate)

(362a) Following the procedures analogous to that used for the preparation of example (300), but using 2-methoxy-5-nitro benzylbromide in step (300i), the title compound was prepared. The product was purified by reverse phase HPLC on a Vydac C-18 semiprep column eluting an acetonitrile:water:TFA gradient, to give the hydroxamic acid product (0.065 g, 25%) as a white amorphous solid. MS $(M-NH_2)^+$=470.

Example 363

[1(R)]-3-amino-3-[4-[(5-quinolinyl)methoxy]
phenyl]-N-hydroxy-alpha-(2-methylpropyl)-2-oxo-1-
pyrrolidineacetamide mono(trifluoroacetate)

(363a) Following the procedures analogous to that used for the preparation of example (300), but using 5-chloromethyl quinoline in step (300i), the title compound was prepared. The product was purified by reverse phase HPLC on a Vydac C-18 semiprep column eluting an acetonitrile:water:TFA gradient, to give the hydroxamic acid product (0.055 g, 50%) as a white amorphous solid. MS $(M-NH_2)^+$=446.

Example 364

[1(R)]-3-amino-N-hydroxy-3-[4-[(2-methoxy-5-
nitro-phenyl)methoxy]phenyl]-alpha-[2-
(methylsulfonyl)ethyl]-2-oxo-1-
pyrrolidineacetamide mono(trifluoroacetate)

(364a) Following the procedures analogous to that used for the preparation of example (300), but using methionine methyl ester in step (300f), 2-methoxy-5-nitro-benzylbromide in step (300i) and oxidation similiar to step (322a) the title compound was prepared. The product was purified by reverse phase HPLC on a Vydac C-18 semiprep column eluting an acetonitrile:water:TFA gradient, to give the hydroxamic acid product (0.17 g, 60%) as a white amorphous solid. MS (M+H)⁺=543, MS (M−NH2)⁺=520.

Example 365

[1(R)]-3-amino-N-hydroxy-3-[4-[(2-nitro-4,5-dimethoxy-phenyl)methoxy]phenyl]-alpha-[2-(methylsulfonyl)ethyl]-2-oxo-1-pyrrolidineacetamide mono(trifluoroacetate)

(365a) Following the procedures analogous to that used for the preparation of example (300), but using methionine methyl ester in step (300f), 2-nitro-4,5-dimethoxy benzylbromide in step (300i) and oxidation similiar to step (322a) the title compound was prepared. The product was purified by reverse phase HPLC on a Vydac C-18 semiprep column eluting an acetonitrile:water:TFA gradient, to give the hydroxamic acid product (0.075 g, 42%) as a white amorphous solid. MS (M+H)⁺=567, MS (M−NH2)⁺=550.

Example 366

[1(R)]-3-amino-N-hydroxy-3-[4-[(2-phenyl]-4-quinolinyl)methoxy]phenyl]-alpha-[2-(methylsulfonyl)ethyl]-2-oxo-1-pyrrolidineacetamide mono(trifluoroacetate)

(366a) Following the procedures analogous to that used for the preparation of example (300), but using methionine methyl ester in step (300f), 2-phenyl-4-bromomethyl quinoline in step (300i) and oxidation similiar to step (322a) the title compound was prepared. The product was purified by reverse phase HPLC on a Vydac C-18 semiprep column eluting an acetonitrile:water:TFA gradient, to give the hydroxamic acid product (0.07 g, 25%) as a white amorphous solid. MS (M+H)⁺=589.

Example 367

[1(R)]-3-amino-N-hydroxy-3-[4-[(3,5-dimethyl-4-isoxazolyl)methoxy]phenyl]-alpha-2-(methylsulfonyl)ethyl]-2-oxo-1-pyrrolidineacetamide mono(trifluoroacetate)

(367a) Following the procedures analogous to that used for the preparation of example (300), but using methionine methyl ester in step (300f), 4-(chloromethyl)3,5-dimethyl-isoxazole in step (300i) and oxidation similiar to step (322a) the title compound was prepared. The product was purified by reverse phase MPLC on a Vydac C-18 semiprep column eluting an acetonitrile:water:TFA gradient, to give the hydroxamic acid product (0.12 g, 55%) as a white amorphous solid. MS (M+H)⁺=481, MS (M−NH2)⁺=464.

Example 368

[1(R)]-3-amino-3-[4-[(phenyl)methoxy]phenyl]-N-hydroxy-alpha-[(4-hydroxyphenyl)methyl]-2-oxo-1-pyrrolidineacetamide mono(trifluoroacetate)

(368a) Following the procedures analogous to that used for the preparation of example (300), but using tyrosine methyl ester in step (300f), the title compound was prepared. The product was purified by reverse phase HPLC on a Vydac C-18 semiprep column eluting an acetonitrile:water:TFA gradient, to give the hydroxamic acid product (0.10 g, 50%) as a white amorphous solid. MS (M+H)⁺=462, MS (M−NH2)⁺=445.

Example 369

[1(R)]-3-amino-3-[4-[(2-methyl-4-quinolinyl)methoxy]phenyl]-N-hydroxy-alpha-[(4-methoxyphenyl)methyl]-2-oxo-1-pyrrolidineacetamide mono(trifluoroacetate)

(369a) Following the procedures analogous to that used for the preparation of example (300), but using O-methyl tyrosine methyl ester in step (300f) and 2-methyl-4-bromomethyl quinoline in step (300i) the title compound was prepared. The product was purified by reverse phase HPLC on a Vydac C-18 semiprep column eluting an acetonitrile:water:TFA gradient, to give the hydroxamic acid product (0.075 g, 53%) as a white amorphous solid. MS (M+H)⁺=541, MS (M−NH2)⁺=524.

Example 370

[1(R)]-3-amino-3-[4-[(2,6-dimethyl-4-pyridinyl)methoxy]phenyl]-N-hydroxy-alpha-[(4-methoxyphenyl)methyl]-2-oxo-1-pyrrolidineacetamide mono(trifluoroacetate)

(370a) Following the procedures analogous to that used for the preparation of example (300), but using O-methyl tyrosine methyl ester in step (300f) and 2,6-dimethyl-4-bromomethyl pyridine in step (300i) the title compound was prepared. The product was purified by reverse phase HPLC on a Vydac C-18 semiprep column eluting an acetonitrile:water:TFA gradient, to give the hydroxamic acid product (0.095 g, 77%) as a white amorphous solid. MS (M+H)⁺=505, MS (M−NH2)⁺=488.

Example 371

[1(R)]-3-amino-3-[4-[(phenyl)methoxy]phenyl]-N-hydroxy-alpha-[(4-methoxyphenyl)methyl]-2-oxo-1-pyrrolidineacetamide mono(trifluoroacetate)

(371a) Following the procedures analogous to that used for the preparation of example (300), but using O-methyl tyrosine methyl ester in step (300f) the title compound was prepared. The product was purified by reverse phase HPLC on a Vydac C-18 semiprep column eluting an acetonitrile:water:TFA gradient, to give the hydroxamic acid product (0.051 g, 25%) as a white amorphous solid. MS (M+H)⁺=476, MS (M−NH2)⁺=459.

Example 450

[1(R)]-3-(aminomethyl)-3-[4-[(2,6-dimethyl-4-pyridinyl)methoxy]phenyl]-N-hydroxy-alpha-(2-methylpropyl)-2-oxo-1-pyrrolidineacetamide bis(trifluoroacetate)

(450a) 4-Hydroxybenzyl cyanide (2.5 g, 18.77 mmol), benzyl bromide (3.8 g, 22.5 mmol) and potassium carbonate (45 mmol) were combined in acetone (50 mL) and heated to reflux for 8 h. The reaction was allowed to cool to rt, diluted with ethyl acetate and filtered to remove the solids. The organic layer, was concentrated in vacuo to give an oil. The crude benzyl ether was purified by chromatography on silica gel eluting hexane: ethyl acetate (90:10, v:v) to give 4-benzyloxybenzyl cyanide (4.0 g, 95%) which solidified. MS (M+NH4)+=241.

(450b) The 4-benzyloxybenzyl cyanide from step (450a)(3.2 g, 14.33 mmol), sodium ethoxide (1.07 g, 15.7 mmol), and diethyl carbonate (2.23 g, 18.9 mmol) were combined in toluene (100 mL), heated to reflux for 3 h, cooled to rt, and partitioned between ethyl acetate and 1 N HCl. The organic layer was washed with brine, dried over magnesium sulfate and concentrated in vacuo. The crude was purified by chromatography on silica gel eluting hexane: ethyl acetate (80:20, v:v) to give ethyl 2-(4-benzyloxyphenyl)cyanoacetate (4.2 g, 99%) as an oil. MS (M+NH4)+=313.

(450c) The ethyl 2-(4-benzyloxyphenyl)cyanoacetate from step (450b) (3.7 g, 12.5 mmol) in DMF (20 mL) was added to a suspension of hexane washed sodium hydride (0.36 g, 15.0 mmol) in DMF (35 mL) cooled in an ice bath under nitrogen. The reaction was allowed to stir for 1 h and the allyl bromide (2.9 g, 24.0 mmol) was added. The reaction was allowed to warm to rt and was stirred for 1 h. The reaction was partitioned between ethyl acetate and 1 N HCl. The organic layer was washed with brine, dried over magnesium sulfate and concentrated to give an oil. The crude was purified by chromatography on silica gel eluting hexane: ethylacetate (90:10, v:v) to give ethyl 2-(4-benzyloxyphenyl)-2-allyl cyanoacetate (4.0 g, 95%) as an oil. MS (M+NH4)+=353.

(450d) Lithium hydroxide hydrate (1.13 g, 26.8 mmol) in water (20 mL) was added to a solution of ethyl 2-(4-benzyloxyphenyl)-2-allyl cyanoacetate from step (450c) (4.5 g, 13.42 mmol) in methanol (100 mL) at rt. The reaction was stirred for 5 h, partitioned between ethyl acetate and 1 N HCL. The organic layer was washed with brine, dried over magnesium sulfate and concentrated to give 2-(4-benzyloxyphenyl)-2-allyl cyanoacetic acid (4.1 g, 100%) as an oil. MS (M+NH4)+=325.

(450e) The 2-(4-benzyloxyphenyl)-2-allyl cyanoacetic acid from step (450d) (2.34 g, 12.88 mmol), TBTU(5.17 g, 16.11 mmol), NMM (4 eq) and DMF (50 mL) were combined and stirred for 15 minutes then the leucine methyl ester (2.34 g, 12.86 mmol) was added. The reaction was allowed to stir at rt for 18 h, partitioned between ethyl acetate and 1 N HCl. The organic layer was washed with brine, dried over magnesium sulfate and concentrated to give an oil. The crude was purified by chromatography on silica gel eluting hexane: ethyl acetate (80:20, v:v) to give the amide (1.9 g, 34%) as an oil. MS (M+NH4)+=452.

(450f) Ozone was bubbled through a solution of the amide from step (450e) (1.9 g, 4.37 mmol) and methylene chloride (50 mL) cooled to −78° C. After 20 minutes the reaction turned blue, oxygen and then nitrogen were bubbled through the reaction solution. The triphenylphosphine (1.15 g, 4.37 mmol) was added and the reaction was allowed to warm to rt and stirred for 4 h. The reaction was concentrated in vacuo to give an oil. The crude product was purified by chromatography on silica gel eluting ethyl ether (100%) to give the aldehyde (1.9 g, 100%) as an oil. MS (M+Na)+=459.

(450g) The aldehyde of step (450f) (1.9 g, 4.37 mmol) was dissolved in methylene chloride (15 mL), triethylsilane (5 mL), and TFA (2 mL) at rt under nitrogen. The reaction was stirred for 4 h and was concentrated in vacuo to give an oil. The crude product was purified by chromatography on silica gel eluting hexane: ethyl acetate (70:30, v:v) to give the cyano lactam (1.55 g, 68%) as an oil. MS (M+NH4)+=438.

(450h) The cyano lactam from step (450g) (1.55 g, 3.68 mmol) was dissolved in methanol (50 mL) degassed with nitrogen, then HCl (conc) (5 drops) and 10% Pd/C were added, the reaction was charged to 50 PSI hydrogen and shaken for 18 h. The catalyst was removed over celite, the organic layer concentrated in vacuo to give the aminomethyl lactam (1.2 g, 97%) as a foam. MS (M+Na)+=335.

(450i) The di-t-butyl dicarbonate (0.85 g, 3.88 mmol) was added to a solution of aminomethyl lactam from step (450h) (1.2 g, 3.24 mmol) and TEA (4 eq) in DMF (20 mL) at rt. The reaction was stirred for 4 h, partitioned between ethyl acetate and 1 N HCl. The organic layer was washed with brine, dried over magnesium sulfate and concentrated to give an oil. The crude was purified by chromatography on silica gel eluting hexane: ethyl acetate (50:50, v:v) to give the N-Boc aminomethyl lactam (0.9 g, 64%) as a foam. MS (M+Na)+=457.

(450j) Following the procedures analogous to that used for the preparation of example (300), but using 3,5-dimethyl-4-picolyl chloride hydrochloride in step (300i), the removal of the N-Boc protecting group similar to step (300j) the compound from step (450i) was converted to the aminomethyl lactam methyl ester (0.64 g, 100%) isolated as an oil. MS (M+H)+=454.

(450k) Following the procedures analogous to that used for the preparation of example (1f), the aminomethyl lactam methyl ester from step (450j) (0.10 g, 0.146 mmol) was converted to title compound. The product was purified by reverse phase HPLC on a Vydac C-18 semiprep column eluting an acetonitrile:water:TFA gradient, to give the hydroxamic acid product (0.03 g, 30%) as a white amorphous solid. MS (M+H)+=455.

Example 451

[1(R)]-3-[4-[(2,6-dimethyl-4-pyridinyl)methoxy]phenyl]-N-hydroxy-alpha-(2-methylpropyl)-2-oxo-3-[[[(2-thiazolylamino)carbonyl]amino]methyl]-1-pyrrolidineacetamide mono(trifluoroacetate)

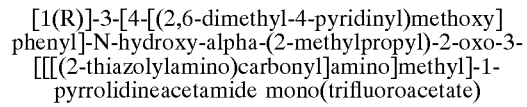

(451a) Following the procedures analogous to that used for the preparation of example (450), the aminomethyl lactam methyl ester from step (450j) was reacted with 2-isocyano thiazole similar to step (302b), to prepare the title compound. The product was purified by reverse phase HPLC on a Vydac C-18 semiprep column eluting an acetonitrile:water:TFA gradient, to give the hydroxamic acid product (0.075 g, 60%) as a white amorphous solid. MS (M+H)+= 581.

Example 452

[1(R)]-3-(aminomethyl)-3-[4-[(2,6-dichloro-4-pyridinyl)methoxy]phenyl]-N-hydroxy-alpha-methyl-2-oxo-1-pyrrolidineacetamide mono (trifluoroacetate)

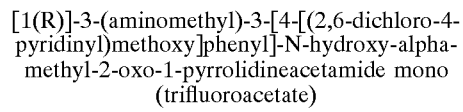

(452a) Following the procedures analogous to that used for the preparation of example (450), but using alanine methyl ester in step (450e) and 3,5-dichloro-4-picolyl chloride hydrochloride in step (450j), the title compound was prepared. The product was purified by reverse phase HPLC on a Vydac C-18 semiprep column eluting an acetonitrile:water:TFA gradient, to give the hydroxamic acid product (0.035 g, 35%) as a white amorphous solid. MS (M+H)+=453,455.

Example 453

[1(R)]-3-[4-[(2,6-dichloro-4-pyridinyl)methoxy]phenyl]-N-hydroxy-alpha-methyl-2-oxo-3-[[[2-thiazolylamino)carbonyl]amino]methyl]-1-pyrrolidineacetamide

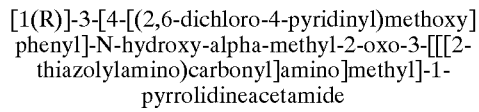

(453a) Following the procedures analogous to that used for the preparation of example (450), but using alanine methyl ester in step (450e) and 3,5-dichloro-4-picolyl chloride hydrochloride in step (450j), the aminomethyl lactam methyl ester similar step (450j) was reacted with 2-isocyano thiazole similar to step (302b), to prepare the title compound. The product was purified by reverse phase HPLC on a Vydac C-18 semiprep column eluting an acetonitrile:water:TFA gradient, to give the hydroxamic acid product (0.03 g, 47%) as a white amorphous solid. MS (M+H)$^+$=579,581.

Example 454

[1(R)]-4-[4-[(3,5-dimethylphenyl)methoxy]phenyl]-N-hydroxy-alpha,4-dimethyl-5-oxo-1-imidazolidineacetamide mono(trifluoroacetate)

(454a) Following the procedures analogous to that used for the preparation of example (300), but using 3,5-dimethyl benzyl bromide in step (300c) and methyl iodide in step (300d) the 4-(3,5-dimethylbenzyloxy) phenyl glycine methyl ester was prepared (1.65 g, 80%) as an oil. MS (M+H, -t-but)$^+$=357.

(454b) Following the procedures analogous to that used for step (450d), the methyl ester from step (454a) was converted to the 4-(3,5-dimethylbenzyloxy) phenyl glycine acid (1.5 g, 97%) as an oil. MS (M+Na)$^+$=422.

(454c) Following the procedures analogous to that used for step (450e), but using alanine methyl ester the 4-(3,5-dimethylbenzyloxy) phenyl glycine acid form step (454b) (1.5 g, 97%) was converted to the diamino acid. The crude was purified by chromatography on silica gel eluting hexane: ethyl acetate (75:25, v:v) to give the alanine-phenyl glycine compound (1.4 g, 75%) as a foam. MS (M+H)$^+$=485.

(454d) Following the procedures similar to that used for step (300j), the N-Boc group of the alanine-phenyl glycine compound from step (454c) was removed to give the amino compound (1.2 gm, 97%) as an oil. MS (M+H)$^+$=385, MS (M-NH2)$^+$=368.

(454e) Paraformaldehyde (0.006 g, 0.2 mmol) was added to a solution of the amino compound from step (454d) in toluene (5 mL) and NMM (2 eq), the reaction was heated to 80° C. for 4.5 h. The reaction was concentrated in vacuo to give the cyclic compound (0.1 g, 100%) as an oil. MS (M+H)$^+$=397.

(454f) Following the procedures similar to that used for step (1f), but using the cyclic compound from step (454e) the title compound was prepared. The product was purified by reverse phase HPLC on a Vydac C-18semiprep column eluting an acetonitrile:water:TFA gradient, to give the hydroxamic acid product (0.015 g, 20%) as a white amorphous solid. MS (M+H)$^+$=398.

Example 455

[1(R)]-3-[4-[(3,5-dimethylphenyl)methoxy]phenyl]-N-hydroxy-3-(hydroxymethyl)-alpha-methyl-2-oxo-1-pyrrolidineacetamide (455a) Methyl 4-hydroxyphenylacetate (8.0 g, 48.0 mmol), 3,5-dimethyl benzyl bromide (12.0 g, 60.0 mmol) and potassium carbonate (8.0 g, 58.0 mmol) were combined in acetone (120 mL) and heated to reflux for 8 h. The reaction was allowed to cool, diluted with ethyl acetate and filtered to remove the solids. The organic solvent was removed in vacuo to give an oil. The crude was purified by chromatography on silica gel eluting hexane: ethyl acetate (95:5, v:v) to give the methyl 4-(2,5-dimethylbenzyloxy)phenyl acetate compound (13.58 g, 99%) as an oil. MS (M+NH4)$^+$=302.

(455b) LDA (2.0 M in hexane, 3.5 mL, 7.0 mmol) was added to a solution of methyl 4-(2,5-dimethylbenzyloxy phenylacetate compound from step (455a), (2.0 g, 7.0 mmol) in THF (75 mL) cooled to −78° C. under a nitrogen atmosphere. The reaction was stirred for 40 minutes and the allyl bromide (0.73 mL, 8.4 mmol) was added. The reaction was stirred at −78° C. for 5 h, allowed to warm to rt overnight and was partitioned between ethyl acetate and 1N HCl. The organic layer was washed with brine, dried over magnesium sulfate and concentrated in vacuo. The crude was purified by chromatography on silica gel eluting hexane: ethyl acetate (93:2, v:v) to give the methyl 2-allyl-[4-(2,5-dimethylbenzyloxy)phenyl]acetate compound (1.2 g, 53%) as an oil. MS (M+NH4)$^+$=342.

(455c) Sodium methoxide (25% in methanol, 0.08 mL, 0.35 mmol) was added dropwise to a solution of the 2-allyl phenylacetate from step (455b) (1.2 g, 3.7 mmol) and parformaldehyde (0.135 g, 4.5 mmol) in DMSO (20 mL) at rt. The reaction was stirred for 1.2 h, diluted with water, acidified with 1N HCl, and extracted with ethyl acetate. The organic layer was washed with brine, dried over magnesium sulfate and concentrated in vacuo, to give the 2-hydroxymethylene-2-allyl phenylacetate (0.91 g, 68%) as an oil. MS (M+NH4−OCH3)$^+$=342.

(455d) Following the procedures analogous to that used for step (450d), the methyl ester from step (455c) was converted to the 2-hydroxymethylene-2-allyl phenylacetic acid (0.45 g, 53%) as an oil. MS (M+Na)$^+$=.

(455e) Following the procedures analogous to that used for step (450e), but using alanine methyl ester, the 2-hydroxymethylene-2-allyl phenylacetic acid from step (455d) (0.4 g, 1.2 mmol) was converted to the diamino acid. The crude was purified by chromatography on silica gel eluting hexane: ethyl acetate (75:25, v:v) to give the hydroxymethylene phenylacetamide compound (0.36 g, 71%) as an oil. MS (M−H)$^-$=339.

(455f) The hydroxymethylene compound from step (455e) (0.35 g, 0.82 mmol) was combined with TEA (1.3 eq), DMAP (0.025 g, 0.2 mmol), and t-butyldimethylchlorosilane (0.136 g, 0.90 mmol) in DMF (10 mL) at rt. The reaction was stirred for 48 h, diluted with ethyl acetate, washed with saturated ammonium chloride, dried over magnesium sulfate and concentrated to give an oil. The crude was purified by chromatography on silica gel eluting hexane: ethyl acetate (75:25, v:v) to give the O-t-butyldimethylsilyl hydroxymethylene compound (0.16 g, 36%) as an oil. MS (M+Na)$^+$=539.

(455g) Following the procedures analogous to that used for step (450f), but using allyl phenylacetamide from step (455f) (0.4 g, 0.74 mmol) the aldehyde was prepared. The crude was purified by chromatography on silica gel eluting hexane: ethyl ether (95:5, v:v) to give the aldehyde phenylacetamide compound (0.35 g, 87%) as an oil. MS (M+Na)$^+$=564.

(455h) Following the procedures analogous to that used for step (450g), but using aldehyde phenylacetamide compound from step (455g) (0.35 g, 0.65 mmol) the hydroxymethylene lactam was prepared. The crude was purified by chromatography on silica gel eluting methylene chloride: methanol (99:1, v:v) to give the hydroxymethylene lactam compound (0.185 g, 69%) as an oil. MS (M+H)$^+$=412.

(455i) Following the procedures analogous to that used for step (450d), but using hydroxymethylene lactam methyl ester compound from step (455h) (0.35 g, 0.65 mmol) the hydroxymethylene lactam acid (0.18 g, 100%) was prepared as an oil. MS (M+Na)$^+$=420.

(455i) Following the procedures analogous to that used for the preparation of step (450e), but using hydroxylamine hydrochloride and the hydroxymethylene lactam acid compound from step (455i) the title compound was prepared. The product was purified by reverse phase HPLC on a Vydac C-18 semiprep column eluting an acetonitrile:water:TFA gradient, to give the hydroxamic acid product (0.055 g, 30%) as a white amorphous solid. MS (M+Na)$^+$=435.

Example 456

[1(R)]-[3-[4-[(3,5-dimethylphenyl)methoxy]phenyl]-1-[2-(hydroxyamino)-1-methyl-2-oxoethyl]-2-oxo-3-pyrrolidinyl]methyl ethylcarbamate (456a) Following the procedures analogous to that used for the preparation of step (302b), but using ethyl isocyanate the hydroxymethylene lactam from step (455h), the lactam carbamate methyl ester compound (0.058 g, 100%) was prepared as an oil. MS (M+Na)$^+$=505.

(456b) Following the procedures similar to that used for step (1f), but using the carbamate lactam compound from step (456a), the title compound was prepared. The product was purified by reverse phase HPLC on a Vydac C-18 semiprep column eluting an acetonitrile:water:TFA gradient, to give the hydroxamic acid product (0.019 g, 36%) as a white amorphous solid. MS (M+Na)$^+$=506.

Example 457

[1(R)]-3-[4-[(2,6-dichloro-4-pyridinyl)methoxy]phenyl]-N-hydroxy-3-(hydroxymethyl)-alpha-methyl-2-oxo-1-pyrrolidineacetamide mono (trifluoroacetate)

(457a) Following the procedures analogous to that used for the preparation of step (300h), but using the hydroxymethylene lactam from step (455h) and 3,5-dichloro-4-picolyl bromide hydrochloride similar to step (300i) and procedures similar to steps (455i and 455j) the title compound was prepared. The product was purified by reverse phase HPLC on a Vydac C-18 semiprep column eluting an acetonitrile:water:TFA gradient, to give the hydroxamic acid product (0.03 g, 18%) as a white amorphous solid. MS (M+Na)$^+$=476,478.

Example 458

[1(R)]-3-[4-[(3,5-dimethylphenyl)methoxy]phenyl]-N-hydroxy-alpha,3-dimethyl-2-oxo-1-azetidineacetamide (458a) Following the procedures analogous to that used for the preparation of example (455), but using methyl iodide in step (455b) the hydroxymethylene acetamide methyl ester (0.10 g, 0.25 mmol) from step (e) was reacted with methanesulfonyl chloride (0.025 mL, 0.32 mmol) in pyridine at rt, to give the methanesulfonylmethyl acetamide (0.1 g, 84%) as an oil. MS (M+Na)$^+$=500.

(458b) The methanesulfonylmethyl acetamide (0.1 g, o,21 mmol) from step (458a) was combined with potassium carbonate (0.125 g, 0.9 mmol) in acetone (3 mL), heated to reflux for 6 h, allowed to cool to rt, diluted with ethyl acetate, filtered to remove the solids and concentrated to give an oil. The crude was purified by chromatography on silica gel eluting hexane: ethyl acetate (80:20, v:v) to give the beta-lactam compound (0.05 g, 63%) as an oil. MS (M+H)$^+$=382.

(458c) Following the procedures similar to that used for steps (455i and 455j), but using the beta-lactam compound from step (458b) the title compound was prepared. The product was purified by reverse phase HPLC on a Vydac C-18 semiprep column eluting an acetonitrile:water:TFA gradient, to give the hydroxamic acid product (0.03 g, 80%) as a white amorphous solid. MS (M+H)$^+$=381.

Example 459

[1(R)]-3-(5-[(3,5-dimethylphenoxy)methyl]-2-thiazolyl]-N-hydroxy-alpha,3-dimethyl-2-oxo-1-pyrrolidineacetamide (459a) Following the procedures similar to that used for step (300a), but using thiopheneacetic acid (7.5 g, 52.7 mmol), the methyl ester was prepared. The crude ester was purified by chromatography on silica gel eluting hexane: ethyl acetate (90:10, v:v) to give the methyl thiopheneacetate (7.5 g, 92%) as a foam. MS (M+H)$^+$=157.

(459b) Following the procedures similar to that used for step (455b), but using the methyl thiopheneacetate from step (459a), the methyl 2-allyl thiopheneacetate was prepared. The crude ester was purified by chromatography on silica gel eluting hexane: ethyl acetate (95:5, v:v) to give the methyl ally thiopheneacetate (5.9 g, 73%) as a foam. MS (M+H)$^+$=197.

(459c) Following the procedures similar to that used for step (455b), but using methyl iodide and the methyl allyl thiopheneacetate from step (459b), the methyl 2-allyl-2-methyl thiopheneacetate was prepared. The crude ester was purified by chromatography on silica gel eluting hexane: ethyl acetate (95:5, v:v) to give the methyl 2-ally-2-methyl thiopheneacetate (5.6 g, 89%) as an oil. MS (M+NH4)$^+$=228.

(459d) Following the procedures similar to that used for step (450d), but using methyl 2-ally-2-methyl thiopheneacetate from step (459c), the 2-allyl-2-methyl thiopheneacetic acid was prepared. The crude ester was purified by chromatography on silica gel eluting toluene: ethyl acetate:acetic acid (60:40:2, v:v:v) to give the thiopheneacetic acid (2.5 g, 99%) as an oil. MS (M+NH4)$^+$=214.

(459e) Following the procedures similar to that used for step (450e), but using 2-ally-2-methyl thiopheneacetic acid from step (459d) and alanine methyl ester, the thiopheneacetamide compound was prepared. The crude ester was purified by chromatography on silica gel eluting hexane: ethyl acetate (80:20, v:v) to give the thiopheneacetamide (1.5 g, 83%) as an oil. MS (M+NH4)$^+$=299.

(459f) Osmium tetraoxide (catalytic) was added to a solution of thiopheneacetamide compound from step (459e) (1.5 g, 5.3 mmol), N-methyl morpholine N-oxide (1.25 g, 10.6 mmol), THF (25 mL) and water (2 mL) at rt under a nitrogen atmosphere. The reaction was stirred overnight, poured into 10% NaHSO3 and 1N HCl (50 mL) and was extracted with ethyl acetate. The organic layer was washed with brine, dried over magnesium sulfate and concentrated to give an oil. The crude oil was dissolved in methylene chloride (25 mL) and water (5 mL). The NaIO4 (2.28 g, 10.6 mmol) was added and the reaction was stirred vigorously for 4 h. This was diluted with ethyl acetate, washed with brine, dried over magnesium sulfate and concentrated to give the aldehyde (1.5 g, 99%) as an oil. MS (M+H−H20)$^+$=266.

(459g) Following the procedures similar to that used for step (450g), but using aldehyde thiopheneacetacetamide from step (459f) the lactam compound was prepared. The crude ester was purified by chromatography on silica gel eluting hexane: ethyl acetate (70:30, v:v) to give the lactam thiophene (1.1 g, 77%) as an oil. MS (M+H)$^+$=268.

(459h) Phosphorous oxychloride (0.95 g, 6.17 mmol) was added slowly to a solution of lactam thiophene from step (451g), (1.1 g, 4.11 mmol) in DMF (0.45 g, 6.17 mmol) and heated to 85° C. for 4 h. The reaction was allowed to cool, partitioned between ethyl acetate and ice water. The organic layer was washed with brine, dried over magnesium sulfate and concentrated in vacuo to to the thiophene aldehyde (0.75 g, 62%) as an oil.

(459i) Sodium borohydride (0.059 g, 1.69 mmol) was added to a solution of thiophene aldehyde from step (459h) (0.5 g, 1.69 mmol) dissolved in THF (5 mL) and methanol (1 mL), at rt. The reaction was stirred for 20 minutes, partitioned between ethyl acetate and 1N HCl. The organic layer was washed with brine, dried over magnesium sulfate and concentrated in vacuo to give the 5-hydroxymethylene-thiophene (0.5 g, 100%) as an oil.

(459j) The 5-hydroxymethylene-thiophene from step (459i) (5.0 g, 1.69 mmol) was combined with carbon tetrabromide (0.67 g, 2.03 mmol), triphenylphosphine (0.53, 2.03 mmol) in methylene chloride (5 mL) at rt. The reaction was stirred for 4 h and became a dark solution. This was partitioned between methylene chloride and 1N HCl. The organic layer was washed with brine, dried over magnesium sulfate and concentrated in vacuo to give a dark oil. The product was purified by chromatography on silica gel eluting hexane: ethyl acetate (50:50, v:v), to give the 5-bromomethylene thiophene (0.15 g 25 %) as an oil. MS (M+H–Br+OCH3)$^+$=312.

(459k) Following the procedures similar to that used for step (300i), but using 5-bromomethylene thiophene from step (459j) and 3,5-dimethyl phenol, the lactam thiophene compound was prepared. The crude ester was purified by chromatography on silica gel eluting methylene chloride: ethyl acetate (95:5, v:v) to give the lactam thiophene (0.08 g, 47%) as an oil. MS (M+NH4)$^+$419.

(459l) Following the procedures similar to that used for steps (1f), but using the lactam thiophene compound from step (459k) the title compound was prepared. The product was purified by reverse phase HPLC on a Vydac C-18 semiprep column eluting an acetonitrile:water:TFA gradient, to give the hydroxamic acid product (0.015 g, 20%) as a white amorphous solid. MS (M+Na)$^+$=425.

Example 460

[1(R)]-4-[4-[(3,5-dimethylphenyl)methoxy]phenyl]-N-hydroxy-alpha-methyl-2,5-dioxo-4-(2-propenyl)-1-imidazolidineacetamide (460a) Following the procedures similar to that used for step (300j), but using N-Boc phenyl glycine from step (300c) (0.5 g, 1.13 mmol), the deprotected phenyl glycine compound (0.51 g, 99%) was prepared as an oil.

(460b) A solution of alanine methyl ester (0.046 g, 0.33 mmol) in methylene chloride (1 mL) and DIEA (0.130 mL) was added slowly to a solution of triphosgene (0.098 g, 0.33 mmol) in methylene chloride (2 mL) at rt. The reaction was stirred for 0.5 h and a solution of deprotected phenyl glycine from step (460a) in methylene chloride (1 mL) and DIEA (0.13 mL) was added. The reaction was stirred for 2 h, partitioned between ethyl acetate and 1N HCl. The organic layer was washed with brine, dried over magnesium sulfate and concentrated in vacuo to give an oil. The product was purified by chromatography on silica gel eluting methylene chloride: ethyl acetate (90:10, v:v), to give the mixed urea (0.035 g 23 %) as an oil. MS (M+NH4–OCH3)$^+$=454.

(460c) A suspension of the mixed urea from step (460b) (0.035 g, 0.075 mmol) and potassium carbonate (3 eq) in acetone (5 mL) was heated to reflux for 2 h. The reaction was allowed to cool, diluted with ethyl acetate and filtered to remove the solids, washed with brine and concentrated to give the hydantoin compound (0.025 g, 76%) as an oil. MS (M+NH4)$^+$=454.

(460d) Following the procedures similar to that used for steps (1f), but using the hydantoin compound from step (460c) the title compound was prepared. The product was purified by reverse phase HPLC on a Vydac C-18 semiprep column eluting an acetonitrile:water:TFA gradient, to give the hydroxamic acid product (0.015 g, 60%) as a white amorphous solid. MS (M+Na)$^+$=460.

Example 461

[1(R)]-N-hydroxy-alpha,3-dimethyl-2-oxo-3-[[4-(phenylmethoxy)phenyl]methyl]-1-pyrrolidineacetamide (461a) Triphenylphosphine (3.67 g, 14.0 mmol) and carbon tetrabromide (4.46 g, 14.0 mmol) were added to a solution of 4-benzyloxybenzyl alcohol (2.0 g, 9.3 mmol) in dichloromethane (25 mL) at 0° C. The mixture was warmed to rt for 2.5 h and then concentrated. The residue was triturated with ether, and the solids filtered off. Filtrate was concentrated. Residue purified by silica gel chromatography (ethyl acetate:hexanes, 5:95, v:v). Residue from chromatography was purified further with treatment with ether and filtration of solids. Filtrate was concentrated in vacuo to yield the desired bromide (2.34 g, 90%) as a white solid. MS found: (M–Br)$^+$=197.

(461b) A 2.0 M THF solution of lithium diisopropylamide (2.6 mL, 1.15 eq) was added over 10 minutes to a solution of ethyl 2-methyl-4-pentenoate (0.75 mL, 4.6 mmol) in THF (18 mL) at –78° C. The mixture was warmed to –55° C. for 40 minutes then cooled to –78° C. A solution of bromide compound from step (461a) (1.92 g, 6.9 mmol) in THF was added over 5 minutes to the cooled mixture. After 1 h at –78° C. the mixture was warmed to rt and 1 M HCl (30 mL) was added. The mixture was extracted with ethyl acetate (2×30 mL). The combined organic extracts were washed successively with 1N HCl (20 mL), saturated aqueous sodium bicarbonate (20 mL), water (20 mL), brine (20 mL), dried (MgSO4) and concentrated. The residue was purified by silica gel chromatography (hexane, then ethyl acetate:hexanes 2:98, v:v) to give the desired product (950 mg, 60%) as a clear oil. MS found: (M+NH4)$^+$=356.

(461c) Ozone was bubbled through a solution of compound (461b) (0.90 g, 2.6 mmol) in dichloromethane (30 mL) at –78° C. until a blue color persisted in the solution. The mixture was purged with oxygen and treated with triphenylphosphine (0.84 g, 3.2 mmol). The reaction mixture was allowed to warm to rt and stirred for 1 h, then was concentrated in vacuo. The residue was purified by silica gel chromatography (hexane, then ethyl acetate:hexanes 6:94, v:v) to give the desired aldehyde (0.70 g,75%) as a clear oil. MS found: (M+H)$^+$=341.

(461d) Following the procedures similar to that used for steps (1d, 1e and 1f), but using the aldehyde compound from step (461c) (650 mg, 1.9 mmol) the title compound was prepared. The product was purified by reverse phase HPLC on a Vydac C-18 semiprep column eluting an acetonitrile:water:TFA gradient, to give the hydroxamic acid product (0.065 g, 20%) as a white amorphous solid. MS (M+Na)$^+$=405.

Example 462

[1(R)]-3-[4-[(2,6-dimethyl-4-pyridinyl)methoxy] phenyl]-N-hydroxy-3-(methylamino)-alpha-(2-methylpropyl)-2-oxo-1-pyrrolidineacetamide mono (trifluoroacetate)

(462a) Following the procedures analogous to that used for the preparation of example (300), the N-Boc phenyl glycine compound from step (300d) (3.59 g, 8.72 mmol) was treated with sodium hydride (0.42 g, 17.45 mmol) in DMF (25 mL) at 0° C. for 1 h. The methyl iodide (2.47 g, 17.45 mmol) was added, the reaction was allowed to stir for 2 h at rt, partitioned between ethyl acetate and 1 N HCl. The organic layer was washed with brine, dried over magnesium sulfate and concentrated to give the N-methyl-N-Boc phenyl glycine (3.6 g, 97%) as an oil. MS (M+Na)$^+$=448.

(462b) Following the procedures analogous to that used for the preparation of example (300), but using the N-methyl-N-Boc phenyl glycine compound from step (462a) and using 2,6-dimethyl picolyl chloride hydrochloride in step (300i) the title compound was prepared. The product was purified by reverse phase HPLC on a Vydac C-18 semiprep column eluting an acetonitrile:water:TFA gradient, to give the hydroxamic acid product (0.12 g, 34%) an a white amorphous solid. MS (M+H)$^+$=455.

Example 463

[1(R)]-N-hydroxy-3-(methylamino)-alpha-(2-methylpropyl)-3-[4-[(2-methyl-4-quinolinyl) methoxy]phenyl]-2-oxo-1-pyrrolidineacetamide mono(trifluoroacetate)

(463a) Following the procedures analogous to that used for the preparation of example (462), but using 2-methyl-4chloromethyl quinoline hydrochloride in step (300i) the title compound was prepared. The product was purified by reverse phase HPLC on a Vydac C-18 semiprep column eluting an acetonitrile:water:TFA gradient, to give the hydroxamic acid product (0.12 g, 34%) as a white amorphous solid. MS (M+H)$^+$=491.

Example 464

[1(R)]-alpha,3-dimethyl-N-hydroxy-2-oxo-3-[4-(phenylmethoxy)phenyl]-1-piperidineacetamide (464a) Following the procedures analogous to that used for the preparation of example (1), the ester from step (1b) was treated with lithium hydroxide similar to step (450d) to give the carboxylic acid, which was coupled to alanine methyl ester similar to step (450e), to give the alanyl-phenyl glycine diamino acid as an oil. MS (M+H)$^+$=382.

(464b) 9-BBN (5.0 eq) was added to a solution of the olefin from Step (464a) (0.45 g, 1.18 mmol) in THF (10 mL) cooled to 0° C. under nitrogen. The reaction was allowed to warm to rt and stir overnight at rt. The reaction was cooled to 0° C. and water (2 mL) was added. The reaction was stirred for 20 minutes, then sodium acetate (1 g, in 2 mL water) and H2O2 (30%) (2.5 mL) were added simultaneously. This was stirred for 40 minutes, concentrated in vacuo, diluted with ethyl acetate and washed with water, brine, dried over magnesium sulfate and concentrated in vacuo to give the alcohol. The crude product was purified by chromatography on silica gel eluting methylene chloride: ethyl acetate (1:1, v:v) to give the alcohol (0.41 g, 87%) as an oil. MS (M+H)$^+$=400.

(464c) Following the procedure similar to that used for the preparation of step (459j), but using the alcohol from step (464b), the bromide was prepared. The crude product was purified by chromatography on silica gel eluting hexane: ethyl acetate (2:1, v:v) to give the bromide (0.145 g, 71%) as an oil. MS (M+H)$^+$=462,464.

(464d) The bromide from step (464c) (0.145 g, 0.313 mmol) was treated with sodium hydride (0.019 g, 0.47 mmol) in THF (10 mL) cooled to 0° C. under nitrogen. The reaction was stirred for 1.5 h, then partitioned between ethyl acetate and 1N HCl. The organic layer was washed with water, brine, dried over magnesium sulfate and concentrated in vacuo to give the lactam (0.105 g, 84%) as an oil. MS (M+H)$^+$=382.

(464e) Following the procedures analogous to that used for step (1f), but using the lactam from step (464d) the title compound was prepared. The product was purified by reverse phase HPLC on a Vydac C-18 semiprep column eluting an acetonitrile:water:TFA gradient, to give the hydroxamic acid product (0.062 g, 60%) as a white amorphous solid. MS (M+Na)$^+$=405.

Example 501

[1(R)]-α-[3-amino-2-oxo-3-[4-(4-quinolinylmethoxy)phenyl]-1-pyrrolidinyl]-N-hydroxy-4-piperidineacetamide tris(trifluoroacetate)

(501a) Following a procedure analogous to (300f), the aldehyde from (300e) (2.80 g, 6.77 mmol) and amino ester from (142b) (2.42 g, 1.1 eq) were coupled to give the secondary amine as a crude material. MS found: (M+H)$^+$= 670.

(501b) Following a procedure analogous to (300g), the crude amine from (501a) was converted to the lactam. Silica gel chromatography (ethyl acetate-hexane, 20:80 then 30:70) provided the less polar isomer (1.40 g) and the more polar isomer (1.30 g). The total yield is 63% for two steps. MS found: (M+Na)$^+$=660.

(501c) Following a procedure analogous to step (3a), the less polar lactam from (501b) (1.30 g, 2.04 mmol) was hydrogenolized to give the phenol (1.10 g, 98%). MS found: (M+H)$^+$=548.

(501d) Following a procedure analogous to step (6b), the phenol from (501c) (100 mg, 0.183 mmol) was reacted with 4-chloromethylquinoline hydrochloride to give the ether (75.5 mg, 60%). MS found: (M+H)$^+$=689.

(501e) Following a procedure analogous to step (92d), the ester from (501d) (69.0 mg, 0.100 mmol) was reacted with hydroxylamine to give the hydroxamic acid (36.0 mg, 52%). MS found: (M+H)$^+$=690.

(501f) Following a procedure analogous to example 117, the hydroxamic acid from (501e) (30.0 mg, 0.0362 mmol) was reacted with trifluoroacetic acid to give the hydroxamic acid tris(trifluoroacetate) (40.0 mg, 100%). MS found: (M+H)$^+$=490.

Example 502

[1(R)]-α-[3-amino-3-[4-[(2,6-dichloro-4-pyridinyl) methoxy]phenyl]-2-oxo-1-pyrrolidinyl]-N-hydroxy-4-piperidineacetamide bis(trifluoroacetate)

Beginning with the phenol from (501c) and 4-bromomethyl-2,6-dichloropyridine, example 502 was pre-

Example 503

[1(R)]-1,1-dimethylethyl 4-[1-[3-[[(1,1-dimethylethoxy)carbonyl]amino-]3-[4-[(1,1-dimethyl-4-pyridinyl)methoxy]phenyl]-2-oxo-1-pyrrolidinyl]-2-(hydroxyamino)-2-oxoethyl]-1-piperidinecarboxylate mono(trifluoroacetate)

(503a) Following a procedure analogous to step (6b), the phenol from (501c) (1.67 g, 3.05 mmol) was reacted with 4-chloromethyl-2,6-dimethylpyridine hydrochloride to give the picolyl ether (1.576, 77%). MS found: $(M+H)^+=667$.

(503b) Following a procedure analogous to step (92d), the ester from (501d) (76.0 mg, 0.114 mmol) was reacted with hydroxylamine to give the hydroxamic acid (32.6 mg, 37%). MS found: $(M+H)^+=668$.

Example 504

[1(R)]-α-[3-amino-3-[4-[(2,6-dimethyl-4-pyridinyl)methoxy]phenyl]-2-oxo-1-pyrrolidinyl]-N-hydroxy-4-piperidineacetamide tris(trifluoroacetate)

Starting with the hydroxamic acid from example 503, example 504 was prepared in a procedure analogous to example 117. MS found: $(M+H)^+=468$.

Example 505

[1(R)]-α-[3-amino-3-[4-[(2,6-dimethyl-4-pyridinyl)methoxy]phenyl]-2-oxo-1-pyrrolidinyl]-N-hydroxy-1-(methylsulfonyl)-4-piperidineacetamide bis(trifluoroacetate)

(505a) Following a procedure analogous to example 117, the lactam from (503a) (624 mg, 0.936 mmol) was reacted with TFA to give the piperidine tris(trifluoroacetate) (750 mg, 99%). MS found: $(M+H)^+=467$.

(505b) Following a procedure analogous to (49a), the piperidine from (148a) (125 mg, 0.155 mmol) was reacted with methylsulfonyl chloride to give the monosulfonamide (67.0 mg, 80%). MS found: $(M+Na)^+=567$.

(505c) Following a procedure analogous to step (92d), the crude ester from (505b) was reacted with hydroxylamine. The mixture was purified by reverse phase HPLC on a Dynamax C-18 semiprep column eluting an acetonitrile:water:TFA gradient, to give the hydroxamic acid bis(trifluoroacetate) (45.0 mg, 52%). MS found: $(M+H)^+=546$.

Example 506

[1(R)]-1-acetyl-α-[3-amino-3-[4-[(2,6-dimethyl-4-pyridinyl)methoxy]phenyl]-2-oxo-1-pyrrolidinyl]-N-hydroxy-4-piperidineacetamide bis(trifluoroacetate)

Beginning with the piperidine from (505a) and acetyl chloride, example 506 was prepared in an analogous series of reactions to (49a) and (92d). MS found: $(M+H)^+=510$.

Example 507

[1(R)]-α-[3-amino-3-[4-[(2,6-dimethyl-4-pyridinyl)methoxy]phenyl]-2-oxo-1-pyrrolidinyl]-1-(2,2-dimethyl-1-oxopropyl)-N-hydroxy-4-piperidineacetamide bis(trifluoroacetate)

Beginning with the piperidine from (505a) and trimethylacetyl chloride, example 507 was prepared in an analogous series of reactions to (49a) and (92d). MS found: $(M+H)^+=508$.

Example 508

[1(R)]-1,1-dimethylethyl 4-[1-[3-amino-3-[4-[(2,6-dimethyl-4-pyridinyl)methoxy]phenyl]-2-oxo-1-pyrrolidinyl]-2-(hydroxyamino)-2-oxoethyl]-1-piperidinecarboxylate bis(trifluoroacetate)

Beginning with the piperidine from (505a) and di-t-butyl dicarbonate, example 508 was prepared in an analogous series of reactions to (49a) and (92d). MS found: $(M+H)^+=568$.

Example 509

[1(R)]-methyl 4-[1-[3-amino-3-[4-[(2,6-dimethyl-4-pyridinyl)methoxy]phenyl]-2-oxo-1-pyrrolidinyl]-2-(hydroxyamino)-2-oxoethyl]-1-piperidinecarboxylate bis(trifluoroacetate)

Beginning with the piperidine from (505a) and methyl chloroformate, example 509 was prepared in an analogous series of reactions to (49a) and (92d). MS found: $(M+H)^+=526$.

Example 510

[1(R)]-α-[3-amino-3-[4-[(2,6-dimethyl-4-pyridinyl)methoxy]phenyl]-2-oxo-1-pyrrolidinyl]-N-hydroxy-1-methyl-4-piperidineacetamide tris(trifluoroacetate)

Beginning with the piperidine from (505a) and formaldehyde, example 506 was prepared in an analogous series of reactions to (86a) and (92d). MS found: $(M+H)^+=482$.

Example 511

[1(R)]-α-[3-amino-3-[4-[(2,6-dimethyl-4-pyridinyl)methoxy]phenyl]-2-oxo-1-pyrrolidinyl]-1-dimethylcarbamyl-N-hydroxy-4-piperidineacetamide bis(trifluoroacetate)

Beginning with the piperidine from (505a) and dimethylcarbamyl chloride, example 511 was prepared in an analogous series of reactions to (49a) and (92d). MS found: $(M+H)^+=539$.

Example 512

[1(R)]-α-[3-amino-3-[4-[(2,6-dimethyl-4-pyridinyl)methoxy]phenyl]-2-oxo-1-pyrrolidinyl -1-cycloproyanecarbonyl-N-hydroxy-4-piperidineacetamide bis(trifluoroacetate)

Beginning with the piperidine from (505a) and cyclopropanecarbonyl chloride, example 512 was prepared in an analogous series of reactions to (49a) and (92d). MS found: $(M+H)^+=536$.

Example 513

[1(R)]-3-amino-N-hydroxy-α-(1-methylethyl)-2-oxo-3-[4-(4-quinolinylmethoxy)phenyl]-1-pyrrolidineacetamide bis(trifluoroacetate)

(513a) Following a procedure analogous to (300f), the aldehyde from (300e) (8.00 g, 19.3 mmol) and D-Val-OMe were coupled to give the secondary amine as a crude material. MS found: $(M+H)^+=529$.

(513b) Following a procedure analogous to (300g), the crude amine from (513a) was converted to the lactam.

Silica gel chromatography (ethyl acetate-hexane, 20:80 then 25:75) provided the less polar isomer (4.60 g) and the more polar isomer (3.60 g). The total yield is 85% for two steps.

(513c) Following a procedure analogous to step (3a), the less polar lactam from (513b) (4.10 g, 8.27 mmol) was hydrogenolized to give the phenol (3.30, 98%). MS found: $(M+Na)^+=429$.

(513d) Following a procedure analogous to step (6b), the phenol from (513c) (500 mg, 1.23 mmol) was reacted with 4-chloromethylquinoline hydrochloride to give the ether (575 mg, 85%). MS found: $(M+Na)^+=570$.

(513e) Following a procedure analogous to step (92d), the ester from (513d) (575 mg, 1.05 mmol) was reacted with hydroxylamine to give the hydroxamic acid (380 mg, 66%). MS found: $(M-H)^-=547$.

(513f) Following a procedure analogous to example 117, the hydroxamic acid from (513e) (380 mg, 0.693 mmol) was reacted with trifluoroacetic acid. The material was purified by reverse phase HPLC on a Dynamax C-18 semiprep column eluting an acetonitrile:water:TFA gradient, to give the hydroxamic acid bis(trifluoroacetate) (268 mg, 57%). MS found: $(M+H)^+=449$.

Example 514

[1(R)]-3-amino-3-[4-[(2,6-dimethyl-4-pyridinyl)
methoxy]phenyl]-N-hydroxy-α-(1-methylethyl)-2-
oxo-1-pyrrolidineacetamide bis(trifluoroacetate)

Beginning with the phenol from (513c) and 4-chloromethyl-2,6-dimethylpyridine hydrochloride, example 514 was prepared in an analogous series of reactions to (6b), (92d) and example 117. MS found: $(M+H)^+=427$.

Example 515

[1(R)]-3-amino-α-cyclohexyl-N-hydroxy-2-oxo-3-
[4-(4-quinolinylmethoxy)phenyl]-1-
pyrrolidineacetamide bis(trifluoroacetate)

Beginning with the aldehyde from (300e) and D-cyclohexylglycine methyl ester hydrochloride, example 515 was prepared in ananalogous series of reactions to example 513. MS found: $(M+H)^+=589$.

Example 516

[1(R)]-3-amino-α-cyclohexyl-3-[4-[(2,6-dimethyl-4-
pyridinyl)methoxy]phenyl]-N-hydroxy-2-oxo-1-
pyrrolidineacetamide bis(trifluoroacetate)

Beginning with the aldehyde from (300e) and D-cyclohexylglycine methyl ester hydrochloride, example 516 was prepared in an analogous series of reactions to example 513. MS found: $(M+H)^+=467$.

Example 517

3-amino-α-(1,1-dimethylethyl)-3-[4-[(2,6-dimethyl-
4-pyridinyl)methoxy]phenyl]-N-hydroxy-2-oxo-1-
pyrrolidineacetamide bis(trifluoroacetate)

(517a) Following a procedure analogous to (300f), the aldehyde from (300e) (8.40 g, 20.2 mmol) and D-t-Leu-OMe were coupled to give the secondary amine as a crude material. MS found: $(M+H)^+=543$.

(517b) Following a procedure analogous to (300g), the crude amine from (517a) was converted to the lactam. Silica gel chromatography (ethyl acetate-hexane, 15:85 then 20:80) provided the less polar isomer (4.60 g, 45%). MS found: $(M+H)^+=511$.

(517c) Following a procedure analogous to step (3a), the less polar lactam from (517b) (4.50 g, 8.80 mmol) was hydrogenolized to give the phenol (3.62 g, 98%). MS found: $(M+Na)^+=443$.

(517d) Following a procedure analogous to step (6b), the phenol from (517c) (210 mg, 0.500 mmol) was reacted with 4-chloromethyl-2,6-dimethylpyridine hydrochloride to give the ether (240 mg, 89%). MS found: $(M+H)^+=540$.

(517e) The ester from (517d) (220 mg, 0.408 mmol) in concentrate HCl (5 mL) and HOAc (7.5 mL) was heated to 100° C. overnight and concentrated to give the crude carboxylic acid. MS found: $(M-H)^-=424$.

(517f) The carboxylic acid from (517e), hydroxylamine hydrochloride (160 mg, 5.6 eq), NMM (0.5 mL), BOP (300 mg, 1.7 eq) in DMF (8 mL) were stirred at rt for 4 h. Following addition of sat NH4Cl (25 mL), the mixture was extracted with ethyl acetate several times. The extracts were concentrated and purified by reverse phase HPLC on a Dynamax C-18 semiprep column eluting an acetonitrile:water:TFA gradient, to give the hydroxamic acid bis(trifluoroacetate) (140 mg, 51% for 2 steps). MS found: $(M+H)^+=441$.

Example 518

[1(R)]-3-amino-α-(,1,1-dimethylethyl)-N-hydroxy-
2-oxo-3-[4-(4-quinolinylmethoxy)phenyl]-1-
pyrrolidineacetamide bis(trifluoroacetate)

Beginning with the phenol from (517c) and 4-chloromethylquinoline hydrochloride, example 518 was prepared in an analogous series of reactions to (6b), (517e) and (517f). MS found: $(M-H)^-=461$.

Example 519

[1(R)]-3-amino-α-(1,1-dimethylethyl)-N-hydroxy-2-
oxo-3-[4-[(2-methyl-4-quinolinyl)methoxy]phenyl]-
1-pyrrolidineacetamide bis(trifluoroacetate)

Beginning with the phenol from (517c) and 4-chloromethyl-2-methylquinoline hydrochloride, example 519 was prepared in an analogous series of reactions to (6b), (517e) and (517f). MS found: $(M+H)^+=477$.

Example 520

[1(R)]-3-amino-N-hydroxy-α-(1-methylethyl)-2-
oxo-3-[4-[(2-methyl-4-quinolinyl)methoxy]phenyl]-
1-pyrrolidineacetamide bis(trifluoroacetate)

Beginning with the phenol from (513c) and 4-chloromethyl-2-methylquinoline hydrochloride, example 520 was prepared in an analogous series of reactions to (6b), (92d) and example 117. MS found: $(M+H)^+=463$.

Example 521

[1(R)]-3-amino-N-hydroxy-α-(1-methylethyl)-2-
oxo-3-[4-[(2,6-dimethyl-4-quinolinyl)methoxy]
phenyl]-1-pyrrolidineacetamide bis(trifluoroacetate)

Beginning with the phenol from (513c) and 4-chloromethyl-2,6-dimethylquinoline hydrochloride, example 521 was prepared in an analogous series of reactions to (6b), (92d) and example 117. MS found: $(M+H)^+=477$.

Example 522

[1(R)]-N-[4-[1-[3-amino-3-[4-[(2,6-dimethyl-4-pyridinyl)methoxy]phenyl]-2-oxo-1-pyrrolidinyl-2-(hydroxyamino)-2-oxoethyl]-1-piperidine]-4-morpholinecarboxamide bis(trifluoroacetate)

Beginning with the piperidine from (505a) and 4-morpholinecarbonyl chloride, example 522 was prepared in an analogous series of reactions to (49a) and (92d). MS found: $(M+H)^+=581$.

Example 523

[1(R)]-α-[(3-amino-3-[4-[(2,6-dimethyl-4-pyridinyl)methoxy]phenyl]-2-oxo-1-pyrrolidinyl]1-(2-methyl-1-oxopropyl)-N-hydroxy-4-piperidineacetamide bis(trifluoroacetate)

Beginning with the piperidine from (505a) and isobutyryl chloride, example 523 was prepared in an analogous series of reactions to (49a) and (92d). MS found: $(M+H)^+=538$.

Example 524

[1(R)]-3-amino-3-[4-[(2,6-dimethyl-4-pyridinyl)methoxy]phenyl]-N-hydroxy-α-(4-methoxycyclohexyl)-2-oxo-1-pyrrolidineacetamide bis(trifluoroacetate)

(524a) Sodium carbonate (6.13 g, 2 eq) and (BOC)20 (6.30 g, 1 eq) were Succesively added to D-4-hydroxycyclohexylgrycine (5.00 g, 28.9 mmol, Ciba-Geigy, WO9722587, 1994) in water (120 mL) and dioxane (60 mL) at 0° C. The mixture was stirred at rt overnight and then adjusted to pH 5–6 with 6 N HCl. Following removal of dioxane, the mixture was diluted with water (150 mL), acidified to pH 2–3, saturated with solid NaCl, and extracted with ethyl acetate (3×250 mL). The combined extracts were dried (MgSO4), and concentrated to give the BOC-protected amino acid (7.80 g, 99%). MS found: $(M-H)^-=272$.

(524b) A 2.0 M hexane solution of trimethylsilyl diazomethane (18.3 mL, 1.3 eq) was added to the acid from (524a) (7.70 g, 28.8 mmol) in methanol (50 mL) and benzene (200 mL). The mixture was stirred at rt for 30 min, then concentrated. Silica gel chromatography (ethyl acetate-hexane, 50:50) gave the ester (7.40 g, 91%). MS found: $(M+Na)^+=310$.

(524c) The ester from (524b) (7.20 g, 25.2 mmol) was stirred in 4 N dioxane solution of hydrogen chloride (200 mL) for 30 min and then concentrated to give the amino ester hydrochloride (5.70 g, 100%). MS found: $(M+H)^+=188$.

(524d) Following a produce analogous to (300f), the aldehyde from (300e) (2.00 g, 4.83 mmol) and the methyl ester hydrochloride from (525c) were coupled to give the secondary amine as a crude material. MS found: $(M+H)^+=585$.

(524e) Following a procedure analogous to (300 g), the crude amine from (525d) were cyclized to give the lactam as a crude material (2.71 g). MS found: $(M+Na)^+=575$.

(524f) Proton sponge (1.16 g, 3 eq) and trimethyloxonium tetrafluoroborate (803 mg, 3 eq) were added to the crude material from (524d) (1.00 g) in dichloromethane (20 mL). After 4 h at rt, ethyl acetate (200 mL) was added. The mixture was washed with water (2×25 mL), brine (25 mL), dried (MgSO4) and concentrated. Silica gel chromatography (35:65 then 40:60 then 45:55) gave the desired methyl ether (628 mg, 62% for 3 steps). MS found: $(M+Na)^+=589$.

(524a) Following a procedure analogous to step (3a), the lactam from (524f) (838 mg, 1.48 mmol) was hydrogenolized to give the phenol (643.2 mg, 91%). MS found: $(M+Na)^+=499$.

(524h) Following a procedure analogous to step (6b), the phenol from (524 g) (200 mg, 0.420 mmol) was reacted with 4-chloromethyl-2,6-dimethylpyridine hydrochloride to give the ether (197.4 mg, 79%). MS found: $(M+Na)^+=619$.

(524i) Following a procedure analogous to step (92d), the ester from (524h) (185.4 mg, 0.311 mmol) was reacted with, hydroxylamine to give the hydroxamic acid (top isomer: 67.3 mg; bottom isomer: 60.1 mg). The total yield is 127.4 mg (69%). MS found: $(M+H)^+=597$.

(524j) Following a procedure analogous to step (117), the bottom isomer of the hydroxamic acid from (524i) (56.1 mg, 0.094 mmol) was reacted with TFA to give the deprotected hydroxamic acid (68.1 mg, 100%). MS found: $(M+H)^+=497$.

Example 525

[1'(R)]-N-hydroxy-1,2-dihydro-α-(1-methylethyl)-2,2'-dioxo-6-(phenylmethoxy)spiro[3H-indole-3,3'-pyrrolidine]-1'-acetamide (525a) Cesium carbonate (8.86 g, 2 eq) was added to a solution of dimethyl [4-(benzyloxy)-2nitrophenyl] malonate (4.87 g, 13.6 mmol; Warpehosski, et al. *J. Med. Chem.* 1988, 31, 590) and allyl bromide (3.53 mL, 3 eq) in DMSO at rt. After 1 h at this temperature, ether (800 mL) and sat ammonium chloride (100 mL) were added. The organic phase was separated, washed with water (3×50 mL), brine (50 mL), dried (MgSO4) and concentrated. Silica gel chromatography (ethyl acetate-hexane, 15:85 then 20:80) provided the allylated product (5.28 g, 979). MS found: $(M+H)^+=400$.

(525b) Following a procedure analogous to step (1c), the olefin from (219a) (5.18 g, 13.0 mmol) was degraded by ozonolysis. Silica gel chromatography (ethyl acetate-hexane, 20:80 then 30:70 then 35:65 then 40:60) provided the aldehyde (4.96 g, 95%). MS found; $(M+NH_4)^+=419$.

(525c) Following a procedure analogous to (300f), the aldehyde from (525b) (510 mg, 1.27 mmol) and D-valine methyl ester hydrochloride were coupled to give the secondary amine as a crude material.

(525d) Following a procedure analogous to (1d), the crude material from (525c) was treated with zinc in acetic acid at reflux. The crude spirolactam was purified by silica gel chromatography (ethyl acetate-hexane, 40:60 then 50:50) to give less polar isomer (180 mg) and more polar isomer (130 mg). The total yield for two steps is 310 mg (58%). MS found: $(M-H)^-=421$.

(525e) Following a procedure analogous to step (92d), the ester from (525d) (25.5 mg, 0.060 mmol) was reacted with hydroxylamine to give the hydroxamic acid (15.2 mg, 60%). MS found: $(M-H)^-=422$.

Example 526

[1(R)]-α-[3-amino-3-[4-[(2,6-dimethyl-4-pyridinyl)methoxy]phenyl]-2-oxo-1-pyrrolidinyl]-N-hydroxy-1-(phenylcarbonyl)-4-piperidineacetamide bis(trifluoroacetate)

Beginning with the piperidine from (505a) and benzoyl chloride, example 526 was prepared in an analogous series of reactions to (49a) and (92d). MS found: $(M+H)^+=572$.

Example 527

[1-(R)]-α-[3-amino-3-[4-[(2,6-dimethyl-4-pyridinyl)methoxy]phenyl]-2-oxo-1-pyrrolidinyl]-N-hydroxy-1-(1-oxopropyl)-4-piperidineacetamide bis (trifluoroacetate)

Beginning with the piperidine from (505a) and propionyl chloride, example 527 was prepared in an analogous series of reactions to (49a) and (92d). MS found: $(M+H)^+=524$.

Example 528

[1(R)]-α-[3-amino-2-oxo-3-[4-(2-methyl-4-quinolinylmethoxy)phenyl]-1-pyrrolidinyl]-1-acetyl-N-hydroxy-4-piperidineacetamide bis (trifluoroacetate)

Beginning with the phenol from (501c), the title compound was prepared in an analogous series of reactions to (6b), (117), (49a) and (92d), but using 4-chloromethyl-2-methylquinoline in step (6b) and acetyl chloride in step (49a). MS found: $(M+H)^+=546$.

Example 529

[1(R)]-α-[3-amino-2-oxo-3-[4-(2-methyl-4-quinolinylmethoxy)phenyl]-1-pyrrolidinyl]-N-hydroxy-1-(methylsulfonyl)-4-piperidineacetamide bis(trifluoroacetate)

Beginning with the phenol from (501c), the title compound was prepared in an analogous series of reactions to (6b), (117), (49a) and (92d), but using 4-chloromethyl-2-methylquinoline in step (6b) and methanesulfonyl chloride in step (49a). MS found: $(M+H)^+=582$.

Example 530

[1(R)]-α-[3-amino-2-oxo-3-[4-(2-methyl-4-quinolinylmethoxy)phenyl]-1-pyrrolidinyl]-1-(2,2-dimethyl-1-oxopropyl)-N-hydroxy-4-piperidineacetamide bis(trifluoroacetate)

Beginning with the phenol from (501c), the title compound was prepared in an analogous series of reactions to (6b), (1.17), (49a) and (92d), but using 4-chloromethyl-2-methylquinoline in step (6b) and pivolyl chloride in step (49a). MS found: $(M+H)^+=588$.

Example 531

[1(R)]-α-[3-amino-2-oxo-3-[4-(4-quinolinylmethoxy)phenyl]-1-pyrrolidinyl]-1-acetyl-N-hydroxy-4-piperidineacetamide bis (trifluoroacetate)

Beginning with the phenol from (501c), the title compound was prepared in an analogous series of reactions to (6b), (117), (49a) and (92d), but using 4-chloromethylquinoline in step (6b) and acetyl chloride in step (49a). MS found: $(M+H)^+=532$.

Example 532

[1(R)]-α-[3-amino-2-oxo-3-[4-(4-quinolinylmethoxy)phenyl]-1-pyrrolidinyl]-N-hydroxy-1-(methylsulfonyl)-4-piperidineacetamide bis(trifluoroacetate)

Beginning with the phenol from (501c), the title compound was prepared in an analogous series of reactions to (6b), (117), (49a) and (92d), but using 4-chloromethylquinoline in step (6b) and methanesulfonyl chloride in step (49a). MS found: $(M+H)^+=568$.

Example 533

[1(R)]-α-[3-amino-2-oxo-3-[4-[(3,5-dimethoxyphenyl)methoxy]phenyl]-1-pyrrolidinyl]-1-acetyl-N-hydroxy-4-piperidineacetamide trifluoroacetate Beginning with the phenol from (501c), the title compound was prepared in an analogous series of reactions to (6b), (117), (49a) and (92d), but using 3,5-dimethoxybenzyl bromide in step (6b) and acetyl chloride in step (49a). MS found: $(M+H)^+=541$.

Example 534

[1(R)]-α-[3-amino-2-oxo-3-[4-[(5-methyl-3-nitrophenyl)methoxy]phenyl]-1-pyrrolidinyl]-1-acetyl-N-hydroxy-4-piperidineacetamide trifluoroacetate Beginning with the phenol from (501c), the title compound was prepared in an analogous series of reactions to (6b), (117), (49a) and (92d), but using 5-methyl-3-nitrobenzyl bromide in step (6b) and acetyl chloride in step (49a). MS found: $(M+H)^+=540$.

Example 535

[1(R)]-α-[3-amino-2-oxo-3-[4-[3,5-bis(trifluoromethyl)phenoxy]phenyl]-1-pyrrolidinyl]-1-acetyl-N-hydroxy-4-piperidineacetamide trifluoroacetate Beginning with the phenol from (501c), the title compound was prepared in an analogous series of reactions to (61a), (117), (49a) and (92d), but using 3,5-bis(trifluoromethyl)benzene boronic acid in step (61a) and acetyl chloride in step (49a). MS found: $(M+H)^+=603$.

Example 536

[1(R)]-α-[3-amino-2-oxo-3-[4-[(3,5-dichlorophenyl)methoxy]phenyl]-1-pyrrolidinyl]-1-acetyl-N-hydroxy-4-piperidineacetamide trifluoroacetate Beginning with phenol from (501c), the title compound was prepared in an analogous series of reactions to (6b), (117), (49a) and (92d), but using 3,5-dichlorobenzyl bromide in step (6b) and acetyl chloride in step (49a). MS found: $(M+H)^+=549$.

Example 537

[1(R)]-α-[3-amino-2-oxo-3-[4-(6-fluoro-2-methyl-4-quinolinylmethoxy)phenyl]-1-pyrrolidinyl]-1-acetyl-N-hydroxy-4-piperidineacetamide bis (trifluoroacetate)

Beginning with the phenol from (501c), the title compound was prepared in an analogous series of reactions to (6b), (117), (49a) and (92d), but using 4-chloromethyl-6-fluoro-2-methylquinoline in step (6b) and acetyl chloride in step (49a). MS found: $(M+H)^+=564$.

Example 538

[1(R)]-α-[3-amino-2-oxo-3-[4-(7-chloro-2-methyl-4-quinolinylmethoxy)phenyl]-1-pyrrolidinyl]-1-acetyl-N-hydroxy-4-piperidineacetamide bis (trifluoroacetate)

Beginning with the phenol from (501c), the title compound was prepared in an analogous series of reactions to (6b), (117), (49a) and (92d), but using 4-chloromethyl-7-chloro-2-methylquinoline in step (6b) and acetyl chloride in step (49a). MS found: (M+H)$^+$=580.

Example 539

[1(R)]-α-[3-amino-2-oxo-3-[4-(6-chloro-2-methyl-4-quinolinylmethoxy)phenyl]-1-pyrrolidinyl]-1-acetyl-N-hydroxy-4-piperidineacetamide bis (trifluoroacetate)

Beginning with the phenol from (501c), the title compound was prepared in an analogous series of reactions to (6b), (117), (49a) and (92d), but using 4-chloromethyl-6-chloro-2-methylquinoline in step (6b) and acetyl chloride in step (49a). MS found (M+H)$^+$=580.

Example 540

[1(R)]-α-[3-amino-2-oxo-3-[4-(6-methoxy-2-methyl-4-quinolinylmethoxy)phenyl]-1-pyrrolidinyl]-1-acetyl-N-hydroxy-4-piperidineacetamide bis(trifluoroacetate)

Beginning with the phenol from (501c), the title compound was prepared in an analogous series of reactions to (6b), (117), (49a) and (92d), but using 4-chloromethyl-6-methoxy-2-methylquinoline in step (6b) and acetyl chloride in step (49a). MS found: (M+H)$^+$=576.

Example 541

[1(R)]-α-[3-amino-2-oxo-3-[4-(2,7-dimethyl-4-quinolinylmethoxy)phenyl]-1-pyrrolidinyl]-N-hydroxy-4-piperidineacetamide tris(trifluoroacetate)

Beginning with the phenol from (501c), the title compound was prepared in an analogous series of reactions to (6b), (117) and (92d), but using 4-chloromethyl-2,7-dimethylquinoline in step (6b). MS found: (M+H)$^+$=518.

Example 542

[1(R)]-α-[3-amino-2-oxo-3-[4-(2,7-dimethyl-4-quinolinylmethoxy)phenyl]-1-pyrrolidinyl]-1-acetyl-N-hydroxy-4-piperidineacetamide bis (trifluoroacetate)

Beginning with the phenol from (501c), the title compound was prepared in an analogous series of reactions to (6b), (117), (49a) and (92d), but using 4-chloromethyl-2,7-dimethylquinoline in step (6b) and acetyl chloride in step (49a). MS found: (M+H)$^+$=560.

Example 543

[1(R)]-α-[3-amino-2-oxo-3-[4-(2-methoxy4-quinolinylmethoxy)phenyl]-1-pyrrolidinyl]-N-hydroxy-4-piperidineacetamide tris(trifluoroacetate)

Beginning with the phenol from (501c), the title compound was prepared in an analogous series of reactions to (6b), (117) and (92d), but using 4-bromomethyl-2-methoxyquinoline in step (6b). MS found: (M+H)$^+$=520.

Example 544

[1(R)]-α-[3-amino-2-oxo-3-[4-[(3,5-dimethoxyphenyl)methoxy]phenyl]-1-pyrrolidinyl]-N-hydroxy-4-piperidineacetamide bis (trifluoroacetate)

Beginning with the phenol from (501c), the title compound was prepared in an analogous series of reactions to (6b), (117) and (92d), but using 3,5-dimethoxybenzyl bromide in step (6b). MS found: (M+H)$^+$=499.

Example 545

[1(R)]-α-[3-amino-3-[4-[(2,6-diethyl-4-pyridinyl)methoxy]phenyl]-2-oxo-1-pyrrolidinyl]-N-hydroxy-4-piperidineacetamide tris(trifluoroacetate)

Beginning with the phenol from (501c), the title compound was prepared in an analogous series of reactions to (6b), (117) and (92d), but using 4-chloromethyl-2,6-diethylpyridine (prepared from 2,6-dichloro-4-hydroxymethylpyridine following the procedure of Tamao, et al Bull. Chem. Soc. Jpn. 1976, 49, 1958 and subsequent treatment with thionyl chloride) in step (6b). MS found: (M+H)$^+$=496.

Example 546

[1(R)]-α-[3-amino-3-[4-[2,6-diethyl-4-pyridinyl)methoxy]phenyl]-2-oxo-1-pyrrolidinyl]-1-acetyl-N-hydroxy-4-piperidineacetamide tris(trifluoroacetate)

Beginning with the phenol from (501c), the title compound was prepared in an analogous series of reactions to (6b), (117), (49a) and (92d), but using 4-chloromethyl-2,6-diethylpyridine in step (6b) and acetyl chloride in step (49a). MS found: (M+H)$^+$=538.

Example 547

[1(R)]-α-[3-amino-2-oxo-3-[4-(7-methyl-4-quinolinylmethoxy)phenyl]-1-pyrrolidinyl]-N-hydroxy-4-piperidineacetamide tris(trifluoroacetate)

Beginning with the phenol from (501c), the title compound was prepared in an analogous series of reactions to (6b), (117) and (92d), but using 4-chloromethyl-7-methylquinoline in step (6b). MS found: (M+H)$^+$=504.

Example 548

[1(R)]-3-amino-N-hydroxy-α-(4-methoxycyclohexyl)-2-oxo-3-[4-(4-quinolinylmethoxy)phenyl]-1-pyrrolidineacetamide bis(trifluoroacetate)

Beginning with the phenol from (524 g), the title compound was prepared in an analogous series of reactions to (6b), (92d) and (117), but using 4-chloromethylquinoline in step (6b). MS found: (M+H)$^+$=519.

Example 549

[1(R)]-3-amino-α-(1,1-dimethylethyl)-3-[4-[(2,6-dimethyl-4-quinolinyl)methoxy]phenyl]-N-hydroxy-2-oxo-1-pyrrolidineacetamide bis(trifluoroacetate)

Beginning with the phenol from (517c), the title compound was prepared in an analogous series of reactions to (517d–f), but using 4-chloromethyl-2,6-dimethylquinoline in step (517d). MS found: (M+H)$^+$=491.

Example 550

[1(R)]-3-[4-[(2,6-dimethyl-1-oxido-4-pyridinyl)methoxy]phenyl]-N-hydroxy-α,3-dimethyl-2-oxo-1-pyrrolidineacetamide mono(trifluoroacetate)

(550a) Beginning with the phenol from (6a), the picolyl ether was prepared in an analogous reaction to (6b), but using 4-chloromethyl-2,6-dimethylpyridine. MS found: (M+H)$^+$=397.

(550b) A mixture of the picolyl ether from (550a) (100 mg, 0.252 mmol), mCPBA (100 mg, 2 eq), and 40% aqueous HF (0.015 mL), DMF (2 mL) and methanol (0.56 mL) was stirred at rt for 2 h. The mixture was quenched with sat NaHSO3 (1 mL) and sat Na2CO3, and extracted with ethyl acetate. The organic extracts were washed with Na2CO3 (2×), brine (2×), dried (MgSO4) and concentrated to give the pyridine N-oxide (90 mg, 86%). MS found: (M+H)$^+$=413.

(550c) Following procedure analogous to (92d), the material from (550b) was converted to the hydroxamic acid. MS found: (M+H)$^+$=414.

Example 551

[1(R)]-3-amino-α-(1,1-dimethylethyl)-3-[4-[(7-chloro-2-methyl-4-quinolinyl)methoxy]phenyl]-N-hydroxy-2-oxo-1-pyrrolidineacetamide bis(trifluoroacetate)

Beginning with the phenol from (517c), the title compound was prepared in an analogous series of reactions to (517d–f), but using 7-chloro-4-chloromethyl-2-methylquinoline in step (517d). MS found: (M+H)$^+$511.

Example 552

[1(R)]-3-amino-α-(1,1-dimethylethyl)-3-[4-[(6-fluoro-2-methyl-4-quinolinyl)methoxy]phenyl]-N-hydroxy-2-oxo-1-pyrrolidineacetamide bis(trifluoroacetate)

Beginning with the phenol from (517c), the title compound was prepared in an analogous series of reactions to (517d–f), but using 4-chloromethyl-6-fluoro-2-methylquinoline in step (517d). MS found: (M+H)$^+$=495.

Example 553

[1(R)]-3-amino-α-(1,1-dimethylethyl)-3-[4-[(6-chloro-2-methyl-4-quinolinyl)methoxy]phenyl]-N-hydroxy-2-oxo-1-pyrrolidineacetamide bis(trifluoroacetate)

Beginning with the phenol from (517c), the title compound was prepared in an analogous series of reactions to (517d–f), but using 6-chloro-4-chloromethyl-2-methylquinoline in step (517d). MS found: (M+H)$^+$=511.

Example 554

[1(R)]-3-amino-α-(1,1-dimethylethyl)-3-[4-[(6-methoxy-2-methyl-4-quinolinyl)methoxy]phenyl]-N-hydroxy-2-oxo-1-pyrrolidineacetamide bis(trifluoroacetate)

Beginning with the phenol from (517c), the title compound was prepared in an analogous series of reactions to (517d–f), but using 4-chloromethyl-6-methoxy-2-methylquinoline in step (517d). MS found: (M+H)$^+$=507.

Example 555

[1(R)]-3-amino-α-(1,1-dimethylethyl)-3-[4-[(2,7-dimethyl-4-quinolinyl)methoxy]phenyl]-N-hydroxy-2-oxo-1-pyrrolidineacetamide bis(trifluoroacetate)

Beginning with the phenol from (517c), the title compound was prepared in an analogous series of reactions to (517d–f), but using 4-chloromethyl-2,7-dimethylquinoline in step (517d). MS found: (M+H)$^+$=491.

Example 556

[1(R)]-3-amino-α-(1,1-dimethylethyl)-3-[4-[(7-methyl-4-quinolinyl)methoxy]phenyl]-N-hydroxy-2-oxo-1-pyrrolidineacetamide bis(trifluoroacetate)

Beginning with the phenol from (517c), the title compound was prepared in an analogous series of reactions to (517d–f), but using 4-chloromethyl-7-methylquinoline in step (517d). MS found: (M+H)$^+$=477.

Example 557

[1(R)]-3-amino-α-cyclohexyl-N-hydroxy-2-oxo-3-[4-(2-methyl-4-quinolinylmethoxy)phenyl]-1-pyrrolidineacetamide bis(trifluoroacetate)

Beginning with the aldehyde from (300e), the title compound was prepared in an analogous series of reactions to (513a–f), but using D-cyclohexylglycine methyl ester hydrochloride in step (513a) and 4-chloromethyl-2-methylquinoline in step (513d). MS found: (M+H)$^+$=503.

Example 558

[1(R)]-3-amino-α-cyclohexyl-N-hydroxy-2-oxo-3-[4-(2,6-dimethyl-4-quinolinylmethoxy)phenyl]-1-pyrrolidineacetamide bis(trifluoroacetate)

Beginning with the aldehyde from (300e), the title compound was prepared in an analogous series of reactions to (513a–f), but using D-cyclohexylglycine methyl ester hydrochloride in step (513a) and 4-chloromethyl-2,6-dimethylquinoline in step (513d). MS found: (M+H)$^+$=517.

Example 559

[1(R)]-3-amino-3-[4-[(5-methyl-3-nitrophenyl)methoxy]phenyl]-N-hydroxy-α-(1-methylethyl)-2-oxo-1-pyrrolidineacetamide trifluoroacetate Beginning with the phenol from (513c), the title compound was prepared in an analogous series of reactions to (513d–f), but using 5-methyl-3-nitrobenzyl bromide in step (513d). MS found: (M+H)$^+$=457.

Example 560

[1(R)-3-amino-3-[4-[3,5-bis(trifluoromethyl)phenoxy]phenyl]-N-hydroxy-α-(1-methylethyl)-2-oxo-1-pyrrolidineacetamide trifluoroacetate Beginning with the phenol from (513c), the title compound was prepared in an analogous series of reactions to (61a) and (513e–f), but using 3,5-bis(trifluoromethyl)benzene boronic acid in step (61a). MS found: (M+H)$^+$=518.

Example 561

[1(R)]-3-amino-3-[4-[(3,5-bis(trifluoromethyl)phenyl]methoxy]phenyl]-N-hydroxy-α-(1-methylethyl)-2-oxo-1-pyrrolidineacetamide trifluoroacetate Beginning with the phenol from (513c), the title compound was prepared in an analogous series of reactions to (513d–f), but using 3,5-bis(trifluoromethyl)benzyl bromide in step (513d). MS found: (M+H)$^+$=534.

Example 562

[1(R)]-3-amino-3-[4-(3,5-dibromophenoxy)phenyl]-N-hydroxy-α-(1-methylethyl)-2-oxo-1-pyrrolidineacetamide trifluoroacetate Beginning with the phenol from (513c), the title compound was prepared in an analogous series of reactions to (61a) and (513e–f), but using 3,5-dibromobenzeneboronic acid in step (61a). MS found: (M+H)⁺=523.

Example 563

[1(R)]-3-amino-N-hydroxy-α-(1-methylethyl)-2-oxo-3-[4-(6-fluoro-2-methyl-4-quinolinylmethoxy)phenyl]-1-pyrrolidineacetamide bis(trifluoroacetate)

Beginning with the phenol from (513c), the title compound was prepared in an analogous series of reactions to (513d–f), but using 4-chloromethyl-6-fluoro-2-methylquinoline in step (513d). MS found: (M+H)⁺=481.

Example 564

[1(R)]-3-amino-N-hydroxy-α-(1-methylethyl)-2-oxo-3-[4-(6-methoxy-2-methyl-4-quinolinylmethoxy)phenyl]-1-pyrrolidineacetamide bis(trifluoroacetate)

Beginning with the phenol from (513c), the title compound was prepared in an analogous series of reactions to (513d–f), but using 4-chloromethyl-6-methoxy-2-methylquinoline in step (513d). MS found: (M+H)⁺=493.

Example 565

[1(R)]-3-amino-N-hydroxy-α-(1-methylethyl)-2-oxo-3-[4-(7-chloro-2-methyl-4-quinolinylmethoxy)phenyl]-1-pyrrolidineacetamide bis(trifluoroacetate)

Beginning with the phenol from (513c), the title compound was prepared in an analogous series of reactions to (513d–f), but using 7-chloro-4-chloromethyl-2-methylquinoline in step (513d). MS found: (M+H)⁺=497.

Example 566

[1(R)]-3-amino-N-hydroxy-α-(1-methylethyl)-2-oxo-3-[4-(6-chloro-2-methyl-4-quinolinylmethoxy)phenyl]-1-pyrrolidineacetamide bis(trifluoroacetate)

Beginning with the phenol from (513c), the title compound was prepared in an analogous series of reactions to (513d–f), but using 6-chloro-4-chloromethyl-2-methylquinoline in step (513d). MS found: (M+H)⁺=497.

Example 567

[1(R)]-3-amino-N-hydroxy-α-(1-methylethyl)-2-oxo-3-[4-(2-methoxy-4-quinolinylmethoxy)phenyl]-1-pyrrolidineacetamide bis(trifluoroacetate)

Beginning with the phenol from (513c), the title compound was prepared in an analogous series of reactions to (513d–f), but using 4-bromomethyl-2-methoxyquinoline in step (513d). MS found: (M+H)⁺=479.

Example 568

[1(R)]-3-amino-N-hydroxy-α-(1-methylethyl)-2-oxo-3-[4-(2,7-dimethyl-4-quinolinylmethoxy)phenyl]-1-pyrrolidineacetamide bis(trifluoroacetate)

Beginning with the phenol from (513c), the title compound was prepared in an analogous series of reactions to (513d–f), but using 4-chloromethyl-2,7-dimethylquinoline in step (513d). MS found: (M+H)⁺=477.

Example 569

[1(R)]-3-amino-N-hydroxy-α-(1-methylethyl)-2-oxo-3-[4-[(2,6-diethyl-4-pyridinyl)methoxy]phenyl]-1-pyrrolidineacetamide bis(trifluoroacetate)

Beginning with the phenol from (513c), the title compound was prepared in an analogous series of reactions to (513d–f), but using 4-chloromethyl-2,6-diethylpyridine in step (513d). MS found: (M+H)⁺=455.

Example 700

[1(R)]-N-hydroxy-α,3-dimethyl-2-oxo-3-[3-(phenylmethoxy)phenyl]-1-pyrrolidineacetamide (700a) To 0.061 grams of methyl ester, obtained in a manner analogous to examples 1a–d, in 4 mL of anhydrous methanol was added 0.116 grams of hydroxylamine hydrochloride and 0.135 grams of sodium methoxide. The reaction was stirred at ambient temperature overnight at which time it was quenched with acetic acid and the volatiles removed under reduced pressure. The resulting material was purified by C18 reverse phase HPLC affording the hydroxamic acid 700. LRMS found (M–H)⁻=367.

Example 701

[1(R)]-3-[3-[(3,5-dimethylphenyl)methoxy]phenyl]-N-hydroxy-α,3-dimethyl-2-oxo-1-pyrrolidineacetamide (701a) Following the procedures analogous to examples 1a–d, 3a, 6b and 700a the hydroxamic acid 701 was obtained. LRMS found (M+H)⁺=397, (M–H)⁻=395.

Example 702

[1(R)]-N-hydroxy-α,3-dimethyl-3-[3-[(3-methylphenyl)methoxy]phenyl]-2-oxo-1-pyrrolidineacetamide (702a) Following the procedures analogous to examples 1a–d, 3a, 6b and 700a the hydroxamic acid 702 was obtained. LRMS found (M–H)⁻=381.

Example 703

[1(R)]-N-hydroxy-α,3-dimethyl-3-[3-(1-methylethoxy)phenyl]-2-oxo-1-pyrrolidineacetamide (703a) Following the procedures analogous to examples 1a–d, 3a, 6b and 700a the hydroxamic acid 703 was obtained. LRMS found (2M+Na)⁺=663.

Example 704

[1(R)]-3-[3-(heptyloxy)phenyl]-N-hydroxy-α,3-dimethyl-2-oxo-1-pyrrolidineacetamide (704a) Following the procedures analogous to examples 1a–d, 3a, 6b and 700a the hydroxamic acid 704 was obtained. LRMS found (M–H)⁻=375.

Example 705

[1(R)]-3-[4-[(2,6-dichloro-4-pyridinyl)methoxy]phenyl]-N1-hydroxy-α1-methyl-2-oxo-N3-1,3,4-thiadiazol-2-yl-1,3-pyrrolidinediacetamide (705a) To a stirred, cooled (−78° C.) solution of 5 grams methyl ester 705 was added 1.2 eq. of lithium diisopropylamide over 10 minutes. After stirring for 1 hour at −78° C. 1.7 mL of allyl bromide was added over 5 minutes. The reaction was allowed to slowly warm to ambient temperature while stirring overnight. Volatiles were removed under reduced pressure and the resulting material was diluted with ethyl acetate and washed with 1N hydrochloric acid. The aqueous phase was extracted 2 additional times with ethyl acetate. The combined organic phases were washed with brine, saturated aqueous sodium bicarbonate, brine, dried over magnesium sulfate and the volatiles were removed under reduced pressure. The resulting material wag chromatographed on silica gel eluting with 5% ethyl acetate/hexane affording 4.9 grams of 705a as a white solid. LRMS found $(M+H)^+=297$.

(705b) To a stirred, cooled ($-78°$ C.) solution of 5 grams (705a) was added 1.02 eq. of lithium diisopropylamide over 10 minutes. After stirring for 1 hour at $-78°$ C. 2.55 mL of t-butyl bromoacetate was added over 5 minutes. The reaction was allowed to slowly warm to ambient temperature while stirring overnight. Volatiles were removed under reduced pressure and the resulting material was diluted with ethyl acetate and washed with 1N hydrochloric acid. The aqueous phase was extracted 3 additional times with ethyl acetate. The combined organic phases were washed with brine, saturated aqueous sodium bicarbonate, brine, dried over magnesium sulfate and the volatiles were removed under reduced pressure. The resulting material was chromatographed on silica gel eluting with 5% ethyl acetate/hexane affording 5 grams of 705b as a white solid. LRMS found $(M+Na)^+=433$.

(705c) To 55 grams of methyl ester 705b in 600 mL of dimethyl sulfoxide, 400 mL of water and 1000 mL of methanol was added 55 grams of lithium hydroxide monohydrate. The reaction was stirred at 79° C. for 3 hours. The mixture was concentrated to about half original volume and poured into ice. The mixture was acidified with 1N hydrochloric acid and extracted 4 times with diethyl ether. The combined ether extracts were washed three times with water, twice with brine and dried over magnesium sulfate. The volatiles were removed under reduced pressure and the resulting material was recrystallized from acetone/hexane affording 45 grams of the acid 705c as a white solid. LRMS found $(M+Na)^+=419$.

(705d) To 1.3 grams of acid 705c in 20 mL of N,N-dimethylformamide was added 1.44 mL of 4-methylmorpholine and 1.44 grams of O-(7-azabenzotriazol-1-yl)-1,1,3,3-tetramethyluronium hexafluorophosphate. After stirring 30 minutes 0.46 grams of D-alanine methyl ester hydrochloride was added. The reaction was stirred 18 hours at ambient temperature and for 45 minutes at 60° C. The volatiles were removed under reduced pressure and the resulting material was partitioned in ethyl acetate and washed with 1N hydrochloric acid saturated with sodium chloride. The aqueous phase was extracted another two times with ethyl acetate. The combined organic phases were washed with brine, saturated aqueous sodium bicarbonate, brine, dried over magnesium sulfate and the volatiles were removed under reduced pressure. The resulting material was chromatographed on silica gel eluting with 25% ethyl acetate/hexane affording 1.6 grams of 705d. LRMS found $(M+Na)^+=504$.

(705e) To a stirred, cooled ($-78°$ C.) solution of 0.90 grams of 705d in 20 mL of dichloromethane was bubbled ozone until the mixture attained a blue color. Ozone was added for an additional 10 minutes followed by a 15 minute oxygen flush. To this material was added 0.54 grams of triphenylphosphine and the reaction was allowed to slowly warm to ambient temperature while stirring 48 hours. The volatiles were removed under reduced pressure and the resulting material was chromatographed on silica gel eluting with a gradient of 25% ethyl acetate/hexane to 50% ethyl acetate/hexane affording 0.620 grams of 705e as a viscous oil. LRMS found $(M+Na)^+=506$.

(705f) To a stirred cooled ($-20°$ C.: carbon tetrachloride/dry ice) solution of 14.1 grams of 705e in 500 mL of dichloromethane was added 23.3 mL of triethylsilane and 11.2 mL of triflouroacetic acid. The reaction was stirred 1 hour at 0° C. and 2 hours at room temperature. The reaction was made basic by the addition of saturated aqueous sodium bicarbonate and partitioned with chloroform. The aqueous was extracted 3 more times with chloroform. The combined organic phases were washed with brine, dried over magnesium sulfate and the volatiles were removed under reduced pressure affording 11.3 grams of 705f. LRMS found $(M+Na)^+=490$.

(705g) To 3 grams of 705f in 20 mL of methanol was added 0.30 grams of 10% palladium on carbon. The reaction was stirred 3 hours under hydrogen (balloon). The catalyst was filtered through a 0.45 uM PTFE filter and the volatiles were removed under reduced pressure affording 2.4 grams of phenol 705 g. LRMS found $(M+Na)^+=400$.

(705h) To 1.2 grams of 705g in 20 mL of DMSO was added 1.54 grams of 3-bromomethyl 2,5-dichloropyridine and 2.32 grams of cesium carbonate. After stirring for two hours at ambient temperature the reaction was diluted with diethyl ether and washed with brine. The aqueous was extracted an additional three times with ether. All organics were combined and washed with saturated aqueous sodium bicarbonate, water, brine, dried over magnesium sulfate and the volatiles were removed under reduced pressure. The resulting material was chromatographed on silica gel eluting with 2% methanol/chloroform affording 1.1 grams of 705h. LRMS found $(M+H)^+=481$.

(705i) To 1.1 grams of 705h in 50 mL of dichloromethane was added 10 mL of trifluoroacetic acid. After stirring 3 hours the volatiles were removed under reduced pressure affording 1 gram of 705i. LRMS found $(M+Na)^+=503$.

(705j) To 0.50 grams of 705i in 20 mL of N,N-dimethylformamide was added 0.46 mL of 4-methylmorpholine, 0.315 grams of 2-amino-1,3,4-thiadiazole and 0.474 grams of O-(7-azabenzotriazol-1-yl)-1,1,3,3-tetramethyluronium hexafluorophosphate. After stirring 10 hours at room temperature the reaction was heated at 60° C. for 45 minutes. The volatiles were removed under reduced pressure and the resulting material was diluted with ethyl acetate and washed with 1N hydrochloric acid saturated with sodium chloride. The aqueous was extracted 3 times with ethyl acetate and all the organics were combined and extracted with brine, saturated aqueous sodium bicarbonate, brine, dried over magnesium sulfate, and the volatiles were removed under reduced pressure affording 0.60 grams of 705j. LRMS found $(M-H)^-=562$.

(705k) To 0.55 grams of 705j in 20 mL of 1:1 tetrahydrofuran/water was added 0.12 grams of lithium hydroxide monohydrate. After stirring 3 hours at ambient temperature the reaction volume was reduced by half under reduced pressure, diluted with water and washed twice with diethyl ether. The ether phases were combined and extracted twice with water. All aqueous phases were combined, acidified with 1N hydrochloric acid and extracted 3 times with ethyl acetate. The combined ethyl acetate extracts were washed with water, brine, dried over magnesium sulfate and the volatiles were removed under reduced pressure affording 0.52 grams of 705k. LRMS found $(M-H)^-=548$.

(7051) To 0.40 grams of 705k in 20 mL of N,N-dimethylformamide was added 0.8 mL of 4-methyl morpholine, 0.202 grams of hydroxylamine hydrochloride and 0.354 grams of benzotriazol-1-yl-oxy-tris (dimethylamino)phosphoniumhexafluorophosphate. After stirring overnight at ambient temperature the volatiles were removed under reduced pressure and the resulting material was separated on C18 reverse phase HPLC isolating 0.18 grams of faster isomer 705l. LRMS found (M−H)−=563.

Example 706

[1(R)]-1,1-dimethylethyl 1-[2-(hydroxyamino)-1-methyl-2-oxoethyl]-2-oxo-3-[4-(phenylmethoxy) phenyl]-3-pyrrolidineacetate (706a) Following the procedures analogous to examples 705a–j and 700a the hydroxamic acid 706 was obtained and isolated as the faster isomer by reverse phase HPLC. LRMS found (M−H)−=467, (M+H)+=469

Example 707

[1(R)]-1-[2-(hydroxyamino)-1-methyl-2-oxoethyl]-2-oxo-3-[4-(phenylmethoxy)phenyl]-3-pyrrolidineacetic acid (707a) To 0.015 grams of hydroxamic acid 706 in 3 mL of dichloromethane was added 0.5 mL of trifluoroacetic acid. After stirring one hour the volatiles were removed under reduced pressure affording 0.009 grams of 707. LRMS found (M+Na)+=435, (M−H)−411

Example 708

[1(R)]-3-[4-[(3,5-dimethylphenyl)methoxy]phenyl]-N1-hydroxy-α1-methyl-N3-[2-(methylamino)-2-oxoethyl]-2-oxo-1,3-pyrrolidinediacetamide (708a) Following the procedures analogous to examples 705a–j and 700a the hydroxamic acid 708 was obtained and isolated as the faster isomer by reverse phase HPLC. LRMS found (M+Na)+533.

Example 709

[1(R)]-3-[4-[(3,5-dimethylphenyl)methoxy]phenyl]-N1-hydroxy-α1-methyl-2-oxo-N3-2-thiazolyl-1,3-pyrrolidinediacetamide (709a) Following the procedures analogous to examples 705a–j and 700a the hydroxamic acid 709 was obtained and isolated as the faster isomer by reverse phase HPLC. LRMS found (M−H)−=521.

Example 710

[1(R)]-3-[4-[(3,5-dimethylphenyl)methoxy]phenyl]-N-hydroxy-α-methyl-3-[2-(4-morpholinyl)-2-oxoethyl]-2-oxo-1-pyrrolidineacetamide (710a) Following the procedures analogous to examples 705a–j and 700a the hydroxamic acid 710 was obtained and isolated as the faster isomer by reverse phase HPLC. LRMS found (M+Na)+=532.

Example 711

[1(R)]-3-[4-[(2,6-dichloro-4-pyridinyl)methoxy] phenyl]-N1-hydroxy-α1-methyl-2-oxo-N3-2-thiazolyl-1,3-pyrrolidinediacetamide mono (trifluoroacetate)

(711a) Following the procedures analogous to examples 705a–j and 700a the hydroxamic acid 711 was obtained and isolated as the faster isomer by reverse phase HPLC. LRMS found (M+H)+=564.

Example 712

[1(R)]-3-[4-[(2,6-dichloro-4-pyridinyl)methoxy] phenyl]-N1-hydroxy-α1-methyl-2-oxo-N3-[2-(4-morpholinyl)ethyl]-1,3-pyrrolidinediacetamide) bis (trifluoroacetate)

(712a) Following the procedures analogous to examples 705a–j and 700a the hydroxamic acid 712 was obtained and isolated as the faster isomer by reverse phase HPLC. LRMS found.(M+H)+=594

Example 713

[1(R)]-3-[4-[(2,6-dichloro-4-pyridinyl)methoxy] phenyl]-N1-hydroxy-α1-methyl-2-oxo-N3-(4-pyridinylmethyl)-1,3-pyrrolidinediacetamide bis (trifluoroacetate)

(713a) Following the procedures analogous to examples 705a–j and 700a the hydroxamic acid 713 was obtained and isolated as the faster isomer by reverse phase HPLC. LRMS found (M+Na)+=594

Example 714

[1(R)]-3-[4-[(2,6-dimethyl-4-pyridinyl)methoxy] phenyl]-N1-hydroxy-α1-methyl-2-oxo-N3-2-thiazolyl-1,3-pyrrolidinediacetamide mono (trifluoroacetate)

(714a) Following the procedures analogous to examples 705a–j and 700a the hydroxamic acid 714 was obtained and isolated as the faster isomer by reverse phase HPLC. LRMS found (M+H)+=524.

Example 715

[1(R)]-3-[4-[(2,6-dichloro-4-pyridinyl)methoxy] phenyl]-N1-hydroxy-α1-methyl-2-oxo-N3-(3-pyridinylmethyl)-1,3-pyrrolidinediacetamide mono (trifluoroacetate)

(715a) Following the procedures analogous to examples 705a–j and 700a the hydroxamic acid 715 was obtained and isolated as the faster isomer by reverse phase HPLC. LRMS found (M+Na)+=594.

Example 716

[1(R)]-3-[4-[(2,6-dichloro-4-pyridinyl)methoxy] phenyl]-N1-hydroxy-α1-methyl-2-oxo-N3-(2-pyridinylmethyl)-1,3-pyrrolidinediacetamide mono (trifluoroacetate)

(716a) Following the 716 analogous to examples 705a–j and 700a the hydroxamic acid 706 was obtained and isolated as the faster isomer by reverse phase HPLC. LRMS found (M+H)+=572.

Example 717

[1(R)]-3-[4-[(2,6-dichloro-4-pyridinyl)methoxy] phenyl]-N1-hydroxy-α1-methyl-2-oxo-N3-4-pyridinyl-1,3-pyrrolidinediacetamide mono (trifluoroacetate)

(717a) Following the procedures analogous to examples 705a–j and 700a the hydroxamic acid 717 was obtained and isolated as the faster isomer by reverse phase HPLC. LRMS found (M+H)⁺=558.

Example 718

[1(R)]-3-[4-[(2,6-dichloro-4pyridinyl)methoxy]phenyl]-N1-hydroxy-α1-methyl-N3-(3-methyl-5-isothiazolyl)-2-oxo-1,3-pyrrolidinediacetamide (718a) Following the procedures analogous to examples 705a–l the hydroxamic acid 718 was obtained and isolated as the faster isomer by reverse phase HPLC. LRMS found (M−H)⁻=576.

Example 719

[1(R)]-3-[4-[(2,6-dichloro-4-pyridinyl)methoxy]phenyl]-N3-[5-(1,1-dimethylethyl)-1,3,4-thiadizol-2-yl]-N1-hydroxy-α1-methyl-2-oxo-1,3-pyrrolidinediacetamide (719a) Following the procedures analogous to examples 705a–l the hydroxamic acid 719 was obtained and isolated as the faster isomer by reverse phase HPLC. LRMS (M−H)⁻=619.

Example 720

[1(R)]-1,1-dimethylethyl 2-[[[3-[4-[(2,6-dichloro-4-pyridinyl)methoxy]phenyl]-1-[2-(hydroxyamino)-1-methyl-2-oxoethyl]-2-oxo-3-pyrrolidinyl]acetyl]amino]-4-thiazoleacetate (720a) Following the procedures analogous to examples 705a–l the hydroxamic acid 720 was obtained and isolated as the faster isomer by reverse phase HPLC. LRMS (M−H)⁻=676.

Example 721

[1(R)]-2-[[[3-[4-[(2,6-dichloro-4-pyridinyl)methoxy]phenyl]-1-[2-(hydroxyamino)-1-methyl-2-oxoethyl]-2-oxo-3-pyrrolidinyl]acetyl]amino]-4-thiazoleacetic acid (721a) Following the procedures analogous to examples 705a–l and 707a the hydroxamic acid 721 was obtained and isolated as the faster isomer by reverse phase HPLC. LRMS found (M−H)⁻=620.

Example 722

[1(R)]-3-[4-[(2,6-dichloro-4-pyridinyl)methoxy]phenyl]-N1-hydroxy-α1-methyl-N3-[4-[2-(methylamino)-2-oxoethyl]-2-thiazolyl]-2-oxo-1,3-pyrrolidinediacetamide (722a) Following the procedures analogous to examples 705a–j, 707a,705j–l the hydroxamic acid 722 was obtained and isolated as the faster isomer by reverse phase HPLC. LRMS found (M+Na)⁺=657.

Example 723

[1(R)]-3-(1H-benzimidazol-2-ylmethyl)-3-[4-[(2,6-dichloro-4-pyridinyl)methoxy]phenyl]-N-hydroxy-α-methyl-2-oxo-1-pyrrolidineacetamide (723a) To 0.20 grams of acid obtained by procedures analogous to 705a–i in 5 mL of N,N-dimethylformamide was added 0.18 mL of 4-methyl morpholine, 0.135 grams of phenyldiamine, and 0.173 grams of O-(7-azabenzotriazol-1-yl)-1,1,3,3-tetramethyluronium hexafluorophosphate. After stirring for 12 hours at ambient temperature the volatiles were removed under reduced pressure and the resulting material was washed with brine and 1 mL of 10% aqueous citric acid. The aqueous was extracted twice with ethyl acetate and the combined organic phases were washed with brine, saturated aqueous sodium bicarbonate, brine, dried over magnesium sulfate and the volatiles were removed under reduced pressure affording 723a. LRMS found (M+H)⁺=571.

(723b) To 0.20. grams of 723a in 40 mL of 1:1 tetrahydrofuran/acetic acid was heated to reflux for 1.5 hours. The volatiles were removed under reduced pressure and the resulting material was dissolved in ethyl acetate and washed with water. The aqueous phase was extracted twice with ethyl acetate and the combined organic phases were washed with water, saturated aqueous sodium bicarbonate, brine, dried over magnesium sulfate and the volatiles were removed under reduced pressure affording 0.17 grams of 723b. LRMS found (M+H)⁺=553.

(723c) To 0.15 grams of 723b in 6 mL of 1:1 tetrahydrofuran/water was added 0.065 grams of lithium hydroxide monohydrate. After stirring for two hours at ambient temperature the volatiles were removed under reduced pressure and the resulting material was dissolved in ethyl acetate and washed 1N hydrochloric acid. The aqueous was extracted twice with ethyl acetate and the combined organic phases were washed with brine, dried over magnesium sulfate and the volatiles were removed under reduced pressure affording 0.11 grams of 723c. LRMS found (M+H)⁺=539.

(723d) Following the procedure analogous to 705l the hydroxamic acid 723d was obtained and isolated as the faster isomer by C18 reverse phase HPLC. LRMS found (M+H)+=554.

Example 724

[1(R)]-3-[4-[(2,6-dichloro-4-pyridinyl)methoxy]phenyl]-N-hydroxy-3-(3H-imidazo(4,5-c]pyridin-2-ylmethyl)-α-methyl-2-oxo-1pyrrolidineacetamide (724a) Following the procedures analogous to examples 723a–d the hydroxamic acid 724 was obtained and isolated as the faster isomer by reverse phase HPLC. LRMS found (M+H)⁺=555.

Example 725

[1(R)]-3-[4-[3,5bis(trifluoromethyl)phenoxy]phenyl]-N1-hydroxy-α1-methyl-2-oxo-N3-2-thiazolyl-1,3-pyrrolidinediacetamide (725a) Following the procedures analogous to examples 705a–g, 61a, and 705i–l, the hydroxamic acid 725 was obtained and isolated as the faster isomer by reverse phase HPLC. LRMS found (M−H)⁻=615.

Example 726

[1(R)]-3-[4-[3,5-bis(trifluoromethyl)phenoxy]phenyl]-N1-hydroxy-α1-methyl-2-oxo-N3-(4-pyridinylmethyl)-1,3-pyrrolidinediacetamide mono (trifluoroacetate)

(726a) Following the procedures analogous to examples 705a–g, 61a, and 705i–l, the hydroxamic acid 726 was obtained and isolated as the faster isomer by reverse phase HPLC. LRMS found (M+H)$^+$=625.

Example 780

[1(R)]-3-[4-[(2,6-dimethyl-4-pyridinyl)methoxy] phenyl]-N1-hydroxy-α1-(1-methylethyl)-2-oxo-N3-(4-pyridinylmethyl)-1,3-pyrrolidinediacetamide (780a) A 1.0 M tetrahydrofuran solution of sodium bis (trimethylsilyl)amide (192.5 mL, 1.1 eq) was added over 30 min to methyl 4-benzyloxyphenylacetate (44.95 g, 175 mmol) in tetrahydrofuran (900 mL) at −78° C. After 1 h at −78° C., DMPU (52.9 mL, 2.5 eq) was added over 15 min. The cold bath was replaced with an ice-water bath, and 2-benzyloxyethyl iodide (50.45 g, 1.1 eq) in THF (40 mL) was added dropwise. After 2 h at 0° C., sat ammonium chloride (500 mL) was added. Following removal of THF in vacuo, the residue was diluted with water (250 mL) and extracted with 1:2 mixture of ether-hexane (3×500 mL). The combined extracts were washed with water (2×100 mL), brine (100 mL), dried (MgSO4) and concentrated. The residue was filtered through a silica gel pad and the filter cake rinsed with ethyl acetate-hexane (20:80) until free of product. The filtrate was concentrated and used in the next step without purification. MS found: (M+H)$^+$=391.

(780b) Following a procedure analogous to (1a), the crude material from (780a) was reacted with allyl bromide. The crude material was used in the next step without purification. MS found: (M+H)$^+$=431.

(780c) Following a procedure analogous to (1c), the crude material from (780b) was ozonolized. Silica gel chromatography (ethyl acetate-hexane, 15:85 then 20:80 then 25:75) gave the desired aldehyde (43.27 g, 57% for three steps). MS found: (M+H)$^+$=433.

(780d) Following a procedure analogous to (1d), the aldehyde from (780c) (3.00 g, 6.94 mmol) and D-valine ethyl ester hydrochloride was condensed to give the lactam (2.50 g, 68%) as a 1:1 mixture of two isomers. MS found: (M+H)$^+$=530.

(780e) Following a procedure analogous to step (3a), the lactam from (780d) (4.50 g, 8.51 mmol) was hydrogenolized to give the phenol (2.30 g, 77%). MS found: (M+H)$^+$=350.

(780f) Following a procedure analogous to step (6b), the phenol from (780e) (975 mg, 2.79 mmol) was reacted with 4-chloromethyl-2,6-dimethylpyridine hydrochloride to give the picolyl ether (818 mg, 62%). MS found: (M+H)$^+$=455.

(780g) Ruthenium chloride monohydrate (18 mg, 0.05 eq) was added to a mixture of the picolyl ether from (780f) (790 mg, 1.69 mmol), sodium periodate (1.44 g, 4 eq), acetonitrile (2 mL), carbon tetrachloride (2 mL) and water (3.5 mL). After 5 h at rt, the mixture was extracted with chloroform (3×). The extracts were washed with brine, dried (MgSO4) and concentrated to give the crude carboxylic acid (710 mg). MS found: (M+H)$^+$=469.

(780h) Following a procedure analogous to step (705j), the carboxylic acid from (780g) (218 mg, 0.452 mmol) was coupled with 4-picolylamine to give the amide (179 mg, 69%). MS found: (M+H)$^+$=573.

(780i) Following a procedure analogous to step (92d), the ester from (780h) was reacted with hydroxylamine to give the desired hydroxamic acid (40 mg, 23%). MS found: (M+H)$^+$=560.

Example 781

[1(R)]-3-[4-[(2,6-dichloro-4-pyridinyl)methoxy] phenyl]-N1-hydroxy-α1-(1-methylethyl)-2-oxo-N3-(4-pyridinylmethyl)-1,3-pyrrolidinediacetamide Beginning with the phenol from (780e) and 4-bromomethyl-2,6-dichloropyridine, example 781 was prepared in an analogous series of reactions to (780f–i). MS found: (M+H)$^+$=600.

Example 782

[1(R)]-α1-(cyclohexylmethyl)-3-[4-[(2,6-dimethyl-4-pyridinyl)methoxy]phenyl]-N1-hydroxy-2-oxo-N3-(4-pyridinylmethyl)-1,3-pyrrolidinediacetamide Beginning with the aldehyde from (780c) and D-cyclohexylmethylglycine methyl ester, example 782 was prepared in an analogous series of reactions to (780d–i). MS found: (M+H)$^+$=614.

Example 783

[1(R)]-α1-(cyclohexylmethyl)-3-[4-[(2,6-dichloro-4-pyridinyl)methoxy]phenyl]-N1-hydroxy-2-oxo-N3-(4-pyridinylmethyl)-1,3-pyrrolidinediacetamide Beginning with the aldehyde from (780c) and D-cyclohexylmethylglycine methyl ester and using 4-bromomethyl-2,6-dichloropyridine in place of 4-chloromethyl-2,6-dimethylpyridine, example 783 was prepared in an analogous series of reactions to (790d–i). MS found: (M+H)$^+$=654.

Example 784

[1(R)]-1,1-dimethylethyl [5-[3-[4-[(2,6-dimethyl-4-pyridinyl)methoxy]phenyl]-2-oxo-3-[2-oxo-2-[(4-pyridinylmethyl)amino]ethyl]-1-pyrrolidinyl]-6-(hydroxyamino)-6-oxohexyl]carbamate Following a sequence analogous to example 705, example 784 was prepared. MS found: (M+H)$^+$=689.

Example 785

[1(R)]-α1-(4-aminobutyl)-3-[4-[(2,6-dimethyl-4-pyridinyl)methoxy]phenyl]-N1-hydroxy-2-oxo-N3-(4-pyridinylmethyl)-1,3-pyrrolidinediacetamide tris (trifluoroacetate)

Example 785 was prepared from example 784 following a procedure similar to example 117. MS found: (M+2H)$^{2+}$=590.

Example 800

[1(R)]-3-[3-(1H-benzotriazol-1-ylmethoxy)phenyl]-N-hydroxy-α,3-dimethyl-2-oxo-1-pyrrolidineacetamide (800a) To 0.090 grams of methyl ester, obtained in a manner analogous to examples 1a–d, in 1 mL of anhydrous methanol was added 0.153 grams of hydroxylamine hydrochloride and 0.18 grams of sodium methoxide. The reaction was stirred at room temperature overnight at which time it was quenched with hydrochloric acid and the volatiles were removed under reduced pressure. The resulting material was purified by reverse phase HPLC affording the hydroxamic acid 800. LRMS found (M−H)$^-$=408.

Example 801

[1(R)]-N-hydroxy-3,4,4-trimethyl-α-[3-methyl-2-oxo-3[4-(phenylmethoxy)phenyl]-1-pyrrolidinyl]-2,5-dioxo-1-imidazolidinepropanamide (801a) Following the procedures analogous to examples 1a–d, 6b and 800a the hydroxamic acid 801 was obtained. LRMS found (M+H)$^+$509, (M−H)−=507 (M+Na)+=531

Example 802

[1(R)]-1,1-dimethylethyl 1-[(hydroxyamino) carbonyl]-3-methylbutyl]-2-oxo-3-[4-(phenyl]-3-pyrrolidineacetate (802a) Following the procedures analogous to examples 705a–f and 1e the hydroxamic acid was obtained and isolated by reverse phase HPLC. LRMS found (M–H)–= 509, (M+H)+=511, (M+Na)+=533.

Example 803

[1(R)-N1-hydroxy-3-[4-[(3,5-dimethylphenyl) methoxy]phenyl]-N3-[2-(methylamino)-2-oxoethyl]-α-(2methylpropyl)-2-oxo-1,3-pyrrolidinediacetamide (803a) Following the procedures analogous to examples 705a–j and 1e the hydroxamic acid was obtained and isolated by reverse phase HPLC. LRMS found (M+Na)+= 533, (M–H)–=551, (M+H)+=553.

Example 804

[1(R)]-3-[4-[(2,6-dichloro-4-pyridinyl)methoxy] phenyl]-N1-hydroxy-N3-[2-(methylamino)-2-oxoethyl]-alpha1-(2-methylpropyl)-2-oxo-1,3-pyrrolidinediacetamide (804a) Following the procedures analogous to examples 705a–j. and 1e the hydroxamic acid was obtained and isolated by reverse phase HPLC. LRMS found (M+H)+= 595.

Example 805

[1(R)]-3-[4-[(2,6-dichloro-4-pyridinyl)methoxy] phenyl]-N1-hydroxy-α1-(2-methylpropyl)-2-oxo-N3-2-thiazolyl-1,3-pyrrolidinediacetamide (805a) Following the procedures analogous to examples 705a–j and 1e the hydroxamic acid was obtained and isolated by reverse phase HPLC. LRMS found (M+H)+ 607, (M–H)–=605.

Example 806

[1(R)]-3-[4-[3,5-bis(trifluoromethyl)phenoxy] phenyl]-N1-hydroxy-N3-[2-(methylamino)-2-oxoethyl]-α1-(2-methylpropyl)-2-oxo-1,3-pyrrolidinediacetamide (806a) Following the procedures analogous to examples 705a–g, 61a, 705i, 705j, and 1e the hydroxamic acid was obtained and isolated by reverse phase HPLC. LRMS found (M+H)+=647, (M–H)–=645, (M+Na)+=669.

Example 807

[1(R)]-3-[4-[3,5-bis(trifluoromethyl)phenoxy] phenyl]-N1-hydroxy-α1-(2-methylpropyl)-2-oxo-N3-(4-pyridinylmethyl)-1,3-pyrrolidinediacetamide mono(trifluoroacetate)

(807a) Following the procedures analogous to examples 705a–g, 61a, 705i, 705j, and 1e the hydroxamic acid was obtained and isolated by reverse phase HPLC. LRMS found (M+H)+=667.

Example 808

[1(R)]-3-[4-[(2,6-dichloro-4-pyridinyl)methoxy] phenyl]-N1-hydroxy-α1-(2-methylpropyl)-2-oxo-N3-phenyl-1,3-pyrrolidinediacetamide (808a) Following the procedures analogous to examples 705a–l the hydroxamic acid was obtained and isolated by reverse phase HPLC. LRMS found (M+H)+=600.

Example 809

[1(R)]-3-[4-[(2,6-dimethyl-4-pyridinyl)methoxy] phenyl]-N1-hydroxy-N3-methyl-α1-(2-methylpropyl)-2-oxo-1,3-pyrrolidinediacetamide mono(trifluoroacetate)

(809a) Following the procedures analogous to examples 705a–l the hydroxamic acid was obtained and isolated by reverse phase HPLC. LRMS found (M+H)+=497.

Example 810

[1(R)]-3-[4-[(2,6-dimethyl-4-pyridinyl)methoxy] phenyl]-N1-hydroxy-N3-[2-(1H-imidazol-4-yl) ethyl]-α1-(2-methylpropyl)-2-oxo-1,3-pyrrolidinediacetamide bis(trifluoroacetate)

(810a) Following the procedures analogous to examples 705a–l the hydroxamic acid was obtained and isolated by reverse phase HPLC. LRMS found (M+H)+=577.

Example 811

[1(R)]-3-[4-[(2,6-dimethyl-4-pyridinyl)methoxy] phenyl]-N1-hydroxy-α1-(2-methylpropyl)-2-oxo-N3-[1-(phenylmethyl)-4-piperidinyl]-1,3-pyrrolidinediacetamide bis(trifluoroacetate)

(811a) Following the procedures-analogous to examples 705a–l the hydroxamic acid was obtained and isolated by reverse phase HPLC. LRMS found (M+H)+=656.

Example 812

[1(R)]-N3-[2-(dimethylamino)ethyl]-3-[4-[(2,6-dimethyl-4-pyridinyl)methoxy]phenyl]-N1-hydroxy-α1-(2-methylpropyl)-2-oxo-1,3-pyrrolidinediacetamide bis(trifluoroacetate)

(812a) Following the procedures analogous to examples 705a–l the hydroxamic acid was obtained and isolated by reverse phase HPLC. LRMS found (M+H)+=554.

Example 813

[1(R)]-3-[4-[(2,6-dimethyl-4-pyridinyl)methoxy] phenyl]-N1-hydroxy-N3-(4-hydroxyphenyl)-α1-(2-methylpropyl)-2-oxo-1,3-pyrrolidinediacetamide mono(trifluoroacetate)

(813a) Following the procedures analogous to examples 705a–l the hydroxamic acid was obtained and isolated by reverse phase HPLC. LRMS found (M+H)+=575.

Example 814

[1(R)]-3-[4-[(2,6-dimethyl-4-pyridinyl)methoxy] phenyl]-N3-hydroxy-α1-(2-methylpropyl)-2-oxo-N3-2-thiazolyl-1,3-pyrrolidinediacetamide mono (trifluoroacetate)

(814a) Following the procedures analogous to examples 705a–l the hydroxamic acid was obtained and isolated by reverse phase HPLC. LRMS found (M+H)+=566

Example 815

[1(R)-]-[4-[(2,6-dimethyl-4-pyridinyl)methoxy]
phenyl]-N3-hydroxy-3-(2-hydroxyethyl)-α1-(2-
methylpropyl)-2-oxo-1-pyrrolidineacetamide mono
(trifluoroacetate)

(815a) Following the procedures analogous to examples 780 the hydroxamic acid was obtained and isolated by reverse phase HPLC. LRMS found (M+H)+=470.

Example 816

[1(R)]-3-[4-[(2,6-dimethyl-4-pyridinyl)methoxy]
phenyl]-N3-(4,5-dimethyl-2-thiazolyl)-N1-hydroxy-
α1-(2-methylpropyl)-2-oxo-1,3-
pyrrolidinediacetamide mono(trifluoroacetate)

(816a) Following the procedures analogous to examples 705a–l the hydroxamic acid was obtained and isolated by reverse phase HPLC. LRMS found (M+H)+=594.

Example 817

[1(R)]-3-[4-[(2,6-dimethyl-4-pyridinyl)methoxy]
phenyl]-N1-hydroxy-N3-1H-indazol-5-yl-α1-(2-
methylpropyl)-2-oxo-1,3-pyrrolidinediacetamide
mono(trifluoroacetate)

(817a) Following the procedures analogous to examples 705a–l the hydroxamic acid was obtained and isolated by reverse phase HPLC. LRMS found (M+H)+=599.

Example 818

[1(R)]-3-[4-[3,5-bis(trifluoromethyl)phenoxy]
phenyl]-N1-hydroxy-α1-(2-methylpropyl)-2-oxo-
N3-2-thiazolyl-1,3-pyrrolidinediacetamide (818a) Following the procedures analogous to examples 705a–g, 61a, and 705i–l the hydroxamic acid was obtained and isolated by reverse phase HPLC. LRMS found (M+H)+=659.

TABLE 1

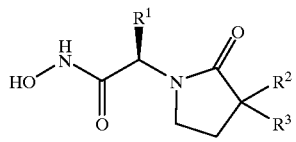

| Ex # | R$^1$ | R$^2$ | R$^3$ | MS |
|---|---|---|---|---|
| 1 | Me | Me | 4-(phenylmethoxy)phenyl | 367 |
| 2 | Me | Me | 4-methoxyphenyl | 291 |
| 3 | Me | Me | 4-(1-isopropoxy)phenyl | 319 |
| 4 | Me | Me | 4-(t-butoxy)phenyl | 333 |
| 5 | Me | Me | 4-cyclohexyloxyphenyl | 359 |
| 6 | Me | Me | 4-[[4-(t-butyl)phenyl]methoxy]phenyl | 423 |
| 7 | Me | Me | 4-[(3-phenyl-2-propen-1-yl)oxy]phenyl | 393 |
| 8 | Me | Me | 4-[(3-methylphenyl)methoxy]phenyl | 381 |
| 9 | Me | Me | 4-[(3,5-dimethylphenyl)methoxy]phenyl | 395 |
| 10 | Me | Me | 4-allyloxyphenyl | 317 |
| 11 | Me | Me | 4-[(3-cyanophenyl)methoxy]phenyl | 392 |
| 12 | Me | Me | 4-[(2-nitrophenyl)methoxy]phenyl | 412 |
| 13 | Me | Me | 4-[(4-nitrophenyl)methoxy]phenyl | 412 |
| 14 | Me | Me | 4-[(3-nitrophenyl)methoxy]phenyl | 412 |
| 15 | Me | Me | 4-[(2-naphthalenyl)methoxy]phenyl | 417 |
| 16 | Me | Me | 4-hydroxyphenyl | 277 |
| 17 | Me | Me | 4-[(2-pyridinyl)methoxy]phenyl | 368 |
| 18 | Me | Me | 4-[(3-pyridinyl)methoxy]phenyl | 368 |
| 19 | Me | Me | 4-[(4-pyridinyl)methoxy]phenyl | 368 |
| 20 | Me | Me | 4-(i-Bu)phenyl | 317 |
| 21 | Me | Me | phenyl | 261 |
| 22 | Me | Me | phenyl | 233 |
| 23 | H | H | phenyl | 247 |
| 24 | H | Me | phenyl | 247 |
| 25 | Me | H | 4-methoxyphenyl | 277 |
| 26 | Me | H | cyclohexyl | 267 |
| 27 | Me | Me | 2-phenylethyl | 289 |
| 28 | Me | Me | 2-cyclohexylethyl | 295 |
| 29 | Me | Me | phenyl | 337 |
| 30 | | | see structure at bottom | 287 |
| 31 | Me | Me | 4-[(3,5-dibromophenyl)methoxy]phenyl | 523 |
| 32 | Me | Me | 4-[[3,5-bis(trifluoromethyl)phenyl]-methoxy]phenyl | 503 |
| 33 | Me | Me | 4-[(3,5-dichlorophenyl)methoxy]phenyl | 435 |
| 34 | Me | Me | 4-[(2-methyl-1-naphthalenyl)methoxy]-phenyl | 455 |
| 35 | Me | Me | 4-[(3,5-dimethoxyphenyl)methoxy]-phenyl | 427 |
| 36 | Me | Me | 4-[[4-chloro-2-(trifluoromethyl)-6-quinolinyl]methoxy]phenyl | 520 |
| 37 | Me | Me | 4-[[4-(1,2,3-thiadiazol-4-yl)phenyl]-methoxy]phenyl | 451 |

TABLE 1-continued

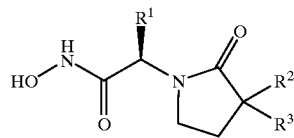

| Ex # | R¹ | R² | R³ | MS |
|---|---|---|---|---|
| 38 | Me | Me | 4-([1,1'-biphenyl]-2-ylmethoxy)phenyl | 443 |
| 39 | Me | Me | 4-[(2,6-dichloro-4-pyridinyl)methoxy]-phenyl | 436 |
| 40 | Me | Me | 4-(1H-benzotriazol-1-ylmethoxy)phenyl | 408 |
| 41 | Me | Me | 4-[(4,6-dimethyl-2-pyrimidinyl)-methoxy]phenyl | 397 |
| 42 | Me | Me | 4-(1,3-benzodioxol-5-ylmethoxy)phenyl | 411 |
| 43 | Me | Me | 4-[(2-chloro-6-ethoxy-4-pyridinyl)-methoxy]phenyl | 446 |
| 44 | Me | Me | 4-(4-quinolinylmethoxy)phenyl | 420 |
| 45 | Me | Me | 4-[(4,5-dimethyl-2-thiazolyl)methoxy]-phenyl | 402 |
| 46 | Me | Me | 4-[(2,6-dimethyl-4-pyridinyl)methoxy]-phenyl | 398 |
| 47 | Me | Me | 4-[(3-methyl-5-nitrophenyl)methoxy]-phenyl | 426 |
| 48 | Me | Me | 4-[(3-amino-5-methylphenyl)methoxy]-phenyl | 396 |
| 49 | Me | Me | 4-[[3-(acetylamino)-5-methylphenyl]-methoxy]phenyl | 438 |
| 50 | Me | Me | 4-[[3-[[[(t-butoxy)carbonyl]amino]-acetyl]amino]-5-methylphenyl]-methoxy]phenyl | 553 |
| 51 | Me | Me | 4-[[3-(aminoacetyl)amino]-5-methyl-phenyl]methoxy]phenyl | 455 |
| 52 | Me | Me | 4-[[3-[[[[(t-butoxy)carbonyl]-amino]acetyl]amino]acetyl]amino]-5-methylphenyl]methoxy]phenyl | 634 |
| 53 | Me | Me | 4-[[3-[[[(aminoacetyl)amino]acetyl]-amino]-5-methylphenyl]methoxy]phenyl | 512 |
| 54 | Me | Me | 4-[[3-[[(4-morpholinyl)carbonyl]-amino]-5-methylphenyl]methoxy]phenyl | 509 |
| 55 | | | see structure at bottom | 479 |
| 56 | Me | Me | [1,1'-biphenyl]-4-yl | 339 |
| 57 | Me | Me | 2'-methyl[1,1'-biphenyl]-4-yl | 353 |
| 58 | Me | Me | 4'-methyl[1,1'-biphenyl]-4-yl | 353 |
| 59 | Me | Me | 3',4'-dimethoxy[1,1'-biphenyl]-4-yl | 397 |
| 60 | Me | Me | 2'-(trifluoromethyl)[1,1'-biphenyl]-4-yl | 405 |
| 61 | Me | Me | 4-(4-methylphenoxy)phenyl | 367 |
| 62 | Me | Me | 4-phenoxyphenyl | 353 |
| 63 | Me | Me | 4-(2-methylphenoxy)phenyl | 367 |
| 64 | Me | Me | 4-(3,5-dichlorophenoxy)phenyl | 421 |
| 65 | Me | Me | 4-(3,4-dimethoxyphenoxy)phenyl | 413 |
| 66 | Me | Me | 4-(1,3-benzodioxol-5-yloxy)phenyl | 397 |
| 67 | Me | Me | 4-[3-(i-Pr)phenoxy]phenyl | 395 |
| 68 | Me | Me | 4-(3-methoxyphenoxy)phenyl | 383 |
| 69 | Me | Me | 4-(3-thienyloxy)phenyl | 359 |
| 70 | Me | Me | 4-(3,4,5-trimethoxyphenoxy)phenyl | 443 |
| 71 | Me | Me | 4-[3,5-bis(trifluoromethyl)phenoxy]-phenyl | 491 |
| 72 | Me | Me | 4-(1-naphthalenyloxy)phenyl | 405 |
| 73 | Me | Me | 4-[3-[(hydroxyimino)methyl]phenoxy]-phenyl | 398 |
| 74 | Me | Me | 4-[4-[1-(hydroxyimino)ethyl]phenoxy]-phenyl | 410 |
| 75 | Me | Me | 4-([1,1'-biphenyl]-4-yloxy)phenyl | 431 |
| 76 | Me | Me | 4-(3,5-dibromophenoxy)phenyl | 510 |
| 77 | Me | Me | 4-[3-(acetylamino)phenoxy]phenyl | 412 |
| 78 | Me | Me | 4-(4-nitrophenoxy)phenyl | 398 |
| 79 | Me | Me | 4-methylphenyl | 275 |
| 80 | Me | Me | 4-[[(2,6-dimethyl-4-pyridinyl)oxy]-methyl]phenyl | 398 |
| 81 | Me | Me | 4-[(4-quinolinyloy)methyl]phenyl | 420 |
| 82 | Me | Me | 4-nitrophenyl | 306 |
| 83 | Me | Me | 4-[(phenylcarbonyl)amino]phenyl | 380 |
| 94 | Me | Me | 4-[(phenylsulfonyl)amino]phenyl | 440 |
| 85 | Me | Me | 4-[[(phenylamino)carbonyl]amino]-phenyl | 419 |

TABLE 1-continued

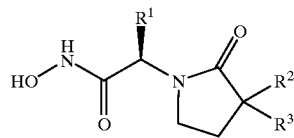

| Ex # | R¹ | R² | R³ | MS |
|---|---|---|---|---|
| 86 | Me | Me | 4-[(1-naphthalenylmethyl)amino]phenyl | 440 |
| 87 | Me | Me | 4-[(4-quinolinylmethyl)amino]phenyl | 419 |
| 88 | Me | Me | 4-[[(3,5-dimethoxyphenyl)methyl]-amino]phenyl | 426 |
| 89 | H | Me | 4-[(3,5-dimethylphenyl)methoxy]phenyl | 405 |
| 90 | H | Me | 4-[(2,6-dichloro-4-pyridinyl)methoxy]-phenyl | 424 |
| 91 | H | Me | 4-[(2,6-dimethyl-4-pyridinyl)methoxy]-phenyl | 384 |
| 92 | i-Pr | Me | 4-(4-quinolinylmethoxy)phenyl | 446 |
| 93 | i-Pr | Me | 4-(phenylmethoxy)phenyl | 395 |
| 94 | i-Pr | Me | 4-[(2,6-dimethyl-4-pyridinyl)methoxy]-phenyl | 426 |
| 95 | i-Bu | Me | 4-[(2,6-dimethyl-4-pyridinyl)methoxy]-phenyl | 440 |
| 96 | i-Bu | Me | 4-[(2,6-dichloro-4-pyridinyl)methoxy]-phenyl | 479 |
| 97 | i-Bu | Me | 4-[[3,5-bis(trifluoromethyl)phenyl]-methoxy]phenyl | 454 |
| 98 | i-Bu | Me | 4-[(3,5-dichlorophenyl)methoxy]phenyl | 479 |
| 99 | i-Bu | Me | 3-(phenylmethoxy)propyl | 375 |
| 101 | i-Bu | Me | 2-methyl-4-(phenylmethoxy)phenyl | 423 |
| 102 | i-Bu | Me | 4-[(2,6-dichloro-4-pyridinyl)methoxy]-2-methylphenyl | 492 |
| 103 | i-Bu | Me | 2-methyl-4-(2-naphthalenylmethoxy)-phenyl | 475 |
| 104 | i-Bu | Me | 2-methyl-4-(4-pyridinylmethoxy)phenyl | 426 |
| 105 | i-Bu | Me | 4-[(2,6-dimethyl-4-pyridinyl)methoxy]-2-methylphenyl | 454 |
| 106 | CH₃SCH₂CH₂ | Me | 4-(phenylmethoxy)phenyl | 427 |
| 107 | | | see structure at bottom | 492 |
| 108 | CH₃SO₂CH₂CH₂ | Me | 4-[3,5-bis(trifluoromethyl)phenoxy]phenyl | 581 |
| 109 | CH₃SO₂CH₂CH₂ | Me | 4-(3,5-dibromophenoxy)phenyl | 603 |
| 110 | CH₃SO₂CH₂CH₂ | Me | 4-[(2,6-dichloro-4-pyridinyl)methoxy]-phenyl | 528 |
| 111 | CH₃SO₂CH₂CH₂ | Me | 4-[(2,6-dimethyl-4-pyridinyl)methoxy]-phenyl | 490 |
| 112 | CH₃SO₂CH₂CH₂ | Me | 4-(4-quinolinylmethoxy)phenyl | 512 |
| 113 | | | see structure at bottom | 379 |
| 114 | (4-HO—phenyl)CH₂ | Me | 4-(phenylmethoxy)phenyl | 395 |
| 115 | HOCH₂CH₂ | Me | 4-[(2,6-dichloro-4-pyridinyl)methoxy]-phenyl | 466 |
| 116 | 4-[(CH₃)₃COC(O)NH₂]butyl | Me | 4-[(2,6-dichloro-4-pyridinyl)methoxy]-phenyl | 593 |
| 117 | 4-aminobutyl | Me phenyl | 4-[(2,6-dichloro-4-pyridinyl)methoxy]- | 495 |
| 118 | 4-(acetylamino)butyl | Me | 4-[(2,6-dichloro-4-pyridinyl)methoxy]-phenyl | 535 |
| 119 | 4-[3-pyridinyl-C(O)NH]butyl | Me | 4-[(2,5-dichloro-4-pyridinyl)methoxy]-phenyl | 600 |
| 120 | 4-[4-morpholinyl-C(O)NH]butyl | Me | 4-[(2,6-dichloro-4-pyridinyl)methoxy]-phenyl | 630 |
| 121 | 4-[CH₃SO₂-amino]butyl | Me | 4-[(2,6-dichloro-4-pyridinyl)methoxy]-phenyl | 595 |
| 122 | 4-(acetylamino)butyl | Me | 4-[(2,6-dimethyl-4-pyridinyl)methoxy]-phenyl | 497 |
| 123 | 4-[(CH₃)₃COC(O)NH]butyl | Me | 4-[(2,6-dimethyl-4-pyridinyl)methoxy]-phenyl | 555 |
| 124 | 4-aminobutyl | Me | 4-[(2,6-dimethyl-4-pyridinyl)methoxy]-phenyl | 455 |
| 125 | 4-[H₂NCH₂C(O)NH]butyl | Me | 4-[(2,6-dimethyl-4-pyridinyl)methoxy]-phenyl | 512 |
| 126 | 4-(acetylamino)butyl | Me | 4-[[3,5-bis(trifluoromethyl)phenyl]-methoxy]phenyl | 626 |
| 127 | 4-[(CH₃)₃COC(O)NH]butyl | Me | 4-(3,5-dibromophenoxy)phenyl | =668 |
| 128 | 4-aminobutyl | Me | 4-(3,5-dibromophenoxy)phenyl | 570 |

TABLE 1-continued

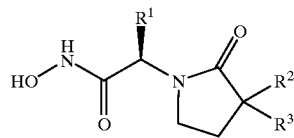

| Ex # | R¹ | R² | R³ | MS |
|---|---|---|---|---|
| 129 | 2-[(CH₃)₃COC(O)NH]ethyl | Me | 4-[(2,6-dichloro-4-pyridinyl)methoxy]phenyl | 565 |
| 130 | 2-aminoethyl | Me | 4-[(2,6-dichloro-4-pyridinyl)methoxy]phenyl | 467 |
| 131 | 2-(acetylamino)ethyl | Me | 4-[(2,6-dichloro-4-pyridinyl)methoxy]phenyl | 508 |
| 132 | 2-[(CH₃)₃COC(O)NH]ethyl | Me | 4-[(2,6-dimethyl-4-pyridinyl)methoxy]phenyl | 527 |
| 133 | 2-aminoethyl | Me | 4-[(2,6-dimethyl-4-pyridinyl)methoxy]phenyl | 427 |
| 134 | 2-[3-pyridinyl-C(O)NH]ethyl | Me | 4-[(2,6-dimethyl-4-pyridinyl)methoxy]phenyl | 523 |
| 135 | 2-[4-morpholinyl-(C(O)NH]ethyl | Me | 4-[(2,6-dimethyl-4-pyridinyl)methoxy]phenyl | 540 |
| 136 | 2-[(CH₃)₃COC(O)NHCH₂C(O)NH]-ethyl | Me | 4-[(2,6-dimethyl-4-pyridinyl)methoxy]phenyl | 584 |
| 137 | 2-[H₂NCH₂C(O)NH]ethyl | Me | 4-[(2,6-dimethyl-4-pyridinyl)methoxy]phenyl | 484 |
| 138 | 2-[(CH₃)₃COC(O)NHCH₂C(O)NH]-ethyl | Me | 4-[(2,6-dimethyl-4-pyridinyl)methoxy]phenyl | 641 |
| 139 | 2-[H₂NCH₂C(O)NHCH₂C(O)NH]-ethyl | Me | 4-[(2,6-dimethyl-4-pyridinyl)methoxy]phenyl | 541 |
| 140 | phenyl-CH₂OCH₂ | Me | 4-(phenylmethoxy)phenyl | 473 |
| 141 | HOCH₂ | Me | 4-[(2,6-dichloro-4-pyridinyl)methoxy]phenyl | 437 |
| 142 | 1-[(CH₃)₃COC(O)]-4-piperidinyl | Me | 4-(4-quinolinylmethoxy)phenyl | 589 |
| 143 | 4-piperidinyl | Me | 4-(4-quinolinylmethoxy)phenyl | 489 |
| 144 | 1-(CH₃SO₂)-4-piperidinyl | Me | 4-(4-quinolinylmethoxy)phenyl | 567 |
| 145 | 1-[(2-furanyl)C(O)]-4-piperidinyl | Me | 4-(4-quinolinylmethoxy)phenyl | 583 |
| 146 | 1-[(CH₃)₃COC(O)]-4-piperidinyl | Me | 4-[(2,6-dimethyl-4-pyridinyl)methoxy]phenyl | 567 |
| 147 | 4-piperidinyl | Me | 4-[(2,6-dimethyl-4-pyridinyl)methoxy]phenyl | 467 |
| 148 | 1-(CH₃C(O))-4-piperidinyl | Me | 4-[(2,6-dimethyl-4-pyridinyl)methoxy]phenyl | 525 |
| 149 | 1-(CH₃SO₂)-4-piperidinyl | Me | 4-[(2,6-dimethyl-4-pyridinyl)methoxy]phenyl | 545 |
| 150 | 1-acetyl-4-piperidinyl | Me | 4-[(2,6-dimethyl-4-pyridinyl)methoxy]phenyl | 509 |
| 151 | 1-(2,2-dimethyl-1-oxopropyl)-4-piperidinyl | Me | 4-[(2,6-dimethyl-4-pyridinyl)methoxy]phenyl | 551 |
| 152 | 1-methyl-4-piperidinyl | Me | 4-[(2,6-dimethyl-4-pyridinyl)methoxy]phenyl | 481 |
| 153 | 1-(i-Pr)-4-piperidinyl | Me | 4-[(2,6-dimethyl-4-pyridinyl)methoxy]phenyl | 510 |
| 300 | i-Bu | amino | 4-(2-quinolinylmethoxy)phenyl | 463 |
| 301 | Me | amino | 4-[(3,5-dimethylphenyl)methoxy]phenyl | 398 |
| 302 | Me | EtNHC(O)NH | 4-[(3,5-dimethylphenyl)methoxy]phenyl | 491 |
| 303 | Me | CH₃SO₂NH | 4-[(3,5-dimethylphenyl)methoxy]phenyl | 498 |
| 304 | Me | [(3-pyridinyl)acetyl]NH | 4-[(3,5-dimethylphenyl)methoxy]phenyl | 517 |
| 305 | Me | 4-pyridinyl-C(O)NH | 4-[(3,5-dimethylphenyl)methoxy]phenyl | 503 |
| 306 | Me | amino | 4-[(2,6-dichloro-4-pyridinyl)methoxy]phenyl | 437 |
| 307 | Me | 4-pyridinyl-C(O)NH | 4-[(2,6-dichloro-4-pyridinyl)methoxy]phenyl | 544 |
| 308 | Me | EtNHC(O)NH | 4-[(2,6-dichloro-4-pyridinyl)methoxy]phenyl | 532 |
| 309 | Me | (CH₃)₃COC(O)NHCH₂C(O)NH | 4-[(2,6-dichloro-4-pyridinyl)methoxy]phenyl | 618 |
| 310 | Me | H₂NCH₂C(O)NH | 4-[(2,6-dichloro-4-pyridinyl)methoxy]phenyl | 496 |
| 311 | Me | (3-pyridinyl)CH₂—C(O)NH | 4-[(2,6-dichloro-4-pyridinyl)methoxy]phenyl | 558 |
| 312 | Me | phenylCH₂NHC(O)NH | 4-[(2,6-dichloro-4-pyridinyl)methoxy]phenyl | 594 |
| 313 | Me | [[(2,4-dimethoxy]phenyl])NHC(O)NH | 4-[(2,6-dichloro-4-pyridinyl)methoxy]phenyl | 640 |

TABLE 1-continued

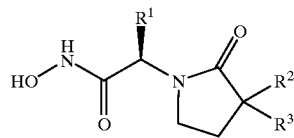

| Ex # | R¹ | R² | R³ | MS |
|---|---|---|---|---|
| 314 | Me | phenyl-NHC(O)NH | 4-[(2,6-dichloro-4-pyridinyl)methoxy]-phenyl | 580 |
| 315 | Me | (CH₃)₃COC(O)NH | 4-[(2,6-dichloro-4-pyridinyl)methoxy]-phenyl | 561 |
| 316 | Me | [2-(4-morpholinyl)ethyl]NHC(O)NH | 4-[(2,6-dichloro-4-pyridinyl)methoxy]-phenyl | 595 |
| 317 | Me | (CH₃)₃COC(O)NHCH₂C(O)NH | 4-[(2,6-dichloro-4-pyridinyl)methoxy]-phenyl | 618 |
| 318 | Me | (2-thiazolyl)NHC(O)NH | 4-[(2,6-dichloro-4-pyridinyl)methoxy]-phenyl | 565 |
| 319 | Me | (4-pyridinyl)NHC(OH)NH | 4-[(2,6-dichloro-4-pyridinyl)methoxy]-phenyl | 581 |
| 320 | Me | (3-HO—phenyl)NHC(O)NH | 4-[(2,6-dichloro-4-pyridinyl)methoxy]-phenyl | 596 |
| 321 | Me | (2,3-dihydro-2-oxo-1H-benzimidazol-5-yl)NHC(O)NH | 4-[(2,6-dichloro-4-pyridinyl)methoxy]-phenyl | 636 |
| 322 | CH₃SO₂CH₂CH₂ | amino | 4-[(2,6-dichloro-4-pyridinyl)methoxy]-phenyl | 532 |
| 323 | CH₃SO₂CH₂CH₂ | amino | 4-[(3,5-dimethylphenyl)methoxy]-phenyl | 491 |
| 324 | CH₃SO₂CH₂CH₂ | [(2-thiazolyl)NH]C(O)NH | 4-[(2,6-dichloro-4-pyridinyl)methoxy]-phenyl | 657 |
| 325 | CH₃SO₂CH₂CH₂ | [(2-thiazolyl)NH]C(O)NH | 4-[(3,5-dimethylphenyl)methoxy]-phenyl | 617 |
| 326 | 4-[(2-propenyl)OC(O)NH]butyl | amino | 4-[(2,6-dichloro-4-pyridinyl)methoxy]-phenyl | 580 |
| 327 | 4-[(2-propenyl)OC(O)NH]butyl | amino | 4-[(2,6-dimethyl-4-pyridinyl)methoxy]-phenyl | 562 |
| 328 | i-Bu | amino | 4-[(2,6-dichloro-4-pyridinyl)methoxy]-phenyl | 481 |
| 329 | i-Bu | [(2-thiazolyl)NH]C(O)NH | 4-[(2,6-dichloro-4-pyridinyl)methoxy]-phenyl | 629 |
| 330 | i-Bu | [(2-thiazolyl)NH]C(O)NH | 4-[(2,6-dimethyl-4-pyridinyl)methoxy]-phenyl | 567 |
| 331 | i-Bu | [(2-pyridinyl)NH]C(O)NH | 4-[(2,6-dichloro-4-pyridinyl)methoxy]-phenyl | 623 |
| 332 | i-Bu | CF₃CH₂C(O)NHC(O)NH | 4-[(2,6-dimethyl-4-pyridinyl)methoxy]-phenyl | 537 |
| 333 | i-Bu | [(2-pyridinyl)NH]C(O)NH | 4-[(2,6-dimethyl-4-pyridinyl)methoxy]-phenyl | 561 |
| 334 | i-Bu | phenylSO₂NHC(O)NH | 4-[(2,6-dichloro-4-pyridinyl)methoxy]-phenyl | 686 |
| 335 | i-Bu | phenylSO₂NHC(O)NH | 4-[(2,6-dimethyl-4-pyridinyl)methoxy]-phenyl | 624 |
| 336 | i-Bu | [[(3-Me-5-isothiazol]yl)NH]C(O)NH | 4-[(2,6-dichloro-4-pyridinyl)methoxy]-phenyl | 621 |
| 337 | i-Bu | 1H-benzimidazol-2-ylNHC(O)NH | 4-[(2,6-dichloro-4-pyridinyl)methoxy]-phenyl | 640 |
| 338 | i-Bu | 1H-benzimidazol-2-ylNHC(O)NH | 4-[(2,6-dimethyl-4-pyridinyl)methoxy]-phenyl | 600 |
| 339 | i-Bu | phenylNHC(O)NH | 4-[(2,6-dimethyl-4-pyridinyl)methoxy]-phenyl | 560 |
| 340 | i-Bu | phenylNHC(O)NH | 4-[(2,6-dichloro-4-pyridinyl)methoxy]-phenyl | 622 |
| 341 | i-Bu | (CH₃)₃N⁺ | (phenylmethoxy)phenyl | 454 |
| 342 | i-Bu | amino | 4-(4-quinolinylmethoxy)phenyl | 446 |
| 343 | i-Bu | amino | 4-(2-oxo-2-phenylethoxy)phenyl | 455 |
| 344 | i-Bu | amino | 4-[(3,5-dimethyl-4-isoxazolyl)-methoxy]phenyl | 431 |
| 345 | i-Bu | amino | 4-[(2,6-dimethyl-4-pyridinyl)methoxy]-phenyl | 441 |
| 346 | i-Bu | amino | 4-[2-(2-benzothiazolylamino)-2-oxo-ethoxy]phenyl | 512 |
| 347 | i-Bu | amino | 4-[(2-methoxy-4-quinolinyl)methoxy]-phenyl | 476 |
| 348 | i-Bu | amino | 4-[(2-phenyl-4-quinolinyl)methoxy]-phenyl | 539 |

TABLE 1-continued

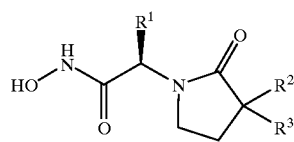

| Ex # | R¹ | R² | R³ | MS |
|---|---|---|---|---|
| 349 | i-Bu | amino | 4-[(2,6-dimethyl-4-quinolinyl)-methoxy]phenyl | 491 |
| 350 | i-Bu | amino | 4-[(2-chloro-4-quinolinyl)methoxy]-phenyl | 497 |
| 351 | i-Bu | amino | 4-[2-(2,5-dimethoxyphenyl)-2-(hydroxyimino)ethoxy]phenyl | 515 |
| 352 | i-Bu | amino | 4-[(2-methylimidazo[1,2-a]pyridin-3-yl)methoxy]phenyl | 466 |
| 353 | i-Bu | amino | 4-[[1,4-dimethyl-2-(methylthio)-1H-imidazol-5-yl]methoxy]phenyl | 476 |
| 354 | i-Bu | amino | 4-[[1,5-dimethyl-2-(methylthio)-1H-imidazol-4-yl]methoxy]phenyl | 476 |
| 355 | i-Bu | amino | 4-[(2,4-dimethyl-5-thiazolyl)methoxy]-phenyl | 447 |
| 356 | i-Bu | amino | 4-[(2-methyl-4-quinolinyl)methoxy]-phenyl | 477 |
| 357 | $CH_3SO_2CH_2CH_2$ | amino | 4-[(2-chloro-4-quinolinyl)methoxy]-phenyl | 547 |
| 358 | $CH_3SO_2CH_2CH_2$ | amino | 4-[(2-methyl-4-quinolinyl)methoxy]-phenyl | 527 |
| 359 | $CH_3SO_2CH_2CH_2$ | amino | 4-[(3,5-dimethoxyphenyl)methoxy]-phenyl | 522 |
| 360 | $CH_3SO_2CH_2CH_2$ | amino | 4-[(2-methoxy-4-quinolinyl)methoxy]-phenyl | 526 |
| 361 | i-Bu | amino | 4-[(3,5-dimethoxyphenyl)methoxy]-phenyl | 455 |
| 362 | i-Bu | amino | 4-[(2-$CH_3O$-5-nitrophenyl)methoxy]-phenyl | 470 |
| 363 | i-Bu | amino | 4-[(5-quinolinyl)methoxy]phenyl | 446 |
| 364 | 2-($CH_3SO_2$)ethyl | amino | 4-[(2-$CH_3O$-5-nitrophenyl)methoxy]-phenyl | 520 |
| 365 | 2-($CH_3SO_2$)ethyl | amino | 4-[(2-nitro-4,5-dimethoxyphenyl)-methoxy]phenyl | 567 |
| 366 | 2-($CH_3SO_2$)ethyl | amino | 4-[(2-phenyl-4-quinolinyl)methoxy]phenyl | 589 |
| 367 | 2-($CH_3SO_2$)ethyl | amino | 4-[(3,5-dimethyl-4-isoxazolyl)-methoxy]phenyl | 481 |
| 368 | (4-HO—phenyl)methyl | amino | 4-[(phenyl)methoxy]phenyl | 462 |
| 369 | (4-$CH_3O$—phenyl)methyl | 4-[(2-methyl-4-quinolinyl)methoxy]-phenyl | | 541 |
| 370 | (4-$CH_3O$—phenyl)methyl | amino | 4-[(2,6-dimethyl-4-pyridinyl)methoxy]-phenyl | 505 |
| 371 | (4-$CH_3O$—phenyl)methyl | amino | 4-[(phenyl)methoxy]phenyl | 476 |
| 450 | i-Bu | aminomethyl | 4-[(2,6-dimethyl-4-pyridinyl)methoxy]-phenyl | 455 |
| 451 | i-Bu | 2-thiazolylNHC(O)NHCH₂ | 4-[(2,6-dimethyl-4-pyridinyl)methoxy]-phenyl | 581 |
| 452 | Me | aminomethyl | 4-[(2,6-dichloro-4-pyridinyl)methoxy]-phenyl | 453 |
| 453 | Me | 2-thiazolylNHC(O)NHCH₂ | 4-[(2,6-dichloro-4-pyridinyl)methoxy]-phenyl | 579 |
| 454 | | | see structure at bottom | 398 |
| 455 | Me | HOCH₂ | 4-[(3,5-dimethylphenyl)methoxy]-phenyl | 435 |
| 456 | Me | $CH_3CH_2NHC(O)OCH_2$ | 4-[(3,5-dimethylphenyl)methoxy]-phenyl | 506 |
| 457 | Me | HOCH₂ | 4-[(2,6-dichloro-4-pyridinyl)methoxy]-phenyl | 476 |
| 458 | | | see structure at bottom | 381 |
| 459 | Me | Me | 5-[(3,5-dimethylphenoxy)methyl]-2-thienyl | 425 |
| 460 | | | see structure at bottom | 460 |
| 461 | Me | Me | [4-(phenylmethoxy)phenyl]methyl | 405 |
| 462 | i-Bu | CH₃NH | 4-[(2,6-dimethyl-4-pyridinyl)methoxy]-phenyl | 455 |
| 463 | i-Bu | CH₃NH | 4-[(2-methyl-4-quinolinyl)methoxy]-phenyl | 491 |
| 464 | | | see structure at bottom | 405 |

TABLE 1-continued

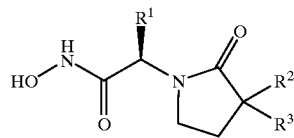

| Ex # | R¹ | R² | R³ | MS |
|---|---|---|---|---|
| 501 | 4-piperidinyl | amino | 4-(4-quinolinylmethoxy)phenyl | 490 |
| 502 | 4-piperidinyl | amino | 4-[(2,6-chloro-4-pyridinyl)methoxy]-phenyl | 508 |
| 503 | 1-[(CH₃)₃COC(O)]-4-piperidinyl | (CH₃)₃COC(O)NH | 4-[(2,6-dimethyl-4-pyridinyl)methoxy]-phenyl | 668 |
| 504 | 4-piperidinyl | amino | 4-[(2,6-dimethyl-4-pyridinyl)methoxy]-phenyl | 468 |
| 505 | 1-(CH₃SO₂)-4-piperidinyl | amino | 4-[(2,6-dimethyl-4-pyridinyl)methoxy]-phenyl | 546 |
| 506 | 1-acetyl-4-piperidinyl | amino | 4-[(2,6-dimethyl-4-pyridinyl)methoxy]-phenyl | 510 |
| 507 | 1-(2,2-dimethyl-1-oxopropyl)-4-piperidinyl | amino | 4-[(2,6-dimethyl-4-pyridinyl)methoxy]-phenyl | 552 |
| 508 | 1-[(CH₃)₃COC(O)]-4-piperidinyl | amino | 4-[(2,6-dimethyl-4-pyridinyl)methoxy]-phenyl | 568 |
| 509 | 1-(CH₃OC(O))-4-piperidinyl | amino | 4-[(2,6-dimethyl-4-pyridinyl)methoxy]-phenyl | 526 |
| 510 | 1-methyl-4-piperidinyl | amino | 4-[(2,6-dimethyl-4-pyridinyl)methoxy]-phenyl | 482 |
| 511 | 1-dimethylcarbamyl-4-piperidinyl | amino | 4-[(2,6-dimethyl-4-pyridinyl)methoxy]-phenyl | 539 |
| 512 | 1-cycPr-C(O)-4-piperidinyl | amino | 4-[(2,6-dimethyl-4-pyridinyl)methoxy]-phenyl | 536 |
| 513 | i-Pr | amino | 4-(4-quinolinylmethoxy)phenyl | 449 |
| 514 | i-Pr | amino | 4-[(2,6-dimethyl-4-pyridinyl)methoxy]-phenyl | 427 |
| 515 | cyclohexyl | amino | 4-(4-quinolinylmethoxy)phenyl | 589 |
| 516 | cyclohexyl | amino | 4-[(2,6-dimethyl-4-pyridinyl)methoxy]-phenyl | 467 |
| 517 | t-Bu | amino | 4-[(2,6-dimethyl-4-pyridinyl)methoxy]-phenyl | 441 |
| 518 | t-Bu | amino | 4-(4-quinolinylmethoxy)phenyl | 461 |
| 519 | t-Bu | amino | 4-(2-methyl-4-quinolinylmethoxy)-phenyl | 477 |
| 520 | i-Pr | amino | 4-(2-methyl-4-quinolinylmethoxy)-phenyl | 463 |
| 521 | i-Pr | amino | 4-(2,6-dimethyl-4-quinolinylmethoxy)-phenyl | 477 |
| 522 | 1-(4-morpholino-C(O))-4-piperidinyl | amino | 4-[(2,6-dimethyl-4-pyridinyl)methoxy]-phenyl | 581 |
| 523 | 1-(2-methyl-1-oxopropyl)-4-piperidinyl | amino | 4-[(2,6-dimethyl-4-pyridinyl)methoxy]-phenyl | 538 |
| 524 | 4-CH₃O-cycHex | amino | 4-[(2,6-dimethyl-4-pyridinyl)methoxy]-phenyl | 497 |
| 525 |  |  | see structure at bottom | 422 |
| 526 | 1-(phenyl-C(O))-4-piperidinyl | amino | 4-[(2,6-dimethyl-4-pyridinyl)methoxy]-phenyl | 572 |
| 527 | 1-(1-oxopropyl)-4-piperidinyl | amino | 4-[(2,6-dimethyl-4-pyridinyl)methoxy]-phenyl | 524 |
| 528 | 1-acetyl-4-piperidinyl | amino | 4-(2-methyl-4-quinolinylmethoxy)-phenyl | 546 |
| 529 | 1-(CH₃SO₂)-4-piperidinyl | amino | 4-(2-methyl-4-quinolinylmethoxy)-phenyl | 582 |
| 530 | 1-(2,2-di-CH₃-1-oxopropyl)-4-piperidinyl | amino | 4-(2-methyl-4-quinolinylmethoxy)-phenyl | 588 |
| 531 | 1-acetyl-4-piperidinyl | amino | 4-(4-quinolinylmethoxy)phenyl | 532 |
| 532 | 1-(CH₃SO₂)-4-piperidinyl | amino | 4-(4-quinolinylmethoxy)phenyl | 568 |
| 533 | 1-acetyl-4-piperidinyl | amino | 4-[(3,5-dimethoxyphenyl)methoxy]-phenyl | 541 |
| 534 | 1-acetyl-4-piperidinyl | amino | 4-[(5-methyl-3-nitrophenyl)methoxy]-phenyl | 540 |
| 535 | 1-acetyl-4-piperidinyl | amino | 4-[3,5-bis(trifluoromethyl)phenoxy]-phenyl | 603 |
| 536 | 1-acetyl-4-piperidinyl | amino | 4-[(3,5-dichlorophenyl)methoxy]phenyl | 549 |
| 537 | 1-acetyl-4-piperidinyl | amino | 4-(6-fluoro-2-methyl-4-quinolinyl-methoxy)phenyl | 564 |
| 538 | 1-acetyl-4-piperidinyl | amino | 4-(7-chloro-2-methyl-4-quinolinyl-methoxy)phenyl | 580 |

TABLE 1-continued

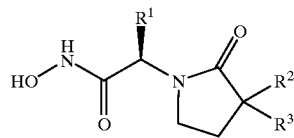

| Ex # | R¹ | R² | R³ | MS |
|---|---|---|---|---|
| 539 | 1-acetyl-4-piperidinyl | amino | 4-(6-chloro-2-methyl-4-quinolinyl-methoxy)phenyl | 580 |
| 540 | 1-acetyl-4-piperidinyl | amino | 4-(6-methoxy-2-methyl-3-quinolinyl-methoxy)phenyl | 576 |
| 541 | 4-piperidinyl | amino | 4-(2,7-dimethyl-4-quinolinylmethoxy)-phenyl | 518 |
| 542 | 1-acetyl-4-piperidinyl | amino | 4-(2,7-dimethyl-4-quinolinylmethoxy)-phenyl | 560 |
| 543 | 4-piperidinyl | amino | 4-(2-$CH_3O$-4-quinolinylmethoxy)-phenyl | 520 |
| 544 | 4-piperidinyl | amino | 4-[(3,5-dimethoxyphenyl)methoxy]-phenyl | 499 |
| 545 | 4-piperidinyl | amino | 4-[(2,6-diethyl-4-pyridinyl)methoxy]-phenyl | 496 |
| 546 | 1-acetyl-4-piperidinyl | amino | 4-[(2,6-diethyl-4-pyridinyl)methoxy]-phenyl | 538 |
| 547 | 4-piperidinyl | amino | 4-(7-methyl-4-quinolinylmethoxy)-phenyl | 504 |
| 548 | 4-methoxy-cycHex | amino | 4-(4-quinolinylmethoxy)phenyl | 519 |
| 549 | t-Bu | amino | 4-(2,6-dimethyl-4-quinolinylmethoxy)-phenyl | 491 |
| 550 | methyl | methyl | 4-[(2,6-dimethyl-1-oxido-4-pyridinyl)-methoxy]phenyl | 414 |
| 551 | t-Bu | amino | 4-(7-chloro-2-methyl-4-quinolinyl-methoxy)phenyl | 511 |
| 552 | t-Bu | amino | 4-(6-fluoro-2-methyl-4-quinolinyl-methoxy)phenyl | 495 |
| 553 | t-Bu | amino | 4-(6-chloro-2-methyl-4-quinolinyl-methoxy)phenyl | 511 |
| 554 | t-Bu | amino | 4-(6-methoxy-2-methyl-4-quinolinyl-methoxy)phenyl | 507 |
| 555 | t-Bu | amino | 4-(2,7-dimethyl-4-quinolinylmethoxy)-phenyl | 491 |
| 556 | t-Bu | amino | 4-(7-methyl-4-quinolinylmethoxy)-phenyl | 477 |
| 557 | cycHex | amino | 4-(2-methyl-4-quinolinylmethoxy)-phenyl | 503 |
| 558 | cycHex | amino | 4-(2,6-dimethyl-4-quinolinylmethoxy)-phenyl | 517 |
| 559 | i-Pr | amino | 4-[(5-methyl-3-nitrophenyl)methoxy]-phenyl | 457 |
| 560 | i-Pr | amino | 4-[3,5-bis(trifluoromethyl)phenoxy]-phenyl | 518 |
| 561 | i-Pr | amino | 4-[[3,5-bis(trifluoromethyl)phenyl]-methoxy]phenyl | 534 |
| 562 | i-Pr | amino | 4-(3,5-dibromophenoxy)phenyl | 523 |
| 563 | i-Pr | amino | 4-(6-fluoro-2-methyl-4-quinolinyl-methoxy)phenyl | 481 |
| 564 | i-Pr | amino | 4-(6-$CH_3O$-2-methyl-4-quinolinyl-methoxy)phenyl | 493 |
| 565 | i-Pr | amino | 4-(7-chloro-2-methyl-4-quinolinyl-methoxy)phenyl | 497 |
| 566 | i-Pr | amino | 4-(6-chloro-2-methyl-4-quinolinyl-methoxy)phenyl | 497 |
| 567 | i-Pr | amino | 4-(2-$CH_3O$-4-quinolinylmethoxy)-phenyl | 479 |
| 568 | i-Pr | amino | 4-(2,7-dimethyl-4-quinolinylmethoxy)-phenyl | 477 |
| 569 | i-Pr | amino | 4-[(2,6-diethyl-4-pyridinyl)methoxy]-phenyl | 455 |
| 700 | Me | Me | 3-(phenylmethoxy)phenyl | 367 |
| 701 | Me | Me | 3-[(3,5-dimethylphenyl)methoxy]phenyl | 395 |
| 702 | Me | Me | 3-[(3-methylphenyl)methoxy]phenyl | 381 |
| 703 | Me | Me | 3-(1-methylethoxy)phenyl | 663 |
| 704 | Me | Me | 3-heptyloxyphenyl | 375 |
| 705 | Me | 2-oxo-2-[(1,3,4-thiadiazol-2-yl)NH]ethyl | 4-[(2,6-dichloro-4-pyridinyl)methoxy]-phenyl | 563 |
| 706 | Me | 2-(($CH_3)_3$CO)-2-oxoethyl | 4-(phenylmethoxy)phenyl | 467 |

TABLE 1-continued

| Ex # | R¹ | R² | R³ | MS |
|---|---|---|---|---|
| 707 | Me | 2-HO-2-oxoethyl | 4-(phenylmethoxy)phenyl | 411 |
| 708 | Me | 2-[2-(CH₃NH)-2-oxoethyl]NH]-2-oxoethyl | 4-[(3,5-dimethylphenyl)methoxy]phenyl | 533 |
| 709 | Me | 2-oxo-2-[(2-thiazolyl)NH]ethyl | 4-[(3,5-dimethylphenyl)methoxy]phenyl | 521 |
| 710 | Me | 2-(4-morpholinyl)-2-oxoethyl | 4-[(3,5-dimethylphenyl)methoxy]phenyl | 532 |
| 711 | Me | 2-oxo-2-[(2-thiazolyl)NH]ethyl | 4-[(3,5-dichlorophenyl)methoxy]phenyl | 564 |
| 712 | Me | 2-]2-[(4-morpholinyl)ethyl]NH]-2-oxoethyl | 4-[(3,5-dichlorophenyl)methoxy]phenyl | 594 |
| 713 | Me | 2-oxo-2-[(4-pyridinyl)CH₂NH]ethyl | 4-[(3,5-dichlorophenyl)methoxy]phenyl | 594 |
| 714 | Me | 2-oxo-2-[(2-thiazolyl)NH]ethyl | 4-[(3,5-dimethylphenyl)methoxy]phenyl | 524 |
| 715 | Me | 2-oxo-2-[(3-pyridinyl)CH₂NH]ethyl | 4-[(3,5-dichlorophenyl)methoxy]phenyl | 594 |
| 716 | Me | 2-oxo-2-[[(2-pyridinyl)]CH₂NH]ethyl | 4-[(3,5-dichlorophenyl)methoxy]phenyl | 572 |
| 717 | Me | 2-oxo-2-[(4-pyridinyl)NH]ethyl | 4-[(3,5-dichlorophenyl)methoxy]phenyl | 558 |
| 718 | Me | 2-[(3-Me-5-isothiazolyl)NH]-2-oxoethyl | 4-[(3,5-dichlorophenyl)methoxy]phenyl | 576 |
| 719 | Me | 2-[[5-(t-Bu)-1,3,4-thiadiazol-2-yl]NH]-2-oxoethyl | 4-[(3,5-dichlorophenyl)methoxy]phenyl | 619 |
| 720 | Me | 2-[[4-[2-(t-Butoxyethoxy)-2-oxoethyl]-2-thiazolyl]NH]-2-oxoethyl | 4-[(3,5-dichlorophenyl)methoxy]phenyl | 676 |
| 721 | Me | 2-[[4-(2-HO-2-oxoethyl)-2-thiazolyl]NH]-2-oxoethyl | 4-[(3,5-dichlorophenyl)methoxy]phenyl | 620 |
| 722 | Me | 2-[[4-(2-CH₃NH-2-oxoethyl)-2-thiazolyl]NH]-2-oxoethyl | 4-[(3,5-dichlorophenyl)methoxy]phenyl | 657 |
| 723 | Me | 1H-benzimidazol-2-ylmethyl | 4-[(3,5-dichlorophenyl)methoxy]phenyl | 554 |
| 724 | Me | 3H-imidazo[4,5-c]pyridin-2-ylmethyl | 4-[(3,5-dichlorophenyl)methoxy]phenyl | 555 |
| 725 | Me | 2-oxo-2-(2-thiazolyl)NH—ethyl | 4-[3,5-bis(trifluoromethyl)phenyloxy]-phenyl | 615 |
| 726 | Me | 2-oxo-2-[(4-pyridinyl)CH₂NH—ethyl | 4-[3,5-bis(trifluoromethyl)phenyloxy]-phenyl | 625 |
| 780 | i-Pr | 2-oxo-2-(4-pyridinylCH₂)NH—ethyl | 4-[(2,6-dimethyl-4-pyridinyl)methoxy]-phenyl | 560 |
| 781 | i-Pr | 2-oxo-2-(4-pyridinylCH₂)NH—ethyl | 4-[(2,6-dichloro-4-pyridinyl)methoxy]-phenyl | 600 |
| 782 | cyclohexylmethyl | 2-oxo-2-(4-pyridinylCH₂)NH—ethyl | 4-[(2,6-dimethyl-4-pyridinyl)methoxy]-phenyl | 614 |
| 783 | cyclohexylmethyl | 2-oxo-2-(4-pyridinylCH₂)NH—ethyl | 4-[(2,6-dichloro-4-pyridinyl)methoxy]-phenyl | 654 |
| 784 | 4-[(CH₃)₃COC(O)NH]butyl | 2-oxo-2-(4-pyridinylCH₂)NH—ethyl | 4-[(2,6-dimethyl-4-pyridinyl)methoxy]-phenyl | 689 |
| 785 | 4-aminobutyl | 2-oxo-2-[(4-pyridinylCH₃)NH—ethyl | 4-[(2,6-dimethyl-4-pyridinyl)methoxy-phenyl | 590 |
| 800 | methyl | methyl | 3-(1H-benzotriazol-1-ylmethoxy)phenyl | 408 |
| 801 | (3,4,4-tri-Me-2,5-dioxo-1-imidazolinyl)CH₂ | methyl | 4-(phenylmethoxy)phenyl | 509 |
| 802 | i-Bu | 2-(t-butoxy)-2-oxoethyl | 4-(phenylmethoxy)phenyl | 509 |
| 803 | i-Bu | 2-[2-(CH₃NH)-2-oxoethyl]NH]-2-oxoethyl | 4-[(3,5-dimethylphenyl)methoxy]phenyl | 533 |
| 804 | i-Bu | 2-[2-(CH₃NH)-2-oxoethyl]NH]-2-oxoethyl | 4-[(2,6-dichloro-4-pyridinyl)methoxy]-phenyl | 595 |
| 805 | i-Bu | 2-oxo-2-(2-thiazolyl)NH—ethyl | 4-[(2,6-dichloro-4-pyridinyl)methoxy]-phenyl | 607 |
| 806 | i-Bu | 2-[2-(CH₃NH)-2-oxoethyl]NH-2-oxoethyl | 4-[3,5-bis(trifluoromethyl)phenyloxy]-phenyl | 647 |
| 807 | i-Bu | 2-oxo-2-[(4-pyridinyl)CH₂]NH—ethyl | 4-[3,5-(trifluoromethyl)phenyloxy]-phenyl | 667 |
| 808 | i-Bu | 2-oxo-2-[phenylNH)ethyl | 4-[(2,6-dichloro-4-pyridinyl)methoxy]-phenyl | 600 |
| 809 | i-Bu | 2-oxo-2-(CH₃NH)ethyl | 4-[(2,6-dimethyl-4-pyridinyl)methoxy]-phenyl | 497 |
| 810 | i-Bu | 2-[2-(1H-imidazol-4-yl)ethyl]NH-2-oxoethyl | 4-[(2,6-dimethyl-4-pyridinyl)methoxy]-phenyl | 577 |
| 811 | i-Bu | 2-2-[1-(phenylCH₂)-4-piperidinylNH]-2-oxoethyl | 4-[(2,6-dimethyl-4-pyridinyl)methoxy]-phenyl | 656 |
| 812 | i-Bu | 2-[2-(dimethylamino)ethyl]NH-2-oxoethyl | 4-[(2,6-dichloro-4-pyridinyl)methoxy]-phenyl | 554 |
| 813 | i-Bu | 2-[(4-HO—phenyl)NH]-2-oxoethyl | 4-[(2,6-dimethyl-4-pyridinyl)methoxy]-phenyl | 575 |
| 814 | i-Bu | 2-oxo-2-(2-thiazolyl)NH—ethyl | 4-[(2,6-dimethyl-4-pyridinyl)methoxy]-phenyl | 566 |
| 815 | i-Bu | 2-HO—ethyl | 4-[(2,6-dimethyl-4-pyridinyl)methoxy]-phenyl | 470 |
| 816 | i-Bu | 2-[(4,5-dimethyl-2-thiazolyl)NH]-2-oxoethyl | 4-[(2,6-dimethyl-4-pyridinyl)methoxy]-phenyl | 594 |
| 817 | i-Bu | 2-[(1H-indazol-5-yl)NH]-2-oxoethyl | 4-[(2,6-dimethyl-4-pyridinyl)methoxy]-phenyl | 599 |

TABLE 1-continued
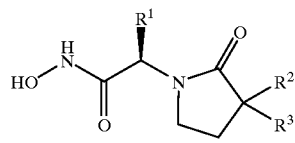
| Ex # | R¹ | R² | R³ | MS |
|---|---|---|---|---|
| 818 | i-Bu | 2-oxo-2-[(2-thiazolyl)NH]ethyl | 4-[3,5-bis(trifluoromethyl)phenyloxy]-phenyl | 659 |
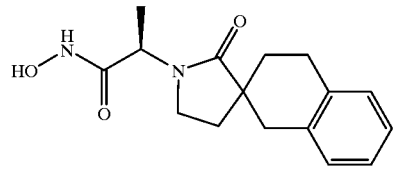
(example 30)
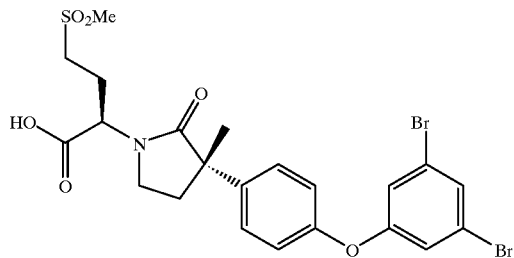
(example 107)
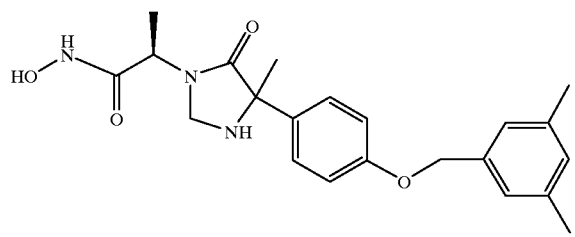
(example 454)
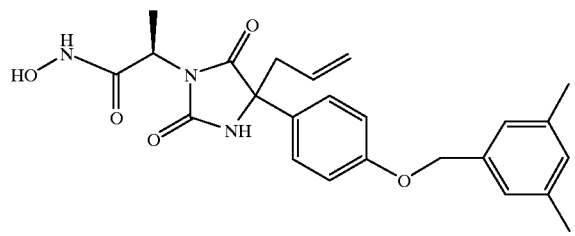
(example 460)

TABLE 1-continued
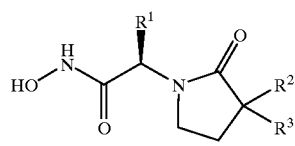
| Ex # | R¹ | R² | R³ | MS |
|---|---|---|---|---|
(example 55)
(example 113)
(example 458)
(example 464)
(example 525)

The following tables contain representative examples of the present invention. Each entry in each table is intended to be paired with each formula at the start of the table. For example, in Table 2, example 1 is intended to be paired with each of formulae A1-FF3.

TABLE 2

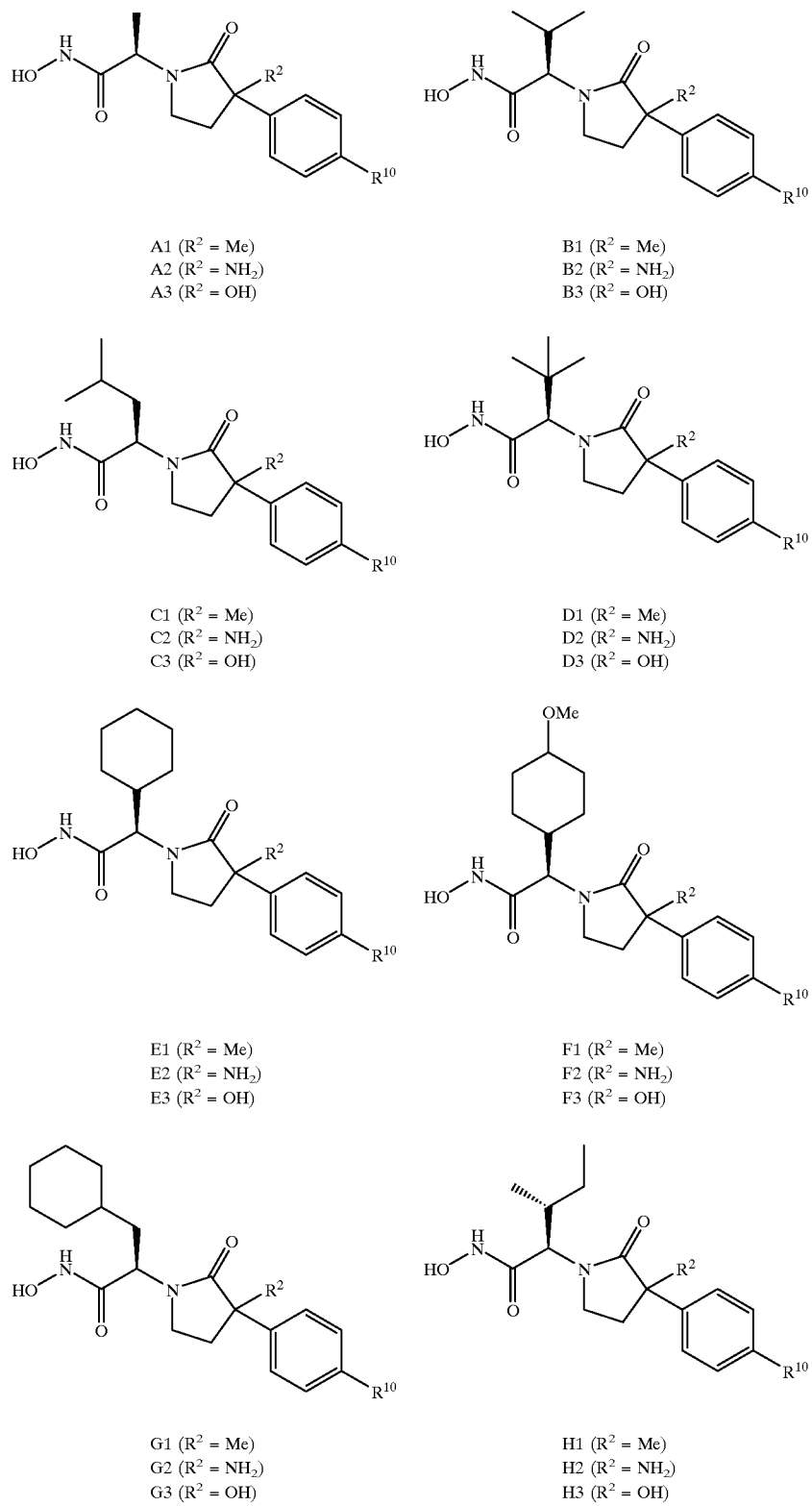

A1 ($R^2$ = Me)
A2 ($R^2$ = $NH_2$)
A3 ($R^2$ = OH)

B1 ($R^2$ = Me)
B2 ($R^2$ = $NH_2$)
B3 ($R^2$ = OH)

C1 ($R^2$ = Me)
C2 ($R^2$ = $NH_2$)
C3 ($R^2$ = OH)

D1 ($R^2$ = Me)
D2 ($R^2$ = $NH_2$)
D3 ($R^2$ = OH)

E1 ($R^2$ = Me)
E2 ($R^2$ = $NH_2$)
E3 ($R^2$ = OH)

F1 ($R^2$ = Me)
F2 ($R^2$ = $NH_2$)
F3 ($R^2$ = OH)

G1 ($R^2$ = Me)
G2 ($R^2$ = $NH_2$)
G3 ($R^2$ = OH)

H1 ($R^2$ = Me)
H2 ($R^2$ = $NH_2$)
H3 ($R^2$ = OH)

TABLE 2-continued
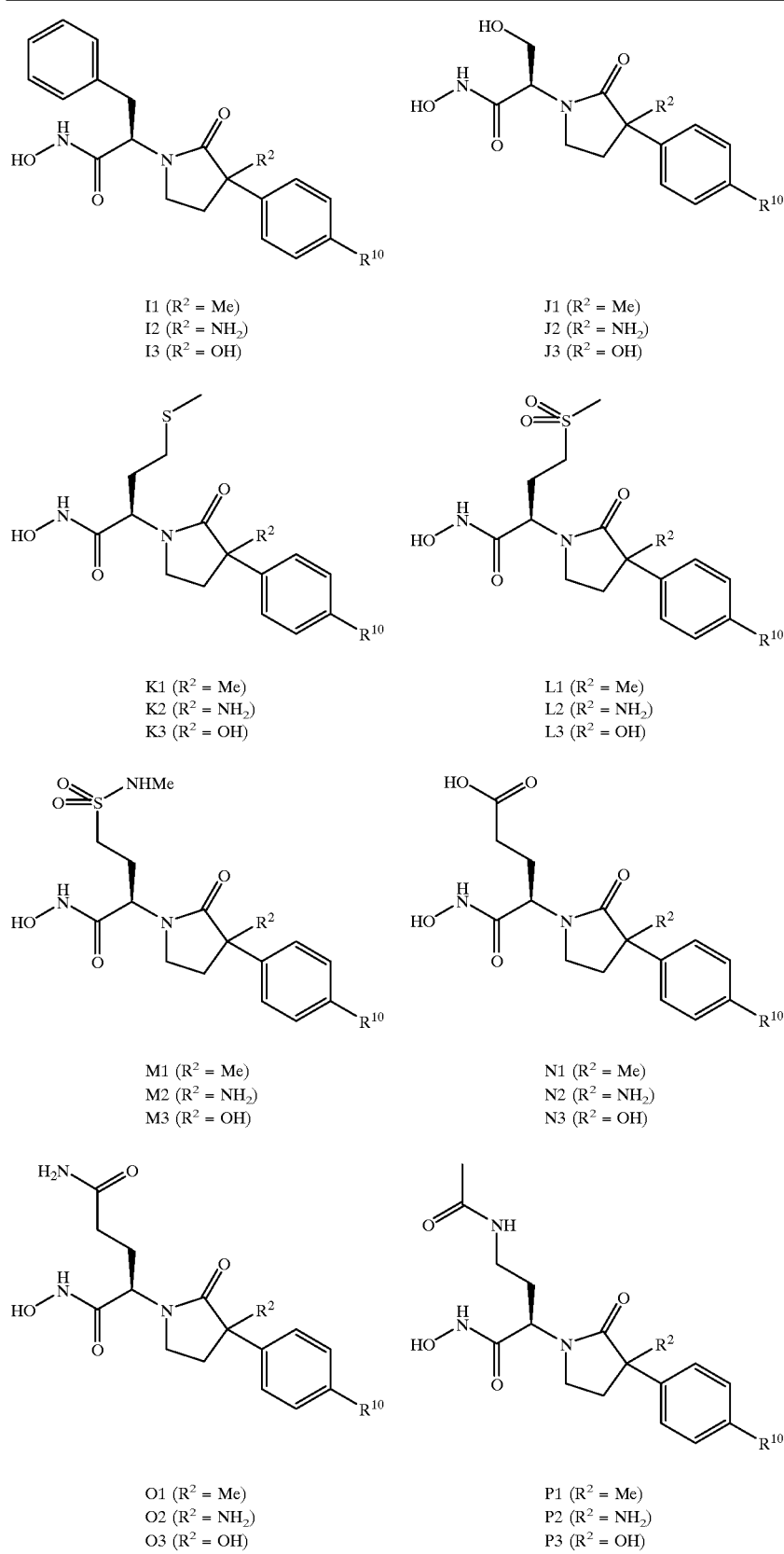
I1 ($R^2$ = Me)
I2 ($R^2$ = $NH_2$)
I3 ($R^2$ = OH)
J1 ($R^2$ = Me)
J2 ($R^2$ = $NH_2$)
J3 ($R^2$ = OH)
K1 ($R^2$ = Me)
K2 ($R^2$ = $NH_2$)
K3 ($R^2$ = OH)
L1 ($R^2$ = Me)
L2 ($R^2$ = $NH_2$)
L3 ($R^2$ = OH)
M1 ($R^2$ = Me)
M2 ($R^2$ = $NH_2$)
M3 ($R^2$ = OH)
N1 ($R^2$ = Me)
N2 ($R^2$ = $NH_2$)
N3 ($R^2$ = OH)
O1 ($R^2$ = Me)
O2 ($R^2$ = $NH_2$)
O3 ($R^2$ = OH)
P1 ($R^2$ = Me)
P2 ($R^2$ = $NH_2$)
P3 ($R^2$ = OH)

TABLE 2-continued
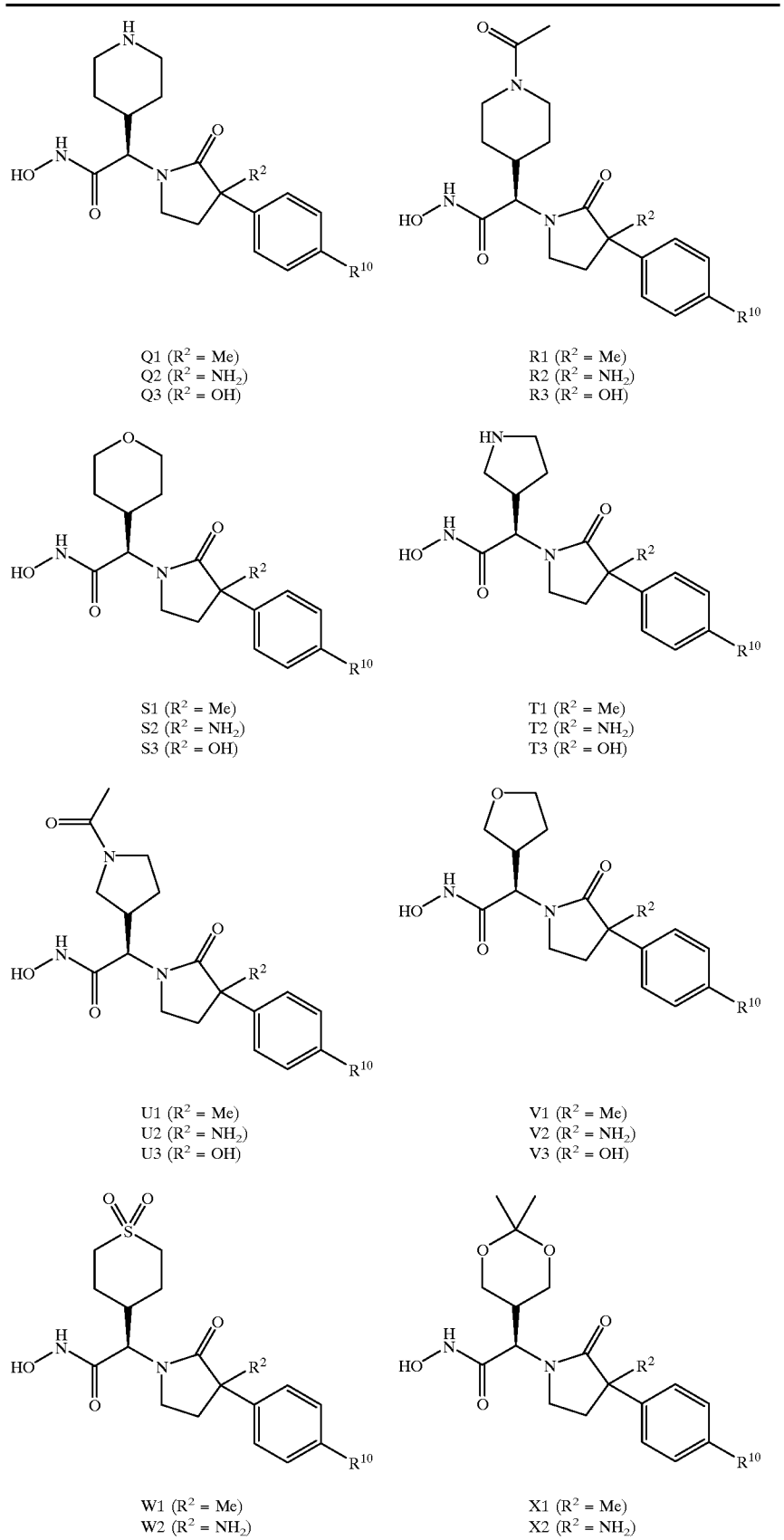
Q1 (R² = Me)
Q2 (R² = NH₂)
Q3 (R² = OH)
R1 (R² = Me)
R2 (R² = NH₂)
R3 (R² = OH)
S1 (R² = Me)
S2 (R² = NH₂)
S3 (R² = OH)
T1 (R² = Me)
T2 (R² = NH₂)
T3 (R² = OH)
U1 (R² = Me)
U2 (R² = NH₂)
U3 (R² = OH)
V1 (R² = Me)
V2 (R² = NH₂)
V3 (R² = OH)
W1 (R² = Me)
W2 (R² = NH₂)
X1 (R² = Me)
X2 (R² = NH₂)

TABLE 2-continued
W3 ($R^2$ = OH)   X3 ($R^2$ = OH)
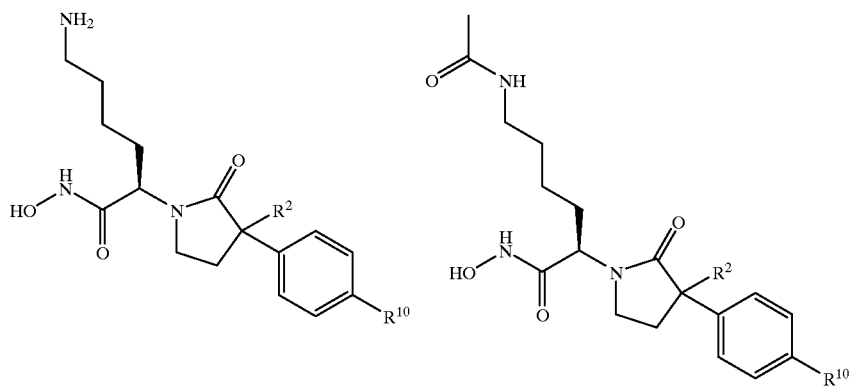
Y1 ($R^2$ = Me)   Z1 ($R^2$ = Me)
Y2 ($R^2$ = $NH_2$)   Z2 ($R^2$ = $NH_2$)
Y3 ($R^2$ = OH)   Z3 ($R^2$ = OH)
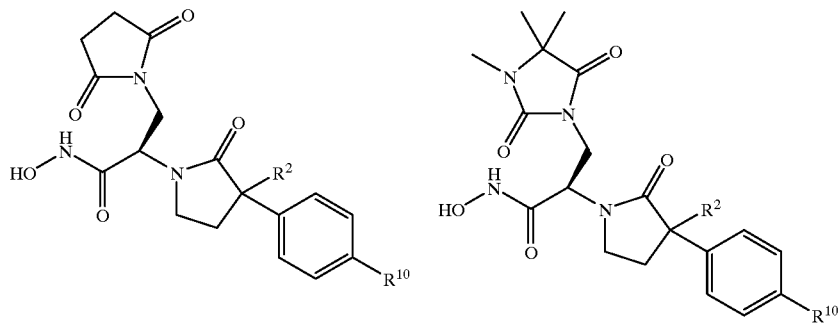
AA1 ($R^2$ = Me)   BB1 ($R^2$ = Me)
AA2 ($R^2$ = $NH_2$)   BB2 ($R^2$ = $NH_2$)
AA3 ($R^2$ = OH)   BB3 ($R^2$ = OH)
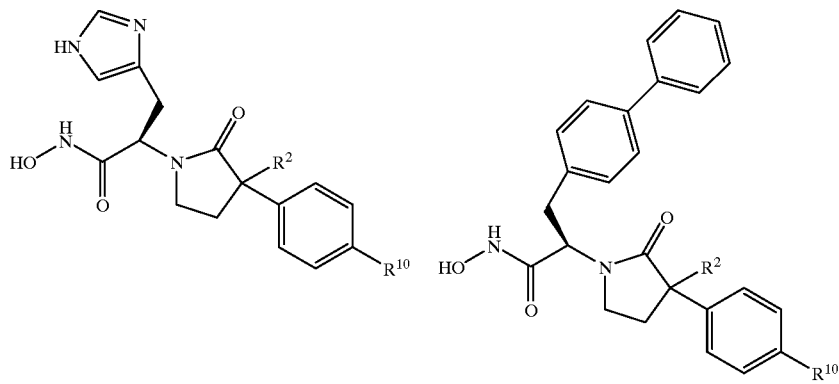
CC1 ($R^2$ = Me)   DD1 ($R^2$ = Me)
CC2 ($R^2$ = $NH_2$)   DD2 ($R^2$ = $NH_2$)
CC3 ($R^2$ = OH)   DD3 ($R^2$ = OH)

TABLE 2-continued

EE1 (R² = Me)
EE2 (R² = NH₂)
EE3 (R² = OH)

FF1 (R² = Me)
FF2 (R² = NH₂)
FF3 (R² = OH)

| Ex# | R¹⁰ |
|---|---|
| 1 | H |
| 2 | methyl |
| 3 | methoxy |
| 4 | 1-methylethyl |
| 5 | 1-methylethoxy |
| 6 | phenyl |
| 7 | [1,1'-biphenyl]-4-yl |
| 8 | phenoxy |
| 9 | 2-phenylethyl |
| 10 | 2-(3,5-dimethylphenyl)ethyl |
| 11 | 1-(2,6-dimethylphenyl)ethyl |
| 12 | 2-phenylethenyl |
| 13 | phenoxymethyl |
| 14 | (2-methylphenyl)methoxy |
| 15 | (3-methylphenyl)methoxy |
| 16 | 3-methylphenoxy |
| 17 | 2,6-dimethylphenoxy |
| 18 | (2,6-dimethylphenyl)methoxy |
| 19 | 3,5-dimethylphenoxy |
| 20 | (3,5-dimethylphenyl)methoxy |
| 21 | 2-(3,5-dimethylphenyl)ethyl |
| 22 | 2-(3,5-dimethylphenyl)ethenyl |
| 23 | (3-amino-5-methylphenyl)methoxy |
| 24 | (2-amino-6-methylphenyl)methoxy |
| 25 | (3-cyano-5-methylphenyl)methoxy |
| 26 | (3-cyano-5-methylphenoxy)methyl |
| 27 | (3-cyano-5-nitrophenyl)methoxy |
| 28 | (3,5-diethoxyphenyl)methoxy |
| 29 | (3,5-dimethoxyphenyl)methoxy |
| 30 | 3,5-dimethoxyphenoxy |
| 31 | 2-(3,5-dimethoxyphenyl)ethyl |
| 32 | 1-(3,5-dimethoxyphenyl)ethoxy |
| 33 | (3,5-dichlorophenyl)methoxy |
| 34 | (2,6-dichlorophenyl)methoxy |
| 35 | (3,5-dibromophenyl)methoxy |
| 36 | 3,5-dibromophenoxy |
| 37 | (3-amino-5-cyanophenyl)methoxy |
| 38 | [2,6-bis(trifluoromethyl)phenyl]methoxy |
| 39 | 2,6-bis(trifluoromethyl)phenoxy |
| 40 | (3-aminocarbonyl-5-methylphenyl)methoxy |
| 41 | ([1,1'-biphenyl]-2-yl)methoxy |
| 42 | ([1,1'-biphenyl]-3-yl)methoxy |
| 43 | [5-methyl-3-(methylsulfonyl)phenyl]methoxy |
| 44 | 5-methyl-3-(methylsulfonyl)phenoxy |
| 45 | (2-pyridinyl)methoxy |
| 46 | (4-pyridinyl)methoxy |
| 47 | (2,6-dimethyl-4-pyridinyl)methoxy |
| 48 | 2,6-dimethyl-4-pyridinyloxy |
| 49 | 1-(2,6-dimethyl-4-pyridinyl)ethoxy |
| 50 | (3,5-dimethyl-4-pyridinyl)methoxy |
| 51 | (2,6-diethyl-4-pyridinyl)methoxy |
| 52 | (2,6-dichloro-4-pyridinyl)methoxy |
| 53 | (2,6-dimethoxy-4-pyridinyl)methoxy |
| 54 | (2-chloro-6-methyl-4-pyridinyl)methoxy |
| 55 | (2-chloro-6-methoxy-4-pyridinyl)methoxy |

TABLE 2-continued

| | |
|---|---|
| 56 | (2-methoxy-6-methyl-4-pyridinyl)methoxy |
| 57 | (1-naphthalenyl)methoxy |
| 58 | 1-naphthalenyloxy |
| 59 | (2-naphthalenyl)methoxy |
| 60 | (2-methyl-1-naphthalenyl)methoxy |
| 61 | (4-methyl-2-naphthalenyl)methoxy |
| 62 | (4-quinolinyl)methoxy |
| 63 | 1-(4-quinolinyl)ethoxy |
| 64 | 4-quinolinyloxy |
| 65 | (4-quinolinyloxy)methyl |
| 66 | 2-(4-quinolinyl)ethyl |
| 67 | (2-methyl-4-quinolinyl)methoxy |
| 68 | 2-methyl-4-quinolinyloxy |
| 69 | (2-chloro-4-quinolinyl)methoxy |
| 70 | (2-methoxy-4-quinolinyl)methoxy |
| 71 | (2-hydroxy-4-quinolinyl)methoxy |
| 72 | (2-trifluoromethyl-4-quinolinyl)methoxy |
| 73 | (2-phenyl-4-quinolinyl)methoxy |
| 74 | (2,6-dimethyl-4-quinolinyl)methoxy |
| 75 | (2,7-dimethyl-4-quinolinyl)methoxy |
| 76 | (5-quinolinyl)methoxy |
| 77 | (7-methyl-5-quinolinyl)methoxy |
| 78 | (7-methoxy-5-quinolinyl)methoxy |
| 79 | (8-quinolinyl)methoxy |
| 80 | 2-(1,2,3-benzotriazol-1-yl)ethyl |
| 81 | (2-benzimidazolyl)methoxy |
| 82 | (1,4-dimethyl-5-imidazolyl)methoxy |
| 83 | (3,5-dimethyl-4-isoxazolyl)methoxy |
| 84 | (4,5-dimethyl-2-oxazolyl)methoxy |
| 85 | (2,5-dimethyl-4-thiazolyl)methoxy |
| 86 | (3,5-dimethyl-1-pyrazolyl)ethyl |
| 87 | (1,3-benzodioxo-4-yl)methoxy |
| 88 | (1,3,5-trimethyl-4-pyrazolyl)methoxy |
| 89 | (2,6-dimethyl-4-pyrimidinyl)methoxy |
| 90 | (4,5-dimethyl-2-furanyl)methoxy |
| 91 | (4,5-dimethyl-2-thiazolyl)methoxy |
| 92 | 2-(2-oxazolyl)ethyl |

TABLE 3

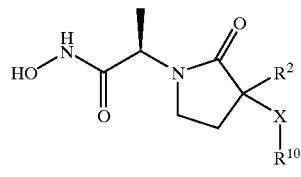 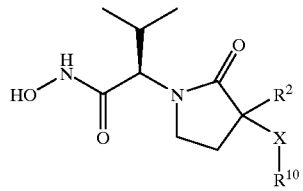

A1 (X = linker Σ)          B1 (X = linker Σ)
A2 (X = linker Δ)          B2 (X = linker Δ)
A3 (X = linker Φ)          B3 (X = linker Φ)
A4 (X = linker Ω)          B4 (X = linker Ω)
A5 (X = linker Π)          B5 (X = linker Π)
A6 (X = linker Ψ)          B6 (X = linker Ψ)
A7 (X = linker Λ)          B7 (X = linker Λ)

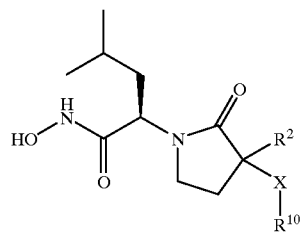 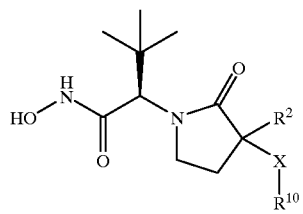

C1 (X = linker Σ)          D1 (X = linker Σ)
C2 (X = linker Δ)          D2 (X = linker Δ)
C3 (X = linker Φ)          D3 (X = linker Φ)
C4 (X = linker Ω)          D4 (X = linker Ω)
C5 (X = linker Π)          D5 (X = linker Π)
C6 (X = linker Ψ)          D6 (X = linker Ψ)

TABLE 3-continued

C7 (X = linker Λ)

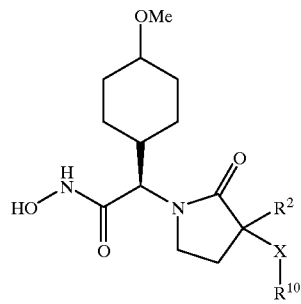

D7 (X = linker Λ)

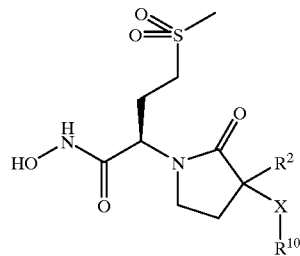

E1 (X = linker Σ)
E2 (X = linker Δ)
E3 (X = linker Φ)
E4 (X = linker Ω)
E5 (X = linker Π)
E6 (X = linker Ψ)
E7 (X = linker Λ)

F1 (X = linker Σ)
F2 (X = linker Δ)
F3 (X = linker Φ)
F4 (X = linker Ω)
F5 (X = linker Π)
F6 (X = linker Ψ)
F7 (X = linker Λ)

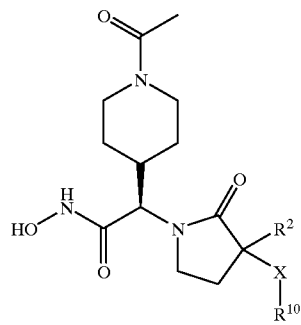

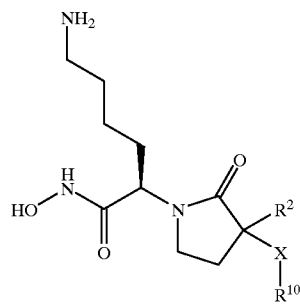

G1 (X = linker Σ)
G2 (X = linker Δ)
G3 (X = linker Φ)
G4 (X = linker Ω)
G5 (X = linker Π)
G6 (X = linker Ψ)
G7 (X = linker Λ)

H1 (X = linker Σ)
H2 (X = linker Δ)
H3 (X = linker Φ)
H4 (X = linker Ω)
H5 (X = linker Π)
H6 (X = linker Ψ)
H7 (X = linker Λ)

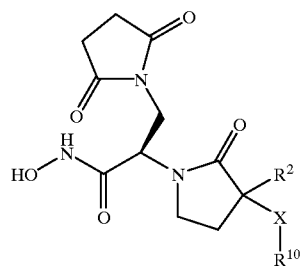

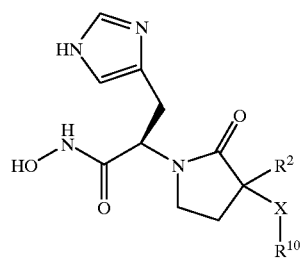

I1 (X = linker Σ)
I2 (X = linker Δ)
I3 (X = linker Φ)
I4 (X = linker Ω)
I5 (X = linker Π)
I6 (X = linker Ψ)
I7 (X = linker Λ)

J1 (X = linker Σ)
J2 (X = linker Δ)
J3 (X = linker Φ)
J4 (X = linker Ω)
J5 (X = linker Π)
J6 (X = linker Ψ)
J7 (X = linker Λ)

TABLE 3-continued
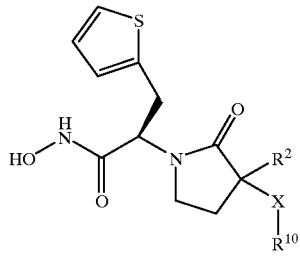 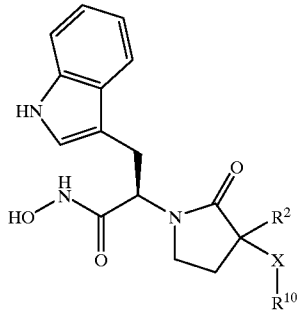
| K1 (X = linker Σ) | L1 (X = linker Σ) |
| K2 (X = linker Λ) | L2 (X = linker Λ) |
| K3 (X = linker Φ) | L3 (X = linker Φ) |
| K4 (X = linker Ω) | L4 (X = linker Ω) |
| K5 (X = linker Π) | L5 (X = linker Π) |
| K6 (X = linker Ψ) | L6 (X = linker Ψ) |
| K7 (X = linker Λ) | L7 (X = linker Λ) |
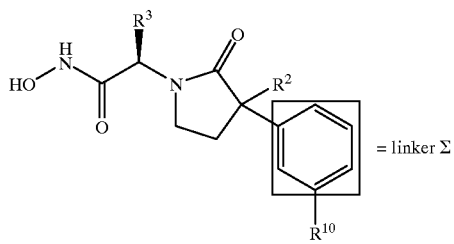 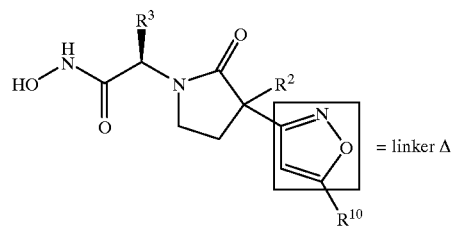
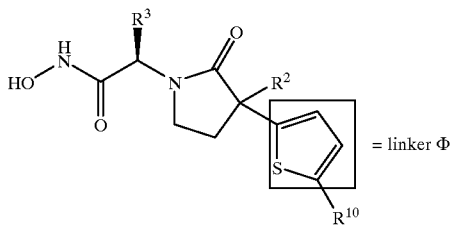 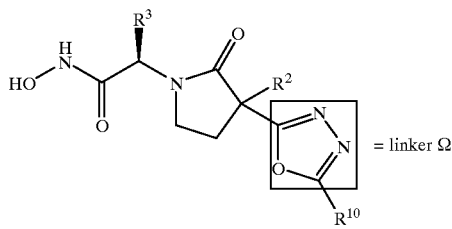
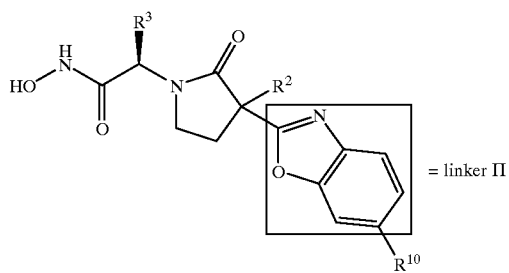 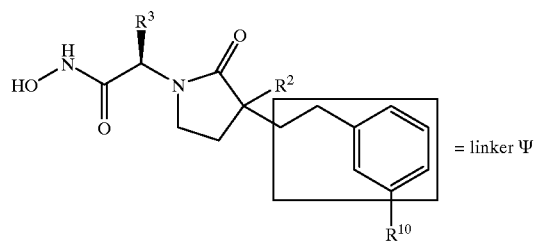
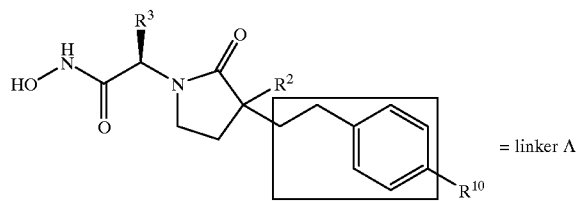
| Ex # | R² | R¹⁰ |
| --- | --- | --- |
| 1 | amino | methoxy |
| 2 | amino | 1-methylethyl |
| 3 | amino | 1-methylethoxy |

TABLE 3-continued

| | | |
|---|---|---|
| 4 | amino | phenyl |
| 5 | amino | phenoxy |
| 6 | amino | 2-phenylethyl |
| 7 | amino | 2-(3,5-dimethylphenyl)ethyl |
| 8 | amino | 2-phenylethenyl |
| 9 | amino | phenoxymethyl |
| 10 | amino | 3,5-dimethylphenoxy |
| 11 | amino | (3,5-dimethylphenyl)methoxy |
| 12 | amino | 2-(3,5-dimethylphenyl)ethyl |
| 13 | amino | 2-(3,5-dimethylphenyl)ethenyl |
| 14 | amino | (3-amino-5-methylphenyl)methoxy |
| 15 | amino | (3,5-dimethoxyphenyl)methoxy |
| 16 | amino | 3,5-dimethoxyphenoxy |
| 17 | amino | 2-(3,5-dimethoxyphenyl)ethyl |
| 18 | amino | (3,5-dichlorophenyl)methoxy |
| 19 | amino | 3,5-dibromophenoxy |
| 20 | amino | [2,6-bis(trifluoromethyl)phenyl]methoxy |
| 21 | amino | 2,6-bis(trifluoromethyl)phenoxy |
| 22 | amino | [5-methyl-3-(methylsulfonyl)phenyl]methoxy |
| 23 | amino | 5-methyl-3-(methylsulfonyl)phenoxy |
| 24 | amino | (2,6-dimethyl-4-pyridinyl)methoxy |
| 25 | amino | 2,6-dimethyl-4-pyridinyloxy |
| 26 | amino | (2,6-dichloro-4-pyridinyl)methoxy |
| 27 | amino | (2-methoxy-6-methyl-4-pyridinyl)methoxy |
| 28 | amino | (1-naphthalenyl)methoxy |
| 29 | amino | 1-naphthalenyloxy |
| 30 | amino | (2-naphthalenyl)methoxy |
| 31 | amino | (2-methyl-1-naphthalenyl)methoxy |
| 32 | amino | (4-methyl-2-naphthalenyl)methoxy |
| 33 | amino | (4-quinolinyl)methoxy |
| 34 | amino | 1-(4-quinolinyl)ethoxy |
| 35 | amino | 4-quinolinyloxy |
| 36 | amino | (4-quinolinyloxy)methyl |
| 37 | amino | (2-methyl-4-quinolinyl)methoxy |
| 38 | amino | 2-methyl-4-quinolinyloxy |
| 39 | amino | (2-methoxy-4-quinolinyl)methoxy |
| 40 | amino | 2-(1,2,3-benzotriazol-1-yl)ethyl |
| 41 | amino | (2-benzimidazolyl)methoxy |
| 42 | amino | (1,4-dimethyl-5-imidazolyl)methoxy |
| 43 | amino | (3,5-dimethyl-4-isoxazolyl)methoxy |
| 44 | amino | (4,5-dimethyl-2-oxazolyl)methoxy |
| 45 | amino | (2,5-dimethyl-4-thiazolyl)methoxy |
| 46 | amino | (3,5-dimethyl-1-pyrazolyl)ethyl |
| 47 | amino | (1,3-benzodioxo-4-yl)methoxy |
| 48 | amino | (1,3,5-trimethyl-4-pyrazolyl)methoxy |
| 49 | amino | (2,6-dimethyl-4-pyrimidinyl)methoxy |
| 50 | amino | (4,5-dimethyl-2-furanyl)methoxy |
| 51 | amino | (4,5-dimethyl-2-thiazolyl)methoxy |
| 52 | amino | 2-(2-oxazolyl)ethyl |
| 53 | methyl | methoxy |
| 54 | methyl | 1-methylethyl |
| 55 | methyl | 1-methylethoxy |
| 56 | methyl | phenyl |
| 57 | methyl | phenoxy |
| 58 | methyl | 2-phenylethyl |
| 59 | methyl | 2-(3,5-dimethylphenyl)ethyl |
| 60 | methyl | 2-phenylethenyl |
| 61 | methyl | phenoxymethyl |
| 62 | methyl | 3,5-dimethylphenyoxy |
| 63 | methyl | (3,5-dimethylphenyl)methoxy |
| 64 | methyl | 2-(3,5-dimethylphenyl)ethyl |
| 65 | methyl | 2-(3,5-dimethylphenyl)ethenyl |
| 66 | methyl | (3-amino-5-methylphenyl)methoxy |
| 67 | methyl | (3,5-dimethoxyphenyl)methoxy |
| 68 | methyl | 3,5-dimethoxyphenoxy |
| 69 | methyl | 2-(3,5-dimethoxyphenyl)ethyl |
| 70 | methyl | (3,5-dichlorophenyl)methoxy |
| 71 | methyl | 3,5-dibromophenoxy |
| 72 | methyl | [2,6-bis(trifluoromethyl)phenyl]methoxy |
| 73 | methyl | 2,6-bis(trifluoromethyl)phenoxy |
| 74 | methyl | [5-methyl-3-(methylsulfonyl)phenyl]methoxy |
| 75 | methyl | 5-methyl-3-(methylsulfonyl)phenoxy |
| 76 | methyl | (2,6-dimethyl-4-pyridinyl)methoxy |
| 77 | methyl | 2,6-dimethyl-4-pyridinyloxy |
| 78 | methyl | (2,6-dichloro-4-pyridinyl)methoxy |
| 79 | methyl | (2-methoxy-6-methyl-4-pyridinyl)methoxy |
| 80 | methyl | (1-naphthalenyl)methoxy |
| 81 | methyl | 1-naphthalenyloxy |
| 82 | methyl | (2-naphthalenyl)methoxy |

TABLE 3-continued

| 83 | methyl | (2-methyl-1-naphthalenyl)methoxy |
| 84 | methyl | (4-methyl-2-naphthalenyl)methoxy |
| 85 | methyl | (4-quinolinyl)methoxy |
| 86 | methyl | 1-(4-quinolinyl)ethoxy |
| 87 | methyl | 4-quinolinyloxy |
| 88 | methyl | (4-quinolinyloxy)methyl |
| 89 | methyl | (2-methyl-4-quinolinyl)methoxy |
| 90 | methyl | 2-methyl-4-quinolinyloxy |
| 91 | methyl | (2-methoxy-4-quinolinyl)methoxy |
| 92 | methyl | 2-(1,2,3-benzotriazol-1-yl)ethyl |
| 93 | methyl | (2-benzimidazolyl)methoxy |
| 94 | methyl | (1,4-dimethyl-5-imidazolyl)methoxy |
| 95 | methyl | (3,5-dimethyl-4-isoxazolyl)methoxy |
| 96 | methyl | (4,5-dimethyl-2-oxazolyl)methoxy |
| 97 | methyl | (2,5-dimethyl-4-thiazolyl)methoxy |
| 98 | methyl | (3,5-dimethyl-1-pyrazolyl)ethyl |
| 99 | methyl | (1,3-benzodioxo-4-yl)methoxy |
| 100 | methyl | (1,3,5-trimethyl-4-pyrazolyl)methoxy |
| 101 | methyl | (2,6-dimethyl-4-pyrimidinyl)methoxy |
| 102 | methyl | (4,5-dimethyl-2-furanyl)methoxy |
| 103 | methyl | (4,5-dimethyl-2-thiazolyl)methoxy |
| 104 | methyl | 2-(2-oxazolyl)ethyl |

TABLE 4

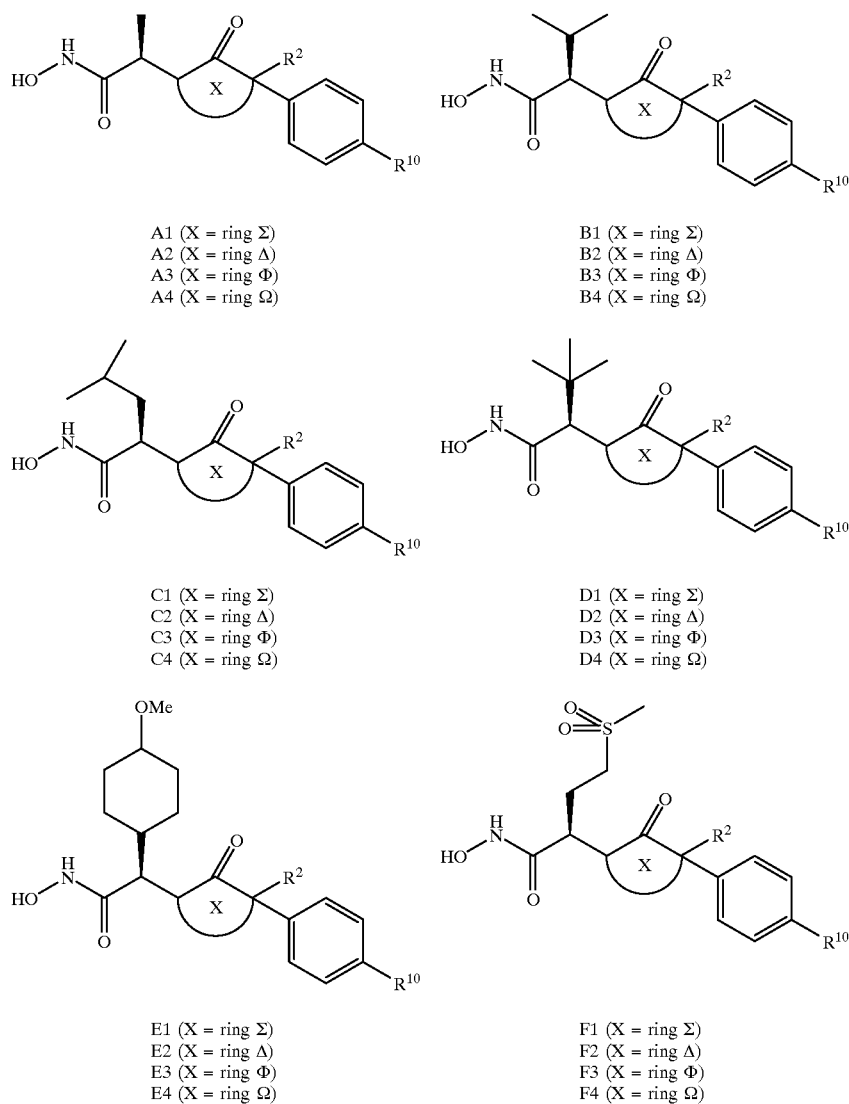

A1 (X = ring Σ)
A2 (X = ring Δ)
A3 (X = ring Φ)
A4 (X = ring Ω)

B1 (X = ring Σ)
B2 (X = ring Δ)
B3 (X = ring Φ)
B4 (X = ring Ω)

C1 (X = ring Σ)
C2 (X = ring Δ)
C3 (X = ring Φ)
C4 (X = ring Ω)

D1 (X = ring Σ)
D2 (X = ring Δ)
D3 (X = ring Φ)
D4 (X = ring Ω)

E1 (X = ring Σ)
E2 (X = ring Δ)
E3 (X = ring Φ)
E4 (X = ring Ω)

F1 (X = ring Σ)
F2 (X = ring Δ)
F3 (X = ring Φ)
F4 (X = ring Ω)

TABLE 4-continued
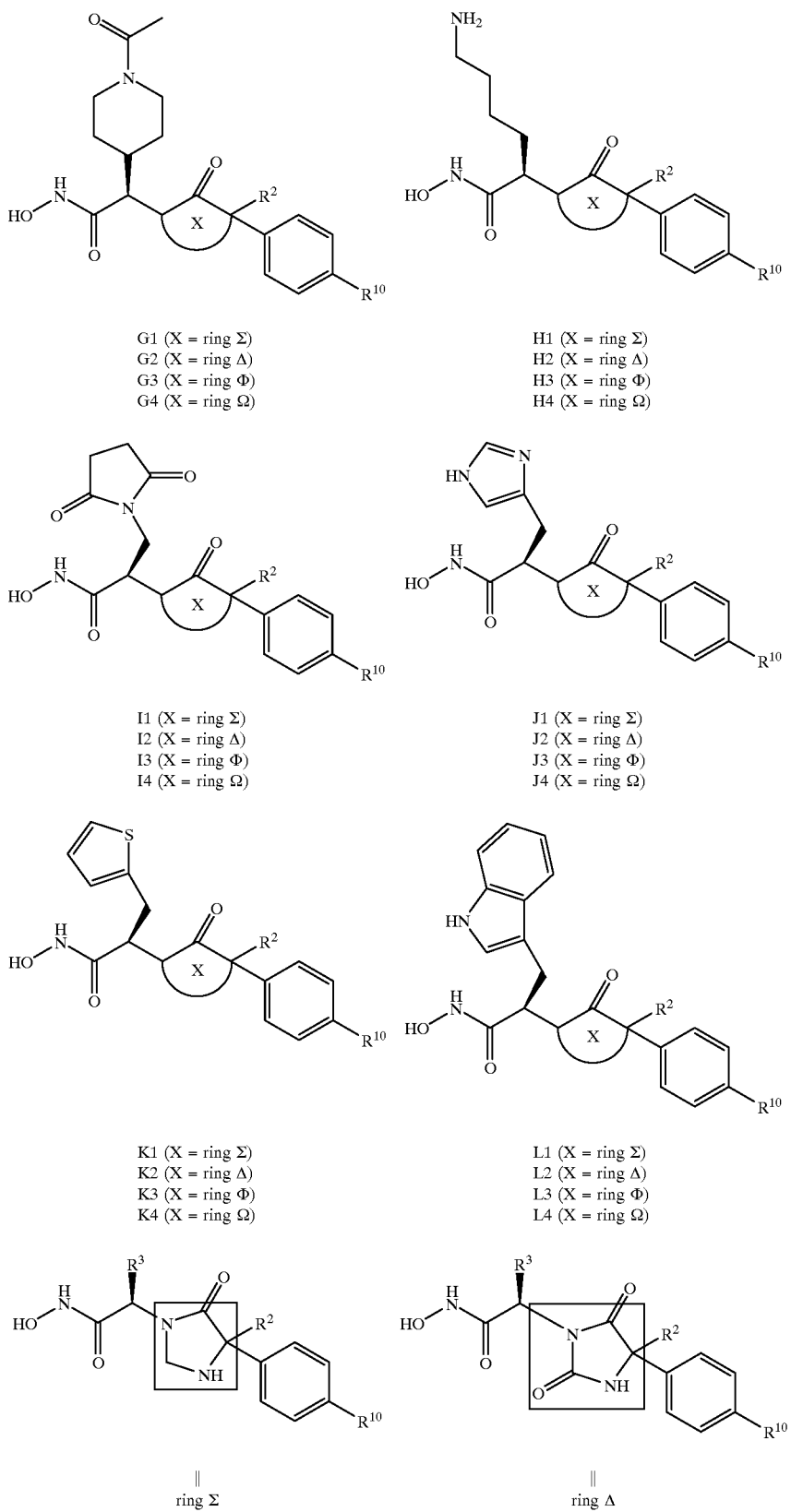
G1 (X = ring Σ)
G2 (X = ring Δ)
G3 (X = ring Φ)
G4 (X = ring Ω)
H1 (X = ring Σ)
H2 (X = ring Δ)
H3 (X = ring Φ)
H4 (X = ring Ω)
I1 (X = ring Σ)
I2 (X = ring Δ)
I3 (X = ring Φ)
I4 (X = ring Ω)
J1 (X = ring Σ)
J2 (X = ring Δ)
J3 (X = ring Φ)
J4 (X = ring Ω)
K1 (X = ring Σ)
K2 (X = ring Δ)
K3 (X = ring Φ)
K4 (X = ring Ω)
L1 (X = ring Σ)
L2 (X = ring Δ)
L3 (X = ring Φ)
L4 (X = ring Ω)
ring Σ
ring Δ

TABLE 4-continued ring Φ / ring Ω

| Ex # | R² | R¹⁰ |
|---|---|---|
| 1 | amino | methoxy |
| 2 | amino | 1-methylethyl |
| 3 | amino | 1-methylethoxy |
| 4 | amino | phenyl |
| 5 | amino | phenoxy |
| 6 | amino | 2-phenylethyl |
| 7 | amino | 2-(3,5-dimethylphenyl)ethyl |
| 8 | amino | 2-phenylethenyl |
| 9 | amino | phenoxymethyl |
| 10 | amino | 3,5-dimethylphenoxy |
| 11 | amino | (3,5-dimethylphenyl)methoxy |
| 12 | amino | 2-(3,5-dimethylphenyl)ethyl |
| 13 | amino | 2-(3,5-dimethylphenyl)ethenyl |
| 14 | amino | (3-amino-5-methylphenyl)methoxy |
| 15 | amino | (3,5-dimethoxyphenyl)methoxy |
| 16 | amino | 3,5-dimethoxyphenoxy |
| 17 | amino | 2-(3,5-dimethoxyphenyl)ethyl |
| 18 | amino | (3,5-dichlorophenyl)methoxy |
| 19 | amino | 3,5-dibromophenoxy |
| 20 | amino | [2,6-bis(trifluoromethyl)phenyl]methoxy |
| 21 | amino | 2,6-bis(trifluoromethyl)phenoxy |
| 22 | amino | [5-methyl-3-(methylsulfonyl)phenyl]methoxy |
| 23 | amino | 5-methyl-3-(methylsulfonyl)phenoxy |
| 24 | amino | (2,6-dimethyl-4-pyridinyl)methoxy |
| 25 | amino | 2,6-dimethyl-4-pyridinyloxy |
| 26 | amino | (2,6-dichloro-4-pyridinyl)methoxy |
| 27 | amino | (2-methoxy-6-methyl-4-pyridinyl)methoxy |
| 28 | amino | (1-naphthalenyl)methoxy |
| 29 | amino | 1-naphthalenyloxy |
| 30 | amino | (2-naphthalenyl)methoxy |
| 31 | amino | (2-methyl-1-naphthalenyl)methoxy |
| 32 | amino | (4-methyl-2-naphthalenyl)methoxy |
| 33 | amino | (4-quinolinyl)methoxy |
| 34 | amino | 1-(4-quinolinyl)ethoxy |
| 35 | amino | 4-quinolinyloxy |
| 36 | amino | (4-quinolinyloxy)methyl |
| 37 | amino | (2-methyl-4-quinolinyl)methoxy |
| 38 | amino | 2-methyl-4-quinolinyloxy |
| 39 | amino | (2-methoxy-4-quinolinyl)methoxy |
| 40 | amino | 2-(1,2,3-benzotriazol-1-yl)ethyl |
| 41 | amino | (2-benzimidazolyl)methoxy |
| 42 | amino | (1,4-dimethyl-5-imidazolyl)methoxy |
| 43 | amino | (3,5-dimethyl-4-isoxazolyl)methoxy |
| 44 | amino | (4,5-dimethyl-2-oxazolyl)methoxy |
| 45 | amino | (2,5-dimethyl-4-thiazolyl)methoxy |
| 46 | amino | (3,5-dimethyl-1-pyrazolyl)ethyl |
| 47 | amino | (1,3-benzodioxo-4-yl)methoxy |
| 48 | amino | (1,3,5-trimethyl-4-pyrazolyl)methoxy |
| 49 | amino | (2,6-dimethyl-4-pyrimidinyl)methoxy |
| 50 | amino | (4,5-dimethyl-2-furanyl)methoxy |
| 51 | amino | (4,5-dimethyl-2-thiazolyl)methoxy |
| 52 | amino | 2-(2-oxazolyl)ethyl |
| 53 | methyl | methoxy |
| 54 | methyl | 1-methylethyl |
| 55 | methyl | 1-methylethoxy |
| 56 | methyl | phenyl |
| 57 | methyl | phenoxy |
| 58 | methyl | 2-phenylethyl |
| 59 | methyl | 2-(3,5-dimethylphenyl)ethyl |
| 60 | methyl | 2-phenylethenyl |
| 61 | methyl | phenoxymethyl |
| 62 | methyl | 3,5-dimethylphenoxy |

TABLE 4-continued

| | | |
|---|---|---|
| 63 | methyl | (3,5-dimethylphenyl)methoxy |
| 64 | methyl | 2-(3,5-dimethylphenyl)ethyl |
| 65 | methyl | 2-(3,5-dimethylphenyl)ethenyl |
| 66 | methyl | (3-amino-5-methylphenyl)methoxy |
| 67 | methyl | (3,5-dimethoxyphenyl)methoxy |
| 68 | methyl | 3,5-dimethoxyphenoxy |
| 69 | methyl | 2-(3,5-dimethoxyphenyl)ethyl |
| 70 | methyl | (3,5-dichlorophenyl)methoxy |
| 71 | methyl | 3,5-dibromophenoxy |
| 72 | methyl | [2,6-bis(trifluoromethyl)phenyl]methoxy |
| 73 | methyl | 2,6-bis(trifluoromethyl)phenoxy |
| 74 | methyl | [5-methyl-3-(methylsulfonyl)phenyl]methoxy |
| 75 | methyl | 5-methyl-3-(methylsulfonyl)phenoxy |
| 76 | methyl | (2,6-dimethyl-4-pyridinyl)methoxy |
| 77 | methyl | 2,6-dimethyl-4-pyridinyloxy |
| 78 | methyl | (2,6-dichloro-4-pyridinyl)methoxy |
| 79 | methyl | (2-methoxy-6-methyl-4-pyridinyl)methoxy |
| 80 | methyl | (1-naphthalenyl)methoxy |
| 81 | methyl | 1-naphthalenyloxy |
| 82 | methyl | (2-naphthalenyl)methoxy |
| 83 | methyl | (2-methyl-1-naphthalenyl)methoxy |
| 84 | methyl | (4-methyl-2-naphthalenyl)methoxy |
| 85 | methyl | (4-quinolinyl)methoxy |
| 86 | methyl | 1-(4-quinolinyl)ethoxy |
| 87 | methyl | 4-quinolinyloxy |
| 88 | methyl | (4-quinolinyloxy)methyl |
| 89 | methyl | (2-methyl-4-quinolinyl)methoxy |
| 90 | methyl | 2-methyl-4-quinolinyloxy |
| 91 | methyl | (2-methoxy-4-quinolinyl)methoxy |
| 92 | methyl | 2-(1,2,3-benzotriazol-1-yl)ethyl |
| 93 | methyl | (2-benzimidazolyl)methoxy |
| 94 | methyl | (1,4-dimethyl-5-imidazolyl)methoxy |
| 95 | methyl | (3,5-dimethyl-4-isoxazolyl)methoxy |
| 96 | methyl | (4,5-dimethyl-2-oxazolyl)methoxy |
| 97 | methyl | (2,5-dimethyl-4-thiazolyl)methoxy |
| 98 | methyl | (3,5-dimethyl-1-pyrazolyl)ethyl |
| 99 | methyl | (1,3-benzodioxo-4-yl)methoxy |
| 100 | methyl | (1,3,5-trimethyl-4-pyrazolyl)methoxy |
| 101 | methyl | (2,6-dimethyl-4-pyrimidinyl)methoxy |
| 102 | methyl | (4,5-dimethyl-2-furanyl)methoxy |
| 103 | methyl | (4,5-dimethyl-2-thiazolyl)methoxy |
| 104 | methyl | 2-(2-oxazolyl)ethyl |

TABLE 5

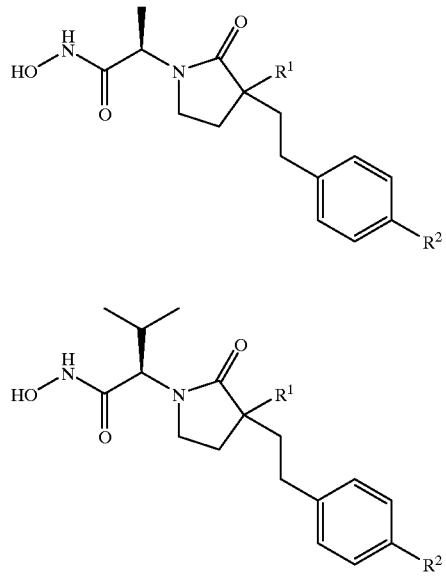
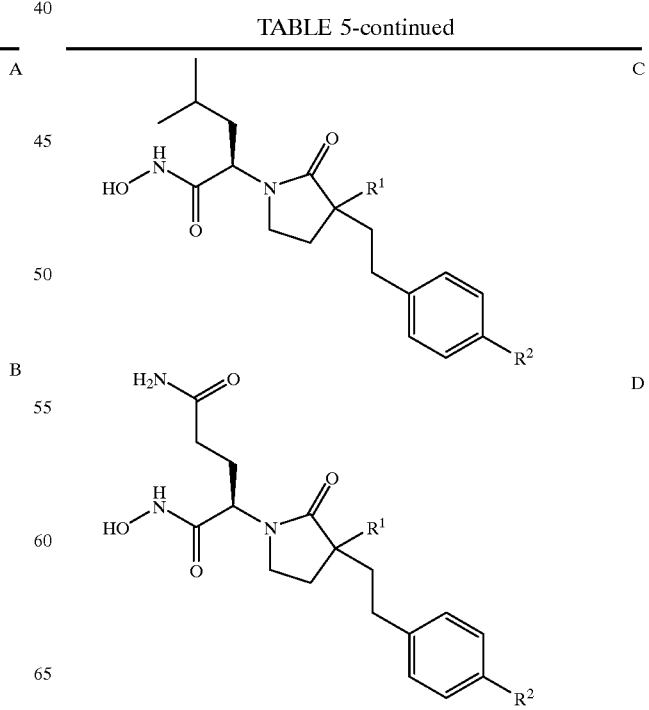

TABLE 5-continued
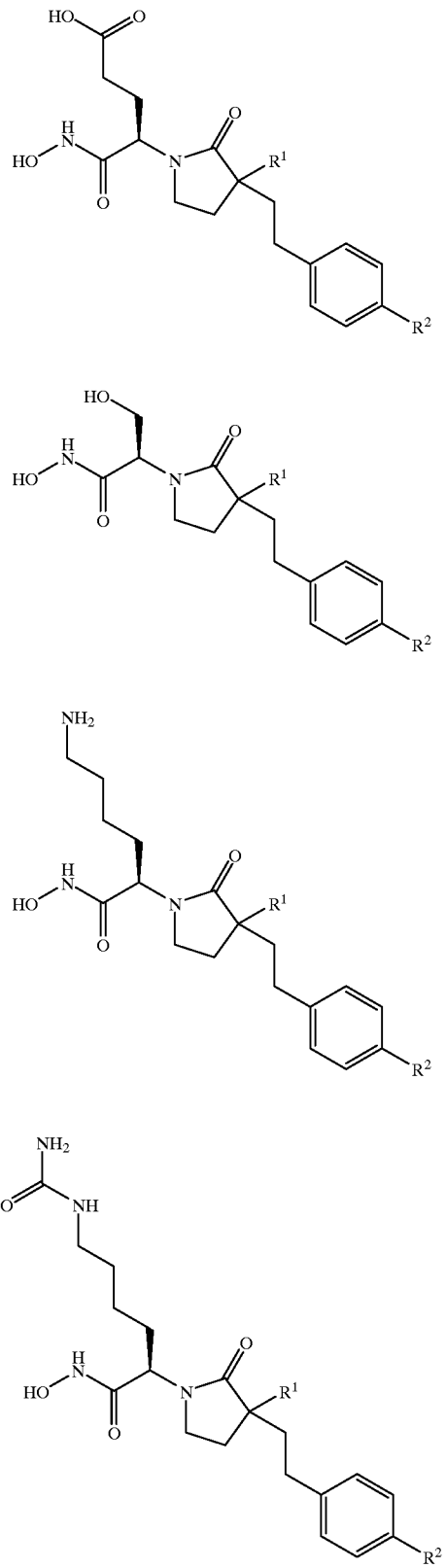
TABLE 5-continued
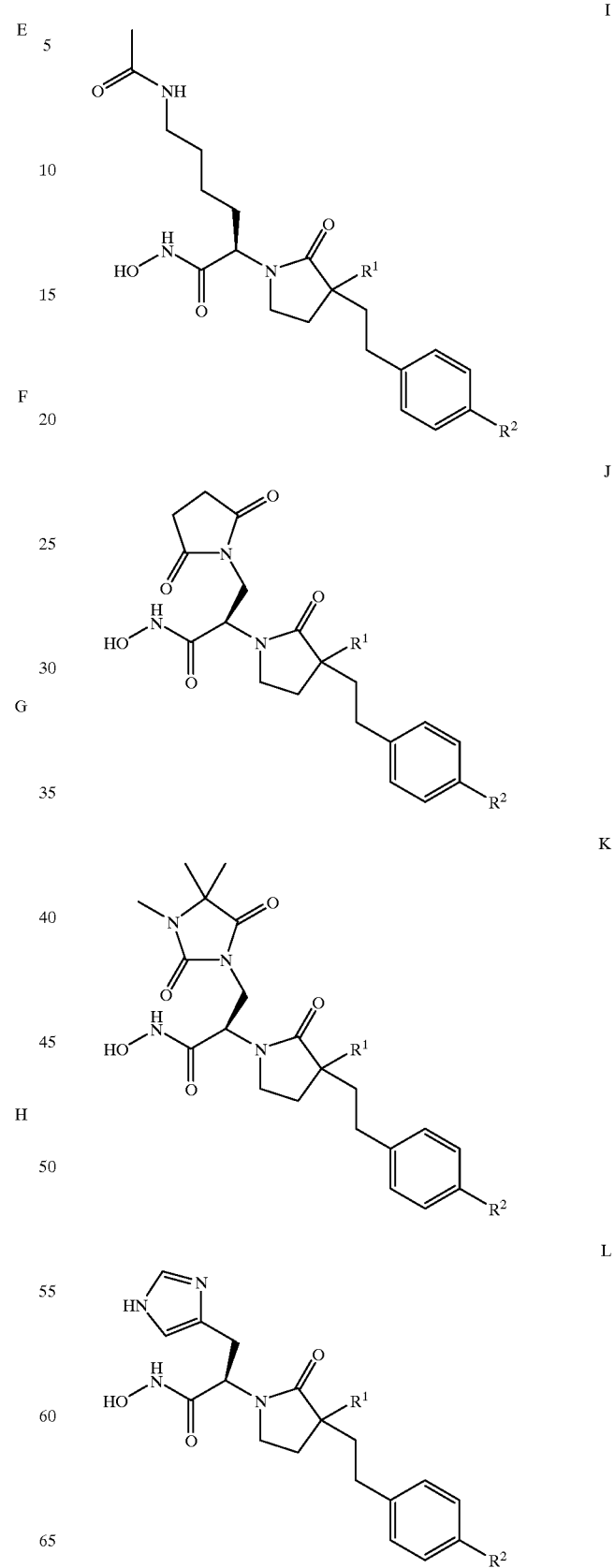

TABLE 5-continued
M
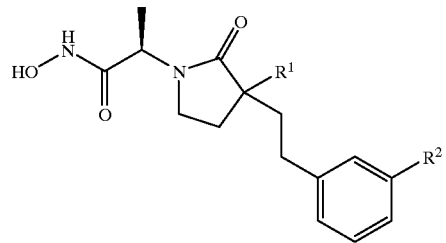
N
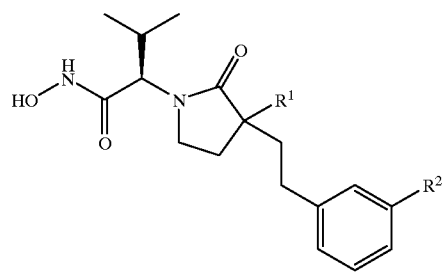
O
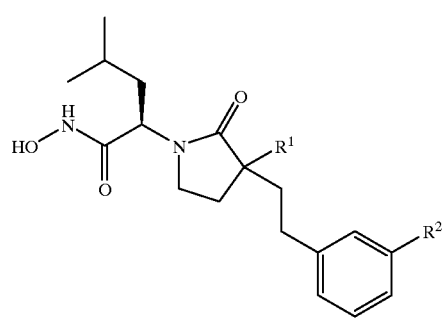
P
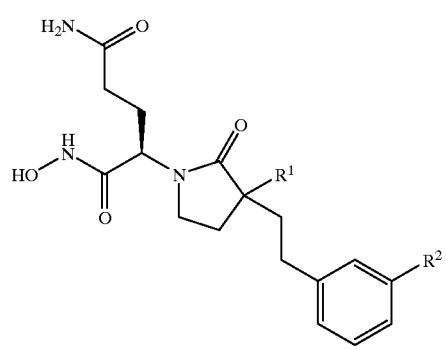
TABLE 5-continued
Q
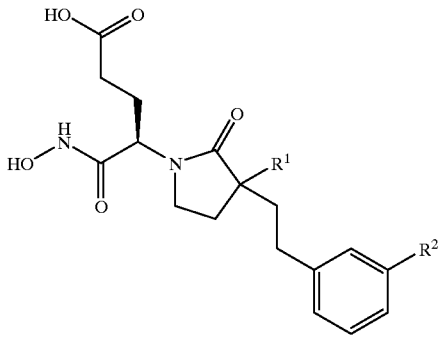
R
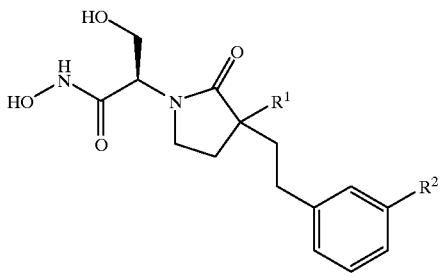
S
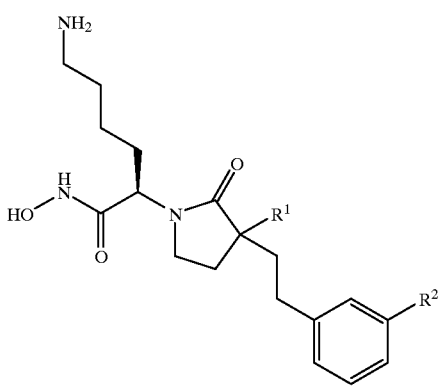
T
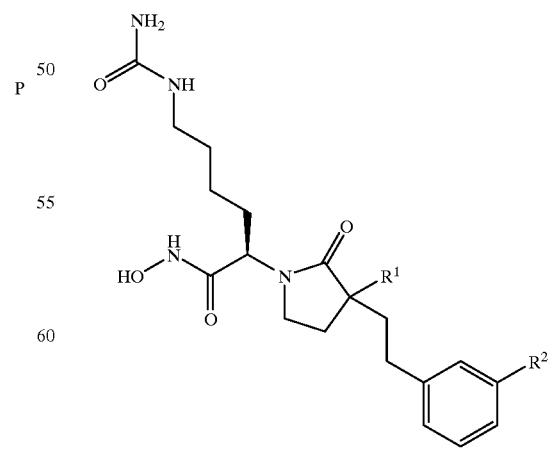

TABLE 5-continued
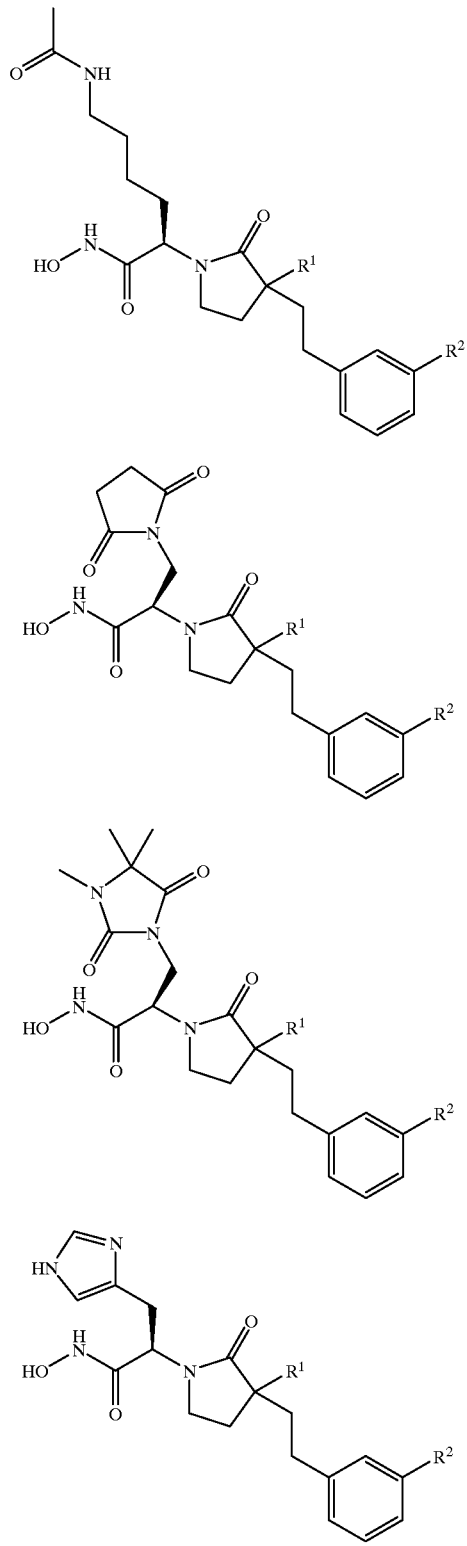
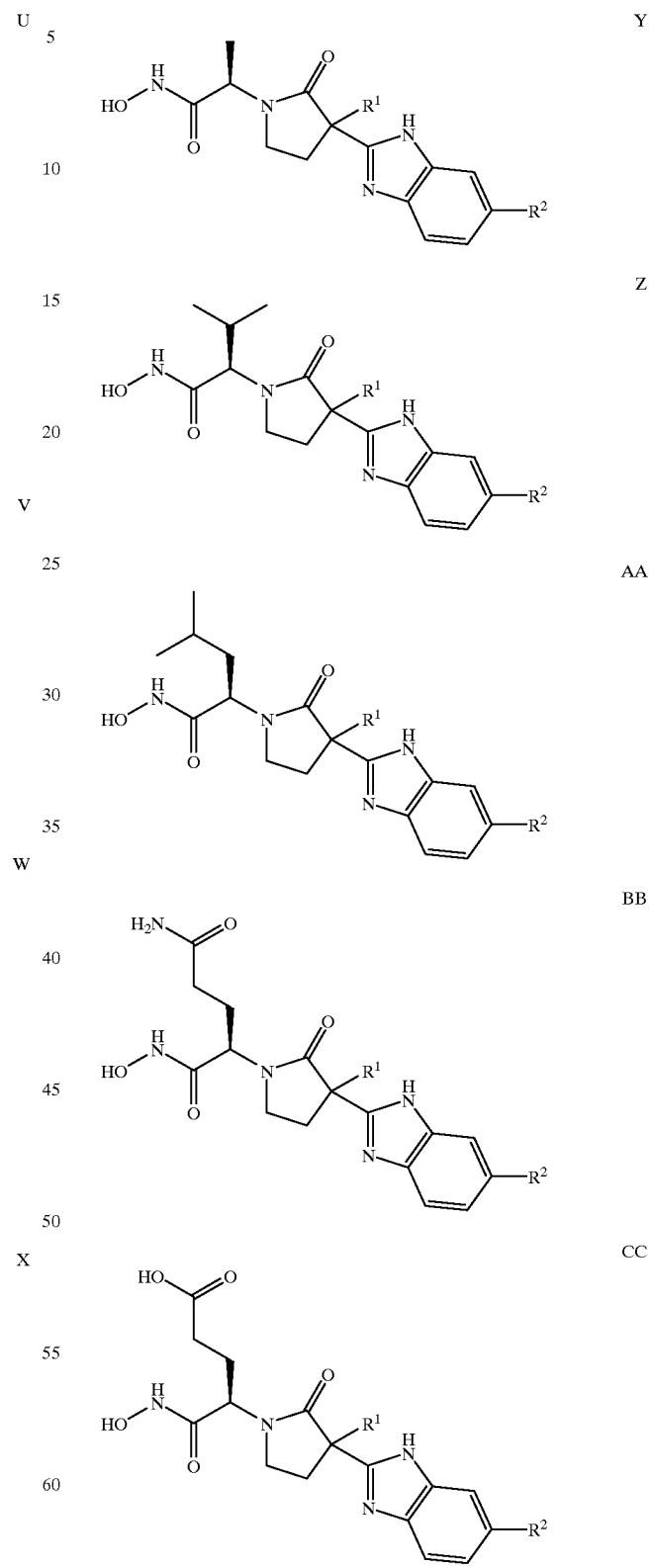

TABLE 5-continued

| Ex # | R¹ | R² |
|------|-----|-----|
| 1 | Me | H |
| 2 | OH | H |
| 3 | NH₂ | H |
| 4 | Me | methyl |
| 5 | OH | methyl |
| 6 | NH₂ | methyl |
| 7 | Me | ethyl |
| 8 | OH | ethyl |
| 9 | NH₂ | ethyl |
| 10 | Me | isopropyl |
| 11 | OH | isopropyl |
| 12 | NH₂ | isopropyl |
| 13 | Me | phenyl |
| 14 | OH | phenyl |
| 15 | NH₂ | phenyl |
| 16 | Me | benzyl |
| 17 | OH | benzyl |
| 18 | NH₂ | benzyl |
| 19 | Me | 2-phenylethyl |
| 20 | OH | 2-phenylethyl |
| 21 | NH₂ | 2-phenylethyl |
| 22 | Me | 2-(2-methylphenyl)ethyl |
| 23 | OH | 2-(2-methylphenyl)ethyl |
| 24 | NH₂ | 2-(2-methylphenyl)ethyl |
| 25 | Me | 2-(3-methylphenyl)ethyl |

TABLE 5-continued

| | | |
|---|---|---|
| 26 | OH | 2-(3-methylphenyl)ethyl |
| 27 | NH₂ | 2-(3-methylphenyl)ethyl |
| 28 | Me | 2-(2,6-dimethylphenyl)ethyl |
| 29 | OH | 2-(2,6-dimethylphenyl)ethyl |
| 30 | NH₂ | 2-(2,6-dimethylphenyl)ethyl |
| 31 | Me | 2-(3,5-dimethylphenyl)ethyl |
| 32 | OH | 2-(3,5-dimethylphenyl)ethyl |
| 33 | NH₂ | 2-(3,5-dimethylphenyl)ethyl |
| 34 | Me | 2-(3-amino-5-methylphenyl)ethyl |
| 35 | OH | 2-(3-amino-5-methylphenyl)ethyl |
| 36 | NH₂ | 2-(3-amino-5-methylphenyl)ethyl |
| 37 | Me | 2-(pyridin-4-yl)ethyl |
| 38 | OH | 2-(pyridin-4-yl)ethyl |
| 39 | NH₂ | 2-(pyridin-4-yl)ethyl |
| 40 | Me | 2-(2,6-dimethylpyridin-4-yl)ethyl |
| 41 | OH | 2-(2,6-dimethylpyridin-4-yl)ethyl |
| 42 | NH₂ | 2-(2,6-dimethylpyridin-4-yl)ethyl |
| 43 | Me | 2-(3,5-dimethylpyridin-4-yl)ethyl |
| 44 | OH | 2-(3,5-dimethylpyridin-4-yl)ethyl |
| 45 | NH₂ | 2-(3,5-dimethylpyridin-4-yl)ethyl |
| 46 | Me | styryl |
| 47 | OH | styryl |
| 48 | NH₂ | styryl |
| 49 | Me | hydroxy |
| 50 | OH | hydroxy |
| 51 | NH₂ | hydroxy |
| 52 | Me | methoxy |
| 53 | OH | methoxy |
| 54 | NH₂ | methoxy |
| 55 | Me | ethoxy |
| 56 | OH | ethoxy |
| 57 | NH₂ | ethoxy |
| 58 | Me | isopropyloxy |
| 59 | OH | isopropyloxy |
| 60 | NH₂ | isopropyloxy |
| 61 | Me | tert-butyoxy |
| 62 | OH | tert-butyoxy |
| 63 | NH₂ | tert-butyoxy |
| 64 | Me | cyclohexyloxy |
| 65 | OH | cyclohexyloxy |
| 66 | NH₂ | cyclohexyloxy |
| 67 | Me | phenoxy |
| 68 | OH | phenoxy |
| 69 | NH₂ | phenoxy |
| 70 | Me | o-methylphenoxy |
| 71 | OH | o-methylphenoxy |
| 72 | NH₂ | o-methylphenoxy |
| 73 | Me | m-methylphenoxy |
| 74 | OH | m-methylphenoxy |
| 75 | NH₂ | m-methylphenoxy |
| 76 | Me | cinnamyloxy |
| 77 | OH | cinnamyloxy |
| 78 | NH₂ | cinnamyloxy |
| 79 | Me | benzyloxy |
| 80 | OH | benzyloxy |
| 81 | NH₂ | benzyloxy |
| 82 | Me | phenoxymethyl |
| 83 | OH | phenoxymethyl |
| 84 | NH₂ | phenoxymethyl |
| 85 | Me | o-methylbenzyloxy |
| 86 | OH | o-methylbenzyloxy |
| 87 | NH₂ | o-methylbenzyloxy |
| 88 | Me | m-methylbenzyloxy |
| 89 | OH | m-methylbenzyloxy |
| 90 | NH₂ | m-methylbenzyloxy |
| 91 | Me | o,o-dimethylbenzyloxy |
| 92 | OH | o,o-dimethylbenzyloxy |
| 93 | NH₂ | o,o-dimethylbenzyloxy |
| 94 | Me | (2,6-dimethylphenoxy)methyl |
| 95 | OH | (2,6-dimethylphenoxy)methyl |
| 96 | NH₂ | (2,6-dimethylphenoxy)methyl |
| 97 | Me | m,m-dimethylbenzyloxy |
| 98 | OH | m,m-dimethylbenzyloxy |
| 99 | NH₂ | m,m-dimethylbenzyloxy |
| 100 | Me | (3,5-dimethylphenoxy)methyl |
| 101 | OH | (3,5-dimethylphenoxy)methyl |
| 102 | NH₂ | (3,5-dimethylphenoxy)methyl |
| 103 | Me | o,o-dicyanobenzyloxy |
| 104 | OH | o,o-dicyanobenzyloxy |
| 105 | NH₂ | o,o-dicyanobenzyloxy |
| 106 | Me | m,m-dicyanobenzyloxy |
| 107 | OH | m,m-dicyanobenzyloxy |
| 108 | NH₂ | m,m-dicyanobenzyloxy |
| 109 | Me | (2,6-dicyanophenoxy)methyl |
| 110 | OH | (2,6-dicyanophenoxy)methyl |
| 111 | NH₂ | (2,6-dicyanophenoxy)methyl |
| 112 | Me | (3,5-dicyanophenoxy)methyl |
| 113 | OH | (3,5-dicyanophenoxy)methyl |
| 114 | NH₂ | (3,5-dicyanophenoxy)methyl |
| 115 | Me | o-amino-o-cyanobenzyloxy |
| 116 | OH | o-amino-o-cyanobenzyloxy |
| 117 | NH₂ | o-amino-o-cyanobenzyloxy |
| 118 | Me | m-amino-m-cyanobenzyloxy |
| 119 | OH | m-amino-m-cyanobenzyloxy |
| 120 | NH₂ | m-amino-m-cyanobenzyloxy |
| 121 | Me | o-amino-o-nitrobenzyloxy |
| 122 | OH | o-amino-o-nitrobenzyloxy |
| 123 | NH₂ | o-amino-o-nitrobenzyloxy |
| 124 | Me | m-amino-m-nitrobenzyloxy |
| 125 | OH | m-amino-m-nitrobenzyloxy |
| 126 | NH₂ | m-amino-m-nitrobenzyloxy |
| 127 | Me | p-amino-m,m-dimethylbenzyloxy |
| 128 | OH | p-amino-m,m-dimethylbenzyloxy |
| 129 | NH₂ | p-amino-m,m-dimethylbenzyloxy |
| 130 | Me | o-amino-o-methylbenzyloxy |
| 131 | OH | o-amino-o-methylbenzyloxy |
| 132 | NH₂ | o-amino-o-methylbenzyloxy |
| 133 | Me | m-amino-m-methylbenzyloxy |
| 134 | OH | m-amino-m-methylbenzyloxy |
| 135 | NH₂ | m-amino-m-methylbenzyloxy |
| 136 | Me | o-cyano-o-methylbenzyloxy |
| 137 | OH | o-cyano-o-methylbenzyloxy |
| 138 | NH₂ | o-cyano-o-methylbenzyloxy |
| 139 | Me | m-cyano-m-methylbenzyloxy |
| 140 | OH | m-cyano-m-methylbenzyloxy |
| 141 | NH₂ | m-cyano-m-methylbenzyloxy |
| 142 | Me | o-cyano-o-nitrobenzyloxy |
| 143 | OH | o-cyano-o-nitrobenzyloxy |
| 144 | NH₂ | o-cyano-o-nitrobenzyloxy |
| 145 | Me | (2-cyano-6-nitrophenoxy)methyl |
| 146 | OH | (2-cyano-6-nitrophenoxy)methyl |
| 147 | NH₂ | (2-cyano-6-nitrophenoxy)methyl |
| 148 | Me | m-cyano-m-nitrobenzyloxy |
| 149 | OH | m-cyano-m-nitrobenzyloxy |
| 150 | NH₂ | m-cyano-m-nitrobenzyloxy |
| 151 | Me | (3-cyano-5-nitrophenoxy)methyl |
| 152 | OH | (3-cyano-5-nitrophenoxy)methyl |
| 153 | NH₂ | (3-cyano-5-nitrophenoxy)methyl |
| 154 | Me | m,m-dimethoxybenzyloxy |
| 155 | OH | m,m-dimethoxybenzyloxy |
| 156 | NH₂ | m,m-dimethoxybenzyloxy |
| 157 | Me | m,m-dichlorobenzyloxy |
| 158 | OH | m,m-dichlorobenzyloxy |
| 159 | NH₂ | m,m-dichlorobenzyloxy |
| 160 | Me | (3,5-dichlorophenoxy)methyl |
| 161 | OH | (3,5-dichlorophenoxy)methyl |
| 162 | NH₂ | (3,5-dichlorophenoxy)methyl |
| 163 | Me | m,m-dibromobenzyloxy |
| 164 | OH | m,m-dibromobenzyloxy |
| 165 | NH₂ | m,m-dibromobenzyloxy |
| 166 | Me | m,m-bis(trifluoromethyl)benzyloxy |
| 167 | OH | m,m-bis(trifluoromethyl)benzyloxy |
| 168 | NH₂ | m,m-bis(trifluoromethyl)benzyloxy |
| 169 | Me | [3,5-bis(trifluoromethyl)phenoxy]methyl |
| 170 | OH | [3,5-bis(trifluoromethyl)phenoxy]methyl |
| 171 | NH₂ | [3,5-bis(trifluoromethyl)phenoxy]methyl |
| 172 | Me | m-carboxamido-m-methylbenzyloxy |
| 173 | OH | m-carboxamido-m-methylbenzyloxy |
| 174 | NH₂ | m-carboxamido-m-methylbenzyloxy |
| 175 | Me | (3-carboxamido-5-methylphenoxy)methyl |
| 176 | OH | (3-carboxamido-5-methylphenoxy)methyl |
| 177 | NH₂ | (3-carboxamido-5-methylphenoxy)methyl |
| 178 | Me | m-hydroxycarbonyl-m-methylbenzyloxy |
| 179 | OH | m-hydroxycarbonyl-m-methylbenzyloxy |
| 180 | NH₂ | m-hydroxycarbonyl-m-methylbenzyloxy |
| 181 | Me | (3-hydroxycarbonyl-5-methylphenoxy)methyl |
| 182 | OH | (3-hydroxycarbonyl-5-methylphenoxy)methyl |
| 183 | NH₂ | (3-hydroxycarbonyl-5-methylphenoxy)methyl |

TABLE 5-continued

| | | |
|---|---|---|
| 184 | Me | o-phenylbenzyloxy |
| 185 | OH | o-phenylbenzyloxy |
| 186 | NH$_2$ | o-phenylbenzyloxy |
| 187 | Me | m-phenylbenzyloxy |
| 188 | OH | m-phenylbenzyloxy |
| 189 | NH$_2$ | m-phenylbenzyloxy |
| 190 | Me | (naphth-1-yl)methoxy |
| 191 | OH | (naphth-1-yl)methoxy |
| 192 | NH$_2$ | (naphth-1-yl)methoxy |
| 193 | Me | (naphth-2-yl)methoxy |
| 194 | OH | (naphth-2-yl)methoxy |
| 195 | NH$_2$ | (naphth-2-yl)methoxy |
| 196 | Me | (2-methylnaphth-1-yl)methoxy |
| 197 | OH | (2-methylnaphth-1-yl)methoxy |
| 198 | NH$_2$ | (2-methylnaphth-1-yl)methoxy |
| 199 | Me | (4-methylnaphth-2-yl)methoxy |
| 200 | OH | (4-methylnaphth-2-yl)methoxy |
| 201 | NH$_2$ | (4-methylnaphth-2-yl)methoxy |
| 202 | Me | (pyridin-3-yl)methoxy |
| 203 | OH | (pyridin-3-yl)methoxy |
| 204 | NH$_2$ | (pyridin-3-yl)methoxy |
| 205 | Me | (pyridin-4-yl)methoxy |
| 206 | OH | (pyridin-4-yl)methoxy |
| 207 | NH$_2$ | (pyridin-4-yl)methoxy |
| 208 | Me | (3,5-dichloropyridin-4-yl)methoxy |
| 209 | OH | (3,5-dichloropyridin-4-yl)methoxy |
| 210 | NH$_2$ | (3,5-dichloropyridin-4-yl)methoxy |
| 211 | Me | (3,5-dimethylpyridin-4-yl)methoxy |
| 212 | OH | (3,5-dimethylpyridin-4-yl)methoxy |
| 213 | NH$_2$ | (3,5-dimethylpyridin-4-yl)methoxy |
| 214 | Me | (1,2,3-benzotriazol-1-yl)methoxy |
| 215 | OH | (1,2,3-benzotriazol-1-yl)methoxy |
| 216 | NH$_2$ | (1,2,3-benzotriazol-1-yl)methoxy |
| 217 | Me | benzhydroxy |
| 218 | OH | benzhydroxy |
| 219 | NH$_2$ | benzhydroxy |
| 220 | Me | p-(1,2,3-thiadiazol-5-yl)benzyloxy |
| 221 | OH | p-(1,2,3-thiadiazol-5-yl)benzyloxy |
| 222 | NH$_2$ | p-(1,2,3-thiadiazol-5-yl)benzyloxy |
| 223 | Me | o-(tetrazol-5-yl)benzyloxy |
| 224 | OH | o-(tetrazol-5-yl)benzyloxy |
| 225 | NH$_2$ | o-(tetrazol-5-yl)benzyloxy |
| 226 | Me | m-(tetrazol-5-yl)benzyloxy |
| 227 | OH | m-(tetrazol-5-yl)benzyloxy |
| 228 | NH$_2$ | m-(tetrazol-5-yl)benzyloxy |
| 229 | Me | [3-methyl-5-(tetrazol-5-yl)phenoxy]methyl |
| 230 | OH | [3-methyl-5-(tetrazol-5-yl)phenoxy]methyl |
| 231 | NH$_2$ | [3-methyl-5-(tetrazol-5-yl)phenoxy]methyl |
| 232 | Me | m-methyl-m-(tetrazol-5-yl)benzyloxy |
| 233 | OH | m-methyl-m-(tetrazol-5-yl)benzyloxy |
| 234 | NH$_2$ | m-methyl-m-(tetrazol-5-yl)benzyloxy |
| 235 | Me | 2-oxo-2-phenylethoxy |
| 236 | OH | 2-oxo-2-phenylethoxy |
| 237 | NH$_2$ | 2-oxo-2-phenylethoxy |
| 238 | Me | carbo-t-butoxymethoxy |
| 239 | OH | carbo-t-butoxymethoxy |
| 240 | NH$_2$ | carbo-t-butoxymethoxy |
| 241 | Me | (benzimidazol-2-yl)methoxy |
| 242 | OH | (benzimidazol-2-yl)methoxy |
| 243 | NH$_2$ | (benzimidazol-2-yl)methoxy |
| 244 | Me | (imidazol-2-yl)methoxy |
| 245 | OH | (imidazol-2-yl)methoxy |
| 246 | NH$_2$ | (imidazol-2-yl)methoxy |
| 247 | Me | (1,4-dimethylimidazol-5-yl)methoxy |
| 248 | OH | (1,4-dimethylimidazol-5-yl)methoxy |
| 249 | NH$_2$ | (1,4-dimethylimidazol-5-yl)methoxy |
| 250 | Me | (thiazol-4-yl)methoxy |
| 251 | OH | (thiazol-4-yl)methoxy |
| 252 | NH$_2$ | (thiazol-4-yl)methoxy |
| 253 | Me | (quinolin-2-yl)methoxy |
| 254 | OH | (quinolin-2-yl)methoxy |
| 255 | NH$_2$ | (quinolin-2-yl)methoxy |
| 256 | Me | (1,3-benzodioxo-5-yl)methoxy |
| 257 | OH | (1,3-benzodioxo-5-yl)methoxy |
| 258 | NH$_2$ | (1,3-benzodioxo-5-yl)methoxy |
| 259 | Me | (3,5-dimethylisoxazol-4-yl)methoxy |
| 260 | OH | (3,5-dimethylisoxazol-4-yl)methoxy |
| 261 | NH$_2$ | (3,5-dimethylisoxazol-4-yl)methoxy |
| 262 | Me | (3,5-dimethylpyrazol-1-yl)methoxy |
| 263 | OH | (3,5-dimethylpyrazol-1-yl)methoxy |
| 264 | NH$_2$ | (3,5-dimethylpyrazol-1-yl)methoxy |
| 265 | Me | (1,3,5-trimethylpyrazol-4-yl)methoxy |
| 266 | OH | (1,3,5-trimethylpyrazol-4-yl)methoxy |
| 267 | NH$_2$ | (1,3,5-trimethylpyrazol-4-yl)methoxy |

TABLE 6

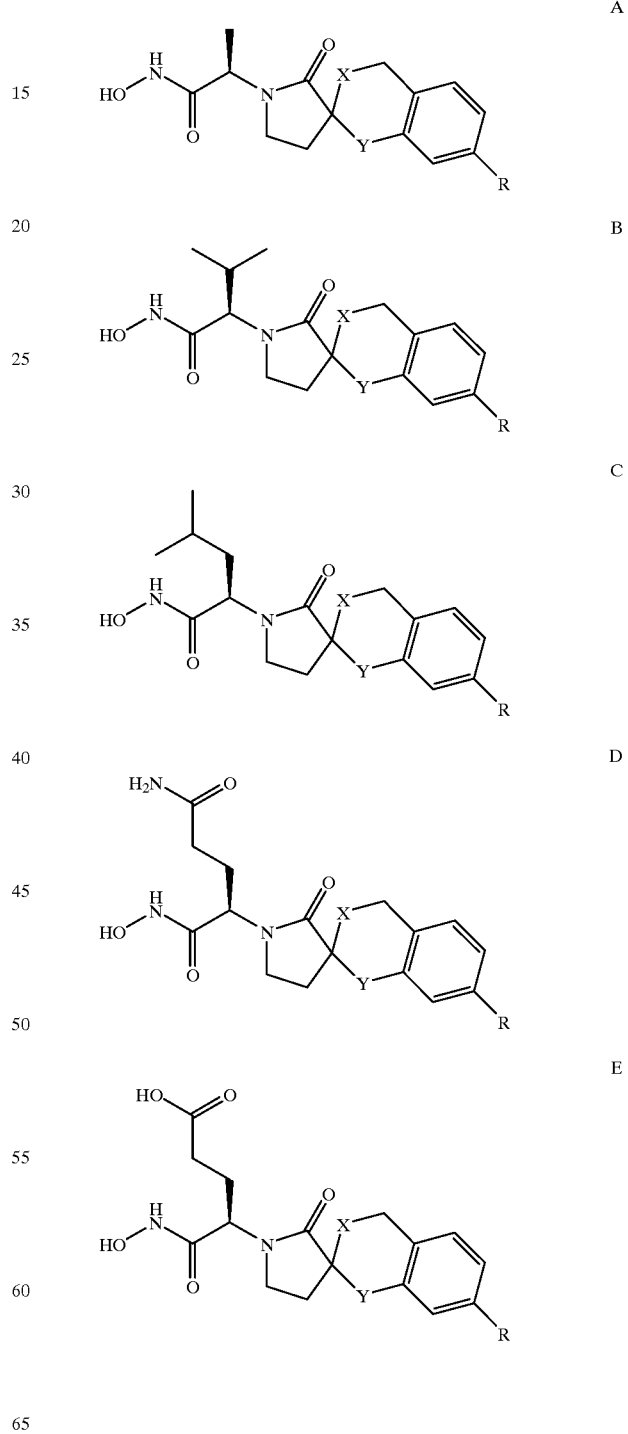

TABLE 6-continued
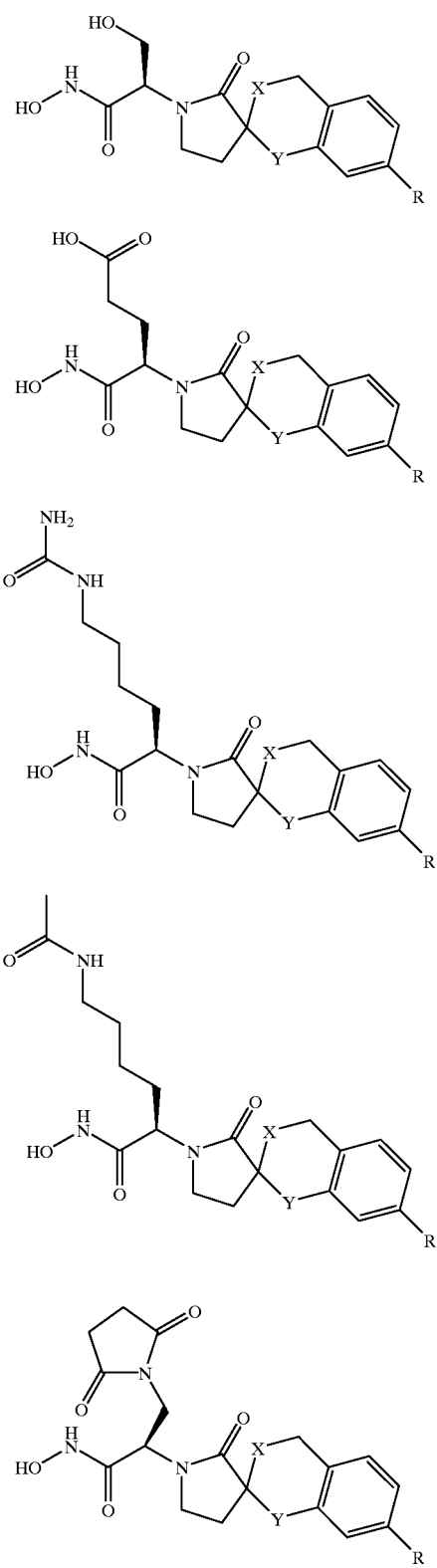
TABLE 6-continued
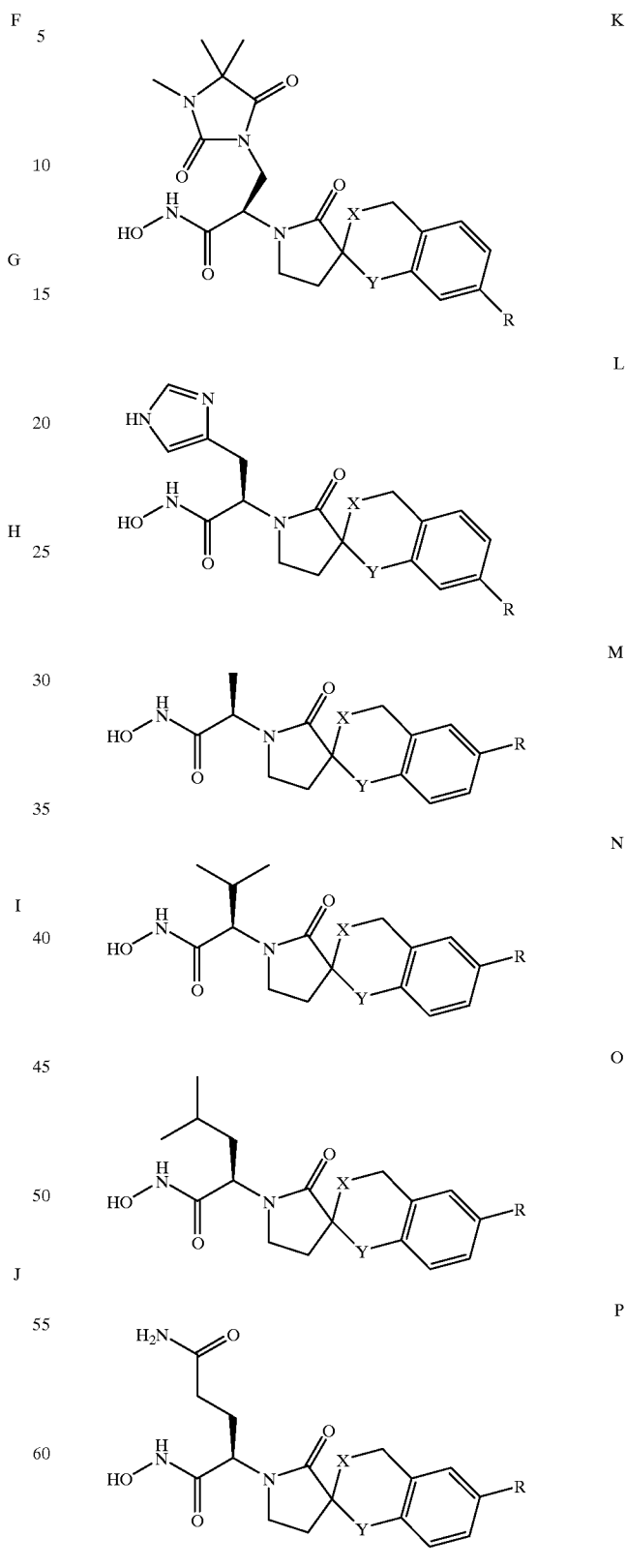

TABLE 6-continued

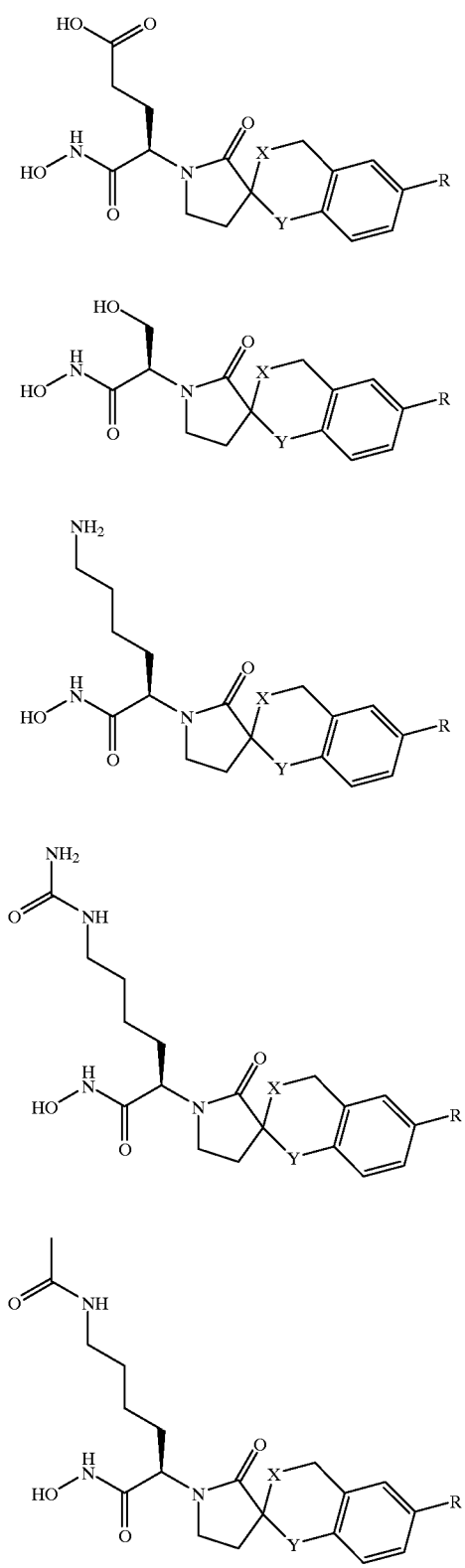

| Ex # | X | Y | R |
|---|---|---|---|
| 1 | CH₂ | CH₂ | H |
| 2 | CH₂ | O | H |
| 3 | O | CH₂ | H |
| 4 | CH₂ | CH₂ | methyl |
| 5 | CH₂ | O | methyl |
| 6 | O | CH₂ | methyl |
| 7 | CH₂ | CH₂ | ethyl |
| 8 | CH₂ | O | ethyl |
| 9 | O | CH₂ | ethyl |
| 10 | CH₂ | CH₂ | isopropyl |
| 11 | CH₂ | O | isopropyl |
| 12 | O | CH₂ | isopropyl |
| 13 | CH₂ | CH₂ | phenyl |
| 14 | CH₂ | O | phenyl |
| 15 | O | CH₂ | phenyl |
| 16 | CH₂ | CH₂ | benzyl |
| 17 | CH₂ | O | benzyl |
| 18 | O | CH₂ | benzyl |
| 19 | CH₂ | CH₂ | o-methylbenzyl |
| 20 | CH₂ | O | o-methylbenzyl |
| 21 | O | CH₂ | o-methylbenzyl |
| 22 | CH₂ | CH₂ | m-methylbenzyl |
| 23 | CH₂ | O | m-methylbenzyl |
| 24 | O | CH₂ | m-methylbenzyl |
| 25 | CH₂ | CH₂ | o,o-dimethylbenzyl |
| 26 | CH₂ | O | o,o-dimethylbenzyl |
| 27 | O | CH₂ | o,o-dimethylbenzyl |
| 28 | CH₂ | CH₂ | m,m-dimethylbenzyl |
| 29 | CH₂ | O | m,m-dimethylbenzyl |
| 30 | O | CH₂ | m,m-dimethylbenzyl |
| 31 | CH₂ | CH₂ | 2-phenylethyl |
| 32 | CH₂ | O | 2-phenylethyl |
| 33 | O | CH₂ | 2-phenylethyl |

TABLE 6-continued

| | | | |
|---|---|---|---|
| 34 | CH$_2$ | CH$_2$ | 2-(2-methylphenyl)ethyl |
| 35 | CH$_2$ | O | 2-(2-methylphenyl)ethyl |
| 36 | O | CH$_2$ | 2-(2-methylphenyl)ethyl |
| 37 | CH$_2$ | CH$_2$ | 2-(3-methylphenyl)ethyl |
| 38 | CH$_2$ | O | 2-(3-methylphenyl)ethyl |
| 39 | O | CH$_2$ | 2-(3-methylphenyl)ethyl |
| 40 | CH$_2$ | CH$_2$ | 2-(2,6-dimethylphenyl)ethyl |
| 41 | CH$_2$ | O | 2-(2,6-dimethylphenyl)ethyl |
| 42 | O | CH$_2$ | 2-(2,6-dimethylphenyl)ethyl |
| 43 | CH$_2$ | CH$_2$ | 2-(3,5-dimethylphenyl)ethyl |
| 44 | CH$_2$ | O | 2-(3,5-dimethylphenyl)ethyl |
| 45 | O | CH$_2$ | 2-(3,5-dimethylphenyl)ethyl |
| 46 | CH$_2$ | CH$_2$ | 2-(3-amino-5-methylphenyl)ethyl |
| 47 | CH$_2$ | O | 2-(3-amino-5-methylphenyl)ethyl |
| 48 | O | CH$_2$ | 2-(3-amino-5-methylphenyl)ethyl |
| 49 | CH$_2$ | CH$_2$ | 2-(pyridin-4-yl)ethyl |
| 50 | CH$_2$ | O | 2-(pyridin-4-yl)ethyl |
| 51 | O | CH$_2$ | 2-(pyridin-4-yl)ethyl |
| 52 | CH$_2$ | CH$_2$ | 2-(2,6-dimethylpyridin-4-yl)ethyl |
| 53 | CH$_2$ | O | 2-(2,6-dimethylpyridin-4-yl)ethyl |
| 54 | O | CH$_2$ | 2-(2,6-dimethylpyridin-4-yl)ethyl |
| 55 | CH$_2$ | CH$_2$ | 2-(3,5-dimethylpyridin-4-yl)ethyl |
| 56 | CH$_2$ | O | 2-(3,5-dimethylpyridin-4-yl)ethyl |
| 57 | O | CH$_2$ | 2-(3,5-dimethylpyridin-4-yl)ethyl |
| 58 | CH$_2$ | CH$_2$ | styryl |
| 59 | CH$_2$ | O | styryl |
| 60 | O | CH$_2$ | styryl |
| 61 | CH$_2$ | CH$_2$ | hydroxy |
| 62 | CH$_2$ | O | hydroxy |
| 63 | O | CH$_2$ | hydroxy |
| 64 | CH$_2$ | CH$_2$ | methoxy |
| 65 | CH$_2$ | O | methoxy |
| 66 | O | CH$_2$ | methoxy |
| 67 | CH$_2$ | CH$_2$ | ethoxy |
| 68 | CH$_2$ | O | ethoxy |
| 69 | O | CH$_2$ | ethoxy |
| 70 | CH$_2$ | CH$_2$ | isopropyloxy |
| 71 | CH$_2$ | O | isopropyloxy |
| 72 | O | CH$_2$ | isopropyloxy |
| 73 | CH$_2$ | CH$_2$ | tert-butoxy |
| 74 | CH$_2$ | O | tert-butoxy |
| 75 | O | CH$_2$ | tert-butoxy |
| 76 | CH$_2$ | CH$_2$ | cyclohexyloxy |
| 77 | CH$_2$ | O | cyclohexyloxy |
| 78 | O | CH$_2$ | cyclohexyloxy |
| 79 | CH$_2$ | CH$_2$ | phenoxy |
| 80 | CH$_2$ | O | phenoxy |
| 81 | O | CH$_2$ | phenoxy |
| 82 | CH$_2$ | CH$_2$ | o-methylphenoxy |
| 83 | CH$_2$ | O | o-methylphenoxy |
| 84 | O | CH$_2$ | o-methylphenoxy |
| 85 | CH$_2$ | CH$_2$ | m-methylphenoxy |
| 86 | CH$_2$ | O | m-methylphenoxy |
| 87 | O | CH$_2$ | m-methylphenoxy |
| 88 | CH$_2$ | CH$_2$ | o,o-dimethylphenoxy |
| 89 | CH$_2$ | O | o,o-dimethylphenoxy |
| 90 | O | CH$_2$ | o,o-dimethylphenoxy |
| 91 | CH$_2$ | CH$_2$ | m,m-dimethylphenoxy |
| 92 | CH$_2$ | O | m,m-dimethylphenoxy |
| 93 | O | CH$_2$ | m,m-dimethylphenoxy |
| 94 | CH$_2$ | CH$_2$ | cinnamyloxy |
| 95 | CH$_2$ | O | cinnamyloxy |
| 96 | O | CH$_2$ | cinnamyloxy |
| 97 | CH$_2$ | CH$_2$ | benzyloxy |
| 98 | CH$_2$ | O | benzyloxy |
| 99 | O | CH$_2$ | benzyloxy |
| 100 | CH$_2$ | CH$_2$ | phenoxymethyl |
| 101 | CH$_2$ | O | phenoxymethyl |
| 102 | O | CH$_2$ | phenoxymethyl |
| 103 | CH$_2$ | CH$_2$ | o-methylbenzyloxy |
| 104 | CH$_2$ | O | o-methylbenzyloxy |
| 105 | O | CH$_2$ | o-methylbenzyloxy |
| 106 | CH$_2$ | CH$_2$ | m-methylbenzyloxy |
| 107 | CH$_2$ | O | m-methylbenzyloxy |
| 108 | O | CH$_2$ | m-methylbenzyloxy |
| 109 | CH$_2$ | CH$_2$ | o,o-dimethylbenzyloxy |
| 110 | CH$_2$ | O | o,o-dimethylbenzyloxy |
| 111 | O | CH$_2$ | o,o-dimethylbenzyloxy |
| 112 | CH$_2$ | CH$_2$ | (2,6-dimethylphenoxy)methyl |
| 113 | CH$_2$ | O | (2,6-dimethylphenoxy)methyl |
| 114 | O | CH$_2$ | (2,6-dimethylphenoxy)methyl |
| 115 | CH$_2$ | CH$_2$ | m,m-dimethylbenzyloxy |
| 116 | CH$_2$ | O | m,m-dimethylbenzyloxy |
| 117 | O | CH$_2$ | m,m-dimethylbenzyloxy |
| 118 | CH$_2$ | CH$_2$ | (3,5-dimethylphenoxy)methyl |
| 119 | CH$_2$ | O | (3,5-dimethylphenoxy)methyl |
| 120 | O | CH$_2$ | (3,5-dimethylphenoxy)methyl |
| 121 | CH$_2$ | CH$_2$ | o,o-dicyanobenzyloxy |
| 122 | CH$_2$ | O | o,o-dicyanobenzyloxy |
| 123 | O | CH$_2$ | o,o-dicyanobenzyloxy |
| 124 | CH$_2$ | CH$_2$ | m,m-dicyanobenzyloxy |
| 125 | CH$_2$ | O | m,m-dicyanobenzyloxy |
| 126 | O | CH$_2$ | m,m-dicyanobenzyloxy |
| 127 | CH$_2$ | CH$_2$ | (2,6-dicyanophenoxy)methyl |
| 128 | CH$_2$ | O | (2,6-dicyanophenoxy)methyl |
| 129 | O | CH$_2$ | (2,6-dicyanophenoxy)methyl |
| 130 | CH$_2$ | CH$_2$ | (3,5-dicyanophenoxy)methyl |
| 131 | CH$_2$ | O | (3,5-dicyanophenoxy)methyl |
| 132 | O | CH$_2$ | (3,5-dicyanophenoxy)methyl |
| 133 | CH$_2$ | CH$_2$ | o-amino-o-cyanobenzyloxy |
| 134 | CH$_2$ | O | o-amino-o-cyanobenzyloxy |
| 135 | O | CH$_2$ | o-amino-o-cyanobenzyloxy |
| 136 | CH$_2$ | CH$_2$ | m-amino-m-cyanobenzyloxy |
| 137 | CH$_2$ | O | m-amino-m-cyanobenzyloxy |
| 138 | O | CH$_2$ | m-amino-m-cyanobenzyloxy |
| 139 | CH$_2$ | CH$_2$ | o-amino-o-nitrobenzyloxy |
| 140 | CH$_2$ | O | o-amino-o-nitrobenzyloxy |
| 141 | O | CH$_2$ | o-amino-o-nitrobenzyloxy |
| 142 | CH$_2$ | CH$_2$ | m-amino-m-nitrobenzyloxy |
| 143 | CH$_2$ | O | m-amino-m-nitrobenzyloxy |
| 144 | O | CH$_2$ | m-amino-m-nitrobenzyloxy |
| 145 | CH$_2$ | CH$_2$ | p-amino-m,m-dimethylbenzyloxy |
| 146 | CH$_2$ | O | p-amino-m,m-dimethylbenzyloxy |
| 147 | O | CH$_2$ | p-amino-m,m-dimethylbenzyloxy |
| 148 | CH$_2$ | CH$_2$ | o-amino-o-methylbenzyloxy |
| 149 | CH$_2$ | O | o-amino-o-methylbenzyloxy |
| 150 | O | CH$_2$ | o-amino-o-methylbenzyloxy |
| 151 | CH$_2$ | CH$_2$ | m-amino-m-methylbenzyloxy |
| 152 | CH$_2$ | O | m-amino-m-methylbenzyloxy |
| 153 | O | CH$_2$ | m-amino-m-methylbenzyloxy |
| 154 | CH$_2$ | CH$_2$ | o-cyano-o-methylbenzyloxy |
| 155 | CH$_2$ | O | o-cyano-o-methylbenzyloxy |
| 156 | O | CH$_2$ | o-cyano-o-methylbenzyloxy |
| 157 | CH$_2$ | CH$_2$ | m-cyano-m-methylbenzyloxy |
| 158 | CH$_2$ | O | m-cyano-m-methylbenzyloxy |
| 159 | O | CH$_2$ | m-cyano-m-methylbenzyloxy |
| 160 | CH$_2$ | CH$_2$ | o-cyano-o-nitrobenzyloxy |
| 161 | CH$_2$ | O | o-cyano-o-nitrobenzyloxy |
| 162 | O | CH$_2$ | o-cyano-o-nitrobenzyloxy |
| 163 | CH$_2$ | CH$_2$ | (2-cyano-6-nitrophenoxy)methyl |
| 164 | CH$_2$ | O | (2-cyano-6-nitrophenoxy)methyl |
| 165 | O | CH$_2$ | (2-cyano-6-nitrophenoxy)methyl |
| 166 | CH$_2$ | CH$_2$ | m-cyano-m-nitrobenzyloxy |
| 167 | CH$_2$ | O | m-cyano-m-nitrobenzyloxy |
| 168 | O | CH$_2$ | m-cyano-m-nitrobenzyloxy |
| 169 | CH$_2$ | CH$_2$ | (3-cyano-5-nitrophenoxy)methyl |
| 170 | CH$_2$ | O | (3-cyano-5-nitrophenoxy)methyl |
| 171 | O | CH$_2$ | (3-cyano-5-nitrophenoxy)methyl |
| 172 | CH$_2$ | CH$_2$ | m,m-dimethoxybenzyloxy |
| 173 | CH$_2$ | O | m,m-dimethoxybenzyloxy |
| 174 | O | CH$_2$ | m,m-dimethoxybenzyloxy |
| 175 | CH$_2$ | CH$_2$ | m,m-dichlorobenzyloxy |
| 176 | CH$_2$ | O | m,m-dichlorobenzyloxy |
| 177 | O | CH$_2$ | m,m-dichlorobenzyloxy |
| 178 | CH$_2$ | CH$_2$ | (3,5-dichlorophenoxy)methyl |
| 179 | CH$_2$ | O | (3,5-dichlorophenoxy)methyl |
| 180 | O | CH$_2$ | (3,5-dichlorophenoxy)methyl |
| 181 | CH$_2$ | CH$_2$ | m,m-dibromobenzyloxy |
| 182 | CH$_2$ | O | m,m-dibromobenzyloxy |
| 183 | O | CH$_2$ | m,m-dibromobenzyloxy |
| 184 | CH$_2$ | CH$_2$ | m,m-bis(trifluoromethyl)benzyloxy |
| 185 | CH$_2$ | O | m,m-bis(trifluoromethyl)benzyloxy |
| 186 | O | CH$_2$ | m,m-bis(trifluoromethyl)benzyloxy |
| 187 | CH$_2$ | CH$_2$ | [3,5-bis(trifluoromethyl)phenoxy]methyl |
| 188 | CH$_2$ | O | [3,5-bis(trifluoromethyl)phenoxy]methyl |
| 189 | O | CH$_2$ | [3,5-bis(trifluoromethyl)phenoxy]methyl |
| 190 | CH$_2$ | CH$_2$ | m-carboxamido-m-methylbenzyloxy |
| 191 | CH$_2$ | O | m-carboxamido-m-methylbenzyloxy |

TABLE 6-continued

| | | | |
|---|---|---|---|
| 192 | O | CH₂ | m-carboxamido-m-methylbenzyloxy |
| 193 | CH₂ | CH₂ | (3-carboxamido-5-methylphenoxy)methyl |
| 194 | CH₂ | O | (3-carboxamido-5-methylphenoxy)methyl |
| 195 | O | CH₂ | (3-carboxamido-5-methylphenoxy)methyl |
| 196 | CH₂ | CH₂ | m-hydroxycarbonyl-m-methylbenzyloxy |
| 197 | CH₂ | O | m-hydroxycarbonyl-m-methylbenzyloxy |
| 198 | O | CH₂ | m-hydroxycarbonyl-m-methylbenzyloxy |
| 199 | CH₂ | CH₂ | (3-hydroxycarbonyl-5-methylphenoxy)methyl |
| 200 | CH₂ | O | (3-hydroxycarbonyl-5-methylphenoxy)methyl |
| 201 | O | CH₂ | (3-hydroxycarbonyl-5-methylphenoxy)methyl |
| 202 | CH₂ | CH₂ | o-phenylbenzyloxy |
| 203 | CH₂ | O | o-phenylbenzyloxy |
| 204 | O | CH₂ | o-phenylbenzyloxy |
| 205 | CH₂ | CH₂ | m-phenylbenzyloxy |
| 206 | CH₂ | O | m-phenylbenzyloxy |
| 207 | O | CH₂ | m-phenylbenzyloxy |
| 208 | CH₂ | CH₂ | (naphth-1-yl)methoxy |
| 209 | CH₂ | O | (naphth-1-yl)methoxy |
| 210 | O | CH₂ | (naphth-1-yl)methoxy |
| 211 | CH₂ | CH₂ | (naphth-2-yl)methoxy |
| 212 | CH₂ | O | (naphth-2-yl)methoxy |
| 213 | O | CH₂ | (naphth-2-yl)methoxy |
| 214 | CH₂ | CH₂ | (2-methylnaphth-1-yl)methoxy |
| 215 | CH₂ | O | (2-methylnaphth-1-yl)methoxy |
| 216 | O | CH₂ | (2-methylnaphth-1-yl)methoxy |
| 217 | CH₂ | CH₂ | (4-methylnaphth-2-yl)methoxy |
| 218 | CH₂ | O | (4-methylnaphth-2-yl)methoxy |
| 219 | O | CH₂ | (4-methylnaphth-2-yl)methoxy |
| 220 | CH₂ | CH₂ | (pyridin-3-yl)methoxy |
| 221 | CH₂ | O | (pyridin-3-yl)methoxy |
| 222 | O | CH₂ | (pyridin-3-yl)methoxy |
| 223 | CH₂ | CH₂ | (pyridin-4-yl)methoxy |
| 224 | CH₂ | O | (pyridin-4-yl)methoxy |
| 225 | O | CH₂ | (pyridin-4-yl)methoxy |
| 226 | CH₂ | CH₂ | (3,5-dichloropyridin-4-yl)methoxy |
| 227 | CH₂ | O | (3,5-dichloropyridin-4-yl)methoxy |
| 228 | O | CH₂ | (3,5-dichloropyridin-4-yl)methoxy |
| 229 | CH₂ | CH₂ | (3,5-dimethylpyridin-4-yl)methoxy |
| 230 | CH₂ | O | (3,5-dimethylpyridin-4-yl)methoxy |
| 231 | O | CH₂ | (3,5-dimethylpyridin-4-yl)methoxy |
| 232 | CH₂ | CH₂ | (1,2,3-benzotriazol-1-yl)methoxy |
| 233 | CH₂ | O | (1,2,3-benzotriazol-1-yl)methoxy |
| 234 | O | CH₂ | (1,2,3-benzotriazol-1-yl)methoxy |
| 235 | CH₂ | CH₂ | benzhydroxy |
| 236 | CH₂ | O | benzhydroxy |
| 237 | O | CH₂ | benzhydroxy |
| 238 | CH₂ | CH₂ | p-(1,2,3-thiadiazol-5-yl)benzyloxy |
| 239 | CH₂ | O | p-(1,2,3-thiadiazol-5-yl)benzyloxy |
| 240 | O | CH₂ | p-(1,2,3-thiadiazol-5-yl)benzyloxy |
| 241 | CH₂ | CH₂ | o-(tetrazol-5-yl)benzyloxy |
| 242 | CH₂ | O | o-(tetrazol-5-yl)benzyloxy |
| 243 | O | CH₂ | o-(tetrazol-5-yl)benzyloxy |
| 244 | CH₂ | CH₂ | m-(tetrazol-5-yl)benzyloxy |
| 245 | CH₂ | O | m-(tetrazol-5-yl)benzyloxy |
| 246 | O | CH₂ | m-(tetrazol-5-yl)benzyloxy |
| 247 | CH₂ | CH₂ | [3-methyl-5-(tetrazol-5-yl)phenoxy]methyl |
| 248 | CH₂ | O | [3-methyl-5-(tetrazol-5-yl)phenoxy]methyl |
| 249 | O | CH₂ | [3-methyl-5-(tetrazol-5-yl)phenoxy]methyl |
| 250 | CH₂ | CH₂ | m-methyl-m-(tetrazol-5-yl)benzyloxy |
| 251 | CH₂ | O | m-methyl-m-(tetrazol-5-yl)benzyloxy |
| 252 | O | CH₂ | m-methyl-m-(tetrazol-5-yl)benzyloxy |
| 253 | CH₂ | CH₂ | 2-oxo-2-phenylethoxy |
| 254 | CH₂ | O | 2-oxo-2-phenylethoxy |
| 255 | O | CH₂ | 2-oxo-2-phenylethoxy |
| 256 | CH₂ | CH₂ | carbo-t-butoxymethoxy |
| 257 | CH₂ | O | carbo-t-butoxymethoxy |
| 258 | O | CH₂ | carbo-t-butoxymethoxy |
| 259 | CH₂ | CH₂ | (benzimidazol-2-yl)methoxy |
| 260 | CH₂ | O | (benzimidazol-2-yl)methoxy |
| 261 | O | CH₂ | (benzimidazol-2-yl)methoxy |
| 262 | CH₂ | CH₂ | (imidazol-2-yl)methoxy |
| 263 | CH₂ | O | (imidazol-2-yl)methoxy |
| 264 | O | CH₂ | (imidazol-2-yl)methoxy |
| 265 | CH₂ | CH₂ | (1,4-dimethylimidazol-5-yl)methoxy |
| 266 | CH₂ | O | (1,4-dimethylimidazol-5-yl)methoxy |
| 267 | O | CH₂ | (1,4-dimethylimidazol-5-yl)methoxy |
| 268 | CH₂ | CH₂ | (thiazol-4-yl)methyl |
| 269 | CH₂ | O | (thiazol-4-yl)methyl |
| 270 | O | CH₂ | (thiazol-4-yl)methyl |
| 271 | CH₂ | CH₂ | (quinolin-2-yl)methoxy |
| 272 | CH₂ | O | (quinolin-2-yl)methoxy |
| 273 | O | CH₂ | (quinolin-2-yl)methoxy |
| 274 | CH₂ | CH₂ | (1,3-benzodioxo-5-yl)methoxy |
| 275 | CH₂ | O | (1,3-benzodioxo-5-yl)methoxy |
| 276 | O | CH₂ | (1,3-benzodioxo-5-yl)methoxy |
| 277 | CH₂ | CH₂ | (3,5-dimethylisoxazol-4-yl)methoxy |
| 278 | CH₂ | O | (3,5-dimethylisoxazol-4-yl)methoxy |
| 279 | O | CH₂ | (3,5-dimethylisoxazol-4-yl)methoxy |
| 280 | CH₂ | CH₂ | (3,5-dimethylpyrazol-1-yl)methoxy |
| 281 | CH₂ | O | (3,5-dimethylpyrazol-1-yl)methoxy |
| 282 | O | CH₂ | (3,5-dimethylpyrazol-1-yl)methoxy |
| 283 | CH₂ | CH₂ | (1,3,5-trimethylpyrazol-4-yl)methoxy |
| 284 | CH₂ | O | (1,3,5-trimethylpyrazol-4-yl)methoxy |
| 285 | O | CH₂ | (1,3,5-trimethylpyrazol-4-yl)methoxy |

Utility

The compounds of formula I are expected to be metalloproteinase inhibitors. The MMP-3 inhibitory activity of the compounds of the present invention is demonstrated using assays of MMP-3 activity, for example, using the assay described below for assaying inhibitors of MMP-3 activity. The compounds of the present invention are expected to be bioavailable in vivo as demonstrated, for example, using the ex vivo assay described below. The compounds of formula I are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteinases have also been implicated in the degradation of basement membranes to allow infiltration of cancer cells into the circulation and subsequent penetration into other tissues leading to tumor metastasis. (Stetler-Stevenson, Cancer and Metastasis Reviews, 9, 289–303, 1990.) The compounds of the present invention should be useful for the prevention and treatment of invasive tumors by inhibition of this aspect of metastasis.

The compounds of the present invention should also have utility for the prevention and treatment of osteopenia associated with matrixmetalloproteinase-mediated breakdown of cartilage and bone which occurs in osteoporosis patients.

Compounds which inhibit the production or action of TNF and/or Aggrecanase and/or MP's are potentially useful for the treatment or prophylaxis of various inflammatory, infectious, immunological or malignant diseases. These include, but are not limited to inflammation, fever, cardiovascular effects, hemorrhage, coagulation and acute phase response, an acute infection, septic shock, haemodynamic shock and sepsis syndrome, post ischaemic reperfusion injury, malaria, Crohn's disease, mycobacterial infection, meningitis, psoriasis, periodontits, gingivitis, congestive heart failure, fibrotic disease, cachexia, and aneroxia, graft rejection, cancer, corneal ulceration or tumor invasion by secondary metastases, autoimmune disease, skin inflammatory diseases, multiple osteo and rheumatoid arthritis, multiple sclerosis, radiation damage, HIV, and hyperoxic alveolar injury.

Some compounds of the present invention have been shown to inhibit TNF production in lipopolysacharride stimulated mice, for example, using the assay for TNF Induction in Mice and in human whole blood as described below.

Some compounds of the present invention have been shown to inhibit aggrecanase a key enzyme in cartilage breakdown as determined by the aggrecanase assay described below.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar and "nm" denotes nanometer. "Sigma" stands for the Sigma-Aldrich Corp. of St. Louis, Mo.

A compound is considered to be active if it has an $IC_{50}$ or $K_i$ value of less than about 1 mM for the inhibition of MMP-3.

Aggrecanase Enzymatic Assay

A novel enzymatic assay was developed to detect potential inhibitors of aggrecanase. The assay uses active aggrecanase accumulated in media from stimulated bovine nasal cartilage (BNC) or related cartilage sources and purified cartilage aggrecan monomer or a fragment thereof as a substrate.

The substrate concentration, amount of aggrecanase time of incubation and amount of product loaded for Western analysis were optimized for use of this assay in screening putative aggrecanase inhibitors. Aggrecanase is generated by stimulation of cartilage slices with interleukin-1 (IL-1), tumor necrosis factor alpha (TNF∂) or other stimuli. Matrix metalloproteinases (MMPs) are secreted from cartilage in an inactive, zymogen form following stimulation, although active enzymes are present within the matrix. We have shown that following depletion of the extracellular aggrecan matrix, active MMPs are released into the culture media. (Tortorella, M. D. et. al. Trans. Ortho. Res. Soc. 20, 341, 1995). Therefore, in order to accumulate BNC aggrecanase in culture media, cartilage is first depleted of endogenous aggrecan by stimulation with 500 ng/ml human recombinant IL-β for 6 days with media changes every 2 days. Cartilage is then stimulated for an additional 8 days without media change to allow accumulation of soluble, active aggrecanase in the culture media. In order to decrease the amounts of other matrix metalloproteinases released into the media during aggrecanase accumulation, agents which inhibit MMP-1, -2, -3, and -9 biosynthesis are included during stimulation. This BNC conditioned media, containing aggrecanase activity is then used as the source of aggrecanase for the assay. Aggrecanase enzymatic activity is deteted by monitoring production of aggrecan fragments produced exclusively by cleavage at the Glu373-Ala374 bond within the aggrecan core protein by Western analysis using the monoclonal antibody, BC-3 (Hughes, C E, et al., Biochem J 306:799–804, 1995). This antibody recognizes aggrecan fragments with the N-terminus, 374ARGSVIL, generated upon cleavage by aggrecanase. The BC-3 antibody recognizes this neoepitope only when it is at the N-terminus and not when it is present internally within aggrecan fragments or within the aggrecan protein core. Other proteases produced by cartilage in response to IL-1 do not cleave aggrecan at the Glu373-Ala374 aggrecanase site; therefore, only products produced upon cleavage by aggrecanase are detected. Kinetic studies using this assay yield a Km of 1.5+/−0.35 uM for aggrecanase.

To evaluate inhibition of aggrecanase, compounds are prepared as 10 mM stocks in DMSO, water or other solvents and diluted to appropriate concentrations in water. Drug (50 ul) is added to 50 ul of aggrecanase-containing media and 50 ul of 2 mg/ml aggrecan substrate and brought to a final volume of 200 ul in 0.2 M Tris, pH 7.6, containing 0.4 M NaCl and 40 mM $CaCl_2$. The assay is run for 4 hr at 37° C., quenched with 20 mM EDTA and analyzed for aggrecanase-generated products. A sample containing enzyme and substrate without drug is included as a positive control and enzyme incubated in the absence of substrate serves as a measure of background.

Removal of the glycosaminoglycan side chains from aggrecan is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 ug GAG) for 2 hr at 37° C. and then with keratanase (0.1 units/10 ug GAG) and keratanase II (0.002 units/10 ug GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 ul of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

Bisacetylated Substance P/MMP-3 Fluorescent Assay

A high capacity enzymatic assay was developed to detect potential inhibitors of MMP-3. The assay uses a derivative of a peptide substrate, substance P (Arg-Pro-Lys-Pro-Gln-Gln-Phe-Phe-Gly-Leu-Met), which is cleaved by MMP-3 exclusively at the glutamine-phenylalanine bond. In order to adapt this assay for high throughput screening, we have developed a fluorimetric method of product detection. The production of the hydrolysis product, substance P 7-11, is measured by reaction with fluorescamine, a fluorogenic compound which reacts with the primary amine of this fragment. The substance P substrate is bisacetylated to block the primary amines of the intact substrate. Thus, the resulting fluorescence represents generation of product (7-11peptide) formed upon cleavage by MMP-3, and is quantitated using a standard curve prepared with known concentrations of 7-11 peptide. Kinetic studies using the bisacetylated substrate yield the following parameters for MMP-3: Km=769+/−52 uM; Vmax=0.090+/−0.003 mmoles 7-11 peptide/min.

To evaluate inhibition of MMP-3, compounds were prepared at a concentration of 10 mM in 100% methanol, and then further diluted to a 20× molar stock. Five microliters of each drug stock was added to the assay in the presence of 20 nM truncated MMP-3 in 67.5 mM tricine (pH 7.5), 10 mM $CaCl_2$, 40 mM NaCl, and 0.005% Brij 35 in a final volume of 100 microliters. Bisacetylated substance P (1000 mM) was added, and the assay was run for 1 hour at 25° C. The reaction was quenched with EDTA (20 mM) and product was detected fluorometrically following addition of fluorescamine (0.075 mg/ml). Fluorescence of each sample was converted to an amount of product formed using a substance P 7-11 standard curve. Under these conditions, the assay is linear with respect to MMP-3 amount up to 10 pmoles. Inhibition of MMP-3 was determined by comparing the amount of product generated in the presence and absence of compound.

Selected compounds of the present invention were tested and shown to have activity in the above assay.

Ex vivo Assay for Bioavailability of MMP-3 Inhibitors

Blood was collected by cardiac puncture from rats at different times after dosing I.V., I.P., or P.O. with compound in order to determine the levels of inhibitor present. Plasma was extracted with 10% TCA in 95% methanol, and placed on ice for 10 minutes. The plasma was then centrifuged for 15 minutes at 14,000 rpm in an Eppendorf microcentrifuge. The supernatant was removed, recentrifuged, and the resulting supernatant was diluted 1:10 in 50 mM tricine, pH 8.5. The pH of the sample was adjusted to 7.5, and then assayed in the MMP-3 substance P fluorescent enzymatic assay. Plasma from naive rats was extracted by the same method and used as a negative control. This plasma was also used to prepare a spiked plasma curve of the compound of interest. Known concentration of the compound were added to control plasma, the plasma was extracted by the same method, and then assayed in the MMP-3 enzymatic assay. A standard curve was prepared that related percent inhibition in the MMP-3 assay to the concentration of drug added in the spiked samples. Based on the percent inhibition in the presence of plasma from dosed rats, the concentration of compound was determined using the standard curve.

Acute Cartilage Degradation Rat Model

A novel in vivo model of acute cartilage degradation in rats has been characterized as a method to determine the proteoglycan content in the synovial fluid after the induction of cartilage degradation. Experimental groups exhibit increased levels of proteoglycan content in their synovial fluid versus control rats. The criteria to demonstrate a compound's activity in this model, is the ability to inhibit the demonstration of cartilage degradation, as measured by increased proteoglycan content in the synovial fluid of rats after compound administration. Indomethacin, a non-steroidal anti-inflammatory drug is inactive in this model. Indomethacin administration does not inhibit the demonstration of cartilage degradation in experimental animals. In contrast, administration of a compound of this invention significantly inhibited the demonstration of cartilage degradation in this model.

TNF Human Whole Blood Assay

Blood is drawn from normal donors into tubes containing 143 USP units of heparin/10 ml. 225 ul of blood is plated directly into sterile polypropylene tubes. Compounds are diluted in DMSO/serum free media and added to the blood samples so the final concentration of compounds are 50, 10, 5, 1, 0.5, 0.1, and 0.01 $\mu$M. The final concentration of DMSO does not exceed 0.5%. Compounds are preincubated for 15 minutes before the addition of 100 ng/ml LPS. Plates are incubated for 5 hours in an atmosphere of 5% $CO_2$ in air. At the end of 5 hours, 750 ul of serumfree media is added to each tube and the samples are spun at 1200 RPM for 10 minutes. The supernatant is collected off the top and assayed for TNF-alpha production by a standard sandwich ELISA. The ability of compounds to inhibit TNF-alpha production by 50% compared to DMSO treated cultures is given by the IC50 value.

TNF Induction in Mice

Test compounds are administered to mice either I.P. or P.O. at time zero. Immediately following compound administration, mice receive an I.P. injection of 20 mg of D-galactosamine plus 10 $\mu$g of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action, MMP-3, in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristic of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition. The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidlzing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field. Useful pharmaceutical dosage-forms for administration of the compounds of this invention can be illustrated as follows:

Capsules

Capsules are prepared by conventional procedures so that the dosage unit is 500 milligrams of active ingredient, 100 milligrams of cellulose and 10 milligrams of magnesium stearate.

A large number of unit capsules may also prepared by filling standard two-piece hard gelatin capsules each with 100 milligrams of powdered active ingredient, 150 milligrams of lactose, 50 milligrams of cellulose, and 6 milligrams magnesium stearate.

| Syrup | |
|---|---|
| | Wt. % |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | |
|---|---|
| | Wt. % |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendable Powder | |
|---|---|
| | Wt. % |
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

| Semi-Solid Gel | |
|---|---|
| | Wt. % |
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | |
|---|---|
| | Wt. % |
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | |
|---|---|
| | Wt. % |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

Tablets may be prepared by conventional procedures so that the dosage unit is 500 milligrams of active ingredient, 150 milligrams of lactose, 50 milligrams of cellulose and 10 milligrams of magnesium stearate.

A large number of tablets may also be prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent, especially non-steroidal anti-inflammatory drugs (NSAID's). The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed as new and desired to be secured by Letter Patent of United States is:

1. A compound of formula I:

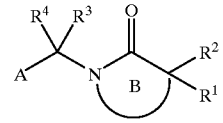

or a stereoisomer or pharmaceutically acceptable salt form thereof, wherein;

A is selected from $COR^5$, $-CO_2H$, $CH_2CO_2H$, $-CO_2R^6$, $-CONHOH$, $-CONHOR^5$, $-CONHOR^6$, $-NHR^a$, $-N(OH)COR^5$, $-SH$, $-CH_2SH$, $-SO_2NHR^a$, $SN_2H_2R^a$, $PO(OH)_2$, and $PO(OH)NHR^a$;

ring B is a 5 membered cyclic amide containing 0–1 additional carbonyl groups and 0–1 double bonds;

$R^1$ is $U-X-Y-Z-U^a-X^a-Y^a-Z^a$;

U is absent or is selected from: O, $NR^a$, C(O), C(O)O, OC(O), $C(O)NR^a$, $NR^aC(O)$, OC(O)O, $OC(O)NR^a$, $NR^aC(O)O$, $NR^aC(O)NR^a$, $S(O)_p$, $S(O)_pNR^a$, $NR^aS(O)_p$, and $NR^aSO_2NR^a$;

X is absent or selected from $C_{1-10}$ alkylene, $C_{2-10}$ alkenylene, and $C_{2-10}$ alkynylene;

Y is absent or selected from O, $NR^a$, $S(O)_p$, and C(O);

Z is selected from a $C_{3-13}$ carbocyclic residue substituted with 0–5 $R^b$ and a 5–14 membered heterocyclic system containing from 1–4 heteroatoms selected from the group consisting of N, O, and S and substituted with 0–5 $R^b$;

$U^a$ is absent or is selected from: O, $NR^a$, C(O), C(O)O, OC(O), $C(O)NR^a$, $NR^aC(O)$, OC(O)O, $OC(O)NR^a$, $NR^aC(O)O$, $NR^aC(O)NR^a$, $S(O)_p$, $S(O)_pNR^a$, $NR^aS(O)_p$, and $NR^aSO_2NR^a$;

$X^a$ is absent or selected from $C_{1-10}$ alkylene, $C_{2-10}$ alkenylene, $C_{2-10}$ alkynylene;

$Y^a$ is absent or selected from O, $NR^a$, $S(O)_p$, and C(O);

$Z^a$ is selected from H, a $C_{3-13}$ carbocyclic residue substituted with 0–5 $R^c$ and a 5–14 membered heterocyclic system containing from 1–4 heteroatoms selected from the group consisting of N, O, and S and substituted with 0–5 $R^c$;

provided that one of Z and $Z^a$ is a heterocycle and $Z^a$ is other than quinolinyl;

$R^2$ is selected from H, Q', $C_{1-10}$ alkylene-Q', $C_{2-10}$ alkenylene-Q', $C_{2-10}$ alkynylene-Q', $(CRR')_rO(CRR')_r$—Q', $(CRR')_rNR^a(CRR')_r$—Q', $(CRR')_rNR^aC(O)(CRR')_r$—Q', $(CRR')_rC(O)NR^a(CRR')_r$—Q', $(CRR')_rC(O)(CRR')_r$—Q', $(CRR')_rC(O)O(CRR')_r$—Q', $(CRR')_rS(O)_p(CRR')_r$—Q', $(CRR')_rSO_2NR^a(CRR')_r$—Q', $(CRR')_rNR^aC(O)NR^a(CRR')_r$—Q', $(CRR')_rOC(O)NR^a(CRR')_r$—Q', and $(CRR')_rNR^aC(O)O(CRR')_r$—Q';

R, at each occurrence, is independently selected from H, $CH_3$, $CH_2CH_3$, $CH=CH_2$, $CH=CHCH_3$, and $CH_2CH=CH_2$;

R', at each occurrence, is independently selected from H, $CH_3$, $CH_2CH_3$, and $CH(CH_3)_2$;

Q' is selected from H and a $C_{3-13}$ carbocyclic residue substituted with 0–5 $R^b$;

$R^3$ is selected from H, Q, $C_{1-10}$ alkylene-Q, $C_{2-10}$ alkenylene-Q, $C_{2-10}$ alkynylene-Q, $(CRR')_rO(CRR')_r$ —Q, (CRR')$_r$NR$^a$(CRR')$_r$—Q, (CRR')$_r$C(O)(CRR')$_r$—Q, (CRR')$_r$C(O)O(CRR')$_r$Q, (CRR')$_r$OC(O) (CRR')$_r$—Q, (CRR')$_r$C(O)NR$^a$(CRR')$_r$—Q, (CRR')$_r$NR$^a$C(O) (CRR')$_r$—Q, (CRR')$_r$OC(O)O(CRR')$_r$—Q, (CRR')$_r$OC(O)NR$^a$(CRR')$_r$—Q, (CRR')$_r$NR$^a$C(O)O(CRR')$_r$—Q, (CRR')$_r$NR$^a$C(O)NR$^a$(CRR')$_r$—Q, (CRR')$_r$S(O)$_p$ (CRR')$_r$—Q, (CRR')$_r$SO$_2$NR$^a$(CRR')$_r$—Q, (CRR')$_r$ NR$^a$SO$_2$(CRR')$_r$—Q, (CRR')$_r$NR$^a$SO$_2$NR$^a$ (CRR')$_r$—Q, (CRR')$_r$NR$^a$C(O) (CRR')$_{r''}$NHQ, (CRR')$_r$NR$^a$C(O)(CRR')$_r$NHC(O)OR$^a$, and (CRR')$_r$NR$^a$C(O) (CRR')$_r$ NHC(O) (CRR')$_r$NHC(O)OR$^a$;

Q is selected from H and a $C_{3-13}$ carbocyclic residue substituted with 0–5 $R^b$;

$R^4$ is selected from H, $C_{1-10}$ alkylene-H, $C_{2-10}$ alkenylene-H, $C_{2-10}$ alkynylene-H, (CRR')$_r$O(CRR')$_r$—H, (CRR')$_r$NR$^a$(CRR')$_r$—H, (CRR')$_r$C(O) (CRR')$_r$—H, (CRR')$_r$C(O)O(CRR')$_r$—H, (CRR')$_r$OC(O)(CRR')$_r$—H, (CRR')$_r$C(O)NR$^a$(CRR')$_r$—H, (CRR')$_r$NR$^a$C(O) (CRR')$_r$—H, (CRR')$_r$OC(O)O(CRR')$_r$—H, (CRR')$_r$OC(O)NR$^a$(CRR')$_r$—H, (CRR')$_r$NR$^a$C(O)O(CRR')$_r$—H, (CRR')$_r$NR$^a$C(O)NR$^a$(CRR')$_r$—H, (CRR')$_r$S(O)$_p$(CRR')$_r$—H, (CRR')$_r$SO$_2$NR$^a$(CRR')$_r$—H, (CRR')$_r$NR$^a$SO$_2$(CRR')$_r$—H, and (CRR')$_{r'}$NR$^a$SO$_2$NR$^a$(CRR')$_r$—H;

alternatively, $R^3$ and $R^4$ combine to form a $C_{3-13}$ carbocyclic residue substituted with $R^{1'}$ and 0–3 $R^b$;

$R^a$, at each occurrence, is independently selected from H, $C_{1-4}$ alkyl, phenyl and benzyl;

$R^{a'}$, at each occurrence, is independently selected from H, $C_{1-4}$ alkyl, phenyl and benzyl;

$R^{a''}$, at each occurrence, is independently selected from H, $C_{1-4}$ alkyl, benzyl, $C_{3-7}$ carbocyclic residue, or a 5 to 6 membered heteroaromatic ring containing 1–4 heteroatoms selected from the group consisting of N, O, and S;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, OR$^a$, Cl, F, Br, I, =O, CN, NO$_2$, NR$^a$R$^{a'}$, C(O)R$^{a''}$, C(O)OR$^a$, C(O)NR$^a$R$^{a'}$, S(O)$_2$NR$^a$R$^{a'}$, S(O)$_p$R$^a$, CF$_3$, and CF$_2$CF$_3$;

$R^c$, at each occurrence, is independently selected from $C_{1-6}$ alkyl, OR$^a$, Cl, F, Br, I, =O, CN, NO$_2$, NR$^a$R$^{a'}$, C(O)R$^a$, C(O)OR$^a$, C(O)NR$^a$R$^{a'}$, NR$^a$C(O)NR$^a$R$^{a'}$, S(O)$_2$NR$^a$R$^{a'}$, S(O)$_p$R$^a$, CF$_3$, CF$_2$CF$_3$, —CH(=NOH), —C(=NOH)CH$_3$, (CRR')$_s$O(CRR')$_s$R$^d$, (CRR')$_s$S(O)$_p$(CRR')$_s$R$^d$, (CRR')$_s$NR$^a$(CRR')$_s$R$^d$, phenyl, and a 5–14 membered heterocyclic system containing from 1–4 heteroatoms selected from the group consisting of N, O, and S;

$R^5$, at each occurrence, is selected from $C_{1-10}$ alkyl substituted with 0–2 $R^b$, and $C_{1-8}$ alkyl substituted with 0–2 $R^d$;

$R^d$, at each occurrence, is independently selected from phenyl substituted with 0–3 $R^b$, biphenyl substituted with 0–2 $R^b$, and naphthyl substituted with 0–3 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, —$C_{1-10}$ alkyl-NR$^7$R$^{7a}$, —CH(R$^8$)OC(=O)R$^9$, and, —CH(R$^8$)OC (=O)OR$^9$;

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-8}$ alkyl substituted with 1–2 $R^e$, $C_{3-8}$ cycloalkyl substituted with 1–2 $R^e$, and phenyl substituted with 0–2 $R^b$;

$R^e$, at each occurrence, is selected from $C_{1-4}$ alkyl, $C_{3-8}$ cycloalkyl, $C_{1-5}$ alkoxy, phenyl substituted with 0–2 $R^b$;

p, at each occurrence, is selected from 0, 1, and 2;

r, at each occurrence, is selected from 0, 1, 2, 3, 4, and 5;

r', at each occurrence, is selected from 0, 1, 2, 3, 4, and 5;

r'', at each occurrence, is selected from 1, 2, and 3;

s, at each occurrence, is selected from 0, 1, 2 and 3; and, s', at each occurrence, is selected from 0, 1, 2, and 3.

2. A compound according to claim 1, wherein:

A is selected from COR$^5$, —CO$_2$H, CH$_2$CO$_2$H, —CONHOH, —CONHOR$^5$, —CONHOR$^6$, —N(OH)COR$^5$, —SH, and —CH$_2$SH;

U is absent;

Y is absent;

Z is selected from a $C_{5-10}$ carbocyclic residue substituted with 0–5 $R^b$ and a 5–10 membered heterocyclic system containing from 1–4 heteroatoms selected from the group consisting of N, O, and S and substituted with 0–5 $R^b$;

$U^a$ is absent or is selected from: O, NR$^a$, C(O), C(O)NR$^a$, NR$^a$C(O), OC(O)NR$^a$, NR$^a$C(O)O, NR$^a$C(O)NR$^a$, S(O)$_p$NR$^a$, and NR$^a$S(O)$_p$;

$R^2$ is selected from H, Q', $C_{1-5}$ alkylene-Q', $C_{2-5}$ alkenylene-Q', $C_{2-5}$ alkynylene-Q', (CRR')$_r$O(CRR')$_r$—Q', (CRR')$_r$NR$^a$(CRR')$_r$—Q', (CRR')$_r$NR$^a$C(O)(CRR')$_r$—Q', (CRR')$_r$C(O)NR$^a$(CRR')$_r$—Q', (CRR')$_r$NR$^a$C(O)NR$^a$(CRR')$_r$—Q', (CRR')$_r$C(O)(CRR')$_r$—Q', (CRR')$_r$C(O)O(CRR')$_r$—Q', (CRR')$_r$S(O)$_p$(CRR')$_r$—Q', and (CRR')$_r$SO$_2$NR$^a$(CRR')$_r$—Q';

Q' is selected from H and phenyl substituted with 0–3 $R^b$;

$R^3$ is selected from H, Q, $C_{1-10}$ alkylene-Q, $C_{2-10}$ alkenylene-Q, $C_{2-10}$ alkynylene-Q, (CRR')$_r$O(CRR')$_r$—Q, (CRR')$_r$NR$^a$(CRR')$_r$—Q, (CRR')$_r$C(O) (CRR')$_r$—Q, (CRR')$_r$C(O)NR$^a$(CRR')$_r$—Q, (CRR')$_r$NR$^a$C(O)(CRR')$_r$—Q, (CRR')$_r$OC(O)NR$^a$(CRR')$_r$—Q, (CRR')$_r$NR$^a$C(O)O(CRR')$_r$—Q, (CRR')$_r$NR$^a$C(O)NR$^a$(CRR')$_r$—Q, (CRR')$_r$S(O)$_p$(CRR')$_r$—Q, (CRR')$_{r'}$ SO$_2$NR$^a$(CRR')$_r$—Q, (CRR')$_{r'}$NR$^a$SO$_2$(CRR')$_r$—Q, and (CRR')$_r$NR$^a$SO$_2$NR$^a$(CRR')$_r$—Q;

R, at each occurrence, is independently selected from H, CH$_3$, and CH$_2$CH$_3$;

R', at each occurrence, is independently selected from H and CH$_3$;

Q is selected from H and a $C_{3-10}$ carbocyclic residue substituted with 0–5 $R^b$; and, $R^c$, at each occurrence, is independently selected from $C_{1-6}$ alkyl, OR$^a$, Cl, F, Br, I, =O, CN, NO$_2$, NR$^a$R$^{a'}$, C(O)R$^a$, C(O)OR$^a$, C(O)NR$^a$R$^{a'}$, S(O)$_2$NR$^a$R$^{a'}$, S(O)$_p$R$^a$, CF$_3$, CF$_2$CF$_3$, and a 5–10 membered heterocyclic system containing from 1–4 heteroatoms selected from the group consisting of N, O, and S.

3. A compound according to claim 2, wherein:

A is selected from —$CO_2H$, $CH_2CO_2H$, —CONHOH, —$CONHOR^5$, and —$N(OH)COR^5$;

Z is selected from a $C_{5-6}$ carbocyclic residue substituted with 0–3 $R^b$ and a 5–9 membered heterocyclic system containing from 1–4 heteroatoms selected from the group consisting of N, O, and S and substituted with 0–5 $R^b$;

$U^a$ is absent or is selected from: O, $NR^a$, C(O), $C(O)NR^a$, $NR^aC(O)$, and $S(O)_pNR^a$;

$X^a$ is absent or $C_{1-10}$ alkylene;

$R^2$ is selected from H, $C_{1-5}$ alkylene-Q', $(CH_2)_rO(CH_2)_r$—Q', $(CH_2)_rNR^a(CH_2)_r$—Q', $(CRR')_rNR^aC(O)(CRR')_r$—Q', $(CH_2)_rC(O)NR^a(CH_2)_r$—Q', $(CRR')_rNR^aC(O)NR^a(CRR')_r$—Q', and $(CH_2)_rC(O)(CH_2)_r$—Q';

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $S(O)_2NR^aR^{a'}$, $S(O)_p R^a$, $CF_3$, $CF_2CF_3$, and a 5–9 membered heterocyclic system containing from 1–4 heteroatoms selected from the group consisting of N, O, and S; and, Q is selected from H and a $C_{5-6}$ carbocyclic residue substituted with 0–5 $R^b$.

4. A compound according to claim 3, wherein:

A is selected from —$CO_2H$, $CH_2CO_2H$, —CONHOH, and —$CONHOR^5$;

X is absent or selected from $C_{1-4}$ alkylene, $C_{2-4}$ alkenylene, and $C_{2-4}$ alkynylene;

Z is selected from phenyl substituted with 0–3 $R^b$ and a 5–9 membered aromatic heterocyclic system containing from 1–4 heteroatoms selected from the group consisting of N, O, and S and substituted with 0–3 $R^b$;

$X^a$ is absent or $C_{1-4}$ alkylene;

$Y^a$ is absent or selected from O and $NR^a$;

$Z^a$ is selected from H, a $C_{5-10}$ carbocyclic residue substituted with 0–5 $R^c$ and a 5–10 membered heterocyclic system containing from 1–4 heteroatoms selected from the group consisting of N, O, and S and substituted with 0–5 $R^c$;

$R^4$ is selected from H, $C_{1-4}$ alkylene-H, $(CH_2)_rO(CH_2)_r$—H, and $(CH_2)_rNR^a(CH_2)_r$—H; and, $R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $S(O)_2NR^aR^{a'}$, $S(O)_p R^a$, $CF_3$, $CF_2CF_3$, and a 5–6 membered heterocyclic system containing from 1–4 heteroatoms selected from the group consisting of N, O, and S.

5. A compound according to claim 1, wherein:

[1(R)]-N-hydroxy-α,3-dimethyl-2-oxo-3-[4-(phenylmethoxy)phenyl]-1-pyrrolidineacetamide;

[1(R)]-N-hydroxy-α,3-dimethyl-2-oxo-3-(4-methoxyphenyl)-1-pyrrolidineacetamide;

[1(R)]-N-hydroxy-α,3-dimethyl-3-[4-(1-methylethoxy)phenyl]-2-oxo-1-pyrrolidineacetamide;

[1(R)]-3-[4-(1,1-dimethylethoxy)phenyl]-N-hydroxy-α,3-dimethyl-2-oxo-1-pyrrolidineacetamide;

[1(R)]-3-(4-(cyclohexyloxy)phenyl]-N-hydroxy-α,3-dimethyl-2-oxo-1-pyrrolidineacetamide;

[1(R)]-N-hydroxy-α,3-dimethyl-2-oxo-3-[4-[4-(1,1-dimethylethyl)phenylmethoxy]phenyl]-1-pyrrolidineacetamide;

[1(R)]-N-hydroxy-α,3-dimethyl-2-oxo-3-[4-(trans-3-phenyl-2-propenyloxy)phenyl]-1-pyrrolidineacetamide;

[1(R)]-3-[4-[(3-methylphenyl)methoxy]phenyl]-N-hydroxy-α,3-dimethyl-2-oxo-1-pyrrolidineacetamide;

[1(R)]-3-[4-[(3,5-dimethylphenyl)methoxy]phenyl]-N-hydroxy-α,3-dimethyl-2-oxo-1-pyrrolidineacetamide;

[1(R)]-N-hydroxy-α,3-dimethyl-2-oxo-3-[4-(2-propenyloxy)phenyl]-1-pyrrolidineacetamide;

[1(R)]-3-[4-[(3-cyanophenyl)methoxy]phenyl]-N-hydroxy-α,3-dimethyl-2-oxo-1-pyrrolidineacetamide;

[1(R)]-N-hydroxy-α-3-dimethyl-3-[4-[(2-nitrophenyl)methoxy]phenyl]-2-oxo-1-pyrrolidineacetamide;

[1(R)]-N-hydroxy-α-3-dimethyl-3-[4-[(3-nitrophenyl)methoxy]phenyl]-2-oxo-1-pyrrolidineacetamide;

[1(R)]-N-hydroxy-α,3-dimethyl-3-[4-[(4-nitrophenyl)methoxy]phenyl]-2-oxo-1-pyrrolidineacetamide;

[1(R)]-N-hydroxy-α,3-dimethyl-3-[4-[(1-naphthalenyl)methoxy]phenyl]-2-oxo-1-pyrrolidineacetamide;

[1(R)]-N-hydroxy-3-(4-hydroxyphenyl)-α,3-dimethyl-2-oxo-1-pyrrolidineacetamide;

[1(R)]-N-hydroxy-α,3-dimethyl-2-oxo-3-[4-[(2-pyridinyl)methoxy]phenyl]-1-pyrrolidineacetamide;

[1(R)]-N-hydroxy-α,3-dimethyl-2-oxo-3-[4-[(3-pyridinyl)methoxy]phenyl]-1-pyrrolidineacetamide;

[1(R)]-N-hydroxy-α,3-dimethyl-2-oxo-3-[4-[(4-pyridinyl)methoxy]phenyl]-1-pyrrolidineacetamide;

[1(R)]-N-hydroxy-α,3-dimethyl-3-[4-(2-methylpropyl)phenyl]-2-oxo-1-pyrrolidineacetamide;

[1(R)]-N-hydroxy-α,3-dimethyl-2-oxo-3-phenyl-1-pyrrolidineacetamide;

N-hydroxy-2-oxo-3-phenyl-1-pyrrolidineacetamide;

(+/−)-N-hydroxy-3-methyl-2-oxo-3-phenyl-1-pyrrolidineacetamide;

[1(R)]-N-hydroxy-α,methyl-2-oxo-3-phenyl-1-pyrrolidineacetamide;

[1(R)]-N-hydroxy-3-(4-methoxyphenyl)-α,methyl-2-oxo-1-pyrrolidineacetamide;

[1(R)]-3-cyclohexyl-N-hydroxy-α,3-dimethyl-2-oxo-1-pyrrolidineacetamide;

[1(R)]-N-hydroxy-α,3-dimethyl-2-oxo-3-(2-phenylethyl)-1-pyrrolidineacetamide;

[1(R)]-3-(2-cyclohexylethyl)-N-hydroxy-α,3-dimethyl-2-oxo-1-pyrrolidineacetamide;

[1(R)]-N-hydroxy-α,methyl-2-oxo-3-phenyl-3-(phenylmethyl)-2-oxo-1-pyrrolidineacetamide;

[1(R)]-3-[4-[(3,5-dibromophenyl)methoxy]phenyl]-N-hydroxy-α,3-dimethyl-2-oxo-1-pyrrolidineacetamide;

[1(R)]-3-[4-[[3,5-bis(trifluoromethyl)phenyl]methoxy]phenyl]-N-hydroxy-α,3-dimethyl-2-oxo-1-pyrrolidineacetamide;

[1(R)]-3-[4-[(3,5-dichlorophenyl)methoxy]phenyl]-N-hydroxy-α,3-dimethyl-2-oxo-1-pyrrolidineacetamide;

[1(R)]-N-hydroxy-α,3-dimethyl-3-[4-[(2-methyl-1-naphthalenyl)methoxy]phenyl]-2-oxo-1-pyrrolidineacetamide;

[1(R)]-3-[4-[(3,5-dimethoxyphenyl)methoxy]phenyl]-N-hydroxy-α, 3-dimethyl-2-oxo-1-pyrrolidineacetamide;

[1(R)]-N-hydroxy-α,3-dimethyl-2-oxo-3-[4-[[4-(1,2,3-thiadiazol-4-yl)phenyl]methoxy]phenyl]-1-pyrrolidineacetamide;

[1(R)]-3-[4-([1,1'-biphenyl]-2-ylmethoxy)phenyl]-N-hydroxy-α,3-dimethyl-2-oxo-1-pyrrolidineacetamide;

[1(R)]-3-[4-[(2,6-dichloro-4-pyridinyl)methoxy]phenyl]-N-hydroxy-α,3-dimethyl-2-oxo-1-pyrrolidineacetamide;

[1(R)]-3-[4-(1H-benzotriazol-1-ylmethoxy)phenyl]-N-hydroxy-α,3-dimethyl-2-oxo-1-pyrrolidineacetamide;

[1(R)]-3-[4-[(4,6-dimethyl-2-pyrimidinyl)methoxy]phenyl]-N-hydroxy-α,3-dimethyl-2-oxo-1-pyrrolidineacetamide;

[1(R)]-3-[4-(1,3-benzodioxol-5-ylmethoxy)phenyl]-N-hydroxy-α,3-dimethyl-2-oxo-1-pyrrolidineacetamide;

[1(R)]-3-[4-[(2-chloro-6-ethoxy-4-pyridinyl)methoxy]phenyl]-N-hydroxy-α,3-dimethyl-2-oxo-1-pyrrolidineacetamide;

[1(R)]-3-[4-[(4,5-dimethyl-2-thiazolyl)methoxy]phenyl]-N-hydroxy-α,3-dimethyl-2-oxo-1-pyrrolidineacetamide;

[1(R)]-3-[4-[(2,6-dimethyl-4-pyridinyl)methoxy]phenyl]-N-hydroxy-α,3-dimethyl-2-oxo-1-pyrrolidineacetamide;

[1(R)]-N-hydroxy-α,3-dimethyl-3-[4-[(3-methyl-5-nitrophenyl)methoxy]phenyl]-2-oxo-1-pyrrolidineacetamide;

[1(R)]-3-[4-[(3-amino-5-methylphenyl)methoxy]phenyl]-N-hydroxy-α,3-dimethyl-2-oxo-1-pyrrolidineacetamide;

[1(R)]-3-[4-[[3-(acetylamino)-5-methylphenyl]methoxy]phenyl]-N-hydroxy-α,3-dimethyl-2-oxo-1-pyrrolidineacetamide;

[1(R)]-1,1-dimethylethyl[2-[[3-[[4-[1-[2-(hydroxyamino)-1-methyl-2-oxoethyl]-3-methyl-2-oxo-3-pyrrolidinyl]phenoxy]methyl]-5-methylphenyl]amino]-2-oxoethyl]carbamate;

[1(R)]-3-[4-[[3-[(aminoacetyl)amino]-5-methylphenyl]methoxy]phenyl]-N-hydroxy-α,3-dimethyl-2-oxo-1-pyrrolidineacetamide;

[1(R)]-1,1-dimethylethyl[2-[[2-[[3-[[4-[1-[2-(hydroxyamino)-1-methyl-2-oxoethyl]-3-methyl-2-oxo-3-pyrrolidinyl]phenoxy]methyl]-5-methylphenyl]amino]-2-oxoethyl]amino]-2-oxoethyl]carbamate;

[1(R)]-3-[4-[[3-[[[(aminoacetyl)amino]acetyl]amino]-5-methylphenyl]methoxy]phenyl]-N-hydroxy-α,3-dimethyl-2-oxo-1-pyrrolidineacetamide;

3-[4-[(2,6-dichloro-4-pyridinyl)methoxy]phenyl]-N-hydroxy-α,α,3-trimethyl-2-oxo-1-pyrrolidineacetamide;

[1(R)]-3-[1,1'-biphenyl]-4-yl-N-hydroxy-α,3-dimethyl-2-oxo-1-pyrrolidineacetamide;

[1(R)]-N-hydroxy-α,3-dimethyl-3-(2'-methyl[1,1'-biphenyl]-4-yl)-2-oxo-1-pyrrolidineacetamide;

[1(R)]-N-hydroxy-α,3-dimethyl-3-(4'-methyl[1,1'-biphenyl]-4-yl)-2-oxo-1-pyrrolidineacetamide;

[1(R)-3-(3',4'-dimethoxy[1,1'-biphenyl]-4-yl)-N-hydroxy-α,3-dimethyl-2-oxo-1-pyrrolidineacetamide;

[1(R)]-N-hydroxy-α,3-dimethyl-2-oxo-3-[2'-(trifluoromethyl)[1,1'-biphenyl]-4-yl]-1-pyrrolidineacetamide;

[1(R)]-N-hydroxy-α,3-dimethyl-3-[4-(4-methylphenoxy)phenyl]-2-oxo-1-pyrrolidineacetamide;

[1(R)]-N-hydroxy-α,3-dimethyl-2-oxo-3-(4-phenoxyphenyl)-1-pyrrolidineacetamide;

[1(R)]-N-hydroxy-α,3-dimethyl-3-[4-(2-methylphenoxy)phenyl]-2-oxo-1-pyrrolidineacetamide;

[1(R)]-3-[4-(3,5-dichlorophenoxy)phenyl]-N-hydroxy-α,3-dimethyl-2-oxo-1-pyrrolidineacetamide;

[1(R)]-3-[4-(3,4-dimethoxyphenoxy)phenyl]-N-hydroxy-α,3-dimethyl-2-oxo-1-pyrrolidineacetamide;

[1(R)]-3-[4-(1,3-benzodioxol-5-yloxy)phenyl]-N-hydroxy-α,3-dimethyl-2-oxo-1-pyrrolidineacetamide;

[1(R)]-N-hydroxy-α,3-dimethyl-3-[4-[3-(1-methylethyl)phenoxy]phenyl]-2-oxo-1-pyrrolidineacetamide;

[1(R)]-N-hydroxy-3-[4-(3-methoxyphenoxy)phenyl]-α,3-dimethyl-2-oxo-1-pyrrolidineacetamide;

[1(R)]-N-hydroxy-α,3-dimethyl-2-oxo-3-[4-(3-thienyloxy)phenyl]-1-pyrrolidineacetamide;

[1(R)]-N-hydroxy-α,3-dimethyl-2-oxo-3-[4-(3,4,5-trimethoxyphenoxy)phenyl]-1-pyrrolidineacetamide;

[1(R)]-3-[4-[3,5-bis(trifluoromethyl)phenoxy]phenyl]-N-hydroxy-α,3-dimethyl-2-oxo-1-pyrrolidineacetamide;

[1(R)]-N-hydroxy-α,3-dimethyl-3-[4-(1-naphthalenyloxy)phenyl]-2-oxo-1-pyrrolidineacetamide;

[1(R)]-N-hydroxy-3-[4-[3-[(hydroxyimino)methyl]phenoxy]phenyl]-α,3-dimethyl-2-oxo-1-pyrrolidineacetamide;

[1(R)]-N-hydroxy-3-[4-[4-[1-(hydroxyimino)ethyl]phenoxy]phenyl]-α,3-dimethyl-2-oxo-1-pyrrolidineacetamide;

[1(R)]-3-[4-([1,1'-biphenyl]-4-yloxy)phenyl]-N-hydroxy-α,3-dimethyl-2-oxo-1-pyrrolidineacetamide;

[1(R)]-3-[4-(3,5-dibromophenoxy)phenyl]-N-hydroxy-α,3-dimethyl-2-oxo-1-pyrrolidineacetamide;

[1(R)]-3-[4-[3-(acetylamino)phenoxy]phenyl]--hydroxy-α,3-dimethyl-2-oxo-1-pyrrolidineacetamide;

[1(R)]-N-hydroxy-α,3-dimethyl-3-[4-(4-nitrophenoxy)phenyl]-2-oxo-1-pyrrolidineacetamide;

[1(R)]-N-hydroxy-α,3-dimethyl-3-(4-methylphenyl)-2-oxo-1-pyrrolidineacetamide;

[1(R)]-3-[4-[[(2,6-dimethyl-4-pyridinyl)oxy]methyl]phenyl]-N-hydroxy-α,3-dimethyl-2-oxo-1-pyrrolidineacetamide;

[1(R)]-N-hydroxy-α,3-dimethyl-3-(4-nitrophenyl)-2-oxo-1-pyrrolidineacetamide;

[1(R)]-N-hydroxy-α,3-dimethyl-2-oxo-3-[4-[(phenylcarbonyl)amino]phenyl]-1-pyrrolidineacetamide;

[1(R)]-N-hydroxy-α,3-dimethyl-2-oxo-3-[4-[(phenylsulfonyl)amino]phenyl]-1-pyrrolidineacetamide;

[1(R)]-N-hydroxy-α,3-dimethyl-2-oxo-3-[4-[[(phenylamino)carbonyl]amino]phenyl]-1-pyrrolidineacetamide;

[1(R)]-N-hydroxy-α,3-dimethyl-3-[4-[(1-naphthalenylmethyl)amino]phenyl]-2-oxo-1-pyrrolidineacetamide;

[1(R)]-3-[4-[[(3,5-dimethoxyphenyl)methyl]amino]phenyl]-N-hydroxy-α,3-dimethyl-2-oxo-1-pyrrolidineacetamide;

3-[4-[(3,5-dimethylphenyl)methoxy]phenyl]-N-hydroxy-3-methyl-2-oxo-1-pyrrolidineacetamide;

3-[4-[(2,6-dichloro-4-pyridinyl)methoxy phenyl]-N-hydroxy-3-methyl-2-oxo-1-pyrrolidineacetamide;

3-[4-[(2,6-dimethyl-4-pyridinyl)methoxy]phenyl]-N-hydroxy-3-methyl-2-oxo-1-pyrrolidineacetamide;

[1(R)]-N-hydroxy-3-methyl-α-(1-methylethyl)-2-oxo-3-[4-(phenylmethoxy)phenyl]-1-pyrrolidineacetamide;

[1(R)]-3-[4-[(2,6-dimethyl-4-pyridinyl)methoxy]phenyl]-N-hydroxy-3-methyl-α-(1-methylethyl)-2-oxo-1-pyrrolidineacetamide;

[1(R)]-3-[4-[(2,6-dimethyl-4-pyridinyl)methoxy]phenyl]-N-hydroxy-3-methyl-α-(2-methylpropyl)-2-oxo-1-pyrrolidineacetamide;

[1(R)]-3-[4-[(2,6-dichloro-4-pyridinyl)methoxy]phenyl]-N-hydroxy-3-methyl-α-(2-methylpropyl)-2-oxo-1-pyrrolidineacetamide;

[1(R)]-3-[4-[[3,5-bis(trifluoromethyl)phenyl]methoxy]phenyl]-N-hydroxy-3-methyl-α-(2-methylpropyl)-2-oxo-1-pyrrolidineacetamide;

[1(R)]-3-[4-[(3,5-dichlorophenyl)methoxy]phenyl]-N-hydroxy- 3-methyl-α-(2-methylpropyl)-2-oxo-1-pyrrolidineacetamide;

[1(R)]-N-hydroxy-3-methyl-α-(2-methylpropyl)-2-oxo-3-[3-(phenylmethoxy)propyl]-1-pyrrolidineacetamide;

[1(R)]-N-hydroxy-3-methyl-3-[2-methyl-4-(phenylmethoxy)phenyl]-α-(2-methylpropyl)-2-oxo-1-pyrrolidineacetamide;

[1(R)]-3-[4-[(2,6-dichloro-4-pyridinyl)methoxy]-2-methylphenyl]-N-hydroxy-3-methyl-α-(2-methylpropyl)-2-oxo-1-pyrrolidineacetamide;

[1(R)]-N-hydroxy-3-methyl-3-[2-methyl-4-(2-naphthalenylmethoxy)phenyl]-α-(2-methylpropyl)-2-oxo-1-pyrrolidineacetamide;

[1(R)]-N-hydroxy-3-methyl-α-(2-methylpropyl)-3-[2-methyl-4-(4-pyridinylmethoxy)phenyl]-2-oxo-1-pyrrolidineacetamide;

[1(R)]-3-[4-[(2,6-dimethyl-4-pyridinyl)methoxy]-2-methylphenyl]-N-hydroxy-3-methyl-α-(2-methylpropyl)-2-oxo-1-pyrrolidineacetamide;

[1(R)]-N-hydroxy-3-methyl-α-[2-(methylthio)ethyl]-2-oxo-3-[4-(phenylmethoxy)phenyl]-1-pyrrolidineacetamide;

[1(R)]-3-[4-(3,5-dibromophenoxy)phenyl]-3-methyl-α-[2-(methylsulfonyl)ethyl]-2-oxo-1-pyrrolidineacetic acid;

[1(R)]-3-[4-[3,5-bis(trifluoromethyl)phenoxy]phenyl]-N-hydroxy-3-methyl-α-[2-(methylsulfonyl)ethyl]-2-oxo-1-pyrrolidineacetamide;

[1(R)]-3-[4-(3,5-dibromophenoxy)phenyl]-N-hydroxy-3-methyl-α-[2-(methylsulfonyl)ethyl]-2-oxo-1-pyrrolidineacetamide;

[1(R)]-3-[4-[(2,6-dichloro-4-pyridinyl)methoxy]phenyl]-N-hydroxy-3-methyl-α-[2-(methylsulfonyl)ethyl]-2-oxo-1-pyrrolidineacetamide;

[1(R)]-3-[4-[(2,6-dimethyl-4-pyridinyl)methoxy]phenyl]-N-hydroxy-3-methyl-α-[2-(methylsulfonyl)ethyl]-2-oxo-1-pyrrolidineacetamide;

N-hydroxy-1-[3-methyl-2-oxo-3-[4-(phenylmethoxy)phenyl]-1-pyrrolidinyl]cyclopropanecarboxamide;

[1(R)]-N-hydroxy-α-[(4-hydroxyphenyl)methyl]-3-methyl-2-oxo-3-[4-(phenylmethoxy)phenyl]-1-pyrrolidineacetamide;

[1(R)]-3-[4-[(2,6-dichloro-4-pyridinyl)methoxy]phenyl]-N-hydroxy-α-(2-hydroxyethyl)-3-methyl-2-oxo-1-pyrrolidineacetamide;

[1(R)]-1,1-dimethylethyl[5-[3-[4-[(2,6-dichloro-4-pyridinyl)methoxy]phenyl]-3-methyl-2-oxo-1-pyrrolidinyl]-6-(hydroxyamino)-6-oxohexyl]carbamate;

[1(R)]-α-(4-aminobutyl)-3-[4-[(2,6-dichloro-4-pyridinyl)methoxy]phenyl]-N-hydroxy-3-methyl-2-oxo-1-pyrrolidineacetamide;

[1(R)]-α,[4-(acetylamino)butyl]-3-[4-[(2,6-dichloro-4-pyridinyl)methoxy]phenyl]-N-hydroxy-3-methyl-2-oxo-1-pyrrolidineacetamide;

[1(R)]-3-[4-[(2,6-dichloro-4-pyridinyl)methoxy]phenyl]-N-hydroxy-3-methyl-α-[4-[(methylsulfonyl)amino]butyl]-2-oxo-1-pyrrolidineacetamide;

[1(R)]-α-[4-(acetylamino)butyl]-3-[4-[(2,6-dimethyl-4-pyridinyl)methoxy]phenyl]-N-hydroxy-3-methyl-2-oxo-1-pyrrolidineacetamide;

[1(R)]-1,1-dimethylethyl[5-[3-[4-[(2,6-dimethyl-4-pyridinyl)methoxy]phenyl]-3-methyl-2-oxo-1-pyrrolidinyl]-6-(hydroxyamino)-6-oxohexyl]carbamate;

[1(R)]-α-(4-aminobutyl)-3-[4-[(2,6-dimethyl-4-pyridinyl)methoxy]phenyl]-N-hydroxy-3-methyl-2-oxo-1-pyrrolidineacetamide;

[1(R)]-α-[4-[(aminoacetyl)amino]butyl]-3-[4-[(2,6-dimethyl-4-pyridinyl)methoxy]phenyl]-N-hydroxy-3-methyl-2-oxo-1-pyrrolidineacetamide;

[1(R)]-α-[4-(acetylamino)butyl]-3-[4-[[3,5-bis(trifluoromethyl)phenyl]methoxy]phenyl]-N-hydroxy-3-methyl-2-oxo-1-pyrrolidineacetamide;

[1(R)]-1,1-dimethylethyl[5-[3-[4-(3,5-dibromophenoxy)phenyl]-3-methyl-2-oxo-1-pyrrolidinyl]-6-(hydroxyamino)-6-oxohexyl]carbamate;

[1(R)]-α-(4-aminobutyl)-3-[4-(3,5-dibromophenoxy)phenyl]-N-hydroxy-3-methyl-2-oxo-1-pyrrolidineacetamide;

[1(R)]-1,1-dimethylethyl[3-[3-[4-[(2,6-dichloro-4-pyridinyl)methoxy]phenyl]-3-methyl-2-oxo-1-pyrrolidinyl]-4-(hydroxyamino)-4-oxobutyl]carbamate;

[1(R)]-α-(2-aminoethyl)-3-[4-[(2,6-dichloro-4-pyridinyl)methoxy]phenyl]-N-hydroxy-3-methyl-2-oxo-1-pyrrolidineacetamide;

[1(R)]-α-[2-(acetylamino)ethyl]-3-[4-[(2,6-dichloro-4-pyridinyl)methoxy]phenyl]-N-hydroxy-3-methyl-2-oxo-1-pyrrolidineacetamide;

[1(R)]-1,1-dimethylethyl[3-[3-[4-[(2,6-dimethyl-4-pyridinyl)methoxy]phenyl]-3-methyl-2-oxo-1-pyrrolidinyl]-4-(hydroxyamino)-4-oxobutyl]carbamate;

[1(R)]-α-(2-aminoethyl)-3-[4-[(2,6-dimethyl-4-pyridinyl)methoxy]phenyl]-N-hydroxy-3-methyl-2-oxo-1-pyrrolidineacetamide;

[1(R)]-1,1-dimethylethyl[2-[[3-[3-[4-[(2,6-dimethyl-4-pyridinyl)methoxy]phenyl]-3-methyl-2-oxo-1-pyrrolidinyl]-4-(hydroxyamino)-4-oxobutyl]amino]-2-oxoethyl]carbamate;

[1(R)]-α-[2-[(aminoacetyl)amino]ethyl]-3-[4-[(2,6-dimethyl-4-pyridinyl)methoxy]phenyl]-N-hydroxy-3-methyl-2-oxo-1-pyrrolidineacetamide;

[1(R)]-1,1-dimethylethyl[2-[[2-[[3-[3-[4-[(2,6-dimethyl-4-pyridinyl)methoxy]phenyl]-3-methyl-2-oxo-1-pyrrolidinyl]-4-(hydroxyamino)-4-oxobutyl]amino]-2-oxoethyl]amino]-2-oxoethyl]carbamate;

[1(R)]-α-[2-[[[(aminoacetyl)amino]acetyl]amino]ethyl]-3-[4-[(2,6-dimethyl-4-pyridinyl)methoxy]phenyl]-N-hydroxy-3-methyl-2-oxo-1-pyrrolidineacetamide;

[1(R)]-N-hydroxy-3-methyl-2-oxo-α-[(phenylmethoxy)methyl]-3-[4-(phenylmethoxy)phenyl]-1-pyrrolidineacetamide;

[1(R)]-3-[4-[(2,6-dichloro-4-pyridinyl)methoxy]phenyl]-N-hydroxy-α-(hydroxymethyl)-3-methyl-2-oxo-1-pyrrolidineacetamide;

[1(R)]-3-amino-3-[4-[(3,5-dimethylphenyl)methoxy]phenyl]-N-hydroxy-alpha-methyl-2-oxo-1-pyrrolidineacetamide;

[1(R)]-3-[4-[(3,5-dimethylphenyl)methoxy]phenyl]-3-[[(ethylamino)carbonyl]amino]-N-hydroxy-alpha-methyl-2-oxo-1-pyrrolidineacetamide;

[1(R)]-3-[4-[(3,5-dimethylphenyl)methoxy]phenyl]-N-hydroxy-alpha-methyl-3-[(methylsulfonyl)amino]-2-oxo-1-pyrrolidineacetamide;

[1(R)]-3-amino-3-[4-[(2,6-dichloro-4-pyridinyl)methoxy]phenyl]-N-hydroxy-alpha-methyl-2-oxo-1-pyrrolidineacetamide;

[1(R)]-3-[4-[(2,6-dichloro-4-pyridinyl)methoxy]phenyl]-3-[[(ethylamino)carbonyl]amino]-N-hydroxy-alpha-methyl-2-oxo-1-pyrrolidineacetamide;

[1(R)]-1,1-dimethylethyl[2-[[3-[4-[(2,6-dichloro-4-pyridinyl)methoxy]phenyl]-1-[2-(hydroxyamino)-1-methyl-2-oxoethyl]-2-oxo-3-pyrrolidinyl]amino]-2-oxoethyl]carbamate;

[1(R)]-3-[(aminoacetyl)amino]-3-[4-[(2,6-dichloro-4-pyridinyl)methoxy]phenyl]-N-hydroxy-alpha-methyl-2-oxo-1-pyrrolidineacetamide;

[1(R)]-3-[4-[(2,6-dichloro-4-pyridinyl)methoxy]phenyl]-N-hydroxy-alpha-methyl--2-oxo-3[[[(phenylmethyl)amino]carbonyl]amino]-1-pyrrolidineacetamide;

[1(R)]-3-[4-[(2,6-dichloro-4-pyridinyl)methoxy]phenyl]-3-[[[(2,4-dimethoxyphenyl)amino]carbonyl]amino]-N-hydroxy-alpha-methyl-2-oxo-1-pyrrolidineacetamide;

[1(R)]-3-[4-[(2,6-dichloro-4-pyridinyl)methoxy]phenyl]-N-hydroxy-alpha-methyl-2-oxo-3-[[(phenylamino)carbonyl]amino]-1-pyrrolidineacetamide;

[1(R)]-1,1-dimethylethyl[3-[4-[(2,6-dichloro-4-pyridinyl)methoxy]phenyl]-1-[2-(hydroxyamino)-1-methyl-2-oxoethyl]-2-oxo-3-pyrrolidinyl]carbamate;

[1(R)]-1,1-dimethylethyl N-[[[3-[4-[(2,6-dichloro-4-pyridinyl)methoxy]phenyl]-1-[2-(hydroxyamino)-1-methyl-2-oxoethyl]-2-oxo-3-pyrrolidinyl]amino]carbonyl]glycine;

[1(R)]-3-[4-[(2,6-dichloro-4-pyridinyl)methoxy]phenyl]-N-hydroxy-3-[[[(3-hydroxyphenyl)amino]carbonyl]amino]-alpha-methyl-2-oxo-1-pyrrolidineacetamide;

[1(R)]-3-amino-3-[4-[(2,6-dichloro-4-pyridinyl)methoxy]phenyl]-N-hydroxy-alpha-[2-(methylsulfonyl)ethyl]-2-oxo-1-pyrrolidineacetamide;

[1(R)]-3-amino-3-[4-[(2,6-dimethyl-4-pyridinyl)methoxy]
  phenyl]-N-hydroxy-alpha-[2-(methylsulfonyl)ethyl]-2-
  oxo-1-pyrrolidine acetamide;
[5(R)]-2-propenyl[5-[3-amino-3-[4-[(2,6-dichloro-4-
  pyridinyl)methoxy]phenyl]-2-oxo-1-pyrrolidinyl]-6-
  (hydroxyamino)-6-oxohexyl]carbamate;
[5(R)]-2-propenyl[5-[3-amino-3-[4-[(2,6-dimethyl-4-
  pyridinyl)methoxy]phenyl]-2-oxo-1-pyrrolidinyl]-6-
  (hydroxyamino)-6-oxohexyl]carbamate;
[1(R)]-3-amino-3-[4-[(2,6-dichloro-4-pyridinyl)methoxy]
  phenyl]-N-hydroxy-alpha-(2-methylpropyl)-2-oxo-1-
  pyrrolidineacetamide;
[1(R)]-3-[4-[(2,6-dimethyl-4-pyridinyl)methoxy]phenyl]-
  N-hydroxy-alpha-(2-methylpropyl)-2-oxo-3-
  [(trifluoroacetyl)amino]-1-pyrrolidineacetamide;
[1(R)]-3-[4-[(2,6-dichloro-4-pyridinyl)methoxy]phenyl]-N-
  hydroxy-alpha-(2-methylpropyl)-2-oxo-3-
  [[[(phenylsulfonyl)amino]carbonyl]amino]-1-
  pyrrolidineacetamide;
[1(R)]-3-[4-[(2,6-dimethyl-4-pyridinyl)methoxy]phenyl]-
  N-hydroxy-alpha-(2-methylpropyl)-2-oxo-3-
  [[[(phenylsulfonyl)amino]carbonyl]amino]-1-
  pyrrolidineacetamide;
[1(R)]-3-[4-[(2,6-dimethyl-4-pyridinyl)methoxy]phenyl]-
  N-hydroxy-alpha-(2-methylpropyl)-2-oxo-3-
  [[(phenylamino)carbonyl]amino]-1-
  pyrrolidineacetamide;
[1(R)]-3-[4-[(2,6-dichloro-4-pyridinyl)methoxy]phenyl]-N-
  hydroxy-alpha-(2-methylpropyl)-2-oxo-3-
  [[(phenylamino)carbonyl]amino]-1-
  pyrrolidineacetamide;
[1(R)]-1-[1-[(hydroxyamino)carbonyl]-3-methylbutyl]-N,
  N,N-trimethyl-2-oxo-3-[4-(phenylmethoxy)phenyl]-1-
  pyrrolidinemethanaminium;
[1(R)]-3-amino-N-hydroxy-alpha-(2-methylpropyl)-2-oxo-
  3-[4-(2-oxo-2-phenylethoxy)phenyl]-1-
  pyrrolidineacetamide;
[1(R)]-3-amino-3-[4-[(3,5-dimethyl-4-isoxazolyl)methoxy]
  phenyl]-N-hydroxy-alpha-(2-methylpropyl)-2-oxo-1-
  pyrrolidineacetamide;
[1(R)]-3-amino-3-[4-[(2,6-dimethyl-4-pyridinyl)methoxy]
  phenyl]-N-hydroxy-alpha-(2-methylpropyl)-2-oxo-1-
  pyrrolidineacetamide;
[1(R)]-3-amino-3-[4-[2-(2-benzothiazolylamino)-2-
  oxoethoxy]phenyl]-N-hydroxy-alpha-(2-methylpropyl)-
  2-oxo-1-pyrrolidineacetamide;
[1(R)]-3-amino-3-[4-[2-(2,5-dimethoxyphenyl)-2-
  (hydroxyimino)ethoxy]phenyl]-N-hydroxy-alpha-(2-
  methylpropyl)-2-oxo-1-pyrrolidineacetamide;
[1(R)]-3-amino-N-hydroxy-3-[4-[(2-methylimidazo[1,2-a]
  pyridin-3-yl)methoxy]phenyl]-alpha-(2-methylpropyl)-2-
  oxo-1-pyrrolidineacetamide;
[1(R)]-3-amino-3-[4-[[1,4-dimethyl-2-(methylthio)-1H-
  imidazol-5-yl]methoxy]phenyl]-N-hydroxy-alpha-(2-
  methylpropyl)-2-oxo-1-pyrrolidineacetamide;
[1(R)]-3-amino-3-[4-[[1,5-dimethyl-2-(methylthio)-1H-
  imidazol-4-yl]methoxy]phenyl]-N-hydroxy-alpha-(2-
  methylpropyl)-2-oxo-1-pyrrolidineacetamide;
[1(R)]-3-amino-3-[4-[(2,4-dimethyl-5-thiazolyl)methoxy]
  phenyl]-alpha-(2-methylpropyl)-2-oxo-1-
  pyrrolidineacetamide;
[1(R)]-3-amino-3-[4-[(3,5-dimethoxyphenyl)methoxy]
  phenyl]-N-hydroxy-alpha-[2-(methylsulfonyl)ethyl]-2-
  oxo-1-pyrrolidineacetamide;
[1(R)]-3-amino-3-[4-[(3,5-dimethoxyphenyl)methoxy]
  phenyl]-N-hydroxy-alpha-(2-methylpropyl)-2-oxo-1-
  pyrrolidineacetamide;
[1(R)]-3-(aminomethyl)-3-[4-[(2,6-dimethyl-4-pyridinyl)
  methoxy]phenyl]-N-hydroxy-alpha-(2-methylpropyl)-2-
  oxo-1-pyrrolidineacetamide;
[1(R)]-3-(aminomethyl)-3-[4-[(2,6-dichloro-4-pyridinyl)
  methoxy]phenyl]-N-hydroxy-alpha-methyl-2-oxo-1-
  pyrrolidineacetamide;
[1(R)]-3-[4-[(3,5-dimethylphenyl)methoxy]phenyl]-N-
  hydroxy-3-(hydroxymethyl)-alpha-methyl-2-oxo-1-
  pyrrolidineacetamide;
[1(R)]-[3-[4-[(3,5-dimethylphenyl)methoxy]phenyl]-1-[2-
  (hydroxyamino)-1-methyl-2-oxoethyl]-2-oxo-3-
  pyrrolidinyl]methyl ethylcarbamate;
[1(R)]-3-[4-[(2,6-dichloro-4-pyridinyl)methoxy]phenyl]-N-
  hydroxy-3-(hydroxymethyl)-alpha-methyl-2-oxo-1-
  pyrrolidineacetamide;
[1(R)]-3-[5-[(3,5-dimethylphenoxy)methyl]-2-thiazolyl]-N-
  hydroxy-alpha, 3-dimethyl-2-oxo-1-
  pyrrolidineacetamide;
[1(R)]-N-hydroxy-alpha, 3-dimethyl-2-oxo-3-[[4-
  (phenylmethoxy)phenyl]methyl]-1-pyrrolidineacetamide;
[1(R)]-3-[4-[(2,6-dimethyl-4-pyridinyl)methoxy]phenyl]-
  N-hydroxy-3-(methylamino)-alpha-(2-methylpropyl)-2-
  oxo-1-pyrrolidineacetamide;
[1(R)]-3-amino-3-[4-[(2,6-dimethyl-4-pyridinyl)methoxy]
  phenyl]-N-hydroxy-α-(1-methylethyl)-2-oxo-1-
  pyrrolidineacetamide;
[1(R)]-3-amino-α-cyclohexyl-3-[4-[(2,6-dimethyl-4-
  pyridinyl)methoxy]phenyl]-N-hydroxy-2-oxo-1-
  pyrrolidineacetamide;
3-amino-α-(1,1-dimethylethyl)-3-[4-[(2,6-dimethyl-4-
  pyridinyl)methoxy]phenyl]-N-hydroxy-2-oxo-1-
  pyrrolidineacetamide;
[1(R)]-3-amino-3-[4-[(2,6-dimethyl-4-pyridinyl)methoxy]
  phenyl]-N-hydroxy-α-(4-methoxycyclohexyl)-2-oxo-1-
  pyrrolidineacetamide;
[1(R)]-N-hydroxy-α,3-dimethyl-2-oxo-3-[3-
  (phenylmethoxy)phenyl]-1-pyrrolidineacetamide;
[1(R)]-3-[3-[(3,5-dimethylphenyl)methoxy]phenyl]-N-
  hydroxy-α,3-dimethyl-2-oxo-1-pyrrolidineacetamide;
[1(R)]-N-hydroxy-α,3-dimethyl-3-[3-[(3-methylphenyl)
  methoxy]phenyl]-2-oxo-1-pyrrolidineacetamide;
[1(R)]-N-hydroxy-α,3-dimethyl-3-[3-(1-methylethoxy)
  phenyl]-2-oxo-1-pyrrolidineacetamide;
[1(R)]-3-[3-(heptyloxy)phenyl]-N-hydroxy-α,3-dimethyl-
  2-oxo-1-pyrrolidineacetamide;
[1(R)]-1,1-dimethylethyl 1-[2-(hydroxyamino)-1-methyl-2-
  oxoethyl]-2-oxo-3-[4-(phenylmethoxy)phenyl]-3-
  pyrrolidineacetate;
[1(R)]-1-[2-(hydroxyamino)-1-methyl-2-oxoethyl]-2-oxo-
  3-[4-(phenylmethoxy)phenyl]-3-pyrrolidineacetic acid;
[1(R)]-3-[4-[(3,5-dimethylphenyl)methoxy]phenyl]-N1-
  hydroxy-α1-methyl-N3-[2-(methylamino)-2-oxoethyl]-
  2-oxo-1,3-pyrrolidinediacetamide;
[1(R)]-3-[3-(1H-benzotriazol-1-ylmethoxy)phenyl]-N-
  hydroxy-α,3-dimethyl-2-oxo-1-pyrrolidineacetamide;
[1(R)]-1,1-dimethylethyl 1-[(hydroxyamino)carbonyl]-3-
  methylbutyl]-2-oxo-3-[4-(phenyl]-3-pyrrolidineacetate;
[1(R)-N1-hydroxy-3-[4-[(3,5-dimethylphenyl)methoxy]
  phenyl]-N3-[2-(methylamino)-2-oxoethyl]-α-(2-
  methylpropyl)-2-oxo-1,3-pyrrolidinediacetamide;
[1(R)]-3-[4-[(2,6-dichloro-4-pyridinyl)methoxy]phenyl]-
  N1-hydroxy-N3-[2-(methylamino)-2-oxoethyl]-alpha1-
  (2-methylpropyl)-2-oxo-1,3-pyrrolidinediacetamide;
[1(R)]-3-[4-[3,5-bis(trifluoromethyl)phenoxy]phenyl]-N1-
  hydroxy-N3-[2-(methylamino)-2-oxoethyl]-α1-(2-
  methylpropyl)-2-oxo-1,3-pyrrolidinediacetamide;
[1(R)]-3-[4-[(2,6-dichloro-4-pyridinyl)methoxy]phenyl]-
  N1-hydroxy-α1-(2-methylpropyl)-2-oxo-N3-phenyl-1,3-
  pyrrolidinediacetamide;

[1(R)]-3-[4-[(2,6-dimethyl-4-pyridinyl)methoxy]phenyl]-N1-hydroxy-N3-methyl-α1-(2-methylpropyl)-2-oxo-1,3-pyrrolidinediacetamide;

[1(R)]-N3-[2-(dimethylamino)ethyl]-3-[4-[(2,6-dimethyl-4-pyridinyl)methoxy]phenyl]-N1-hydroxy-α1-(2-methylpropyl)-2-oxo-1,3-pyrrolidinediacotamide;

[1(R)]-3-[4-[(2,6-dimethyl-4-pyridinyl)methoxy]phenyl]-N1-hydroxy-N3-(4-hydroxyphenyl)-α1-(2-methylpropyl)-2-oxo-1,3-pyrrolidinediacetamide; and,

[1(R)]-3-[4-[(2,6-dimethyl-4-pyridinyl)methoxy]phenyl]-N3-hydroxy-3-(2-hydroxyethyl)-α1-(2-methylpropyl)-2-oxo-1-pyrrolidineacetamide; or a pharmaceutically acceptable salt form thereof.

6. A pharmaceutical composition, comprising: a pharmaceutically acceptable carrier and a therapeutically effective amount of a compound of claim 1 or a pharmaceutically acceptable salt form thereof.

7. A pharmaceutical composition, comprising: a pharmaceutically acceptable carrier and a therapeutically effective amount of a compound of claim 2 or a pharmaceutically acceptable salt form thereof.

8. A pharmaceutical composition, comprising: a pharmaceutically acceptable carrier and a therapeutically effective amount of a compound of claim 3 or a pharmaceutically acceptable salt form thereof.

9. A pharmaceutical composition, comprising: a pharmaceutically acceptable carrier and a therapeutically effective amount of a compound of claim 4 or a pharmaceutically acceptable salt form thereof.

10. A pharmaceutical composition, comprising: a pharmaceutically acceptable carrier and a therapeutically effective amount of a compound of claim 5 or a pharmaceutically acceptable salt form thereof.

11. A method for treating or preventing an inflammatory disorder, comprising: administering to a patient in need thereof a therapeutically effective amount of a compound of claim 1 or a pharmaceutically acceptable salt form thereof.

12. A method of treating according to claim 11, wherein the disorder is a condition or disease mediated by MMPs, TNF, aggrecanase, or a combination thereof in a mammal.

13. A method of treating a condition or disease according to claim 12, wherein the disease or condition is selected from: rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal.

14. A method of treating a condition or disease according to claim 12, wherein the disease or condition is selected from: fever, cardiovascular effects, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of claim 1 or a pharmaceutically acceptable salt form thereof.

15. A method for treating or preventing an inflammatory disorder, wherein the disorder is a condition or disease mediated by MMPs, TNF, aggrecanase, or a combination thereof in a mammal, comprising: administering to the mammal in need of such treatment a therapeutically effective amount of a compound of claim 2 or a pharmaceutically acceptable salt form thereof.

16. A method for treating or preventing an inflammatory disorder, wherein the disorder is a condition or disease mediated by MMPs, TNF, aggrecanase, or a combination thereof in a mammal, comprising: administering to the mammal in need of such treatment a therapeutically effective amount of a compound of claim 3 or a pharmaceutically acceptable salt form thereof.

17. A method for treating or preventing an inflammatory disorder, wherein the disorder is a condition or disease mediated by MMPs, TNF, aggrecanase, or a combination thereof in a mammal, comprising: administering to the mammal in need of such treatment a therapeutically effective amount of a compound of claim 4 or a pharmaceutically acceptable salt form thereof.

18. A method for treating or preventing an inflammatory disorder, wherein the disorder is a condition or disease mediated by MMPs, TNF, aggrecanase, or a combination thereof in a mammal, comprising: administering to the mammal in need of such treatment a therapeutically effective amount of a compound of claim 5 or a pharmaceutically acceptable salt form thereof.

\* \* \* \* \*

UNITED STATES PATENT AND TRADEMARK OFFICE
CERTIFICATE OF CORRECTION

PATENT NO. : 6,403,632 B1
DATED : June 11, 2002
INVENTOR(S) : Jingwu Duan et al.

It is certified that error appears in the above-identified patent and that said Letters Patent is hereby corrected as shown below:

<u>Title page,</u>
Insert Item: -- [73] Assignee: Bristol-Myers Squibb Pharma Company, Princeton NJ (US) --;
Insert        -- Related U.S. Application Data

[62] Division of application No. 09/165,747 October 2, 1998, now U.S. Patent No. 6,057,336
[60] Provisional application No. 60/062,418, filed October 3, 1997 --;

<u>Column 1,</u>
After the title, insert:

-- CROSS REFERENCE TO RELATED APPLICATIONS

This is a divisional of Application No. 09/165,747, filed October 2, 1998, now U.S. Patent No. 6,057,336, which claims priority to Provisional Application No. 60/062,418, filed October 3, 1997. --

Signed and Sealed this

Sixteenth Day of December, 2003

JAMES E. ROGAN
*Director of the United States Patent and Trademark Office*